United States Patent
Mathews et al.

(10) Patent No.: US 6,544,989 B2
(45) Date of Patent: Apr. 8, 2003

(54) BENZAZOLES: BENZOXAZOLE, BENZTHIAZOLE AND BENZIMIDAZOLE DERIVATIVES

(75) Inventors: Christopher John Mathews, Bracknell (GB); Russell Viner, Bracknell (GB); Susan Patricia Barnett, Bracknell (GB); Christopher John Urch, Bracknell (GB); Stephen Christopher Smith, Bracknell (GB); Patrick Jelf Crowley, Bracknell (GB); William Guy Whittingham, Bracknell (GB); Stephen Paul Heaney, Bracknell (GB); John Williams, Bracknell (GB); Torquil Eoghan Macleod Fraser, Bracknell (GB); Eric Daniel Clarke, Bracknell (GB); David John Hughes, Bracknell (GB); Sarah Armstrong, Bracknell (GB); Nigel John Barnes, Bracknell (GB); Alan John Whittle, Camelford (GB); Brian Leslie Pilkington, deceased, late of Maidenhead (GB), by Joan Pilkington, legal representative

(73) Assignee: Syngenta Limited (GB)

( * ) Notice: Subject to any disclaimer, the term of this patent is extended or adjusted under 35 U.S.C. 154(b) by 0 days.

(21) Appl. No.: 09/767,880

(22) Filed: Jan. 23, 2001

(65) Prior Publication Data

US 2002/0049142 A1 Apr. 25, 2002

Related U.S. Application Data

(63) Continuation of application No. PCT/GB99/02377, filed on Jul. 21, 1999.

(30) Foreign Application Priority Data

Jul. 30, 1998 (GB) ............................................. 9816654

(51) Int. Cl.$^7$ .................. C07D 417/12; C07D 417/14; H01N 43/80
(52) U.S. Cl. .................. 514/233.8; 548/159; 548/206; 544/133; 514/367; 514/372
(58) Field of Search .............................. 548/159, 206; 514/367, 233.8, 372; 544/133

(56) References Cited

FOREIGN PATENT DOCUMENTS

| EP | 0 623 282 A1 | 11/1994 |
|---|---|---|
| EP | 0 640 597 A1 | 3/1995 |
| WO | 95/31448 | 11/1995 |
| WO | 97/18198 | 5/1997 |
| WO | 98/02424 | 1/1998 |

*Primary Examiner*—Mukund J. Shah
*Assistant Examiner*—Hong Liu
(74) *Attorney, Agent, or Firm*—Hale and Dorr LLP

(57) ABSTRACT

The invention provides compounds of formula (I):

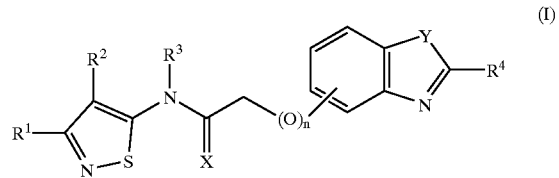

where the substituents are as defined in the specification. The invention also provides processes for preparing the compounds, compositions comprising the compounds, methods of using the compounds and compositions to combat fungal diseases, and methods of using the compounds and compositions to combat or control insect, acarine, mollusc and nematode pests.

30 Claims, No Drawings

BENZAZOLES: BENZOXAZOLE, BENZTHIAZOLE AND BENZIMIDAZOLE DERIVATIVES

This is a continuation of International Application No. PCT. GB99/02377, filed on Jul. 21, 1999, published in English.

The present invention relates to isothiazole derivatives, to processes for preparing them, to fungicidal, insecticidal, acarcidal, molluscicidal and nematicidal compositions comprising them, to methods of using them to combat fungal diseases (especially fungal diseases of plants) and to methods of using them to combat and control insect, acarine, mollusc and nematode pests.

Isothiazole derivatives are disclosed in WO 95/31448, WO 97/18198, WO 98/02424 and WO 98/05670.

The present invention provides a compound of formula (I):

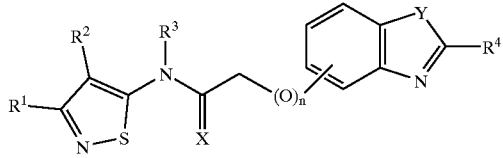

wherein X is O or S; n is 0 or 1; Y is O, S or $NR^7$; $R^1$ is hydrogen, halogen, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{3-6}$ cycloalkyl, $C_{1-6}$ alkoxy($C_{1-6}$)alkyl or $SF_5$; $R^2$ is hydrogen, halogen, $C_{1-6}$ alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{-6}$ haloalkylsulfonyl, $C_{1-6}$ haloalkyl, cyano, nitro, CHO, CH=$NOR^5$, $C_{1-6}$ alkylcarbonyl, $C_{1-6}$ alkoxycarbonyl or $SF_5$; or together $R^1$ and $R^2$ form a five or six merbered saturated or unsaturated carbocyclic ring, optionally substituted by one or two $C_{1-6}$ alkyl groups; $R^3$ is hydrogen, $C_{1-6}$ alkyl, $CH_2(C_{1-4}$ haloalkyl), $C_{1-6}$ cyanoalkyl, $C_{3-6}$ alkenyl, $C_{3-6}$ alkynyl, $C_{1-6}$ alkoxy($C_{1-6}$)alkyl, $C_{1-6}$ alkylthio($C_{1-6}$)alkyl, $C_{1-6}$ alkoxy($C_{1-6}$)alkoxy($C_{1-6}$)alkyl, $C_{1-6}$ alkylcarbonyl, $C_{1-6}$ alkoxycarbonyl, formyl, $C_{1-6}$ alkylcarbonyl($C_{1-6}$)alkyl, $C_{1-6}$ alkoxycarbonyl($C_{1-6}$)alkyl, $C_{1-6}$ alkylaminocarbonyl, di($C_{1-6}$)alkylaminocarbonyl, optionally substituted phenoxycarbonyl, optionally substituted phenyl($C_{1-4}$)alkyl or $S(O)_qR^6$; $R^4$ is hydrogen, halogen, cyano, $C_{1-8}$ alkyl, $C_{1-6}$ haloalkyl, $C_{1-6}$ cyanoalkyl, $C_{2-6}$ alkenyl, $C_{2-6}$ alkynyl, $C_{3-7}$ cycloalkyl, $C_{3-7}$ halocycloalkyl, $C_{3-7}$ cyanocycloalkyl, $C_{1-3}$ alkyl($C_{3-7}$)cycloalkyl, $C_{1-3}$ alkyl($C_{3-7}$)halocycloalkyl, $C_{3-6}$ cycloalkyl($C_{1-6}$)alkyl, $C_{5-6}$ cycloalkenyl, $C_{5-6}$ cycloalkenyl ($C_{1-6}$)alkyl, $C_{1-6}$ haloalkenyl, $C_{1-6}$ cyanoalkenyl, $C_{1-6}$ alkoxy($C_{1-6}$)alkyl, formyl, $C_{1-6}$ carboxyalkyl, $C_{1-6}$ akylcarbonyl($C_{1-6}$)alkyl, $C_{1-6}$ alkoxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)alkyl, di($C_{1-6}$)alkylaminocarbonyl ($C_{1-6}$)alkyl, $C_{1-6}$ alkoxycarbonyl, $C_{1-6}$ alkylcarbonyl, aminocarbonyl, $C_{1-6}$ alkylaminocarbonyl, di($C_{1-6}$) alkylaminocarbonyl, optionally substituted phenyl, optionally substituted phenyl($C_{1-4}$)alkyl, optionally substituted phenyl($C_{2-4}$)alkenyl, optionally substituted heteroaryl, optionally substituted heteroaryl($C_{1-4}$)alkyl, optionally substituted heterocyclyl, optionally substituted heterocyclyl($C_{1-4}$)alkyl, a group $OR^8$, a group SH, a group $S(O)_pR^9$, a group $NR^{10}R^{11}$ or a group $C(R^{12})$=$NOR^{13}$; $R^5$ is hydrogen, $C_{1-6}$ alkyl, optionally substituted phenyl or optionally substituted phenyl($CC_{1-4}$)alkyl; $R^6$ is $C_{1-6}$ alkyl, $C_{1-6}$ haloalkyl or optionally substituted phenyl; $R^7$ is hydrogen, cyano, $C_{1-8}$ alkyl, $C_{1-6}$ haloalkyl, $C_{1-6}$ cyanoalkyl, $C_{2-6}$ alkenyl, $C_{2-6}$ alkynyl, $C_{3-7}$ cycloalkyl, $C_{2-6}$ haloalkenyl, $C_{3-6}$ cycloalkyl($C_{1-6}$)alkyl, $C_{1-6}$ alkoxy($C_{1-6}$) alkyl, $C_{1-6}$ alkoxycarbonyl, $C_{1-6}$ alkylcarbonyl, $C_{1-6}$ alkylaminocarbonyl, di($C_{1-6}$)alkylaminocarbonyl, optionally substituted phenyl or optionally substituted heteroaryl; $R^8$ is hydrogen, $C_{1-6}$ alkyl, $C_{1-6}$ haloalkyl, $C_{3-6}$ alkenyl, $C_{1-4}$ cyanoalkyl, $C_{1-6}$ alkoxycarbonyl($C_{1-6}$)alkyl, optionally substituted phenyl, optionally substituted phenyl($C_{1-4}$)alkyl, optionally substituted heteroaryl, N=$C(CH_3)_2$; $R^9$ is $C_{1-6}$ alkyl, $C_{1-6}$ haloalkyl, $C_{3-6}$ alkenyl, cyano, $C_{1-4}$ cyanoalkyl, $C_{1-6}$ alkoxycarbonyl($C_{1-6}$)alkyl, optionally substituted phenyl, optionally substituted phenyl($C_{1-4}$)alkyl or optionally substituted heteroaryl; $R^{10}$ and $R^{11}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxy($C_{1-6}$)alkyl, $C_{1-6}$ alkoxycarbonyl, optionally substituted phenoxycarbonyl, formyl, $C_{1-6}$ alkylcarbonyl, $C_{1-6}$ alkyl$SO_2$, optionally substituted phenyl$SO_2$ or optionally substituted phenyl($C_{1-4}$) alkyl; $R^{12}$ is $C_{1-3}$ alkyl; $R^{13}$ is $C_{1-6}$ alkyl, optionally substituted phenyl($C_{1-2}$); and p and q are, independently, 0, 1 or 2.

The compounds of formula (I) may exist in different isomeric or tautomeric forms. This invention covers all such isomers and tautomers and mixtures thereof in all proportions.

In a further aspect the present invention provides a compound of formula (I) wherein X is O or S; n is 0 or 1; Y is O, S or $NR^7$; $R^1$ is hydrogen, halogen, $C_{1-6}$ alkyl, $C_{1-6}$ haloalkyl $C_{1-6}$ alkoxy, $C_{1-6}$ haloalkoxy, $C_{1-6}$ alkylthio, $C_{3-6}$ cycloalkyl or $C_{1-6}$ alkoxy($C_{1-6}$)alkyl; $R^2$ is hydrogen, halogen, $C_{1-6}$ alkyl, $C_{1-6}$ haloalkyl, cyano, nitro, CHO, CH=$NOR^5$, $C_{1-6}$ alkylcarbonyl, $C_{1-6}$ alkoxycarbonyl or $C_{1-6}$ alkylS(O)$_x$; or together $R^1$ and $R^2$ form a five or six membered saturated or unsated carbocyclic ring, optionally substituted by one or two $C_{1-6}$ alkyl groups; $R^3$ is hydrogen, $C_{1-6}$ alkyl, $CH_2(C_{1-4}$ haloalkyl), $C_{3-6}$ alkenyl, $C_{3-6}$ alkynyl, $C_{1-6}$ alkoxy($C_{1-6}$)alkyl, $C_{1-6}$ alkylcarbonyl, $C_{1-6}$ alkoxycarbonyl, formyl, optionally substituted phenoxycarbonyl, optionally substituted phenyl($C_{1-4}$)alkyl or $S(O)_xR^{25}$; $R^4$ is hydrogen, halogen, cyano, optionally substituted alkyl, $C_{1-8}$ alkoxy, $C_{1-8}$ haloalkoxy, $C_{1-8}$ alkylthio, $C_{2-6}$ alkenyl, $C_{2-6}$ alkynyl, $C_{3-7}$ cycloalkyl (optionally substituted with halogen or $C_{1-6}$ alkyl), $C_{5-6}$ cycloalkenyl (optionally substituted with halogen or $C_{1-6}$ alkyl), $C_{2-6}$ haloalkenyl, NHSO$_2R^{24}$, NHCOR$^{24}$, CONR$^{20}$R$^{21}$, NR$^{20}$R$^{21}$, COR$^{24}$, CO$_2R^{20}$, optionally substituted phenyl substituted heteroaryl or a group ZR$^{26}$; $R^5$ is hydrogen, $C_{1-6}$ alkyl, optionally substituted phenyl or optionally substituted phenyl($C_{1-4}$)alkyl; $R^5$ is $C_{1-6}$ alkyl, $C_{1-6}$ haloalkyl or optionally substituted phenyl; Z is O, S, SO, SO$_2$ or NR$^{27}$; $R^7$ is hydrogen, cyano, $C_{1-8}$ alkyl, $C_{1-6}$ haloalkyl, $C_{1-6}$ cyanoalkyl, $C_{2-6}$ alkenyl, $C_{2-6}$ alkynyl, $C_{3-7}$ cycloalkyl, $C_{2-6}$ haloalkenyl, $C_{3-6}$ cycloalkyl($C_{1-6}$)alkyl, $C_{1-6}$ alkoxy($C_{1-6}$)alkyl, $C_{1-6}$ alkoxycarbonyl, $C_{1-6}$ alkylcarbonyl, $C_{1-6}$ alkylaminocarbonyl, di($C_{1-6}$) alkylaminocarbonyl, optionally substituted phenyl or optionally substituted heteroaryl; $R^{26}$ and $R^{27}$ are, independently, hydrogen, $C_{1-8}$ alkyl, $C_{3-6}$ alkenyl, $C_{3-6}$ alkynyl, $C_{1-6}$ alkoxy($C_{1-6}$)alkyl, $C_{1-6}$ alkoxycarbonyl, optionally substituted phenoxycarbonyl, $C_{1-6}$ alkycarbonyl or optionally substituted phenyl($C_{1-4}$)alkyl, or $R^{26}$ and $R^{27}$ join to form a 5- or 6-membered saturated or unsaturated ring optionally containing another heteroatom selected from oxygen, sulfur and nitrogen; $R^{20}$ and $R^{21}$ are, independently, hydrogen or $C_{1-6}$ alkyl; $R^{24}$ is $C_{1-6}$ alkyl or phenyl; and x and y are, independently, 0, 1 or 2.

Alkyl is straight or branched chain and is, for example, methyl ethyl, n-propyl, n-butyl, n-pentyl, n-hexyl, iso-propyl, n-butyl, sec-butyl, iso-butyl, tert-butyl or neo-pentyl.

Halogen is fluorine, chlorine, bromine or iodine.

Haloalkyl groups are alkyl groups which are optionally substituted with one or more of the same or different halogen atoms and are, for example, $CF_3$, $CH_2CF_3$ or $CH_2CHF_2$.

Phenyl($C_{1-4}$)alkyl is, for example, 1-phenyleth-1-yl, 2-phenyleth-1-yl, 2-phenylprop-2-yl, 3-phenylprop-1-yl, but is preferably benzyl.

The term heteroaryl refers to an aromatic ring containing one or more heteroatoms (preferably one or two heteroatoms) selected from O, S and N. Examples of such rings include pyridine, pyrimidine, furan, quinazoline, thiophene, thiazole, oxazole and isoxazole.

The term heterocyclyl refers to a non-aromatic ring containing one or more (preferably one or two) heteroatoms selected from O, S and N. Examples of such rings include 1,3-dioxolanyl, tetrahydrofuryl and morpholinyl. It is preferred that heterocyclyl is optionally substituted by $C_{1-6}$ alkyl.

Cycloalkenyl includes cyclopentenyl, cyclohexenyl and cyclohexadienyl.

It is preferred that phenyl moieties and heteroaryl groups are optionally substituted by one or more substituents independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-6}$ cycloalkyl, nitro, cyano, $CO_2H$, $C_{1-6}$ alkylcarbonyl, $C_{1-6}$ alkoxycarbonyl, $R^{14}R^{15}N$ or $R^{16}R^{17}NC(O)$; wherein $R^{14}$, $R^{15}$, $R^{16}$ and $R^{17}$ are, independently hydrogen or $C_{1-6}$ alkyl.

It is preferred that $R^1$ is $C_{1-2}$ alkyl, especially, methyl.

It is preferred that $R^2$ is hydrogen, cyano or halogen, especially, halogen (especially bromo or chloro).

It is preferred that $R^3$ is hydrogen, $C_{1-6}$ alkyl or $C_{1-6}$ alkoxy($C_{1-6}$)alkyl.

It is further preferred that $R^3$ is hydrogen, ethyl or ethoxymethyl.

It is preferred that $R^4$ is $C_{1-6}$ alkoxy($C_{1-6}$)alkyl, $C_{1-6}$ haloalkyl, ($C_{1-6}$ alkyl)amino, di($C_{1-6}$ alkyl)amino (such as $N(C_2H_5)_2$ or $N(C_2H_5)(CH[CH_2]CH_3)$), morpholino, $C_{1-6}$ alkyl or $C_{1-6}$ alkoxy, especially morpholino, $C_{1-6}$ alkyl or $C_{1-6}$ alkoxy.

It is preferred that n is 0.

It is preferred that X is oxygen.

It is preferred that Y is oxygen or sulphur.

It is preferred that the compounds of the invention are of formula (Ia).

In one particular aspect the present invention provides a compound of formula (Ia) wherein $R^1$ is $C_{1-4}$ alkyl (especially methyl or ethyl); $R^2$ is hydrogen, halogen (especially chloro or bromo) or cyano; or $R^1$ and $R^2$ together form a cyclopentyl, cyclohexyl or phenyl ring, $R^3$ is hydrogen, $C_{1-4}$ alkyl (especially methyl or ethyl), $C_{1-6}$ alkenyl (especially allyl), $C_{1-6}$ alkynyl (especially propargyl), or $C_{1-6}$ alkoxy($C_{1-6}$)alkyl (especially methoxymethyl and ethoxymethyl); n is 0; X and Y are both oxygen; and $R^4$ is $C_{1-6}$ alkyl [optionally substituted with halogen, $C_{1-4}$ alkoxy, $C_{1-4}$ alkylthio, $C_{1-4}$ haloalkylthio, alkylamino, dialkylamino (wherein the alkyl groups may form part of a five or six-membered ring, optionally containing one hetero tom such as oxygen or nitrogen), phenyl (itself optionally substituted with halogen), $C_{3-6}$ cycloalkyl, $C_{3-6}$ alkenyl, $C_{3-6}$ alkynyl, $C_{3-6}$ cycloalkyl, phenyl [optionally substituted with halogen, $C_{1-4}$ haloalkyl (especially $CF_3$), nitro, $CO_2H$, or cyano] or heteroaryl (especially pyridyl or pyrimidinyl) [optionally substituted with $C_{1-4}$ alkyl or $C_{1-4}$ haloalkyl]].

In one particular aspect the present invention provides a compound of formula (Ia) wherein $R^1$ is $C_{1-4}$ alkyl (especially methyl or ethyl); $R^2$ is hydrogen, halogen (especially chloro or bromo) or cyano; or $R^1$ and $R^2$ together form a cyclopentyl, cyclohexyl or phenyl ring; $R^3$ is hydrogen, $C_{1-4}$ alkyl (especially methyl or ethyl), phenyl($C_{1-4}$)alkyl (especially benzyl), $C_{1-4}$ alkylcarbonyl (especially acetyl) or $C_{1-4}$ alkylsulfonyl (especially methanesulfonyl); n is 0; X is oxygen; Y is oxygen or sulphur (especially oxygen); $R^4$ is hydrogen, $C_{1-8}$ alkyl [optionally substituted with halogen, $C_{1-4}$ alkoxy, $C_{1-4}$ alkylS(O)$_m$, phenyl (itself optionally substituted with halogen), phenoxy, $NR^{20}R^{21}$, $CO_2H$, $CONR^{22}R^{23}$, cyano, $C_{3-6}$ cycloalkyl or $CO(C_{1-6}$ alkoxy)], $C_{1-8}$ alkoxy (optionally substituted with halogen), $C_{1-8}$ alkylthio, $C_{2-8}$ alkenyl (optionally substituted with halogen), $NHSO_2R^{24}$, $NHCOR^{24}$, $NR^{20}R^{21}$, $COR^{24}$, $CO_2R^{20}$, $C_{2-8}$ alkynyl, $C_{3-6}$ cycloalkyl (optionally substituted with halogen or $C_{1-6}$ alkyl), $C_{5-6}$ cycloalkenyl, phenyl [optionally substituted with halogen, $C_{1-4}$ haloalkyl (especially $CF_3$), $C_{1-4}$ alkoxy, nitro, $CO_2R^{20}$ or cyano] or heteroaryl (especially pyridyl, pyrimidinyl, furanyl or thiophenyl) [optionally substituted with $C_{1-6}$ alkyl, nitro or $C_{1-4}$ haloalkyl]; $R^{21}$, $R^{20}$, $R^{22}$ and $R^{23}$ are, independently, hydrogen or $C_{1-4}$ alkyl; $R^{24}$ is $C_{1-4}$ alkyl or phenyl; and m is 0, 1 or 2.

The physical parameter $K_{o/w}$ concerns the relative solubility of a compound in n-octanol and water and, for a compound [A]:

$$K_{o/w} = \frac{\text{(solubility of compound [A] in } n\text{-octanol)}}{\text{(solubility of compound [A] in water)}}$$

In a further aspect the present invention provides a compound of formula (I) wherein $\log_{10}K_{o/w}$ (calculated using the CLOGP3 program, available from BioByte Corp., 201 West 4th Street, Suite 204, Claremont, Calif. 91711, USA) of the compound is in the range zero to 8, preferably in the range 1 to 6 and more preferably in the range 1.2 to 5.2.

It will readily be seen that the side chain portion of formula XIX):

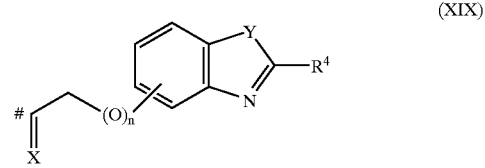

(XIX)

is a portion of a compound of formula (I). The longest bond path of the side chain portion of formula (XIX) is the path involving the minimum number of bonds from the carbon labelled # to the furthest atom of the side chain, having an atomic weight greater than 10 Daltons. If there is more than one longest bond path, each involving the same minimum number of bonds, there is a set of longest bond paths.

In a further aspect of the present invention it is preferred that $R^4$ is hydrogen, SH, $C_{1-6}$ alkyl, $C_{3-6}$ cycloalkyl, $C_{2-6}$ alkenyl, $C_{2-5}$ alkynyl, $C_{1-4}$ haloalkyl, $C_{1-4}$ cyanoalkyl, $C_{2-6}$ haloalkenyl, optionally substituted heterocyclyl($C_{1-4}$)alkyl, $C_{2-6}$ cyanoalkenyl (such as 1-cyano-2-methylpropenyl), phenyl (optionally substituted with fluoro, chloro, bromo, nitro, cyano, $C_{1-6}$ alkyl, $C_{1-2}$ alkoxy, $C_{1-4}$ haloalkyl (such as trifluoromethyl), $C_{1-4}$ haloalko as trifluoromethoxy), methanesulfonyl, methylenedioxy or di($C_{1-4}$ alkyl)amino (such as dimethylamino)), phenyl($C_{1-3}$)alkyl (phenyl optionally substituted with halogen, nitro, cyano, $C_{1-4}$ alkyl, $C_{1-2}$ alkoxy, $C_{1-4}$ haloalkyl (such as trifluoromethyl), $C_{1-4}$ haloalkoxy (such as trifluoromethoxy), methanesulfonyl, or methylenedioxy), formyl, optionally substituted heterocyclyl, optionally substituted heteroaryl, optionally substituted heteroaryl($C_{1-4}$)alkyl, $C_{1-2}$ alkylcarbonyl, $C_{1-4}$ alkoxycarbonyl, $C_{1-5}$ alkoxycarbonyl($C_{1-4}$)alkyl, a group $NR^{10}R^{11}$, a group $OR^8$, $C_{1-4}$ alkoxymethyl, chlorine, a group $SR^9$, or a group $C(R^{12})=NOR^{13}$; $R^8$ is hydrogen, $C_{1-5}$ alkyl, $C_{1-4}$ haloalkyl (such as 2,2,2-trifluoroethyl), $C_{2-4}$ alkenyl (such as allyl), phenyl (optionally substituted with fluoro, chloro, bromo, nitro, cyano, $C_{1-6}$ alkyl, $C_{1-2}$ alkoxy, $C_{1-4}$ haloalkyl (such as trifluoromethyl), $C_{1-4}$ haloalkoxy (such as trifluoromethoxy), methanesulfonyl, or methylenedioxy), phenyl($CH_2$) (phenyl optionally substituted with fluoro, chloro, bromo, nitro, cyano, $C_{1-6}$ alkyl, $C_{1-2}$ alkoxy, $C_{1-4}$ haloalkyl (such as trifluoromethyl), $C_{1-4}$ haloalkoxy (such as trifluoromethoxy), methanesulfonyl, or methylenedioxy), $N=C(CH_3)_2$; $R^9$ is $C_{1-5}$ alkyl, phenyl (optionally substituted with fluoro, chloro, bromo, nitro, cyano, $C_{1-6}$ alkyl, $C_{1-2}$ alkoxy, $C_{1-4}$ haloalkyl (such as trifluoromethyl), $C_{1-4}$ haloalkoxy (such as trifluoromethoxy), methanesulfonyl, methylenedioxy or di($C_{1-4}$ alkyl)amino (such as dimethylamino)), $C_{1-2}$ haloalkyl, cyano, cyanomethyl or $C_{1-2}$ alkoxycarbonylmethyl; $R^{10}$ and $R^{11}$ are, independently, hydrogen, $C_{1-4}$ alkyl, $C_{5-6}$ cycloalkyl, formyl, $C_{1-3}$ alkylcarbonyl, phenoxycarbonyl, $C_{1-2}$ alkylSO$_2$ or phenylSO$_2$; $R^{12}$ is $C_{1-2}$ alkyl; $R^{13}$ is $C_{1-2}$ alkyl or benzyl; heterocyclyl is, for example, tetrahydrofuryl, 1,3-dioxolanyl or morpholinyl; an example of an optional substituent for heterocyclyl is $C_{1-4}$ alkyl; heteroaryl is, for example, thienyl, furyl, pyridyl, quinazolinyl, pyrazolyl or isoxazolyl; and examples of optional substituents for heteroaryl include $C_{1-6}$ alkyl, $C_{1-6}$ haloalkyl and phenoxy.

In a further aspect the present invention provides a compound of formula (I) wherein the side chain portion of formula (XIX) is such that each atom having an atomic weight greater than 10 Daltons in the side chain portion is no more than four bond lengths away from any of the atoms present in the longest bond path or one of the longest bond paths.

In another aspect the present invention provides a compound of formula (Ia) or (Ib) wherein $R^1$ is $C_{1-2}$ alkyl, chloro, CF$_3$, OCH$_3$ or SCH$_3$; $R^2$ is hydrogen, halogen (such as fluorine, chlorine or bromine), cyano, nitro, $C_{1-4}$ alkyl (such as methyl), $C_{1-4}$ alkoxy (such methoxy) or SCH$_3$; or $R^1$ and $R^2$ join to form a $C_{3-7}$ cycloalkyl (such as cyclopentyl or cyclohexyl) or phenyl ring; $R^3$ is hydrogen, $C_{1-6}$ alkyl optionally substituted with cyano, halogen, ($C_{1-6}$) alkoxy, ($C_{1-6}$)alkoxy($C_{1-6}$)alkoxy, $C_{1-4}$ alkoxycarbonyl, phenyl or $C_{1-4}$ alkylthio (such as methyl, ethyl, n-propyl, iso-propyl, cyanomethyl, 2,2,2-tifluoroethyl, ($C_{1-2}$) alkoxymethyl, methoxyethoxymethyl, methoxycarbonylmethyl, phenylmethyl or methylthiomethyl), $C_{3-6}$ alkenyl (such as allyl), $C_{3-6}$ alkynyl (such as propargyl), carbonyl substituted with $C_{1-6}$ alkoxy, $C_{1-4}$ alkylamino or di($C_{1-4}$alkyl)amino (such as $C_{1-2}$ alkoxycarbonyl, methylaminocarbonyl or dimethylaminocarbonyl), $C_{1-4}$ alkylthio (such as methylthio) or phenylthio; X is oxygen or sulphur; Y is oxygen, sulphur or NR$^7$; n is 0; R$^4$ is hydrogen, SH, $C_{1-6}$ alkyl, $C_{3-6}$ cycloalkyl, $C_{2-6}$ alkenyl, $C_{2-5}$ alkynyl, $C_{1-4}$ haloalkyl, $C_{1-4}$ cyanoalkyl, $C_{2-6}$ haloalkenyl, optionally substituted heterocyclyl($C_{1-4}$)alkyl, 1-cyano-2-methylpropenyl, phenyl (optionally substituted with fluoro, chloro, bromo, nitro, cyano, $C_{1-2}$ alkyl, tert-butyl, $C_{1-2}$ alkoxy, trifluoromethyl, trifluoromethoxy, methanesulfonyl, methylenedioxy or dimethylamino), phenyl($C_{1-3}$)alkyl (phenyl optionally substituted with fluorine), formyl, optionally substituted heteroyclyl, optionally substituted heteroaryl, optionally substituted heteroaryl($C_{1-4}$)alkyl, $C_{1-2}$ alkylcarbonyl $C_{1-4}$ alkoxycarbonyl, $C_{1-5}$ alkoxycarbonyl($C_{1-4}$)alkyl, a group $NR^{10}R^{11}$, a group $OR^8$, $C_{1-4}$ alkoxymethyl, chlorine, a group $SR^9$, or a group $C(R^{12})=NOR^{13}$; $R^7$ is hydrogen or $C_{1-4}$ alkyl (such as methyl); $R^8$ is hydrogen, $C_{1-5}$ alkyl, 2,2,2-trifluoroethyl, alkyl, phenyl (optionally substituted with chloro), phenyl(CH$_2$)(phenyl optionally substituted with fluoro, chloro), $N=C(CH_3)_2$; $R^9$ is $C_{1-5}$ alkyl, phenyl, $C_{1-2}$ cycloalkyl, cyano, cyanomethyl or $C_{1-2}$ alkoxycarbonylmethyl; $R^{10}$ and $R^{11}$ are, independently, hydrogen, $C_{1-4}$ alkyl, $C_{5-6}$ cycloalkyl, formyl, $C_{1-3}$ alkylcarbonyl, phenoxycarbonyl, $C_{1-2}$ alkylSO$_2$ or phenylSO$_2$; $R^{12}$ is $C_{1-2}$ alkyl; $R^{13}$ is $C_{1-2}$ alkyl or benzyl; heterocyclyl, for example, tetrahydrofuryl, 1,3-dioxolanyl or morpholinyl; an example of an optional substituent for heterocyclyl is $C_{1-4}$ alkyl; heteroaryl is, for example, thienyl, furyl, pyridyl, quinazolinyl, pyrazolyl or isoxazolyl; and examples of optional substituents for heteroaryl include $C_{1-6}$ alkyl, $C_{1-6}$ haloalkyl and phenoxy. Specific preferred values of $R^4$ are recited in table A1.

The compounds in the following Tables illustrate compounds of the invention. Table A1 provides 352 compounds of formula (Ia) wherein $R^1$ is methyl; $R^2$ is hydrogen; $R^3$ is hydrogen; X and Y are each oxygen; n is 0; and $R^4$ is as defined in the Table.

TABLE A1

| Compound Number | $R^4$ |
| --- | --- |
| 1 | H |
| 2 | CH$_3$ |
| 3 | CH$_2$CH$_3$ |
| 4 | CH$_2$CH$_2$CH$_3$ |
| 5 | CH$_2$CH$_2$CH$_2$CH$_3$ |
| 6 | CH$_2$CH$_2$CH$_2$CH$_2$CH$_3$ |
| 7 | CH$_2$CH$_2$CH$_2$CH$_2$CH$_2$CH$_3$ |
| 8 | CH(CH$_3$)$_2$ |
| 9 | C(CH$_3$)$_3$ |
| 10 | CH(CH$_3$)CH$_2$CH$_3$ |
| 11 | CH$_2$CH(CH$_3$)CH$_2$CH$_3$ |
| 12 | CH(CH$_3$)CH$_2$CH$_2$CH$_3$ |
| 13 | CH(CH$_2$CH$_3$)$_2$ |
| 14 | CH$_2$CH(CH$_3$)$_2$ |
| 15 | CH$_2$C(CH$_3$)$_3$ |
| 16 | CH$_2$CH$_2$CH(CH$_3$)$_2$ |
| 17 | CH$_2$CH$_2$C(CH$_3$)$_3$ |
| 18 | C(CH$_3$)$_2$CH$_3$ |
| 19 | C(CH$_3$)$_2$CH$_2$CH$_3$ |
| 20 | C(CH$_3$)$_2$CH$_2$CH$_2$CH$_3$ |
| 21 | cyclopropyl |
| 22 | 1-methylcyclopropyl |
| 23 | 2-methylcyclopropyl |
| 24 | 1-cyanocyclopropyl |
| 25 | 2,2-dichloro-3,3-dimethylcyclopropyl |
| 26 | 2,2-dichloro-1-ethyl-3-methylcyclopropyl |
| 27 | cyclobutyl |
| 28 | cyclopentyl |
| 29 | 1-methylcyclopentyl |
| 30 | 1-cyclopentenyl |
| 31 | 2-cyclopentenyl |
| 32 | 3-cyclopentenyl |
| 33 | 2-cyclopentenylmethyl |
| 34 | 1-cyclopentenylmethyl |

TABLE A1-continued

| Compound Number | R⁴ |
| --- | --- |
| 35 | cyclohexyl |
| 36 | 1-methylcyclohexyl |
| 37 | 1-cyclohexenyl |
| 38 | 2-cyclohexenyl |
| 39 | cyclohexylmethyl |
| 40 | 2-cyclohexenylmethyl |
| 41 | cyclopropylmethyl |
| 42 | cyclopentylmethyl |
| 43 | 2-cyclopentylethyl |
| 44 | CH=CH$_2$ |
| 45 | CH=CHCH$_3$ |
| 46 | CH=C(CH$_3$)$_2$ |
| 47 | C(CH$_3$)=CHCH$_3$ |
| 48 | CH=CHCH$_2$CH$_3$ |
| 49 | C(CH$_3$)=C(CH$_3$)$_2$ |
| 50 | CH=CHCH(CH$_3$)$_2$ |
| 51 | CH$_2$CH=CH$_2$ |
| 52 | CH$_2$CH=CHCH$_3$ |
| 53 | CH$_2$CH=C(CH$_3$)$_2$ |
| 54 | CH$_2$C(CH$_3$)=CH$_2$ |
| 55 | CH$_2$C(CH$_3$)=CHCH$_3$ |
| 56 | CH$_2$C(CH$_3$)=C(CH$_3$)$_2$ |
| 57 | CH$_2$CH$_2$CH=CH$_2$ |
| 58 | C(CH$_3$)=CHCH$_3$ |
| 59 | C(CH$_3$)$_2$CH=CH$_2$ |
| 60 | C(CH$_3$)=CHCH$_2$CH$_3$ |
| 61 | CH=CHCH=CHCH$_3$ |
| 62 | cyclopentyldienyl |
| 63 | 4-nitrostyryl |
| 64 | C≡CH |
| 65 | C≡CCH$_3$ |
| 66 | C≡CCH$_2$CH$_3$ |
| 67 | CH$_2$C≡CH |
| 68 | CH(CH$_3$)C≡CH |
| 69 | C(CH$_3$)$_2$C≡CH |
| 70 | CH$_2$CH$_2$C≡CH |
| 71 | CH$_2$CH$_2$C≡CCH$_3$ |
| 72 | CH$_2$CH$_2$COCH$_3$ |
| 73 | CH$_2$F |
| 74 | CHF$_2$ |
| 75 | CF$_3$ |
| 76 | CF(CH$_3$)$_2$ |
| 77 | CH$_2$CF$_3$ |
| 78 | CF$_2$CF$_3$ |
| 79 | CF$_2$CHF$_2$ |
| 80 | CF$_2$CF$_2$CF$_3$ |
| 81 | CF$_2$CF$_2$CF$_2$CF$_3$ |
| 82 | CF=CFCF$_2$CF$_3$ |
| 83 | CF$_2$Cl |
| 84 | CF$_2$Br |
| 85 | CFClCF$_3$ |
| 86 | CF$_2$CF$_2$Cl |
| 87 | CF$_2$CFClCF$_3$ |
| 88 | CFBrCF$_3$ |
| 89 | CH$_2$Cl |
| 90 | CH$_2$CH$_2$Cl |
| 91 | CH$_2$CH$_2$CH$_2$Cl |
| 92 | CH$_2$CH$_2$CH$_2$CH$_2$Cl |
| 93 | CH(Cl)CH$_3$ |
| 94 | CH(Cl)—C$_6$H$_5$ |
| 95 | CH(Cl)CH$_2$CH$_3$ |
| 96 | CH(Cl)CH$_2$Cl |
| 97 | CCl(CH$_3$)$_2$ |
| 98 | C(CH$_3$)$_2$CH$_2$Cl |
| 99 | CHCl$_2$ |
| 100 | C(CH$_2$Cl)$_2$CH$_3$ |
| 101 | C(CH$_3$)$_2$CHCl$_2$ |
| 102 | CH$_2$CH(Cl)CH$_3$ |
| 103 | CCl$_3$ |
| 104 | CCl$_2$CCl$_3$ |
| 105 | CH=CHCl |
| 106 | CCl=CH$_2$ |
| 107 | CCl=CCl$_2$ |
| 108 | CH$_2$Br |
| 109 | CHBr$_2$ |
| 110 | C(CH$_3$)$_2$Br |
| 111 | CH(Br)CH(CH$_3$)$_2$ |
| 112 | C(CH$_3$)BrCH$_2$Br |
| 113 | CH$_2$CN |
| 114 | CH$_2$CH$_2$CN |
| 115 | CH(CH$_3$)CN |
| 116 | C(CH$_3$)$_2$CN |
| 117 | CH$_2$CH(CH$_3$)CN |
| 118 | CH$_2$C(CH$_3$)$_2$CN |
| 119 | C(CN)=C(CH$_3$)$_2$ |
| 120 | CH$_2$CO$_2$CH$_3$ |
| 121 | CH$_2$CO$_2$CH$_2$CH$_3$ |
| 122 | CH$_2$CO$_2$C(CH$_3$)$_3$ |
| 123 | CH(CH$_3$)CO$_2$CH$_3$ |
| 124 | CH(CH$_3$)CO$_2$CH$_2$CH$_3$ |
| 125 | CH(CH$_3$)CO$_2$C(CH$_3$)$_3$ |
| 126 | C(CH$_3$)$_2$CO$_2$CH$_3$ |
| 127 | C(CH$_3$)$_2$CO$_2$CH$_2$CH$_3$ |
| 128 | C(CH$_3$)$_2$CO$_2$C(CH$_3$)$_3$ |
| 129 | CH$_2$C(CH$_3$)$_2$CH$_2$CO$_2$CH$_2$CH$_3$ |
| 130 | CH$_2$OCH$_3$ |
| 131 | CH$_2$OCH$_2$CH$_3$ |
| 132 | CH$_2$CH$_2$OCH$_3$ |
| 133 | CH$_2$OCH(CH$_3$)$_2$ |
| 134 | CH$_2$OC(CH$_3$)$_3$ |
| 135 | C(CH$_3$)$_2$OCOCH$_3$ |
| 136 | C(CH$_3$)$_2$OH |
| 137 | CH$_2$OCH$_2$CH$_2$OCH$_3$ |
| 138 | CH$_2$OCH$_2$CH$_2$OCH$_2$CH$_3$ |
| 139 | CH$_2$CH$_2$OH |
| 140 | CH$_2$O—C$_6$H$_5$ |
| 141 | CH(CH$_3$)O—C$_6$H$_5$ |
| 142 | 1-methyl-1-(4-chlorophenoxy)ethyl |
| 143 | 2-nitrophenoxymethyl |
| 144 | 4-nitrophenoxymethyl |
| 145 | 2-tetrahydrofuryl |
| 146 | 3-tetrahydrofuryl |
| 147 | 2-tetrahydrofurylmethyl |
| 148 | 3-tetrahydrofurylmethyl |
| 149 | (1,3-dioxolan-2-yl)methyl |
| 150 | (2-methyl-1,3-dioxolan-2-yl)methyl |
| 151 | (1,3-dioxolan-4-yl)methyl |
| 152 | (2-methyl-1,3-dioxolan-4-yl)methyl |
| 153 | CHO |
| 154 | COCH$_3$ |
| 155 | COCH$_2$CH$_3$ |
| 156 | CO$_2$CH$_3$ |
| 157 | CO$_2$CH$_2$CH$_3$ |
| 158 | CO$_2$CH(CH$_3$)$_2$ |
| 159 | CO$_2$C(CH$_3$)$_3$ |
| 160 | CO$_2$C(CH$_3$)$_2$CH$_2$CH$_3$ |
| 161 | CH$_2$CH$_2$CO$_2$H |
| 162 | CH$_2$CH$_2$CO$_2$CH$_3$ |
| 163 | CH$_2$CH$_2$CO$_2$CH$_2$CH$_3$ |
| 164 | CH$_2$CH$_2$CH$_2$CO$_2$CH$_3$ |
| 165 | CH$_2$CH$_2$CH$_2$CO$_2$CH$_2$CH$_3$ |
| 166 | CH=NOH |
| 167 | C(CH$_3$)=NOCH$_3$ |
| 168 | C(CH$_3$)=NOH |
| 169 | C(CH$_3$)=NOCH$_3$ |
| 170 | C(CH$_3$)=NOCH$_2$—C$_6$H$_5$ |
| 171 | CH$_2$SCH$_3$ |
| 172 | CH$_2$CH$_2$SCH$_3$ |
| 173 | CH$_2$S—C$_6$H$_5$ |
| 174 | Cl |
| 175 | NH$_2$ |
| 176 | NHCH$_3$ |
| 177 | NHCH$_2$CH$_3$ |
| 178 | NHCH$_2$CH$_2$CH$_3$ |
| 179 | N(CH$_3$)$_2$ |
| 180 | N(CH$_3$)CH$_2$CH$_3$ |
| 181 | N(CH$_2$CH$_3$)$_2$ |
| 182 | NHCH(CH$_3$)$_2$ |
| 183 | NHC(CH$_3$)$_3$ |
| 184 | N(CH$_3$)CH(CH$_3$)$_2$ |
| 185 | N(CH$_3$)C(CH$_3$)$_3$ |
| 186 | NH-cyclopentyl |
| 187 | NH-cyclohexyl |
| 188 | N(CH$_3$)-cyclopentyl |

TABLE A1-continued

| Compound Number | R⁴ |
|---|---|
| 189 | N(CH₃)-cyclohexyl |
| 190 | N(CH₂CH₃)-cyclohexyl |
| 191 | morpholino |
| 192 | NHCHO |
| 193 | NHCOCH₃ |
| 194 | NHCOCH₂CH₃ |
| 195 | NHCOCH(CH₃)₂ |
| 196 | NHCO—C₆H₅ |
| 197 | N(CH₃)CHO |
| 198 | N(CH₃)COCH₃ |
| 199 | N(CH₃)COCH₂CH₃ |
| 200 | NHSO₂CH₃ |
| 201 | NHSO₂CH₂CH₃ |
| 202 | NHSO₂—C₆H₅ |
| 203 | OCH₃ |
| 204 | OCH₂CH₃ |
| 205 | OCH₂CH₂CH₃ |
| 206 | OCH(CH₃)₂ |
| 207 | OC(CH₃)₃ |
| 208 | OCH₂CH(CH₃)₂ |
| 209 | OCH(CH₃)CH₂CH₃ |
| 210 | OCH₂CF₃ |
| 211 | OCH₂C(CH₃)₃ |
| 212 | OCH₂—C₆H₅ |
| 213 | 4-fluorobenzyloxy |
| 214 | 2,4-dichlorobenzyloxy |
| 215 | OCH₂CH═CH₂ |
| 216 | O—C₆H₅ |
| 217 | 2-chlorophenoxy |
| 218 | 4-chlorophenoxy |
| 219 | O—N═C(CH₃)₂ |
| 220 | SCH₃ |
| 221 | SCH₂CH₃ |
| 222 | S(CH₂)₂CH₃ |
| 223 | SCH(CH₃)₂ |
| 224 | SC(CH₃)₃ |
| 225 | SCH₂CH(CH₃)₂ |
| 226 | SCH₂C(CH₃)₃ |
| 227 | S—C₆H₅ |
| 228 | SCH₂CN |
| 229 | SCH₂CO₂CH₃ |
| 230 | SCH₂CO₂CH₂CH₃ |
| 231 | SCHF₂ |
| 232 | SCF₃ |
| 233 | SCH₂CF₃ |
| 234 | SCF₂CF₂H |
| 235 | SCN |
| 236 | CH₂C₆H₅ |
| 237 | CH(CH₃)C₆H₅ |
| 238 | C(CH₃)₂C₆H₅ |
| 239 | CH₂C₆F₅ |
| 240 | 3,5-diF—C₆H₃ |
| 241 | 3-CH₃O—C₆H₄ |
| 242 | 4-F—C₆H₄ |
| 243 | 4-F—C₆H₄ |
| 244 | 2,6-diCl-4-CF₃—C₆H₂ |
| 245 | CH(CH₂CH₃)C₆H₅ |
| 246 | CH(C₆H₅)₂ |
| 247 | CH₂CH₂C₆H₅ |
| 248 | C₆H₅ |
| 249 | 2-Br—C₆H₄ |
| 250 | 3-Br—C₆H₄ |
| 251 | 4-Br—C₆H₄ |
| 252 | 4-tert-butyl-C₆H₄ |
| 253 | 2-Cl—C₆H₄ |
| 254 | 3-Cl—C₆H₄ |
| 255 | 4-Cl—C₆H₄ |
| 256 | 2,3-diCl—C₆H₃ |
| 257 | 2,4-diCl—C₆H₃ |
| 258 | 2,5-diCl—C₆H₃ |
| 259 | 2,6-diCl—C₆H₃ |
| 260 | 3,4-diCl—C₆H₃ |
| 261 | 3,5-diCl—C₆H₃ |
| 262 | 2,4,6-triCl—C₆H₂ |
| 263 | C₆Cl₅ |
| 264 | 2-Cl-4-F—C₆H₃ |
| 265 | 2-Cl-6-F—C₆H₃ |
| 266 | 4-Cl-2,5-diF—C₆H₂ |
| 267 | 2-Cl-4-NO₂—C₆H₃ |
| 268 | 2-Cl-4-CF₃—C₆H₃ |
| 269 | 2-Cl-6-CF₃—C₆H₃ |
| 270 | 2-Cl-4-methanesulfonyl-C₆H₃ |
| 271 | 2,4-diCl-5-F—C₆H₂ |
| 272 | 2-F—C₆H₄ |
| 273 | 3-F—C₆H₄ |
| 274 | 4-F—C₆H₄ |
| 275 | 2,3-diF—C₆H₃ |
| 276 | 2,4-diF—C₆H₃ |
| 277 | 2,5-diF—C₆H₃ |
| 278 | 2,6-diF—C₆H₃ |
| 279 | 3,4-diF—C₆H₃ |
| 280 | 3,5-diF—C₆H₃ |
| 281 | 2,3,4-triF—C₆H₂ |
| 282 | 2,3,5-triF—C₆H₂ |
| 283 | 2,3,6-triF—C₆H₂ |
| 284 | 2,4,6-triF—C₆H₂ |
| 285 | 3,4,5-triF—C₆H₂ |
| 286 | 2,3,4,5-tetraF—C₆H |
| 287 | C₆F₅ |
| 288 | 2-F-3-CF₃—C₆H₃ |
| 289 | 2-F-4-CF₃—C₆H₃ |
| 290 | 2-F-5-CF₃—C₆H₃ |
| 291 | 2-F-6-CF₃—C₆H₃ |
| 292 | 4-F-2-CF₃—C₆H₃ |
| 293 | 4-F-3-CF₃—C₆H₃ |
| 294 | 5-F-2-CF₃—C₆H₃ |
| 295 | 2-CN—C₆H₄ |
| 296 | 3-CN—C₆H₄ |
| 297 | 4-CN—C₆H₄ |
| 298 | 4-dimethylaminophenyl |
| 299 | 2-C₂H₅O—C₆H₄ |
| 300 | 3-C₂H₅O—C₆H₄ |
| 301 | 4-C₂H₅O—C₆H₄ |
| 302 | 2-C₂H₅—C₆H₄ |
| 303 | 3-C₂H₅—C₆H₄ |
| 304 | 4-C₂H₅—C₆H₄ |
| 305 | 2-CH₃O—C₆H₄ |
| 306 | 3-CH₃O—C₆H₄ |
| 307 | 4-CH₃O—C₆H₄ |
| 308 | 3,4-diCH₃O—C₆H₃ |
| 309 | 3,5-diCH₃O—C₆H₃ |
| 310 | 2,6-diCH₃O—C₆H₃ |
| 311 | 3,4-(methylenedioxy)phenyl |
| 312 | 2-CH₃—C₆H₄ |
| 313 | 3-CH₃—C₆H₄ |
| 314 | 4-CH₃—C₆H₄ |
| 315 | 2,3-diCH₃—C₆H₃ |
| 316 | 2,4-diCH₃—C₆H₃ |
| 317 | 2,5-diCH₃—C₆H₃ |
| 318 | 2,6-diCH₃—C₆H₃ |
| 319 | 3,4-diCH₃—C₆H₃ |
| 320 | 2,4,6-triCH₃—C₆H₂ |
| 321 | 2-NO₂—C₆H₄ |
| 322 | 3-NO₂—C₆H₄ |
| 323 | 4-NO₂—C₆H₄ |
| 324 | 4-methanesulfonyl-2-nitrophenyl |
| 325 | 3-trifluoromethoxyphenyl |
| 326 | 2-trifluoromethylphenyl |
| 327 | 3-trifluoromethylphenyl |
| 328 | 4-trifluoromethylphenyl |
| 329 | 4-carboxymethylphenyl |
| 330 | 2-thienyl |
| 331 | 3-chloro-2-thienyl |
| 332 | 3,4,5-trichloro-2-thienyl |
| 333 | 2-benzothiophenyl |
| 334 | 2-thienylmethyl |
| 335 | 5-tert-butyl-2-furyl |
| 336 | 5-nitro-2-furyl |
| 337 | pyridin-2-yl |
| 338 | pyridin-3-yl |
| 339 | pyridin-4-yl |
| 340 | 3-chloro-2-pyridyl |
| 341 | 6-chloro-2-pyridyl |
| 342 | 2,6-dichloro-4-pyridyl |

TABLE A1-continued

| Compound Number | R⁴ |
| --- | --- |
| 343 | 2-chloro-3-pyridyl |
| 344 | 2-phenoxy-3-pyridyl |
| 345 | 2-quinazolinyl |
| 346 | 4-biphenyl |
| 347 | 1,3-dimethyl-5-pyrazolyl |
| 348 | 4-chloro-1,3-dimethyl-5-pyrazolyl |
| 349 | 5-isoxazolyl |
| 350 | 6-trifluoromethyl-2-pyridyl |
| 351 | OH |
| 352 | SH |

TABLE A2

Table A2 provides 352 compounds of formula (Ia) wherein $R^1$ is methyl; $R^2$ is fluoro; $R^3$ is hydrogen; X and Y are each oxygen; n is 0; and the values of $R^4$ match those of the correspondingly numbered compounds of Table A1.

TABLE A3

Table A3 provides 352 compounds of formula (Ia) wherein $R^1$ is methyl; $R^2$ is chloro; $R^3$ is hydrogen; X and Y are each oxygen; n is 0; and the values of $R^4$ match those of the correspondingly numbered compounds of Table A1.

TABLE A4

Table A4 provides 352 compounds of formula (Ia) wherein $R^1$ is methyl; $R^2$ is bromo; $R^3$ is hydrogen; X and Y are each oxygen; n is 0; and the values of $R^4$ match those of the correspondingly numbered compounds of Table A1.

TABLE A5

Table A 5 provides 352 compounds of formula (Ia) wherein $R^1$ is methyl; $R^2$ is cyano; $R^3$ is hydrogen; X and Y are each oxygen; n is 0; and the values of $R^4$ match those of the correspondingly numbered compounds of Table A1.

TABLE A6

Table A6 provides 352 compounds of formula (Ia) wherein $R^1$ is ethyl; $R^2$ is hydrogen; $R^3$ is hydrogen; X and Y are each oxygen; n is 0; and the values of $R^4$ match those of the correspondingly numbered compounds of Table A1.

TABLE A7

Table A7 provides 352 compounds of formula (Ia) wherein $R^1$ is ethyl; $R^2$ is fluoro; $R^3$ is hydrogen; X and Y are each oxygen; n is 0; and the values of $R^4$ match those of the correspondingly numbered compounds of Table A1.

TABLE A8

Table A8 provides 352 compounds of formula (Ia) wherein $R^1$ is ethyl; $R^2$ is chloro; $R^3$ is hydrogen; X and Y are each oxygen; n is 0; and the values of $R^4$ match those of the correspondingly numbered compounds of Table A1.

TABLE A9

Table A9 provides 352 compounds of formula (Ia) wherein $R^1$ is ethyl; $R^2$ is bromo; $R^3$ is hydrogen; X and Y are each oxygen; n is 0; and the values of $R^4$ match those of the correspondingly numbered compounds of Table A1.

TABLE A10

Table A10 provides 352 compounds of formula (Ia) wherein $R^1$ is ethyl; $R^2$ is cyano; $R^3$ is hydrogen; X and Y are each oxygen; n is 0; and the values of $R^4$ match those of the correspondingly numbered compounds of Table A1.

TABLE A11

Table A11 provides 352 compounds of formula (Ia) wherein $R^1$ is methyl; $R^2$ is hydrogen; $R^3$ is hydrogen; X is oxygen; Y is sulphur; n is 0; and the values of $R^4$ match those of the correspondingly numbered compounds of Table A1.

TABLE A12

Table A12 provides 352 compounds of formula (Ia) wherein $R^1$ is methyl; $R^2$ is fluoro; $R^3$ is hydrogen; X is oxygen; Y is sulphur; n is 0; and the values of $R^4$ match those of the correspondingly numbered compounds of Table A1.

TABLE13

Table A13 provides 352 compounds of formula (Ia) wherein $R^1$ is methyl; $R^2$ is chloro; $R^3$ is hydrogen; X is oxygen; Y is sulphur; n is 0; and the values of $R^4$ match those of the correspondingly numbered compounds of Table A1.

TABLE A14

Table A14 provides 352 compounds of formula (Ia) wherein $R^1$ is methyl; $R^2$ is bromo; $R^3$ is hydrogen; X is oxygen; Y is sulphur; n is 0; and the values of $R^4$ match those of the correspondingly numbered compounds of Table A1.

TABLE A15

Table A15 provides 352 compounds of formula (Ia) wherein $R^1$ is methyl; $R^2$ is cyano; $R^3$ is hydrogen; X is oxygen; Y is sulphur; n is 0; and the values of $R^4$ match those of the correspondingly numbered compounds of Table A1.

TABLE A16

Table A16 provides 352 compounds of formula (Ia) wherein $R^1$ is ethyl; $R^2$ is hydrogen; $R^3$ is hydrogen; X is oxygen; Y is sulphur; n is 0; and the values of $R^4$ match those of the correspondingly numbered compounds of Table A1.

TABLE A17

Table A17 provides 352 compounds of formula (Ia) wherein $R^1$ is ethyl; $R^2$ is fluoro; $R^3$ is hydrogen; X is oxygen; Y is sulphur; n is 0; and the values of $R^4$ match those of the correspondingly numbered compounds of Table A1.

TABLE A18

Table A18 provides 352 compounds of formula (Ia) wherein $R^1$ is ethyl; $R^2$ is chloro; $R^3$ is hydrogen; X is oxygen; Y is sulphur; n is 0; and the values of $R^4$ match those of the correspondingly numbered compounds of Table A1.

TABLE A19

Table A19 provides 352 compounds of formula (Ia) wherein $R^1$ is ethyl; $R^2$ is bromo; $R^3$ is hydrogen; X is oxygen; Y is sulphur; n is 0; and the values of $R^4$ match those of the correspondingly numbered compounds of Table A1.

TABLE A20

Table A20 provides 352 compounds of formula (Ia) wherein $R^1$ is ethyl; $R^2$ is cyano; $R^3$ is hydrogen; X is oxygen; Y is sulphur; n is 0; and the values of $R^4$ match those of the correspondingly numbered compounds of Table A1.

TABLE A21

Table A21 provides 352 compounds of formula (Ib) wherein $R^1$ is methyl; $R^2$ is hydrogen; $R^3$ is hydrogen; X and Y are each oxygen; n is 0; and the values of $R^4$ match those of the correspondingly numbered compounds of Table A1.

TABLE A22

Table A22 provides 352 compounds of formula (Ib) wherein $R^1$ is methyl; $R^2$ is fluoro; $R^3$ is hydrogen; X and Y are each oxygen; n is 0; and the values of $R^4$ match those of the correspondingly numbered compounds of Table A1.

TABLE A23

Table A23 provides 352 compounds of formula (Ib) wherein $R^1$ is methyl; $R^2$ is chloro; $R^3$ is hydrogen; X and Y are each oxygen; n is 0; and the values of $R^4$ match those of the correspondingly numbered compounds of Table A1.

TABLE A24

Table A24 provides 352 compounds of formula (Ib) wherein $R^1$ is methyl; $R^2$ is bromo; $R^3$ is hydrogen; X and Y are each oxygen; n is 0; and the values of $R^4$ match those of the correspondingly numbered compounds of Table A1.

TABLE A25

Table A25 provides 352 compounds of formula (Ib) wherein $R^1$ is methyl; $R^2$ is cyano; $R^3$ is hydrogen; X and Y are each oxygen; n is 0; and the values of $R^4$ match those of the correspondingly numbered compounds of Table A1.

TABLE A26

Table A26 provides 352 compounds of formula (Ib) wherein $R^1$ is ethyl; $R^2$ is hydrogen; $R^3$ is hydrogen; X and Y are each oxygen; n is 0; and the values of $R^4$ match those of the correspondingly numbered compounds of Table A1.

TABLE A27

Table A27 provides 352 compounds of formula (Ib) wherein $R^1$ is ethyl; $R^2$ is fluoro; $R^3$ is hydrogen; X and Y are each oxygen; n is 0; and the values of $R^4$ match those of the correspondingly numbered compounds of Table A1.

TABLE A28

Table A28 provides 352 compounds of formula (Ib) wherein $R^1$ is ethyl; $R^2$ is chloro; $R^3$ is hydrogen; X and Y are each oxygen; n is 0; and the values of $R^4$ match those of the correspondingly numbered compounds of Table A1.

TABLE A29

Table A29 provides 352 compounds of formula (Ib) wherein $R^1$ is ethyl; $R^2$ is bromo; $R^3$ is hydrogen; X and Y are each oxygen; n is: 0; and the values of $R^4$ match those of the correspondingly numbered compounds of Table A1.

TABLE A30

Table A30 provides 352 compounds of formula (Ib) wherein $R^1$ is ethyl; $R^2$ is cyano; $R^3$ is hydrogen; X and Y are each oxygen; n is 0; and the values of $R^4$ match those of the correspondingly numbered compounds of Table A1.

TABLE A31

Table A31 provides 352 compounds of formula (Ib) wherein $R^1$ is methyl; $R^2$ is hydrogen; $R^3$ is hydrogen; X is oxygen; Y is sulphur; n is 0; and the values of $R^4$ match those of the correspondingly numbered compounds of Table A1.

TABLE A32

Table A32 provides 352 compounds of formula (Ib) wherein $R^1$ is methyl; $R^2$ is fluoro; $R^3$ is hydrogen; X is oxygen; Y is sulphur; n is 0; and the values of $R^4$ match those of the correspondingly numbered compounds of Table A1.

TABLE A33

Table A33 provides 352 compounds of formula (Ib) wherein $R^1$ is methyl; $R^2$ is chloro; $R^3$ is hydrogen; X is oxygen; Y is sulphur; n is 0; and the values of $R^4$ match those of the correspondingly numbered compounds of Table A1.

TABLE A34

Table A34 provides 352 compounds of formula (Ib) wherein $R^1$ is methyl; $R^2$ is bromo; $R^3$ is hydrogen; X is oxygen; Y is sulphur; n is 0; and the values of $R^4$ match those of the correspondingly numbered compounds of Table A1.

TABLE A35

Table A35 provides 352 compounds of formula (Ib) wherein $R^1$ is methyl; $R^2$ is cyano; $R^3$ is hydrogen; X is oxygen; Y is sulphur; n is 0; and the values of $R^4$ match those of the correspondingly numbered compounds of Table A1.

TABLE A36

Table A36 provides 352 compounds of formula (Ib) wherein $R^1$ is ethyl; $R^2$ is hydrogen; $R^3$ is hydrogen; X is oxygen; Y is sulphur; n is 0; and the values of $R^4$ match those of the correspondingly numbered compounds of Table A1.

TABLE A37

Table A37 provides 352 compounds of formula (Ib) wherein $R^1$ is ethyl; $R^2$ is fluoro; $R^3$ is hydrogen; X is oxygen; Y is sulphur; n is 0; and the values of $R^4$ match those of the correspondingly numbered compounds of Table A1.

TABLE A38

Table A38 provides 352 compounds of formula (Ib) wherein $R^1$ is ethyl; $R^2$ is chloro; $R^3$ is hydrogen; X is oxygen; Y is sulphur; n is 0; and the values of $R^4$ match those of the correspondingly numbered compounds of Table A1.

TABLE A39

Table A39 provides 352 compounds of formula (Ib) wherein $R^1$ is ethyl; $R^2$ is bromo; $R^3$ is hydrogen; X is oxygen; Y is sulphur; n is 0; and the values of $R^4$ match those of the correspondingly numbered compounds of Table A1.

TABLE A40

Table A40 provides 352 compounds of formula (Ib) wherein $R^1$ is ethyl; $R^2$ is cyano; $R^3$ is hydrogen; X is oxygen; Y is sulphur; n is 0; and the values of $R^4$ match those of the correspondingly numbered compounds of Table A1.

TABLE A41

Table A41 provides 352 compounds of formula (Ib) wherein $R^1$ is methyl; $R^2$ is hydrogen; $R^3$ is hydrogen; X is oxygen; Y is $NR^7$; $R^7$ is hydrogen; n is 0; and the values of $R^4$ match those of the correspondingly numbered compounds of Table A1.

TABLE A42

Table A42 provides 352 compounds of formula (Ib) wherein $R^1$ is methyl; $R^2$ is fluoro; $R^3$ is hydrogen; X is oxygen; Y is $NR^7$; $R^7$ is hydrogen; n is 0; and the values of $R^4$ match those of the correspondingly numbered compounds of Table A1.

TABLE A43

Table A43 provides 352 compounds of formula (Ib) wherein $R^1$ is methyl; $R^2$ is chloro; $R^3$ is hydrogen; X is oxygen; Y is $NR^7$; $R^7$ is hydrogen; n is 0; and the values of $R^4$ match those of the correspondingly numbered compounds of Table A1.

TABLE A44

Table A44 provides 352 compounds of formula (Ib) wherein $R^1$ is methyl; $R^2$ is bromo; $R^3$ is hydrogen; X is oxygen; Y is $NR^7$; $R^7$ is hydrogen; n is 0; and the values of $R^4$ match those of the correspondingly numbered compounds of Table A1.

TABLE A45

Table A45 provides 352 compounds of formula (Ib) wherein $R^1$ is methyl; $R^2$ is cyano; $R^3$ is hydrogen; X is oxygen; Y is $NR^7$; $R^7$ is hydrogen; n is 0; and the values of $R^4$ match those of the correspondingly numbered compounds of Table A1.

TABLE A46

Table A46 provides 352 compounds of formula (Ib) wherein $R^1$ is ethyl; $R^2$ is hydrogen; $R^3$ is hydrogen; X is oxygen; Y is $NR^7$; $R^7$ is hydrogen; n is 0; and the values of $R^4$ match those of the correspondingly numbered compounds of Table A1.

TABLE A47

Table A47 provides 352 compounds of formula (Ib) wherein $R^1$ is ethyl; $R^2$ is fluoro; $R^3$ is hydrogen; X is oxygen; Y is $NR^7$; $R^7$ is hydrogen; n is 0; and the values of $R^4$ match those of the correspondingly numbered compounds of Table A1.

TABLE A48

Table A48 provides 352 compounds of formula (Ib) wherein $R^1$ is ethyl; $R^2$ is chloro; $R^3$ is hydrogen; X is oxygen; Y is $NR^7$; $R^7$ is hydrogen; n is 0; and the values of $R^4$ match those of the correspondingly numbered compounds of Table A1.

TABLE A49

Table A49 provides 352 compounds of formula (Ib) wherein $R^1$ is ethyl; $R^2$ is bromo; $R^3$ is hydrogen; X is oxygen; Y is $NR^7$; $R^7$ is hydrogen; n is 0; and the values of $R^4$ match those of the correspondingly numbered compounds of Table A1.

TABLE A50

Table A50 provides 352 compounds of formula (Ib) wherein $R^1$ is ethyl; $R^2$ is cyano; $R^3$ is hydrogen; X is oxygen; Y is $NR^7$; $R^7$ is hydrogen; n is 0; and the values of $R^4$ match those of the correspondingly numbered compounds of Table A1.

TABLE A51

Table A51 provides 352 compounds of formula (Ib) wherein $R^1$ is methyl; $R^2$ is hydrogen; $R^3$ is hydrogen; X is oxygen; Y is $NR^7$; $R^7$ is methyl; n is 0; and the values of $R^4$ match those of the correspondingly numbered compounds of Table A1.

TABLE A52

Table A52 provides 352 compounds of formula (Ib) wherein $R^1$ is methyl; $R^2$ is fluoro; $R^3$ is hydrogen; X is oxygen; Y is $NR^7$; $R^7$ is methyl; n is 0; and the values of $R^4$ match those of the correspondingly numbered compounds of Table A1.

TABLE A53

Table A53 provides 352 compounds of formula (Ib) wherein $R^1$ is methyl; $R^2$ is chloro; $R^3$ is hydrogen; X is oxygen; Y is $NR^7$; $R^7$ is methyl; n is 0; and the values of $R^4$ match those of the correspondingly numbered compounds of Table A1.

TABLE A54

Table A54 provides 352 compounds of formula (Ib) wherein $R^1$ is methyl; $R^2$ is bromo; $R^3$ is hydrogen; X is oxygen; Y is $NR^7$; $R^7$ is methyl; n is 0; and the values of $R^4$ match those of the correspondingly numbered compounds of Table A1.

TABLE A55

Table A55 provides 352 compounds of formula (Ib) wherein $R^1$ is methyl; $R^2$ is cyano; $R^3$ is hydrogen; X is oxygen; Y is $NR^7$; $R^7$ is methyl; n is 0; and the values of $R^4$ match those of the correspondingly numbered compounds of Table A1.

TABLE A56

Table A56 provides 352 compounds of formula (Ib) wherein $R^1$ is ethyl; $R^2$ is hydrogen; $R^3$ is hydrogen; X is oxygen; Y is $NR^7$; $R^7$ is methyl; n is 0; and the values of $R^4$ match those of the correspondingly numbered compounds of Table A1.

TABLE A57

Table A57 provides 352 compounds of formula (Ib) wherein $R^1$ is ethyl; $R^2$ is fluoro; $R^3$ is hydrogen; X is oxygen; Y is $NR^7$; $R^7$ is methyl; n is 0; and the values of $R^4$ match those of the correspondingly numbered compounds of Table A1.

TABLE A58

Table A58 provides 352 compounds of formula (Ib) wherein $R^1$ is ethyl; $R^2$ is chloro; $R^3$ is hydrogen; X is oxygen; Y is NR$^7$; R$^7$ is methyl; n is 0; and the values of R$^4$ match those of the correspondingly numbered compounds of Table A1.

TABLE A59

Table A59 provides 352 compounds of formula (Ib) wherein R$^1$ is ethyl; R$^2$ is bromo; R$^3$ is hydrogen; X is oxygen; Y is NR$^7$; R$^7$ is methyl; n is 0; and the values of R$^4$ match those of the correspondingly numbered compounds of Table A1.

TABLE A60

Table A60 provides 352 compounds of formula (Ib) wherein R$^1$ is ethyl; R$^2$ is cyano; R$^3$ is hydrogen; X is oxygen; Y is NR$^7$; R$^7$ is methyl; n is 0; and the values of R$^4$ match those of the correspondingly numbered compounds of Table A1.

TABLE A61

Table A61 provides 352 compounds of formula (Ia) wherein R$^1$ is methyl; R$^2$ is hydrogen; R$^3$ is hydrogen; X is oxygen; Y is NR$^7$; R$^7$ is methyl; n is 0; and the values of R$^4$ match those of the correspondingly numbered compounds of Table A1.

TABLE A62

Table A62 provides 352 compounds of formula (Ia) wherein R$^1$ is methyl; R$^2$ is fluoro; R$^3$ is hydrogen; X is oxygen; Y is NR$^7$; R$^7$ is methyl; n is 0; and the values of R$^4$ match those of the correspondingly numbered compounds of Table A1.

TABLE A63

Table A63 provides 352 compounds of formula (Ia) wherein R$^1$ is methyl; R$^2$ is chloro; R$^3$ is hydrogen; X is oxygen; Y is NR$^7$; R$^7$ is methyl; n is 0; and the values of R$^4$ match those of the correspondingly numbered compounds of Table A1.

TABLE A64

Table A64 provides 352 compounds of formula (Ia) wherein R$^1$ is methyl; R$^2$ is bromo; R$^3$ is hydrogen; X is oxygen; Y is NR$^7$; R$^7$ is methyl; n is 0; and the values of R$^4$ match those of the correspondingly numbered compounds of Table A1.

TABLE A65

Table A65 provides 352 compounds of formula (Ib) wherein R$^1$ is methyl; R$^2$ is cyano; R$^3$ is hydrogen; X is oxygen; Y is NR$^7$; R$^7$ is methyl; n is 0; and the values of R$^4$ match those of the correspondingly numbered compounds of Table A1.

TABLE A66

Table A66 provides 352 compounds of formula (Ia) wherein R$^1$ is ethyl; R$^2$ is hydrogen; R$^3$ is hydrogen; X is oxygen; Y is NR$^7$; R$^7$ is methyl; n is 0; and the values of R$^4$ match those of the correspondingly numbered compounds of Table A1.

TABLE A67

Table A67 provides 352 compounds of formula (Ia) wherein R$^1$ is ethyl; R$^2$ is fluoro; R$^3$ is hydrogen; X is oxygen; Y is NR$^7$; R$^7$ is methyl; n is 0; and the values of R$^4$ match those of the correspondingly numbered compounds of Table A1.

TABLE A68

Table A68 provides 352 compounds of formula (Ia) wherein R$^1$ is ethyl; R$^2$ is chloro; R$^3$ is hydrogen; X is oxygen; Y is NR$^7$; R$^7$ is methyl; n is 0; and the values of R$^4$ match those of the correspondingly numbered compounds of Table A1.

TABLE A69

Table A69 provides 352 compounds of formula (Ia) wherein R$^1$ is ethyl; R$^2$ is bromo; R$^3$ is hydrogen; X is oxygen; Y is NR$^7$; R$^7$ is methyl; n is 0; and the values of R$^4$ match those of the correspondingly numbered compounds of Table A1.

TABLE A70

Table A70 provides 352 compounds of formula (Ia) wherein R$^1$ is ethyl; R$^2$ is cyano; R$^3$ is hydrogen; X is oxygen; Y is NR$^7$; R$^7$ is methyl; n is 0; and the values of R$^4$ match those of the correspondingly numbered compounds of Table A1.

TABLE B1

Table B1 provides 352 compounds of formula (Ia) wherein R$^1$ is methyl; R$^2$ is hydrogen; R$^3$ is methyl; X and Y are each oxygen; n is 0; and the values of R$^4$ match those of the correspondingly numbered compounds of Table A1.

TABLE B2

Table B2 provides 352 compounds of formula (Ia) wherein R$^1$ is methyl; R$^2$ is fluoro; R$^3$ is methyl; X and Y are each oxygen; n is 0; and the values of R$^4$ match those of the correspondingly numbered compounds of Table A1.

TABLE B3

Table B3 provides 352 compounds of formula (Ia) wherein R$^1$ is methyl; R$^2$ is chloro; R$^3$ is methyl; X and Y are each oxygen; n is 0; and the values of R$^4$ match those of the correspondingly numbered compounds of Table A1.

TABLE B4

Table B4 provides 352 compounds of formula (Ia) wherein R$^1$ is methyl, R$^2$ is bromo; R$^3$ is methyl; X and Y are each oxygen; n is 0; and the values of R$^4$ match those of the correspondingly numbered compounds of Table A1.

TABLE B5

Table B5 provides 352 compounds of formula (Ia) wherein R$^1$ is methyl; R$^2$ is cyano; R$^3$ is methyl; X and Y are each oxygen; n is 0; and the values of R$^4$ match those of the correspondingly numbered compounds of Table A1.

TABLE B6

Table B6 provides 352 compounds of formula (Ia) wherein R$^1$ is ethyl; R$^2$ is hydrogen; R$^3$ is methyl; X and Y are each oxygen; n is 0; and the values of R$^4$ match those of the correspondingly numbered compounds of Table A1.

TABLE B7

Table B7 provides 352 compounds of formula (Ia) wherein R$^1$ is ethyl; R$^2$ is fluoro; R$^3$ is methyl; X and Y are

TABLE B8

Table B8 provides 352 compounds of formula (Ia) wherein $R^1$ is ethyl; $R^2$ is chloro; $R^3$ is methyl; X and Y are each oxygen; n is 0; and the values of $R^4$ match those of the correspondingly numbered compounds of Table A1.

TABLE B9

Table B9 provides 352 compounds of formula (Ia) wherein $R^1$ is ethyl; $R^2$ is bromo; $R^3$ is methyl; X and Y are each oxygen; n is 0; and the values of $R^4$ match those of the correspondingly numbered compounds of Table A1.

TABLE B10

Table B10 provides 352 compounds of formula (Ia) wherein $R^1$ is ethyl; $R^2$ is cyano; $R^3$ is methyl; X and Y are each oxygen; n is 0; and the values of $R^4$ match those of the correspondingly numbered compounds of Table A1.

TABLE B11

Table B11 provides 352 compounds of formula (Ia) wherein $R^1$ is methyl; $R^2$ is hydrogen; $R^3$ is methyl; X is oxygen; Y is sulphur; n is 0; and the values of $R^4$ match those of the correspondingly numbered compounds of Table A1.

TABLE B12

Table B12 provides 352 compounds of formula (Ia) wherein $R^1$ is methyl; $R^2$ is fluoro; $R^3$ is methyl; X is oxygen; Y is sulphur; n is 0; and the values of $R^4$ match those of the correspondingly numbered compounds of Table A1.

TABLE B13

Table B13 provides 352 compounds of formula (Ia) wherein $R^1$ is methyl; $R^2$ is chloro; $R^3$ is methyl; X is oxygen; Y is sulphur; n is 0; and the values of $R^4$ match those of the correspondingly numbered compounds of Table A1.

TABLE B14

Table B14 provides 352 compounds of formula (Ia) wherein $R^1$ is methyl; $R^2$ is bromo; $R^3$ is methyl; X is oxygen; Y is sulphur; n is 0; and the values of $R^4$ match those of the correspondingly numbered compounds of Table A1.

TABLE B15

Table B15 provides 352 compounds of formula (Ia) wherein $R^1$ is methyl; $R^2$ is cyano; $R^3$ is methyl; X is oxygen; Y is sulphur; n is 0; and the values of $R^4$ match those of the correspondingly numbered compounds of Table A1.

TABLE B16

Table B16 provides 352 compounds of formula (Ia) wherein $R^1$ is ethyl; $R^2$ is hydrogen; $R^3$ is methyl; X is oxygen; Y is sulphur; n is 0; and the values of $R^4$ match those of the correspondingly numbered compounds of Table A1.

TABLE B17

Table B17 provides 352 compounds of formula (Ia) wherein $R^1$ is ethyl; $R^2$ is fluoro; $R^3$ is methyl; X is oxygen; Y is sulphur; n is 0; and the values of $R^4$ match those of the correspondingly numbered compounds of Table A1.

TABLE B18

Table B18 provides 352 compounds of formula (Ia) wherein $R^1$ is ethyl; $R^2$ is chloro; $R^3$ is methyl; X is oxygen; Y is sulphur; n is 0; and the values of $R^4$ match those of the correspondingly numbered compounds of Table A1.

TABLE B19

Table B19 provides 352 compounds of formula (a) wherein $R^1$ is ethyl; $R^2$ is bromo; $R^3$ is methyl; X is oxygen; Y is sulphur; n is 0; and the values of $R^4$ match those of the correspondingly numbered compounds of Table A1.

TABLE B20

Table B20 provides 352 compounds of formula (Ia) wherein $R^1$ is ethyl; $R^2$ is cyano; $R^3$ is methyl; X is oxygen; Y is sulphur; n is 0; and the values of $R^4$ match those of the correspondingly numbered compounds of Table A1.

TABLE B21

Table B21 provides 352 compounds of formula (Ib) wherein $R^1$ is methyl; $R^2$ is hydrogen; $R^3$ is methyl; X and Y are each oxygen; n is 0; and the values of $R^4$ match those of the correspondingly numbered compounds of Table A1.

TABLE B22

Table B22 provides 352 compounds of formula (Ib) wherein $R^1$ is methyl; $R^2$ is fluoro; $R^3$ is methyl; X and Y are each oxygen; n is 0; and the values of $R^4$ match those of the correspondingly numbered compounds of Table A1.

TABLE B23

Table B23 provides 352 compounds of formula (Ib) wherein $R^1$ is methyl; $R^2$ is chloro; $R^3$ is methyl; X and Y are each oxygen; n is 0; and the values of $R^4$ match those of the correspondingly numbered compounds of Table A1.

TABLE B24

Table B24 provides 352 compounds of formula (Ib) wherein $R^1$ is methyl; $R^2$ is bromo; $R^3$ is methyl; X and Y are each oxygen; n is 0; and the values of $R^4$ match those of the correspondingly numbered compounds of Table A1.

TABLE B25

Table B25 provides 352 compounds of formula (Ib) wherein $R^1$ is methyl; $R^2$ is cyano; $R^3$ is methyl; X and Y are each oxygen; n is 0; and the values of $R^4$ match those of the correspondingly numbered compounds of Table A1.

TABLE B26

Table B26 provides 352 compounds of formula (Ib) wherein $R^1$ is ethyl; $R^2$ is hydrogen; $R^3$ is methyl; X and Y are each oxygen; n is 0; and the values of $R^4$ match those of the correspondingly numbered compounds of Table A1.

TABLE B27

Table B27 provides 352 compounds of formula (Ib) wherein $R^1$ is ethyl; $R^2$ is fluoro; $R^3$ is methyl; X and Y are each oxygen; n is 0; and the values of $R^4$ match those of the correspondingly numbered compounds of Table A1.

TABLE B28

Table B28 provides 352 compounds of formula (Ib) wherein $R^1$ is ethyl; $R^2$ is chloro; $R^3$ is methyl; X and Y are each oxygen; n is 0; and the values of $R^4$ match those of the correspondingly numbered compounds of Table A1.

TABLE B29

Table B29 provides 352 compounds of formula (Ib) wherein $R^1$ is ethyl; $R^2$ is bromo; $R^3$ is methyl; X and Y are each oxygen; n is 0; and the values of $R^4$ match those of the correspondingly numbered compounds of Table A1.

TABLE B30

Table B30 provides 352 compounds of formula (Ib) wherein $R^1$ is ethyl; $R^2$ is cyano; $R^3$ is methyl; X and Y are each oxygen; n is 0; and the values of $R^4$ match those of the correspondingly numbered compounds of Table A1.

TABLE B31

Table B31 provides 352 compounds of formula (Ib) wherein $R^1$ is methyl; $R^2$ is hydrogen; $R^3$ is methyl; X is oxygen; Y is sulphur; n is 0; and the values of $R^4$ match those of the correspondingly numbered compounds of Table A1.

TABLE B32

Table B32 provides 352 compounds of formula (Ib) wherein $R^1$ is methyl; $R^2$ is fluoro; $R^3$ is methyl; X is oxygen; Y is sulphur; n is 0; and the values of $R^4$ match those of the correspondingly numbered compounds of Table A1.

TABLE B33

Table B33 provides 352 compounds of formula (Ib) wherein $R^1$ is methyl; $R^2$ is chloro; $R^3$ is methyl; X is oxygen; Y is sulphur; n is 0; and the values of $R^4$ match those of the correspondingly numbered compounds of Table A1.

TABLE B34

Table B34 provides 352 compounds of formula (Ib) wherein $R^1$ is methyl; $R^2$ is bromo; $R^3$ is methyl; X is oxygen; Y is sulphur; n is 0; and the values of $R^4$ match those of the correspondingly numbered compounds of Table A1.

TABLE B35

Table B35 provides 352 compounds of formula (Ib) wherein $R^1$ is methyl; $R^2$ is cyano; $R^3$ is methyl; X is oxygen; Y is sulphur; n is 0; and the values of $R^4$ match those of the correspondingly numbered compounds of Table A1.

TABLE B36

Table B36 provides 352 compounds of formula (Ib) wherein $R^1$ is ethyl; $R^2$ is hydrogen; $R^3$ is methyl; X is oxygen; Y is sulphur; n is 0; and the values of $R^4$ match those of the correspondingly numbered compounds of Table A1.

TABLE B37

Table B37 provides 352 compounds of formula (Ib) wherein $R^1$ is ethyl; $R^2$ is fluoro; $R^3$ is methyl; X is oxygen; Y is sulphur; n is 0; and the values of $R^4$ match those of the correspondingly numbered compounds of Table A1.

TABLE B38

Table B38 provides 352 compounds of formula (Ib) wherein $R^1$ is ethyl; $R^2$ is chloro; $R^3$ is methyl; X is oxygen; Y is sulphur; n is 0; and the values of $R^4$ match those of the correspondingly numbered compounds of Table A1.

TABLE B39

Table B39 provides 352 compounds of formula (Ib) wherein $R^1$ is ethyl; $R^2$ is bromo; $R^3$ is methyl; X is oxygen; Y is sulphur; n is 0; and the values of $R^4$ match those of the correspondingly numbered compounds of Table A1.

TABLE B40

Table B40 provides 352 compounds of formula (Ib) wherein $R^1$ is ethyl; $R^2$ is cyano; $R^3$ is methyl; X is oxygen; Y is sulphur; n is 0; and the values of $R^4$ match those of the correspondingly numbered compounds of Table A1.

TABLE41

Table B41 provides 352 compounds of formula (Ib) wherein $R^1$ is methyl; $R^2$ is hydrogen; $R^3$ is methyl; X is oxygen; Y is $NR^7$; $R^7$ is hydrogen; n is 0; and the values of $R^4$ match those of the correspondingly numbered compounds of Table A1.

TABLE B42

Table B42 provides 352 compounds of formula (Ib) wherein $R^1$ is methyl; $R^2$ is fluoro; $R^3$ is methyl; X is oxygen; Y is $NR^7$; $R^7$ is hydrogen; n is 0; and the values of $R^4$ match those of the correspondingly numbered compounds of Table A1.

TABLE B43

Table B43 provides 352 compounds of formula (Ib) wherein $R^1$ is methyl; $R^2$ is chloro; $R^3$ is methyl; X is oxygen; Y is $NR^7$; $R^7$ is hydrogen; n is 0; and the values of $R^4$ match those of the correspondingly numbered compounds of Table A1.

TABLE B44

Table B44 provides 352 compounds of formula (Ib) wherein $R^1$ is methyl; $R^2$ is bromo; $R^3$ is methyl; X is oxygen; Y is $NR^7$; $R^7$ is hydrogen; n is 0; and the values of $R^4$ match those of the correspondingly numbered compounds of Table A1.

TABLE B45

Table B45 provides 352 compounds of formula (Ib) wherein $R^1$ is methyl; $R^2$ is cyano; $R^3$ is methyl; X is oxygen; Y is $NR^7$; $R^7$ is hydrogen; n is 0; and the values of $R^4$ match those of the correspondingly numbered compounds of Table A1.

TABLE B46

Table B46 provides 352 compounds of formula (Ib) wherein $R^1$ is ethyl; $R^2$ is hydrogen; $R^3$ is methyl; X is oxygen; Y is $NR^7$; $R^7$ is hydrogen; n is 0; and the values of $R^4$ match those of the correspondingly numbered compounds of Table A1.

TABLE B47

Table B47 provides 352 compounds of formula (Ib) wherein $R^1$ is ethyl; $R^2$ is fluoro; $R^3$ is methyl; X is oxygen;

TABLE B48

Table B48 provides 352 compounds of formula (Ib) wherein $R^1$ is ethyl; $R^2$ is chloro; $R^3$ is methyl; X is oxygen; Y is $NR^7$; $R^7$ is hydrogen; n is 0; and the values of $R^4$ match those of the correspondingly numbered compounds of Table A1.

TABLE B49

Table B49 provides 352 compounds of formula (Ib) wherein $R^1$ is ethyl; $R^2$ is bromo; $R^3$ is methyl; X is oxygen; Y is $NR^7$; $R^7$ is hydrogen; n is 0; and the values of $R^4$ match those of the correspondingly numbered compounds of Table A1.

TABLE B50

Table B50 provides 352 compounds of formula (Ib) wherein $R^1$ is ethyl; $R^2$ is cyano; $R^3$ is methyl; X is oxygen; Y is $NR^7$; $R^7$ is hydrogen; n is 0; and the values of $R^4$ match those of the correspondingly numbered compounds of Table A1.

TABLE B51

Table B51 provides 352 compounds of formula (Ib) wherein $R^1$ is methyl; $R^2$ is hydrogen; $R^3$ is methyl; X is oxygen; Y is $NR^7$; $R^7$ is methyl; n is 0; and the values of $R^4$ match those of the correspondingly numbered compounds of Table A1.

TABLE B52

Table B52 provides 352 compounds of formula (Ib) wherein $R^1$ is methyl; $R^2$ is fluoro; $R^3$ is methyl; X is oxygen; Y is $NR^7$; $R^7$ is methyl; n is 0; and the values of $R^4$ match those of the correspondingly numbered compounds of Table A1.

TABLE B53

Table B53 provides 352 compounds of formula (Ib) wherein $R^1$ is methyl; $R^2$ is chloro; $R^3$ is methyl; X is oxygen; Y is $NR^7$; $R^7$ is methyl; n is 0; and the values of $R^4$ match those of the correspondingly numbered compounds of Table A1.

TABLE B54

Table B54 provides 352 compounds of formula (Ib) wherein $R^1$ is methyl; $R^2$ is bromo; $R^3$ is methyl; X is oxygen; Y is $NR^7$; $R^7$ is methyl; n is 0; and the values of $R^4$ match those of the correspondingly numbered compounds of Table A1.

TABLE B55

Table B55 provides 352 compounds of formula (Ib) wherein $R^1$ is methyl; $R^2$ is cyano; $R^3$ is methyl; X is oxygen; Y is $NR^7$; $R^7$ is methyl; n is 0; and the values of $R^4$ match those of the correspondingly numbered compounds of Table A1.

TABLE B56

Table B56 provides 352 compounds of formula (Ib) wherein $R^1$ is ethyl; $R^2$ is hydrogen; $R^3$ is methyl; X is oxygen; Y is $NR^7$; $R^7$ is methyl; n is 0; and the values of $R^4$ match those of the correspondingly numbered compounds of Table A1.

TABLE B57

Table B57 provides 352 compounds of formula (Ib) wherein $R^1$ is ethyl; $R^2$ is fluoro; $R^3$ is methyl; X is oxygen; Y is $NR^7$; $R^7$ is methyl; n is 0; and the values of $R^4$ match those of the correspondingly numbered compounds of Table A1.

TABLE B58

Table B58 provides 352 compounds of formula (Ib) wherein $R^1$ is ethyl; $R^2$ is chloro; $R^3$ is methyl; X is oxygen; Y is $NR^7$; $R^7$ is methyl; n is 0; and the values of $R^4$ match those of the correspondingly numbered compounds of Table A1.

TABLE B59

Table B59 provides 352 compounds of formula (Ib) wherein $R^1$ is ethyl; $R^2$ is bromo; $R^3$ is methyl; X is oxygen; Y is $NR^7$; $R^7$ is methyl; n is 0; and the values of $R^4$ match those of the correspondingly numbered compounds of Table A1.

TABLE B60

Table B60 provides 352 compounds of formula (Ib) wherein $R^1$ is ethyl; $R^2$ is cyano; $R^3$ is methyl; X is oxygen; Y is $NR^7$; $R^7$ is methyl; n is 0; and the values of $R^4$ match those of the correspondingly numbered compounds of Table A1.

TABLE B61

Table B61 provides 352 compounds of formula (Ia) wherein $R^1$ is methyl; $R^2$ is hydrogen; $R^3$ is methyl; X is oxygen; Y is $NR^7$; $R^7$ is methyl; n is 0; and the values of $R^4$ match those of the correspondingly numbered compounds of Table A1.

TABLE B62

Table B62 provides 352 compounds of formula (Ia) wherein $R^1$ is methyl; $R^2$ is is fluoro; $R^3$ is methyl; X is oxygen; Y is $NR^7$; $R^7$ is methyl; n is 0; and the values of $R^4$ match those of the correspondingly numbered compounds of Table A1.

TABLE B63

Table B63 provides 352 compounds of formula (Ia) wherein $R^1$ is methyl; $R^2$ is chloro; $R^3$ is methyl; X is oxygen; Y is $NR^7$; $R^7$ is methyl; n is 0; and the values of $R^4$ match those of the correspondingly numbered compounds of Table A1.

TABLE B64

Table B64 provides 352 compounds of formula (Ia) wherein $R^1$ is methyl; $R^2$ is bromo; $R^3$ is methyl; X is oxygen; Y is $NR^7$; $R^7$ is methyl; n is 0; and the values of $R^4$ match those of the correspondingly numbered compounds of Table A1.

TABLE B65

Table B65 provides 352 compounds of formula (Ib) wherein $R^1$ is methyl; $R^2$ is cyano; $R^3$ is methyl; X is oxygen; Y is $NR^7$; $R^7$ is methyl; n is 0; and the values of $R^4$ match those of the correspondingly numbered compounds of Table A1.

TABLE B66

Table B66 provides 352 compounds of formula (Ia) wherein $R^1$ is ethyl; $R^2$ is hydrogen; $R^3$ is methyl; X is oxygen; Y is $NR^7$; $R^7$ is methyl; n is 0; and the values of $R^4$ match those of the correspondingly numbered compounds of Table A1.

TABLE B67

Table B67 provides 352 compounds of formula (Ia) wherein $R^1$ is ethyl; $R^2$ is fluoro; $R^3$ is methyl; X is oxygen; Y is $NR^7$; $R^7$ is methyl; n is 0; and the values of $R^4$ match those of the correspondingly numbered compounds of Table A1.

TABLE B68

Table B68 provides 352 compounds of formula (Ia) wherein $R^1$ is ethyl; $R^2$ is chloro; $R^3$ is methyl; X is oxygen; Y is $NR^7$; $R^7$ is methyl; n is 0; and the values of $R^4$ match those of the correspondingly numbered compounds of Table A1.

TABLE B69

Table B69 provides 352 compounds of formula (Ia) wherein $R^1$ is ethyl; $R^2$ is bromo; $R^3$ is methyl; X is oxygen; Y is $NR^7$; $R^7$ is methyl; n is 0; and the values of $R^4$ match those of the correspondingly numbered compounds of Table A1.

TABLE B70

Table B70 provides 352 compounds of formula (Ia) wherein $R^1$ is ethyl; $R^2$ is cyano; $R^3$ is methyl; X is oxygen; Y is $NR^7$; $R^7$ is methyl; n is 0; and the values of $R^4$ match those of the correspondingly numbered compounds of Table A1.

TABLE C1

Table C1 provides 352 compounds of formula (Ia) wherein $R^1$ is methyl; $R^2$ is hydrogen; $R^3$ is ethyl; X and Y are each oxygen; n is 0; and the values of $R^4$ match those of the correspondingly numbered compounds of Table A1.

TABLE C2

Table C2 provides 352 compounds of formula (Ia) wherein $R^1$ is methyl; $R^2$ is fluoro; $R^3$ is ethyl; X and Y are each oxygen; n is 0; and the values of $R^4$ match those of the correspondingly numbered compounds of Table A1.

TABLE C3

Table C3 provides 352 compounds of formula (Ia) wherein $R^1$ is methyl; $R^2$ is chloro; $R^3$ is ethyl; X and Y are each oxygen; n is 0; and the values of $R^4$ match those of the correspondingly numbered compounds of Table A1.

TABLE C4

Table C4 provides 352 compounds of formula (Ia) wherein $R^1$ is methyl; $R^2$ is bromo; $R^3$ is ethyl; X and Y are each oxygen; n is 0; and the values of $R^4$ match those of the correspondingly numbered compounds of Table A1.

TABLE C5

Table C5 provides 352 compounds of formula (Ia) wherein $R^1$ is methyl; $R^2$ is cyano; $R^3$ is ethyl; X and Y are each oxygen; n is 0; and the values of $R^4$ match those of the correspondingly numbered compounds of Table A1.

TABLE C6

Table C6 provides 352 compounds of formula (Ia) wherein $R^1$ is ethyl; $R^2$ is hydrogen; $R^3$ is ethyl; X and Y are each oxygen; n is 0; and the values of $R^4$ match those of the correspondingly numbered compounds of Table A1.

TABLE C7

Table C7 provides 352 compounds of formula (Ia) wherein $R^1$ is ethyl; $R^2$ is fluoro; $R^3$ is ethyl; X and Y are each oxygen; n is 0; and the values of $R^4$ match those of the correspondingly numbered compounds of Table A1.

TABLE C8

Table C8 provides 352 compounds of formula (Ia) wherein $R^1$ is ethyl; $R^2$ is chloro; $R^3$ is ethyl; X and Y are each oxygen; n is 0; and the values of $R^4$ match those of the correspondingly numbered compounds of Table A1.

TABLE C9

Table C9 provides 352 compounds of formula (Ia) wherein $R^1$ is ethyl; $R^2$ is bromo; $R^3$ is ethyl; X and Y are each oxygen; n is 0; and the values of $R^4$ match those of the correspondingly numbered compounds of Table A1.

TABLE C10

Table C10 provides 352 compounds of formula (Ia) wherein $R^1$ is ethyl; $R^2$ is cyano; $R^3$ is ethyl; X and Y are each oxygen; n is 0; and the values of $R^4$ match those of the correspondingly numbered compounds of Table A1.

TABLE C11

Table C11 provides 352 compounds of formula (Ia) wherein $R^1$ is methyl; $R^2$ is hydrogen; $R^3$ is ethyl; X is oxygen; Y is sulphur; n is 0; and the values of $R^4$ match those of the correspondingly numbered compounds of Table A1.

TABLE C12

Table C12 provides 352 compounds of formula (Ia) wherein $R^1$ is methyl; $R^2$ is fluoro; $R^3$ is ethyl; X is oxygen; Y is sulphur; n is 0; and the values of $R^4$ match those of the correspondingly numbered compounds of Table A1.

TABLE C13

Table C13 provides 352 compounds of formula (Ia) wherein $R^1$ is methyl; $R^2$ is chloro; $R^3$ is ethyl; X is oxygen; Y is sulphur; n is 0; and the values of $R^4$ match those of the correspondingly numbered compounds of Table A1.

TABLE C14

Table C14 provides 352 compounds of formula (Ia) wherein $R^1$ is methyl; $R^2$ is bromo; $R^3$ is ethyl; X is oxygen; Y is sulphur; n is 0; and the values of $R^4$ match those of the correspondingly numbered compounds of Table A1.

TABLE C15

Table C15 provides 352 compounds of formula (Ia) wherein $R^1$ is methyl; $R^2$ is cyano; $R^3$ is ethyl; X is oxygen; Y is sulphur; n is 0; and the values of $R^4$ match those of the correspondingly numbered compounds of Table A1.

TABLE C16

Table C16 provides 352 compounds of formula (Ia) wherein $R^1$ is ethyl; $R^2$ is hydrogen; $R^3$ is ethyl; X is oxygen; Y is sulphur; n is 0; and the values of $R^4$ match those of the correspondingly numbered compounds of Table A1.

TABLE C17

Table C17 provides 352 compounds of formula (Ia) wherein $R^1$ is ethyl; $R^2$ is fluoro; $R^3$ is ethyl; X is oxygen; Y is sulphur; n is 0; and the values of $R^4$ match those of the correspondingly numbered compounds of Table A1.

TABLE C18

Table C18 provides 352 compounds of formula (Ia) wherein $R^1$ is ethyl; $R^2$ is chloro; $R^3$ is ethyl; X is oxygen; Y is sulphur; n is 0; and the values of $R^4$ match those of the correspondingly numbered compounds of Table A1.

TABLE C19

Table C19 provides 352 compounds of formula (Ia) wherein $R^1$ is ethyl; $R^2$ is bromo; $R^3$ is ethyl; X is oxygen; Y is sulphur; n is 0; and the values of $R^4$ match those of the correspondingly numbered compounds of Table A1.

TABLE C20

Table C20 provides 352 compounds of formula (Ia) wherein $R^1$ is ethyl; $R^2$ is cyano; $R^3$ is ethyl; X is oxygen; Y is sulphur; n is 0; and the values of $R^4$ match those of the correspondingly numbered compounds of Table A1.

TABLE C21

Table C21 provides 352 compounds of formula (Ib) wherein $R^1$ is methyl; $R^2$ is hydrogen; $R^3$ is ethyl; X and Y are each oxygen; n is 0; and the values of $R^4$ match those of the correspondingly numbered compounds of Table A1.

TABLE C22

Table C22 provides 352 compounds of formula (Ib) wherein $R^1$ is methyl; $R^2$ is fluoro; $R^3$ is ethyl; X and Y are each oxygen; n is 0; and the values of $R^4$ match those of the correspondingly numbered compounds of Table A1.

TABLE C23

Table C23 provides 352 compounds of formula (Ib) wherein $R^1$ is methyl; $R^2$ is chloro; $R^3$ is ethyl; X and Y are each oxygen; n is 0; and the values of $R^4$ match those of the correspondingly numbered compounds of Table A1.

TABLE C24

Table C24 provides 352 compounds of formula (Ib) wherein $R^1$ is methyl; $R^2$ is bromo; $R^3$ is ethyl; X and Y are each oxygen; n is 0; and the values of $R^4$ match those of the correspondingly numbered compounds of Table A1.

TABLE C25

Table C25 provides 352 compounds of formula (Ib) wherein $R^1$ is methyl; $R^2$ is cyano; $R^3$ is ethyl; X and Y are each oxygen; n is 0; and the values of $R^4$ match those of the correspondingly numbered compounds of Table A1.

TABLE C26

Table C26 provides 352 compounds of formula (Ib) wherein $R^1$ is ethyl; $R^2$ is hydrogen; $R^3$ is ethyl; X and Y are each oxygen; n is 0; and the values of $R^4$ match those of the correspondingly numbered compounds of Table A1.

TABLE C27

Table C27 provides 352 compounds of formula (Ib) wherein $R^1$ is ethyl; $R^2$ is fluoro; $R^3$ is ethyl; X and Y are each oxygen; n is 0; and the values of $R^4$ match those of the correspondingly numbered compounds of Table A1.

TABLE C28

Table C28 provides 352 compounds of formula (Ib) wherein $R^1$ is ethyl; $R^2$ is chloro; $R^3$ is ethyl; X and Y are each oxygen; n is 0; and the values of $R^4$ match those of the correspondingly numbered compounds of Table A1.

TABLE C29

Table C29 provides 352 compounds of formula (Ib) wherein $R^1$ is ethyl; $R^2$ is bromo; $R^3$ is ethyl; X and Y are each oxygen; n is 0; and the values of $R^4$ match those of the correspondingly numbered compounds of Table A1.

TABLE C30

Table C30 provides 352 compounds of formula (Ib) wherein $R^1$ is ethyl; $R^2$ is cyano; $R^3$ is ethyl; X and Y are each oxygen; n is 0; and the values of $R^4$ match those of the correspondingly numbered compounds of Table A1.

TABLE C31

Table C31 provides 352 compounds of formula (Ib) wherein $R^1$ is methyl; $R^2$ is hydrogen; $R^3$ is ethyl; X is oxygen; Y is sulphur; n is 0; and the values of $R^4$ match those of the correspondingly numbered compounds of Table A1.

TABLE C32

Table C32 provides 352 compounds of formula (Ib) wherein $R^1$ is methyl; $R^2$ is fluoro; $R^3$ is ethyl; X is oxygen; Y is sulphur; n is 0; and the values of $R^4$ match those of the correspondingly numbered compounds of Table A1.

TABLE C33

Table C33 provides 352 compounds of formula (Ib) wherein $R^1$ is methyl; $R^2$ is chloro; $R^3$ is ethyl; X is oxygen; Y is sulphur; n is 0; and the values of $R^4$ match those of the correspondingly numbered compounds of Table A1.

TABLE C34

Table C34 provides 352 compounds of formula (Ib) wherein $R^1$ is methyl; $R^2$ is bromo; $R^3$ is ethyl; X is oxygen; Y is sulphur; n is 0; and the values of $R^4$ match those of the correspondingly numbered compounds of Table A1.

TABLE C35

Table C35 provides 352 compounds of formula (Ib) wherein $R^1$ is methyl; $R^2$ is cyano; $R^3$ is ethyl; X is oxygen; Y is sulphur; n is 0; and the values of $R^4$ match those of the correspondingly numbered compounds of Table A1.

TABLE C36

Table C36 provides 352 compounds of formula (Ib) wherein $R^1$ is ethyl; $R^2$ is hydrogen; $R^3$ is ethyl; X is oxygen; Y is sulphur; n is 0; and the values of $R^4$ match those of the correspondingly numbered compounds of Table A1.

TABLE C37

Table C37 provides 352 compounds of formula (Ib) wherein $R^1$ is ethyl; $R^2$ is fluoro; $R^3$ is ethyl; X is oxygen; Y is sulphur; n is 0; and the values of $R^4$ match those of the correspondingly numbered compounds of Table A1.

TABLE C38

Table C38 provides 352 compounds of formula (Ib) wherein $R^1$ is ethyl; $R^2$ is chloro; $R^3$ is ethyl; X is oxygen; Y is sulphur; n is 0; and the values of $R^4$ match those of the correspondingly numbered compounds of Table A1.

TABLE C39

Table C39 provides 352 compounds of formula (Ib) wherein $R^1$ is ethyl; $R^2$ is bromo; $R^3$ is ethyl; X is oxygen; Y is sulphur; n is 0; and the values of $R^4$ match those of the correspondingly numbered compounds of Table A1.

TABLE C40

Table C40 provides 352 compounds of formula (Ib) wherein $R^1$ is ethyl; $R^2$ is cyano; $R^3$ is ethyl; X is oxygen; Y is sulphur; n is 0; and the values of $R^4$ match those of the correspondingly numbered compounds of Table A1.

TABLE C41

Table C41 provides 352 compounds of formula (Ib) wherein $R^1$ is methyl; $R^2$ is hydrogen; $R^3$ is ethyl; X is oxygen; Y is $NR^7$; $R^7$ is hydrogen; n is 0; and the values of $R^4$ match those of the correspondingly numbered compounds of Table A1.

TABLE C42

Table C42 provides 352 compounds of formula (Ib) wherein $R^1$ is methyl; $R^2$ is fluoro; $R^3$ is ethyl; X is oxygen; Y is $NR^7$; $R^7$ is hydrogen; n is 0; and the values of $R^4$ match those of the correspondingly numbered compounds of Table A1.

TABLE C43

Table C43 provides 352 compounds of formula (Ib) wherein $R^1$ is methyl; $R^2$ is chloro; $R^3$ is ethyl; X is oxygen; Y is $NR^7$; $R^7$ is hydrogen; n is 0; and the values of $R^4$ match those of the correspondingly numbered compounds of Table A1.

TABLE C44

Table C44 provides 352 compounds of formula (Ib) wherein $R^1$ is methyl; $R^2$ is bromo; $R^3$ is ethyl; X is oxygen; Y is $NR^7$; $R^7$ is hydrogen; n is 0; and the values of $R^4$ match those of the correspondingly numbered compounds of Table A1.

TABLE C45

Table C45 provides 352 compounds of formula (Ib) wherein $R^1$ is methyl; $R^2$ is cyano; $R^3$ is ethyl; X is oxygen; Y is $NR^7$; $R^7$ is hydrogen; n is 0; and the values of $R^4$ match those of the correspondingly numbered compounds of Table A1.

TABLE C46

Table C46 provides 352 compounds of formula (Ib) wherein $R^1$ is ethyl; $R^2$ is hydrogen; $R^3$ is ethyl; X is oxygen; Y is $NR^7$; $R^7$ is hydrogen; n is 0; and the values of $R^4$ match those of the correspondingly numbered compounds of Table A1.

TABLE C47

Table C47 provides 352 compounds of formula (Ib) wherein $R^1$ is ethyl; $R^2$ is fluoro; $R^3$ is ethyl; X is oxygen; Y is $NR^7$; $R^7$ is hydrogen; n is 0; and the values of $R^4$ match those of the correspondingly numbered compounds of Table A1.

TABLE C48

Table C48 provides 352 compounds of formula (Ib) wherein $R^1$ is ethyl; $R^2$ is chloro; $R^3$ is ethyl; X is oxygen; Y is $NR^7$; $R^7$ is hydrogen; n is 0; and the values of $R^4$ match those of the correspondingly numbered compounds of Table A1.

TABLE C49

Table C49 provides 352 compounds of formula (Ib) wherein $R^1$ is ethyl; $R^2$ is bromo; $R^3$ is ethyl; X is oxygen; Y is $NR^7$; $R^7$ is hydrogen; n is 0; and the values of $R^4$ match those of the correspondingly numbered compounds of Table A1.

TABLE C50

Table C50 provides 352 compounds of formula (Ib) wherein $R^1$ is ethyl; $R^2$ is cyano; $R^3$ is ethyl; X is oxygen; Y is $NR^7$; $R^7$ is hydrogen; n is 0; and the values of $R^4$ match those of the correspondingly numbered compounds of Table A1.

TABLE C51

Table C51 provides 352 compounds of formula (Ib) wherein $R^1$ is methyl; $R^2$ is hydrogen; $R^3$ is ethyl; X is oxygen; Y is $NR^7$; $R^7$ is methyl; n is 0; and the values of $R^4$ match those of the correspondingly numbered compounds of Table A1.

TABLE C52

Table C52 provides 352 compounds of formula (Ib) wherein $R^1$ is methyl; $R^2$ is fluoro; $R^3$ is ethyl; X is oxygen; Y is $NR^7$; $R^7$ is methyl; n is 0; and the values of $R^4$ match those of the correspondingly numbered compounds of Table A1.

TABLE C53

Table C53 provides 352 compounds of formula (Ib) wherein $R^1$ is methyl; $R^2$ is chloro; $R^3$ is ethyl; X is oxygen; Y is $NR^7$; $R^7$ is methyl; n is 0; and the values of $R^4$ match those of the correspondingly numbered compounds of Table A1.

TABLE C54

Table C54 provides 352 compounds of formula (Ib) wherein $R^1$ is methyl; $R^2$ is bromo; $R^3$ is ethyl; X is oxygen; Y is $NR^7$; $R^7$ is methyl; n is 0; and the values of $R^4$ match those of the correspondingly numbered compounds of Table A1.

TABLE C55

Table C55 provides 352 compounds of formula (Ib) wherein $R^1$ is methyl; $R^2$ is cyano; $R^3$ is ethyl; X is oxygen;

TABLE C56

Table C56 provides 352 compounds of formula (Ib) wherein $R^1$ is ethyl; $R^2$ is hydrogen; $R^3$ is ethyl; X is oxygen; Y is $NR^7$; $R^7$ is methyl; n is 0; and the values of $R^4$ match those of the correspondingly numbered compounds of Table A1.

TABLE C57

Table C57 provides 352 compounds of formula (Ib) wherein $R^1$ is ethyl; $R^2$ is fluoro; $R^3$ is ethyl; X is oxygen; Y is $NR^7$; $R^7$ is methyl; n is 0; and the values of $R^4$ match those of the correspondingly numbered compounds of Table A1.

TABLE C58

Table C58 provides 352 compounds of formula (Ib) wherein $R^1$ is ethyl; $R^2$ is chloro; $R^3$ is ethyl; X is oxygen; Y is $NR^7$; $R^7$ is methyl; n is 0; and the values of $R^4$ match those of the correspondingly numbered compounds of Table A1.

TABLE C59

Table C59 provides 352 compounds of formula (Ib) wherein $R^1$ is ethyl; $R^2$ is bromo; $R^3$ is ethyl; X is oxygen; Y is $NR^7$; $R^7$ is methyl; n is 0; and the values of $R^4$ match those of the correspondingly numbered compounds of Table A1.

TABLE C60

Table C60 provides 352 compounds of formula (Ib) wherein $R^1$ is ethyl; $R^2$ is cyano; $R^3$ is ethyl; X is oxygen; Y is $NR^7$; $R^7$ is methyl; n is 0; and the values of $R^4$ match those of the correspondingly numbered compounds of Table A1.

TABLE C61

Table C61 provides 352 compounds of formula (Ia) wherein $R^1$ is methyl; $R^2$ is hydrogen; $R^3$ is ethyl; X is oxygen; Y is $NR^7$; $R^7$ is methyl; n is 0; and the values of $R^4$ match those of the correspondingly numbered compounds of Table A1.

TABLE C62

Table C62 provides 352 compounds of formula (Ia) wherein $R^1$ is methyl; $R^2$ is fluoro; $R^3$ is ethyl; X is oxygen; Y is $NR^7$; $R^7$ is methyl; n is 0; and the values of $R^4$ match those of the correspondingly numbered compounds of Table A1.

TABLE C63

Table C63 provides 352 compounds of formula (Ia) wherein $R^1$ is methyl; $R^2$ is chloro; $R^3$ is ethyl; X is oxygen; Y is $NR^7$; $R^7$ is methyl; n is 0; and the values of $R^4$ match those of the correspondingly numbered compounds of Table A1.

TABLE C64

Table C64 provides 352 compounds of formula (Ia) wherein $R^1$ is methyl; $R^2$ is bromo; $R^3$ is ethyl; X is oxygen; Y is $NR^7$; $R^7$ is methyl; n is 0; and the values of $R^4$ match those of the correspondingly numbered compounds of Table A1.

TABLE C65

Table C65 provides 352 compounds of formula (Ib) wherein $R^1$ is methyl; $R^2$ is cyano; $R^3$ is ethyl; X is oxygen; Y is $NR^7$; $R^7$ is methyl; n is 0; and the values of $R^4$ match those of the correspondingly numbered compounds of Table A1.

TABLE C66

Table C66 provides 352 compounds of formula (Ia) wherein $R^1$ is ethyl; $R^2$ is hydrogen; $R^3$ is ethyl; X is oxygen; Y is $NR^7$; $R^7$ is methyl; n is 0; and the values of $R^4$ match those of the correspondingly numbered compounds of Table A1.

TABLE C67

Table C67 provides 352 compounds of formula (Ia) wherein $R^1$ is ethyl; $R^2$ is fluoro; i s $R^3$ is ethyl; X is oxygen; Y is $NR^7$; $R^7$ is methyl; n is 0; and the values of $R^4$ match those of the correspondingly numbered compounds of Table A1.

TABLE C68

Table C68 provides 352 compounds of formula (Ia) wherein $R^1$ is ethyl; $R^2$ is chloro; $R^3$ is ethyl; X is oxygen; Y is $NR^7$; $R^7$ is methyl; n is 0; and the values of $R^4$ match those of the correspondingly numbered compounds of Table A1.

TABLE C69

Table C69 provides 352 compounds of formula (Ia) wherein $R^1$ is ethyl; $R^2$ is bromo; $R^3$ is ethyl; X is oxygen; Y is $NR^7$; $R^7$ is methyl; n is 0; and the values of $R^4$ match those of the correspondingly numbered compounds of Table A1.

TABLE C70

Table C70 provides 352 compounds of formula (Ia) wherein $R^1$ is ethyl; $R^2$ is cyano; $R^3$ is ethyl; X is oxygen; Y is $NR^7$; $R^7$ is methyl; n is 0; and the values of $R^4$ match those of the correspondingly numbered compounds of Table A1.

TABLE D1

Table D1 provides 352 compounds of formula (Ia) wherein $R^1$ is methyl; $R^2$ is hydrogen; $R^3$ is $CH_2CH_2CH_3$; X and Y are each oxygen; n is 0; and the values of $R^4$ match those of the correspondingly numbered compounds of Table A1.

TABLE D2

Table D2 provides 352 compounds of formula (Ia) wherein $R^1$ is methyl; $R^2$ is fluoro; $R^3$ is $CH_2CH_2CH_3$; X and Y are each oxygen; n is 0; and the values of $R^4$ match those of the correspondingly numbered compounds of Table A1.

TABLE D3

Table D3 provides 352 compounds of formula (Ia) wherein $R^1$ is methyl; $R^2$ is chloro; $R^3$ is $CH_2CH_2CH_3$; X and Y are each oxygen; n is 0; and the values of $R^4$ match those of the correspondingly numbered compounds of Table A1.

TABLE D4

Table D4 provides 352 compounds of formula (Ia) wherein $R^1$ is methyl; $R^2$ is bromo; $R^3$ is $CH_2CH_2CH_3$; X and Y are each oxygen; n is 0; and the values of $R^4$ match those of the correspondingly numbered compounds of Table A1.

TABLE D5

Table D5 provides 352 compounds of formula (Ia) wherein $R^1$ is methyl; $R^2$ is cyano; $R^3$ is $CH_2CH_2CH_3$; X and Y are each oxygen; n is 0; and the values of $R^4$ match those of the correspondingly numbered compounds of Table A1.

TABLE D6

Table D6 provides 352 compounds of formula (Ia) wherein $R^1$ is ethyl; $R^2$ is hydrogen; $R^3$ is $CH_2CH_2CH_3$; X and Y are each oxygen; n is 0, and the values of $R^4$ match those of the correspondingly numbered compounds of Table A1.

TABLE D7

Table D7 provides 352 compounds of formula (Ia) wherein $R^1$ is ethyl; $R^2$ is fluoro; $R^3$ is $CH_2CH_2CH_3$; X and Y are each oxygen; n is 0; and the values of $R^4$ match those of the correspondingly numbered compounds of Table A1.

TABLE D8

Table D8 provides 352 compounds of formula (Ia) wherein $R^1$ is ethyl; $R^2$ is chloro; $R^3$ is $CH_2CH_2CH_3$; X and Y are each oxygen; n is 0; and the values of $R^4$ match those of the correspondingly numbered compounds of Table A1.

TABLE D9

Table D9 provides 352 compounds of formula (Ia) wherein $R^1$ is ethyl; $R^2$ is bromo; $R^3$ is $CH_2CH_2CH_3$; X and Y are each oxygen; n is 0; and the values of $R^4$ match those of the correspondingly numbered compounds of Table A1.

TABLE D10

Table D10 provides 352 compounds of formula (Ia) wherein $R^1$ is ethyl; $R^2$ is cyano; $R^1$ is $CH_2CH_2CH_3$; X and Y are each oxygen; n is 0; and the values of $R^4$ match those of the correspondingly numbered compounds of Table A1.

TABLE D11

Table D11 provides 352 compounds of formula (Ia) wherein $R^1$ is methyl; $R^2$ is hydrogen; $R^3$ is $CH_2CH_2CH_3$; X is oxygen; Y is sulphur; n is 0; and the values of $R^4$ match those of the correspondingly numbered compounds of Table A1.

TABLE D12

Table D12 provides 352 compounds of formula (Ia) wherein $R^1$ is methyl; $R^2$ is fluoro; $R^3$ is $CH_2CH_2CH_3$; X is oxygen; Y is sulphur; n is 0; and the values of $R^4$ match those of the correspondingly numbered compounds of Table A1.

TABLE D13

Table D13 provides 352 compounds of formula (Ia) wherein $R^1$ is methyl; $R^2$ is chloro; $R^3$ is $CH_2CH_2CH_3$; X is oxygen; Y is sulphur; n is 0; and the values of $R^4$ match those of the correspondingly numbered compounds of Table A1.

TABLE D14

Table D14 provides 352 compounds of formula (Ia) wherein $R^1$ is methyl; $R^2$ is bromo; $R^3$ is $CH_2CH_2CH_3$; X is oxygen; Y is sulphur; n is 0; and the values of $R^4$ match those of the correspondingly numbered compounds of Table A1.

TABLE D15

Table D15 provides 352 compounds of formula (Ia) wherein $R^1$ is methyl; $R^2$ is cyano; $R^3$ is $CH_2CH_2CH_3$; X is oxygen; Y is sulphur; n is 0; and the values of $R^4$ match those of the correspondingly numbered compounds of Table A1.

TABLE D16

Table D16 provides 352 compounds of formula (Ia) wherein $R^1$ is ethyl; $R^2$ is hydrogen; $R^3$ is $CH_2CH_2CH_3$; X is oxygen; Y is sulphur; n is 0; and the values of $R^4$ match those of the correspondingly numbered compounds of Table A1.

TABLE D17

Table D17 provides 352 compounds of formula (Ia) wherein $R^1$ is ethyl; $R^2$ is fluoro; $R^3$ is $CH_2CH_2CH_3$; X is oxygen; Y is sulphur; n is 0; and the values of $R^4$ match those of the correspondingly numbered compounds of Table A1.

TABLE D18

Table D18 provides 352 compounds of formula (Ia) wherein $R^1$ is ethyl; $R^2$ is chloro; $R^3$ is $CH_2CH_2CH_3$; X is oxygen; Y is sulphur; n is 0; and the values of $R^4$ match those of the correspondingly numbered compounds of Table A1.

TABLE D19

Table D19 provides 352 compounds of formula (Ia) wherein $R^1$ is ethyl; $R^2$ is bromo; $R^3$ is $CH_2CH_2CH_3$; X is oxygen; Y is sulphur; n is 0; and the values of $R^4$ match those of the is correspondingly numbered compounds of Table A1.

TABLE D20

Table D20 provides 352 compounds of formula (Ia) wherein $R^1$ is ethyl; $R^2$ is cyano; $R^3$ is $CH_2CH_2CH_3$; X is oxygen; Y is sulphur; n is 0; and the values of $R^4$ match those of the correspondingly numbered compounds of Table A1.

TABLE D21

Table D21 provides 352 compounds of formula (Ib) wherein $R^1$ is methyl; $R^2$ is hydrogen; $R^3$ is $CH_2CH_2CH_3$; X and Y are each oxygen; n is 0, and the values of $R^4$ match those of the correspondingly numbered compounds of Table A1.

TABLE D22

Table D22 provides 352 compounds of formula (Ib) wherein $R^1$ is methyl; $R^2$ is fluoro; $R^3$ is $CH_2CH_2CH_3$; X and Y are each oxygen; n is 0; and the values of $R^4$ match those of the correspondingly numbered compounds of Table A1.

TABLE D23

Table D23 provides 352 compounds of formula (Ib) wherein $R^1$ is methyl; $R^2$ is chloro; $R^3$ is $CH_2CH_2CH_3$; X and Y are each oxygen; n is 0; and the values of $R^4$ match those of the correspondingly numbered compounds of Table A1.

TABLE D24

Table D24 provides 352 compounds of formula (Ib) wherein $R^1$ is methyl; $R^2$ is bromo; $R^3$ is $CH_2CH_2CH_3$; X and Y are each oxygen; n is 0; and the values of $R^4$ match those of the correspondingly numbered compounds of Table A1.

TABLE D25

Table D25 provides 352 compounds of formula (Ib) wherein $R^1$ is methyl; $R^2$ is cyano; $R^3$ is $CH_2CH_2CH_3$; X and Y are each oxygen; n is 0; and the values of $R^4$ match those of the correspondingly numbered compounds of Table A1.

TABLE D26

Table D26 provides 352 compounds of formula (Ib) wherein $R^1$ is ethyl; $R^2$ is hydrogen; $R^3$ is $CH_2CH_2CH_3$; X and Y are each oxygen; n is 0; and the values of $R^4$ match those of the correspondingly numbered compounds of Table A1.

TABLE D27

Table D27 provides 352 compounds of formula (Ib) wherein $R^1$ is ethyl; $R^2$ is fluoro; $R^3$ is $CH_2CH_2CH_3$; X and Y are each oxygen; n is 0; and the values of $R^4$ match those of the correspondingly numbered compounds of Table A1.

TABLE D28

Table D28 provides 352 compounds of formula (Ib) wherein $R^1$ is ethyl; $R^2$ is chloro; $R^3$ is $CH_2CH_2CH_3$; X and Y are each oxygen; n is 0; and the values of $R^4$ match those of the correspondingly numbered compounds of Table A1.

TABLE D29

Table D29 provides 352 compounds of formula (Ib) wherein $R^1$ is ethyl; $R^2$ is bromo; $R^3$ is $CH_2CH_2CH_3$; X and Y are each oxygen; n is 0; and the values of $R^4$ match those of the correspondingly numbered compounds of Table A1.

TABLE D30

Table D30 provides 352 compounds of formula (Ib) wherein $R^1$ is ethyl; $R^2$ is cyano; $R^3$ is $CH_2CH_2CH_3$; X and Y are each oxygen; n is 0; and the values of $R^4$ match those of the correspondingly numbered compounds of Table A1.

TABLE D31

Table D31 provides 352 compounds of formula (Ib) wherein $R^1$ is methyl; $R^2$ is hydrogen; $R^3$ is $CH_2CH_2CH_3$; X is oxygen; Y is sulphur; n is 0; and the values of $R^4$ match those of the correspondingly numbered compounds of Table A1.

TABLE D32

Table D32 provides 352 compounds of formula (Ib) wherein $R^1$ is methyl; $R^2$ is fluoro; $R^3$ is $CH_2CH_2CH_3$; X is oxygen; Y is sulphur; n is 0; and the values of $R^4$ match those of the correspondingly numbered compounds of Table A1.

TABLE D33

Table D33 provides 352 compounds of formula (Ib) wherein $R^1$ is methyl; $R^2$ is chloro; $R^3$ is $CH_2CH_2CH_3$; X is oxygen; Y is sulphur; n is 0; and the values of $R^4$ match those of the correspondingly numbered compounds of Table A1.

TABLE D34

Table D34 provides 352 compounds of formula (Ib) wherein $R^1$ is methyl; $R^2$ is bromo; $R^3$ is $CH_2CH_2CH_3$; X is oxygen; Y is sulphur; n is 0; and the values of $R^4$ match those of the correspondingly numbered compounds of Table A1.

TABLE D35

Table D35 provides 352 compounds of formula (Ib) wherein $R^1$ is methyl; $R^2$ is cyano; $R^3$ is $CH_2CH_2CH_3$; X is oxygen; Y is sulphur; n is 0; and the values of $R^4$ match those of the correspondingly numbered compounds of Table A1.

TABLE D36

Table D36 provides 352 compounds of formula (Ib) wherein $R^1$ is ethyl; $R^2$ is hydrogen; $R^3$ is $CH_2CH_2CH_3$; X is oxygen; Y is sulphur; n is 0, and the values of $R^4$ match those of the correspondingly numbered compounds of Table A1.

TABLE D37

Table D37 provides 352 compounds of formula (Ib) wherein $R^1$ is ethyl; $R^2$ is fluoro; $R^3$ is $CH_2CH_2CH_3$; X is oxygen; Y is sulphur; n is 0; and the values of $R^4$ match those of the correspondingly numbered compounds of Table A1.

TABLE D38

Table D38 provides 352 compounds of formula (Ib) wherein $R^1$ is ethyl; $R^2$ is chloro; $R^3$ is $CH_2CH_2CH_3$; X is oxygen; Y is sulphur; n is 0; and the values of $R^4$ match those of the correspondingly numbered compounds of Table A1.

TABLE D39

Table D39 provides 352 compounds of formula (Ib) wherein $R^1$ is ethyl; $R^2$ is bromo; $R^3$ is $CH_2CH_2CH_3$; X is oxygen; Y is sulphur; n is 0; and the values of $R^4$ match those of the correspondingly numbered compounds of Table A1.

TABLE D40

Table D40 provides 352 compounds of formula (Ib) wherein $R^1$ is ethyl; $R^2$ is cyano; $R^3$ is $CH_2CH_2CH_3$; X is oxygen; Y is sulphur; n is 0; and the values of $R^4$ match those of the correspondingly numbered compounds of Table A1.

TABLE D41

Table D41 provides 352 compounds of formula (Ib) wherein $R^1$ is methyl; $R^2$ is hydrogen; $R^3$ is $CH_2CH_2CH_3$;

X is oxygen; Y is NR$^7$; R$^7$ is hydrogen; n is 0; and the values of R$^4$ match those of the correspondingly numbered compounds of Table A1.

TABLE D42

Table D42 provides 352 compounds of formula (Ib) wherein R$^1$ is methyl; R$^2$ is fluoro; R$^3$ is CH$_2$CH$_2$CH$_3$; X is oxygen; Y is NR$^7$; R$^7$ is hydrogen; n is 0; and the values of R$^4$ match those of the correspondingly numbered compounds of Table A1.

TABLE D43

Table D43 provides 352 compounds of formula (Ib) wherein R$^1$ is methyl; R$^2$ is chloro; R$^3$ is CH$_2$CH$_2$CH$_3$; X is oxygen; Y is NR$^7$; R$^7$ is hydrogen; n is 0; and the values of R$^4$ match those of the correspondingly numbered compounds of Table A1.

TABLE D44

Table D44 provides 352 compounds of formula (Ib) wherein R$^1$ is methyl; R$^2$ is bromo; R$^3$ is CH$_2$CH$_2$CH$_3$; X is oxygen; Y is NR$^7$; R$^7$ is hydrogen; n is 0; and the values of R$^4$ match those of the correspondingly numbered compounds of Table A1.

TABLE D45

Table D45 provides 352 compounds of formula (Ib) wherein R$^1$ is methyl; R$^2$ is cyano; R$^3$ is CH$_2$CH$_2$CH$_3$; X is oxygen; Y is NR$^7$; R$^7$ is hydrogen; n is 0; and the values of R$^4$ match those of the correspondingly numbered compounds of Table A1.

TABLE D46

Table D46 provides 352 compounds of formula (Ib) wherein R$^1$ is ethyl; R$^2$ is hydrogen; R$^3$ is CH$_2$CH$_2$CH$_3$; X is oxygen; Y is NR$^7$; R$^7$ is hydrogen; n is 0; and the values of R$^4$ match those of the correspondingly numbered compounds of Table A1.

TABLE D47

Table D47 provides 352 compounds of formula (Ib) wherein R$^1$ is ethyl; R$^2$ is fluoro; R$^3$ is CH$_2$CH$_2$CH$_3$; X is oxygen; Y is NR$^7$; R$^7$ is hydrogen; n is 0; and the values of R$^4$ match those of the correspondingly numbered compounds of Table A1.

TABLE D48

Table D48 provides 352 compounds of formula (Ib) wherein R$^1$ is ethyl; R$^2$ is chloro; R$^3$ is CH$_2$CH$_2$CH$_3$; X is oxygen; Y is NR$^7$; R$^7$ is hydrogen; n is 0; and the values of R$^4$ match those of the correspondingly numbered compounds of Table A1.

TABLE D49

Table D49 provides 352 compounds of formula (Ib) wherein R$^1$ is ethyl; R$^2$ is bromo; R$^3$ is CH$_2$CH$_2$CH$_3$; X is oxygen; Y is NR$^7$; R$^7$ is hydrogen; n is 0; and the values of R$^4$ match those of the correspondingly numbered compounds of Table A1.

TABLE D50

Table D50 provides 352 compounds of formula (Ib) wherein R$^1$ is ethyl; R$^2$ is cyano; R$^3$ is CH$_2$CH$_2$CH$_3$; X is oxygen; Y is NR$^7$; R$^7$ is hydrogen; n is 0; and the values of R$^4$ match those of the correspondingly numbered compounds of Table A1.

TABLE D51

Table D51 provides 352 compounds of formula (Ib) wherein R$^1$ is methyl; R$^2$ is hydrogen; R$^3$ is CH$_2$CH$_2$CH$_3$; X is oxygen; Y is NR$^7$; R$^7$ is methyl; n is 0; and the values of R$^4$ match those of the correspondingly numbered compounds of Table A1.

TABLE D52

Table D52 provides 352 compounds of formula (Ib) wherein R$^1$ is methyl; R$^2$ is fluoro; R$^3$ is CH$_2$CH$_2$CH$_3$; X is oxygen; Y is NR$^7$; R$^7$ is methyl; n is 0; and the values of R$^4$ match those of the correspondingly numbered compounds of Table A1.

TABLE D53

Table D53 provides 352 compounds of formula (Ib) wherein R$^1$ is methyl; R$^2$ is chloro; R$^3$ is CH$_2$CH$_2$CH$_3$; X is oxygen; Y is NR$^7$; R$^7$ is methyl; n is 0; and the values of R$^4$ match those of the correspondingly numbered compounds of Table A1.

TABLE D54

Table D54 provides 352 compounds of formula (Ib) wherein R$^1$ is methyl; R$^2$ is bromo; R$^3$ is CH$_2$CH$_2$CH$_3$; X is oxygen; Y is NR$^7$; R$^7$ is methyl; n is 0; and the values of R$^4$ match those of the correspondingly numbered compounds of Table A1.

TABLE D55

Table D55 provides 352 compounds of formula (Ib) wherein R$^1$ is methyl; R$^2$ is cyano; R$^3$ is CH$_2$CH$_2$CH$_3$; X is oxygen; Y is NR$^7$; R$^7$ is methyl; n is 0; and the values of R$^4$ match those of the correspondingly numbered compounds of Table A1.

TABLE D56

Table D56 provides 352 compounds of formula (Ib) wherein R$^1$ is ethyl; R$^2$ is hydrogen; R$^3$ is CH$_2$CH$_2$CH$_3$; X is oxygen; Y is NR;$^7$R$^7$ is methyl; n is 0; and the values of R$^4$ match those of the correspondingly numbered compounds of Table A1.

TABLE D57

Table D57 provides 352 compounds of formula (Ib) wherein R$^1$ is ethyl; R$^2$ is fluoro; R$^3$ is CH$_2$CH$_2$CH$_3$; X is oxygen; Y is NR$^7$; R$^7$ is methyl; n is 0; and the values of R$^4$ those of the correspondingly numbered compounds of Table A1.

TABLE D 58

Table D58 provides 352 compounds of formula (Ib) wherein R$^1$ is ethyl; R$^2$ is chloro; R$^3$ is CH$_2$CH$_2$CH$_3$; X is oxygen; Y is NR$^7$; R$^7$ is methyl; n is 0; and the values of R$^4$ match those of the correspondingly numbered compounds of Table A1.

TABLE D59

Table D59 provides 352 compounds of formula (Ib) wherein R$^1$ is ethyl; R$^2$ is bromo; R$^3$ is CH$_2$CH$_2$CH$_3$; X is

TABLE D60

Table D60 provides 352 compounds of formula (Ib) wherein $R^1$ is ethyl; $R^2$ is cyano; $R^3$ is $CH_2CH_2CH_3$; X is oxygen; Y is $NR^7$; $R^7$ is methyl; n is 0; and the values of $R^4$ match those of the correspondingly numbered compounds of Table A1.

TABLE D61

Table D61 provides 352 compounds of formula (Ia) wherein $R^1$ is methyl; $R^2$ is hydrogen; $R^3$ is $CH_2CH_2CH_3$; X is oxygen; Y is $NR^7$; $R^7$ is methyl; n is 0; and the values of $R^4$ match those of the correspondingly numbered compounds of Table A1.

TABLE D62

Table D62 provides 352 compounds of formula (Ia) wherein $R^1$ is methyl; $R^2$ is fluoro; $R^3$ is $CH_2CH_2CH_3$; X is oxygen; Y is $NR^7$; $R^7$ is methyl; n is 0; and the values of $R^4$ match those of the correspondingly numbered compounds of Table A1.

TABLE D63

Table D63 provides 352 compounds of formula (Ia) wherein $R^1$ is methyl; $R^2$ is chloro; $R^3$ is $CH_2CH_2CH_3$; X is oxygen; Y is $NR^7$; $R^7$ is methyl; n is 0; and the values of $R^4$ match those of the correspondingly numbered compounds of Table A1.

TABLE D64

Table D64 provides 352 compounds of formula (Ia) wherein $R^1$ is methyl; $R^2$ is bromo; $R^3$ is $CH_2CH_2CH_3$; X is oxygen; Y is $NR^7$; $R^7$ is methyl; n is 0; and the values of $R^4$ match those of the correspondingly numbered compounds of Table A1.

TABLE D65

Table D65 provides 352 compounds of formula (Ib) wherein $R^1$ is methyl; $R^2$ is cyano; $R^3$ is $CH_2CH_2CH_3$; X is oxygen; Y is $NR^7$; $R^7$ is methyl; n is 0; and the values of $R^4$ match those of the correspondingly numbered compounds of Table A1.

TABLE D66

Table D66 provides 352 compounds of formula (Ia) wherein $R^1$ is ethyl; $R^2$ is hydrogen; $R^3$ is $CH_2CH_2CH_3$; X is oxygen; Y is $NR^7$; $R^7$ is methyl; n is 0; and the values of $R^4$ match those of the correspondingly numbered compounds of Table A1.

TABLE D67

Table D67 provides 352 compounds of formula (Ia) wherein $R^1$ is ethyl; $R^2$ is fluoro; $R^3$ is $CH_2CH_2CH_3$; X is oxygen; Y is $NR^7$; $R^7$ is methyl; n is 0; and the values of $R^4$ match those of the correspondingly numbered compounds of Table A1.

TABLE D68

Table D68 provides 352 compounds of formula (Ia) wherein $R^1$ is ethyl; $R^2$ is chloro; $R^3$ is $CH_2CH_2CH_3$; X is oxygen; Y is $NR^7$; $R^7$ is methyl; n is 0; and the values of $R^4$ match those of the correspondingly numbered compounds of Table A1.

TABLE D69

Table D69 provides 352 compounds of formula (Ia) wherein $R^1$ is ethyl; $R^2$ is bromo; $R^3$ is $CH_2CH_2CH_3$; X is oxygen; Y is $NR^7$; $R^7$ is methyl; n is 0; and the values of $R^4$ match those of the correspondingly numbered compounds of Table A1.

TABLE D70

Table D70 provides 352 compounds of formula (Ia) wherein $R^1$ is ethyl; $R^2$ is cyano; $R^3$ is $CH_2CH_2CH_3$; X is oxygen; Y is $NR^7$; $R^7$ is methyl; n is 0; and the values of $R^4$ match those of the correspondingly numbered compounds of Table A1.

TABLE E1

Table E1 provides 352 compounds of formula (Ia) wherein $R^1$ is methyl; $R^2$ is hydrogen; $R^3$ is $CH_2CH=CH_2$; X and Y are each oxygen; n is 0; and the values of $R^4$ match those of the correspondingly numbered compounds of Table A1.

TABLE E2

Table E2 provides 352 compounds of formula (Ia) wherein $R^1$ is methyl; $R^2$ is fluoro; is $R^3$ is $CH_2CH=CH_2$; X and Y are each oxygen; n is 0; and the values of $R^4$ match those of the correspondingly numbered compounds of Table A1.

TABLE E3

Table E3 provides 352 compounds of formula (Ia) wherein $R^1$ is methyl; $R^2$ is chloro; $R^3$ is $CH_2CH=CH_2$; X and Y are each oxygen; n is 0; and the values of $R^4$ match those of the correspondingly numbered compounds of Table A1.

TABLE E4

Table E4 provides 352 compounds of formula (Ia) wherein $R^1$ is methyl; $R^2$ is bromo; $R^3$ is $CH_2CH=CH_2$; X and Y are each oxygen; n is 0; and the values of $R^4$ match those of the correspondingly numbered compounds of Table A1.

TABLE E5

Table E 5 provides 352 compounds of formula (Ia) wherein $R^1$ is methyl; $R^2$ is cyano; $R^3$ is $CH_2CH=CH_2$; X and Y are each oxygen; n is 0; and the values of $R^4$ match those of the correspondingly numbered compounds of Table A1.

TABLE E6

Table E6 provides 352 compounds of formula (Ia) wherein $R^1$ is ethyl; $R^2$ is hydrogen; $R^3$ is $CH_2CH=CH_2$; X and Y are each oxygen; n is 0; and the values of $R^4$ match those of the correspondingly numbered compounds of Table A1.

TABLE E7

Table E7 provides 352 compounds of formula (Ia) wherein $R^1$ is ethyl; $R^2$ is fluoro; $R^3$ is $CH_2CH=CH_2$; X and Y are each oxygen; n is 0; and the values of $R^4$ match those of the correspondingly numbered compounds of Table A1.

TABLE E8

Table E8 provides 352 compounds of formula (Ia) wherein $R^1$ is ethyl; $R^2$ is chloro; $R^3$ is $CH_2CH=CH_2$; X and Y are each oxygen; n is 0; and the values of $R^4$ match those of the correspondingly numbered compounds of Table A1.

TABLE E9

Table E9 provides 352 compounds of formula (Ia) wherein $R^1$ is ethyl; $R^2$ is bromo; $R^3$ is $CH_2CH=CH_2$; X and Y are each oxygen; n is 0; and the values of $R^4$ match those of the correspondingly numbered compounds of Table A1.

TABLE E10

Table E10 provides 352 compounds of formula (Ia) wherein $R^1$ is ethyl; $R^2$ is cyano; $R^3$ is $CH_2CH=CH_2$; X and Y are each oxygen; n is 0; and the values of $R^4$ match those of the correspondingly numbered compounds of Table A1.

TABLE E11

Table E11 provides 352 compounds of formula (Ia) wherein $R^1$ is methyl; $R^2$ is hydrogen; $R^3$ is $CH_2CH=CH_2$; X is oxygen; Y is sulphur; n is 0; and the values of $R^4$ match those of the correspondingly numbered compounds of Table A1.

TABLE E12

Table E12 provides 352 compounds of formula (Ia) wherein $R^1$ is methyl; $R^2$ is fluoro; $R^3$ is $CH_2CH=CH_2$; X is oxygen; Y is sulphur; n is 0; and the values of $R^4$ match those of the correspondingly numbered compounds of Table A1.

TABLE E13

Table E13 provides 352 compounds of formula (Ia) wherein $R^1$ is methyl; $R^2$ is chloro; $R^3$ is $CH_2CH=CH_2$; X is oxygen; Y is sulphur; n is 0; and the values of $R^4$ match those of the correspondingly numbered compounds of Table A1.

TABLE E14

Table E14 provides 352 compounds of formula (Ia) wherein $R^1$ is methyl; $R^2$ is bromo; $R^3$ is $CH_2CH=CH_2$; X is oxygen; Y is sulphur; n is 0; and the values of $R^4$ match those of the correspondingly numbered compounds of Table A1.

TABLE E15

Table E15 provides 352 compounds of formula (Ia) wherein $R^1$ is methyl; $R^2$ is cyano; $R^3$ is $CH_2CH=CH_2$; X is oxygen; Y is sulphur; n is 0; and the values of $R^4$ match those of the correspondingly numbered compounds of Table A1.

TABLE E16

Table E16 provides 352 compounds of formula (Ia) wherein $R^1$ is ethyl; $R^2$ is hydrogen; $R^3$ is $CH_2CH=CH_2$; X is oxygen; Y is sulphur; n is 0; and the values of $R^4$ match those of the correspondingly numbered compounds of Table A1.

TABLE E17

Table E17 provides 352 compounds of formula (Ia) wherein $R^1$ is ethyl; $R^2$ is fluoro; $R^3$ is $CH_2CH=CH_2$; X is oxygen; Y is sulphur; n is 0; and the values of $R^4$ match those of the correspondingly numbered compounds of Table A1.

TABLE E18

Table E18 provides 352 compounds of formula (Ia) wherein $R^1$ is ethyl; $R^2$ is chloro; $R^3$ is $CH_2CH=CH_2$; X is oxygen; Y is sulphur; n is 0; and the values of $R^4$ match those of the correspondingly numbered compounds of Table A1.

TABLE E19

Table E19 provides 352 compounds of formula (Ia) wherein $R^1$ is ethyl; $R^2$ is bromo; $R^3$ is $CH_2CH=CH_2$; X is oxygen; Y is sulphur; n is 0; and the values of $R^4$ match those of the correspondingly numbered compounds of Table A1.

TABLE E20

Table E20 provides 352 compounds of formula (Ia) wherein $R^1$ is ethyl; $R^2$ is cyano; $R^3$ is $CH_2CH=CH_2$; X is oxygen; Y is sulphur; n is 0; and the values of $R^4$ match those of the correspondingly numbered compounds of Table A1.

TABLE E21

Table E21 provides 352 compounds of formula (Ib) wherein $R^1$ is methyl; $R^2$ is hydrogen; $R^3$ is $CH_2CH=CH_2$; X and Y are each oxygen; n is 0; and the values of $R^4$ match those of the correspondingly numbered compounds of Table A1.

TABLE E22

Table E22 provides 352 compounds of formula (Ib) wherein $R^1$ is methyl; $R^2$ is fluoro; $R^3$ is $CH_2CH=CH_2$; X and Y are each oxygen; n is 0; and the values of $R^4$ match those of the correspondingly numbered compounds of Table A1.

TABLE E23

Table E23 provides 352 compounds of formula (Ib) wherein $R^1$ is methyl; $R^2$ is chloro; $R^3$ is $CH_2CH=CH_2$; X and Y are each oxygen; n is 0; and the values of $R^4$ match those of the correspondingly numbered compounds of Table A1.

TABLE E24

Table E24 provides 352 compounds of formula (Ib) wherein $R^1$ is methyl; $R^2$ is bromo; $R^3$ is $CH_2CH=CH_2$; X and Y are each oxygen; n is 0; and the values of $R^4$ match those of the correspondingly numbered compounds of Table A1.

TABLE E25

Table E25 provides 352 compounds of formula (Ib) wherein $R^1$ is methyl; $R^2$ is cyano; $R^3$ is $CH_2CH=CH_2$; X and Y are each oxygen; n is 0; and the values of $R^4$ match those of the correspondingly numbered compounds of Table A1.

TABLE E26

Table E26 provides 352 compounds of formula (Ib) wherein $R^1$ is ethyl; $R^2$ is hydrogen; $R^3$ is $CH_2CH=CH_2$; X

TABLE E27

Table E27 provides 352 compounds of formula (Ib) wherein $R^1$ is ethyl; $R^2$ is fluoro; $R^3$ is $CH_2CH=CH_2$; X and Y are each oxygen; n is 0; and the values of $R^4$ match those of the correspondingly numbered compounds of Table A1.

TABLE E28

Table E28 provides 352 compounds of formula (Ib) wherein $R^1$ is ethyl; $R^2$ is chloro; $R^3$ is $CH_2CH=CH_2$; X and Y are each oxygen; n is 0; and the values of $R^4$ match those of the correspondingly numbered compounds of Table A1.

TABLE E29

Table E29 provides 352 compounds of formula (Ib) wherein $R^1$ is ethyl; $R^2$ is bromo; $R^3$ is $CH_2CH=CH_2$; X and Y are each oxygen; n is 0; and the values of $R^4$ match those of the correspondingly numbered compounds of Table A1.

TABLE E30

Table E30 provides 352 compounds of formula (Ib) wherein $R^1$ is ethyl; $R^2$ is cyano; $R^3$ is $CH_2CH=CH_2$; X and Y are each oxygen; n is 0; and the values of $R^4$ match those of the correspondingly numbered compounds of Table A1.

TABLE E31

Table E31 provides 352 compounds of formula (Ib) wherein $R^1$ is methyl; $R^2$ is hydrogen; $R^3$ is $CH_2CH=CH_2$; X is oxygen; Y is sulphur; n is 0; and the values of $R^4$ match those of the correspondingly numbered compounds of Table A1.

TABLE E32

Table E32 provides 352 compounds of formula (Ib) wherein $R^1$ is methyl; $R^2$ is fluoro; $R^3$ is $CH_2CH=CH_2$; X is oxygen; Y is sulphur; n is 0; and the values of $R^4$ match those of the correspondingly numbered compounds of Table A1.

TABLE E33

Table E33 provides 352 compounds of formula (Ib) wherein $R^1$ is methyl; $R^2$ is chloro; $R^3$ is $CH_2CH=CH_2$; X is oxygen; Y is sulphur; n is 0; and the values of $R^4$ match those of the correspondingly numbered compounds of Table A1.

TABLE E34

Table E34 provides 352 compounds of formula (Ib) wherein $R^1$ is methyl; $R^2$ is bromo; $R^3$ is $CH_2CH=CH_2$; X is oxygen; Y is sulphur; n is 0; and the values of $R^4$ match those of the correspondingly numbered compounds of Table A1.

TABLE E35

Table E35 provides 352 compounds of formula (Ib) wherein $R^1$ is methyl; $R^2$ is cyano; $R^3$ is $CH_2CH=CH_2$; X is oxygen; Y is sulphur; n is 0; and the values of $R^4$ match those of the correspondingly numbered compounds of Table A1.

TABLE E36

Table E36 provides 352 compounds of formula (Ib) wherein $R^1$ is ethyl; $R^2$ is hydrogen; $R^3$ is $CH_2CH=CH_2$; X is oxygen; Y is sulphur; n is 0; and the values of $R^4$ match those of the correspondingly numbered compounds of Table A1.

TABLE E37

Table E37 provides 352 compounds of formula (Ib) wherein $R^1$ is ethyl; $R^2$ is fluoro; $R^3$ is $CH_2CH=CH_2$; X is oxygen; Y is sulphur; n is 0; and the values of $R^4$ match those of the correspondingly numbered compounds of Table A1.

TABLE E38

Table E38 provides 352 compounds of formula (Ib) wherein $R^1$ is ethyl; $R^2$ is chloro; $R^3$ is $CH_2CH=CH_2$; X is oxygen; Y is sulphur; n is 0; and the values of $R^4$ match those of the correspondingly numbered compounds of Table A1.

TABLE E39

Table E39 provides 352 compounds of formula (Ib) wherein $R^1$ is ethyl; $R^2$ is bromo; $R^3$ is $CH_2CH=CH_2$; X is oxygen; Y is sulphur; n is 0; and the values of $R^4$ match those of the correspondingly numbered compounds of Table A1.

TABLE E40

Table E40 provides 352 compounds of formula (Ib) wherein $R^1$ is ethyl; $R^2$ is cyano; $R^3$ is $CH_2CH=CH_2$; X is oxygen; Y is sulphur; n is 0; and the values of $R^4$ match those of the correspondingly numbered compounds of Table A1.

TABLE E41

Table E41 provides 352 compounds of formula (Ib) wherein $R^1$ is methyl; $R^2$ is hydrogen; $R^3$ is $CH_2CH=CH_2$; X is oxygen; Y is $NR^7$; $R^7$ is hydrogen; n is 0; and the values of $R^4$ match those of the correspondingly numbered compounds of Table A1.

TABLE E42

Table E42 provides 352 compounds of formula (Ib) wherein $R^1$ is methyl; $R^2$ is fluoro; $R^3$ is $CH_2CH=CH_2$; X is oxygen; Y is $NR^7$; $R^7$ is hydrogen; n is 0; and the values of $R^4$ match those of the correspondingly numbered compounds of Table A1.

TABLE E43

Table E43 provides 352 compounds of formula (Ib) wherein $R^1$ is methyl; $R^2$ is chloro; $R^3$ is $CH_2CH=CH_2$; X is oxygen; Y is $NR^7$; $R^7$ is hydrogen; n is 0; and the values of $R^4$ match those of the correspondingly numbered compounds of Table A1.

TABLE E44

Table E44 provides 352 compounds of formula (Ib) wherein $R^1$ is methyl; $R^2$ is bromo; $R^3$ is $CH_2CH=CH_2$; X is oxygen; Y is $NR^7$; $R^7$ is hydrogen; n is 0; and the values of $R^4$ match those of the correspondingly numbered compounds of Table A1.

TABLE E45

Table E45 provides 352 compounds of formula (Ib) wherein $R^1$ is methyl; $R^2$ is cyano; $R^3$ is $CH_2CH=CH_2$; X is oxygen; Y is NR$^7$; R$^7$ is hydrogen; n is 0; and the values of R$^4$ match those of the correspondingly numbered compounds of Table A1.

TABLE E46

Table E46 provides 352 compounds of formula (Ib) wherein R$^1$ is ethyl; R$^2$ is hydrogen; R$^3$ is CH$_2$CH=CH$_2$; X is oxygen; Y is NR$^7$; R$^7$ is hydrogen; n is 0; and the values of R$^4$ match those of the correspondingly numbered compounds of Table A1.

TABLE E47

Table E47 provides 352 compounds of formula (Ib) wherein R$^1$ is ethyl; R$^2$ is fluoro; R$^3$ is CH$_2$CH=CH$_2$; X is oxygen; Y is NR$^7$; R$^7$ is hydrogen; n is 0; and the values of R$^4$ match those of the correspondingly numbered compounds of Table A1.

TABLE E48

Table E48 provides 352 compounds of formula (Ib) wherein R$^1$ is ethyl; R$^2$ is chloro; R$^3$ is CH$_2$CH=CH$_2$; X is oxygen; Y is NR$^7$; R$^7$ is hydrogen; n is 0; and the values of R$^4$ match those of the correspondingly numbered compounds of Table A1.

TABLE E9

Table E49 provides 352 compounds of formula (Ib) wherein R$^1$ is ethyl; R$^2$ is bromo; R$^3$ is CH$_2$CH=CH$_2$; X is oxygen; Y is NR$^7$; R$^7$ is hydrogen; n is 0; and the values of R$^4$ match those of the correspondingly numbered compounds of Table A1.

TABLE E50

Table E50 provides 352 compounds of formula (Ib) wherein R$^1$ is ethyl; R$^2$ is cyano; R$^3$ is CH$_2$CH=CH$_2$; X is oxygen; Y is NR$^7$; R$^7$ is hydrogen; n is 0; and the values of R$^4$ match those of the correspondingly numbered compounds of Table A1.

TABLE E51

Table E51 provides 352 compounds of formula (Ib) wherein R$^1$ is methyl; R$^2$ is hydrogen; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E52

Table E52 provides 352 compounds of formula (Ib) wherein R$^1$ is methyl; R$^2$ is fluoro; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E53

Table E53 provides 352 compounds of formula (Ib) wherein R$^1$ is methyl; R$^2$ is chloro; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E54

Table E54 provides 352 compounds of formula (Ib) wherein R$^1$ is methyl; R$^2$ is bromo; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E55

Table E55 provides 352 compounds of formula (Ib) wherein R$^1$ is methyl; R$^2$ is cyano; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E56

Table E56 provides 352 compounds of formula (Ib) wherein R$^1$ is ethyl; R$^2$ is hydrogen; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E57

Table E57 provides 352 compounds of formula (Ib) wherein R$^1$ is ethyl; R$^2$ is fluoro; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E58

Table E58 provides 352 compounds of formula (Ib) wherein R$^1$ is ethyl; R$^2$ is chloro; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E59

Table E59 provides 352 compounds of formula (Ib) wherein R$^1$ is ethyl; R$^2$ is bromo; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E60

Table E60 provides 352 compounds of formula (Ib) wherein R$^1$ is ethyl; R$^2$ is cyano; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E61

Table E61 provides 352 compounds of formula (Ia) wherein R$^1$ is methyl; R$^2$ is hydrogen; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E62

Table E62 provides 352 compounds of formula (Ia) wherein R$^1$ is methyl; R$^2$ is fluoro; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E63

Table E63 provides 352 compounds of formula (Ia) wherein R$^1$ is methyl; R$^2$ is chloro; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E64

Table E64 provides 352 compounds of formula (Ia) wherein R$^1$ is methyl; R$^2$ is bromo; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E65

Table E65 provides 352 compounds of formula (Ib) wherein R$^1$ is methyl; R$^2$ is cyano; R$^3$ is CH$_2$CH=CH$_2$; X is oxygen; Y is NkR$^7$; R$^7$ is methyl; n is 0; and the values of R$^4$ match those of the correspondingly numbered compounds of Table A1.

TABLE E66

Table E66 provides 352 compounds of formula (Ia) wherein R$^1$ is ethyl; R$^2$ is hydrogen; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E67

Table E67 provides 352 compounds of formula (Ia) wherein R$^1$ is ethyl; R$^2$ is fluoro; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E68

Table E68 provides 352 compounds of formula (Ia) wherein R$^1$ is ethyl; R$^2$ is chloro; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE E69

Table E69 provides 352 compounds of formula (Ia) wherein R$^1$ is ethyl; R$^2$ is bromo; R$^3$ is CH$_2$CH=CH$_2$; X is oxygen; Y is NR$^7$; R$^7$ is methyl; n is 0; and the values of R$^4$ match is those of the correspondingly numbered compounds of Table A1.

TABLE E70

Table E70 provides 352 compounds of formula (Ia) wherein R$^1$ is ethyl; R$^2$ is cyano; R$^3$ is CH$_2$CH=CH$_2$; X is oxygen; Y is NR$^7$; R$^7$ is methyl; n is 0; and the values of R$^4$ match those of the correspondingly numbered compounds of Table A1.

TABLE F1

Table F1 provides 352 compounds of formula (Ia) wherein R$^1$ is methyl; R$^2$ is hydrogen; R$^3$ is CH$_2$C.CH; X and Y are each oxygen; n is 0; and the values of R$^4$ match hose of the correspondingly numbered compounds of Table A1.

TABLE F2

Table F2 provides 352 compounds of formula (Ia) wherein R$^1$ is methyl; R$^2$ is fluoro; R$^3$ is CH$_2$C.CH; X and Y are each oxygen; n is 0; and the values of R$^4$ match those of the correspondingly numbered compounds of Table A1.

TABLE F3

Table F3 provides 352 compounds of formula (Ia) wherein R$^1$ is methyl; R$^2$ is chloro; R$^3$ is CH$_2$C.CH; X and Y are each oxygen; n is 0; and the values of R$^4$ match those of the correspondingly numbered compounds of Table A1.

TABLE F4

Table F4 provides 352 compounds of formula (Ia) wherein R$^1$ is methyl; R$^2$ is bromo; R$^3$ is CH$_2$C.CH; X and Y are each oxygen; n is 0; and the values of R$^4$ match those of the correspondingly numbered compounds of Table A1.

TABLE F5

Table F5 provides 352 compounds of formula (Ia) wherein R$^1$ is methyl; R$^2$ is cyano; R$^3$ is CH$_2$C.CH; X and Y are each oxygen; n is 0; and the values of R$^4$ match those of the correspondingly numbered compounds of Table A1.

TABLE F6

Table F6 provides 352 compounds of formula (Ia) wherein R$^1$ is ethyl; R$^2$ is hydrogen; R$^3$ is CH$_2$C.CH; X and Y are each oxygen; n is 0; and the values of R$^4$ match those of the correspondingly numbered compounds of Table A1.

TABLE F7

Table F7 provides 352 compounds of formula (Ia) wherein R$^1$ is ethyl; R$^2$ is fluoro; R$^3$ is CH$_2$C.CH; X and Y are each oxygen; n is 0; and the values of R$^4$ match those of the correspondingly numbered compounds of Table A1.

TABLE F8

Table F8 provides 352 compounds of formula (Ia) wherein R$^1$ is ethyl; R$^2$ is chloro; R$^3$ is CH$_2$C.CH; X and Y are each oxygen; n is 0; and the values of R$^4$ match those of the correspondingly numbered compounds of Table A1.

TABLE F9

Table F9 provides 352 compounds of formula (I) wherein R$^1$ is ethyl; R$^2$ is bromo; R$^3$ is CH$_2$C.CH; X and Y are each oxygen; n is 0, and the values of R$^4$ match those of the correspondingly numbered compounds of Table A1.

TABLE F10

Table F10 provides 352 compounds of formula (Ia) wherein R$^1$ is ethyl; R$^2$ is cyano; R$^3$ is CH$_2$C.CH; X and Y are each oxygen; n is 0; and the values of R$^4$ match those of the correspondingly numbered compounds of Table A1.

TABLE F11

Table F11 provides 352 compounds of formula (Ia) wherein R$^1$ is methyl; R$^2$ is hydrogen; R$^3$ is CH$_2$C.CH; X is oxygen; Y is sulphur; n is 0; and the values of R$^4$ match those of the correspondingly numbered compounds of Table A1.

TABLE F12

Table F12 provides 352 compounds of formula (Ia) wherein R$^1$ is methyl; R$^2$ is fluoro; R$^3$ is CH$_2$C.CH; X is oxygen; Y is sulphur; n is 0; and the values of R$^4$ match those of the correspondingly numbered compounds of Table A1.

TABLE F13

Table F13 provides 352 compounds of formula (Ia) wherein $R^1$ is methyl; $R^2$ is chloro; $R^3$ is $CH_2C.CH$; X is oxygen; Y is sulphur; n is 0; and the values of $R^4$ match those of the correspondingly numbered compounds of Table A1.

TABLE F14

Table F14 provides 352 compounds of formula (Ia) wherein $R^1$ is methyl; $R^2$ is bromo; $R^3$ is $CH_2C.CH$; X is oxygen; Y is sulphur; n is 0; and the values of $R^4$ match those of the correspondingly numbered compounds of Table A1.

TABLE F15

Table F15 provides 352 compounds of formula (Ia) wherein $R^1$ is methyl; $R^2$ is cyano; $R^3$ is $CH_2C.CH$; X is oxygen; Y is sulphur; n is 0, and the values of $R^4$ match those of the correspondingly numbered compounds of Table A1.

TABLE F16

Table F16 provides 352 compounds of formula (Ia) wherein $R^1$ is ethyl; $R^2$ is hydrogen; $R^3$ is $CH_2C.CH$; X is oxygen; Y is sulphur; n is 0; and the values of $R^4$ match those of the correspondingly numbered compounds of Table A1.

TABLE F17

Table F17 provides 352 compounds of formula (Ia) wherein $R^1$ is ethyl; $R^2$ is fluoro; $R^3$ is $CH_2C.CH$; X is oxygen; Y is sulphur; n is 0; and the values of $R^4$ match those of the correspondingly numbered compounds of Table A1.

TABLE F18

Table F18 provides 352 compounds of formula (Ia) wherein $R^1$ is ethyl; $R^2$ is chloro; $R^3$ is $CH_2C.CH$; X is oxygen; Y is sulphur; n is 0; and the values of $R^4$ match those of the correspondingly numbered compounds of Table A1.

TABLE F19

Table F19 provides 352 compounds of formula (Ia) wherein $R^1$ is ethyl; $R^2$ is bromo; $R^3$ is $CH_2C.CH$; X is oxygen; Y is sulphur; n is 0; and the values of $R^4$ match those of the correspondingly numbered compounds of Table A1.

TABLE F20

Table F20 provides 352 compounds of formula (Ia) wherein $R^1$ is ethyl; $R^2$ is cyano; $R^3$ is $CH_2C.CH$; X is oxygen; Y is sulphur; n is 0; and the values of $R^4$ match those of the correspondingly numbered compounds of Table A1.

TABLE F21

Table F21 provides 352 compounds of formula (Ib) wherein $R^1$ is methyl; $R^2$ is hydrogen; $R^3$ is $CH_2C.CH$; X and Y are each oxygen; n is 0; and the values of $R^4$ match those of the correspondingly numbered compounds of Table A1.

TABLE F22

Table F22 provides 352 compounds of formula (Ib) wherein $R^1$ is methyl; $R^2$ is fluoro; $R^3$ is $CH_2C.CH$; X and Y are each oxygen; n is 0; and the values of $R^4$ match those of the correspondingly numbered compounds of Table A1.

TABLE F23

Table F23 provides 352 compounds of formula (Ib) wherein $R^1$ is methyl; $R^2$ is chloro; $R^3$ is $CH_2C.CH$; X and Y are each oxygen; n is 0; and the values of $R^4$ match those of the correspondingly numbered compounds of Table A1.

TABLE F24

Table F24 provides 352 compounds of formula (Ib) wherein $R^1$ is methyl; $R^2$ is bromo; $R^3$ is $CH_2C.CH$; X and Y are each oxygen; n is 0; and the values of $R^4$ match those of the correspondingly numbered compounds of Table A1.

TABLE F25

Table F25 provides 352 compounds of formula (Ib) wherein $R^1$ is methyl; $R^2$ is cyano; $R^3$ is $CH_2C.CH$; X and Y are each oxygen; n is 0; and the values of $R^4$ match those of the correspondingly numbered compounds of Table A1.

TABLE F26

Table F26 provides 352 compounds of formula (Ib) wherein $R^1$ is ethyl; $R^2$ is hydrogen; $R^3$ is $CH_2C.CH$; X and Y are each oxygen; n is 0; and the values of $R^4$ match those of the correspondingly numbered compounds of Table A1.

TABLE F27

Table F27 provides 352 compounds of formula (Ib) wherein $R^1$ is ethyl; $R^2$ is fluoro; $R^3$ is $CH_2C.CH$; X and Y are each oxygen; n is 0; and the values of $R^4$ match those of the correspondingly numbered compounds of Table A1.

TABLE F28

Table F28 provides 352 compounds of formula (Ib) wherein $R^1$ is ethyl; $R^2$ is chloro; $R^3$ is $CH_2C.CH$; X and Y are each oxygen; n is 0; and the values of $R^4$ match those of the correspondingly numbered compounds of Table A1.

TABLE F29

Table F29 provides 352 compounds of formula (Ib) wherein $R^1$ is ethyl; $R^2$ is bromo; $R^3$ is $CH_2C.CH$; X and Y are each oxygen; n is 0; and the values of $R^4$ match those of the correspondingly numbered compounds of Table A1.

TABLE F30

Table F30 provides 352 compounds of formula (b) wherein $R^1$ is ethyl; $R^2$ is cyano; $R^3$ is $CH_2C.CH$; X and Y are each oxygen; n is 0; and the values of $R^4$ match those of the correspondingly numbered compounds of Table A1.

TABLE F31

Table F31 provides 352 compounds of formula (Ib) wherein $R^1$ is methyl; $R^2$ is hydrogen; $R^3$ is $CH_2C.CH$; X is oxygen; Y is sulphur; n is 0; and the values of $R^4$ match those of the correspondingly numbered compounds of Table A1.

TABLE F32

Table F32 provides 352 compounds of formula (Ib) wherein $R^1$ is methyl; $R^2$ is fluoro; $R^3$ is $CH_2C.CH$; X is oxygen; Y is sulphur; n is 0; and the values of $R^4$ match those of the correspondingly numbered compounds of Table A1.

TABLE F33

Table F33 provides 352 compounds of formula (Ib) wherein $R^1$ is methyl; $R^2$ is chloro; $R^3$ is $CH_2.C.CH$; X is oxygen; Y is sulphur; n is 0; and the values of $R^4$ match those of the correspondingly numbered compounds of Table A1.

TABLE F34

Table F34 provides 352 compounds of formula (Ib) wherein $R^1$ is methyl; $R^2$ is bromo; $R^3$ is $CH_2.C.CH$; X is oxygen; Y is sulphur; n is 0; and the values of $R^4$ match those of the correspondingly numbered compounds of Table A1.

TABLE F35

Table F35 provides 352 compounds of formula (Ib) wherein $R^1$ is methyl; $R^2$ is cyano; $R^3$ is $CH_2.C.CH$; X is oxygen; Y is sulphur; n is 0; and the values of $R^4$ match those of the correspondingly numbered compounds of Table A1.

TABLE F36

Table F36 provides 352 compounds of formula (Ib) wherein $R^1$ is ethyl; $R^2$ is hydrogen; $R^3$ is $CH_2.C.CH$; X is oxygen; Y is sulphur; n is 0; and the values of $R^4$ match those of the correspondingly numbered compounds of Table A1.

TABLE F37

Table F37 provides 352 compounds of formula (Ib) wherein $R^1$ is ethyl; $R^2$ is fluoro; $R^3$ is $CH_2.C.CH$; X is oxygen; Y is sulphur; n is 0; and the values of $R^4$ match those of the correspondingly numbered compounds of Table A1.

TABLE F38

Table F38 provides 352 compounds of formula (Ib) wherein $R^1$ is ethyl; $R^2$ is chloro; $R^3$ is $CH_2.C.CH$; X is oxygen; Y is sulphur; n is 0; and the values of $R^4$ match those of the correspondingly numbered compounds of Table A1.

TABLE F39

Table F39 provides 352 compounds of formula (Ib) wherein $R^1$ is ethyl; $R^2$ is bromo; $R^3$ is $CH_2.C.CH$; X is oxygen; Y is sulphur; n is 0; and the values of $R^4$ match those of the correspondingly numbered compounds of Table A1.

TABLE F40

Table F40 provides 352 compounds of formula (Ib) wherein $R^1$ is ethyl; $R^2$ is cyano; $R^3$ is $CH_2.C.CH$; X is oxygen; Y is sulphur; n is 0; and the values of $R^4$ match those of the correspondingly numbered compounds of Table A1.

TABLE F41

Table F41 provides 352 compounds of formula (Ib) wherein $R^1$ is methyl; $R^2$ is hydrogen; $R^3$ is $CH_2.C.CH$; X is oxygen; Y is $NR^7$; $R^7$ is hydrogen; n is 0; and the values of $R^4$ match those of the correspondingly numbered compounds of Table A1.

TABLE F42

Table F42 provides 352 compounds of formula (Ib) wherein $R^1$ is methyl; $R^2$ is fluoro; $R^3$ is $CH_2.C.CH$; X is oxygen; Y is $NR^7$; $R^7$ is hydrogen; n is 0; and the values of $R^4$ match those of the correspondingly numbered compounds of Table A1.

TABLE F43

Table F43 provides 352 compounds of formula (Ib) wherein $R^1$ is methyl; $R^2$ is chloro; $R^3$ is $CH_2.C.CH$; X is oxygen; Y is $NR^7$; $R^7$ is hydrogen; n is 0; and the values of $R^4$ match those of the correspondingly numbered compounds of Table A1.

TABLE F44

Table F44 provides 352 compounds of formula (Ib) wherein $R^1$ is methyl; $R^2$ is bromo; $R^3$ is $CH_2.C.CH$; X is oxygen; Y is $NR^7$; $R^7$ is hydrogen; n is 0; and the values of $R^4$ match those of the correspondingly numbered compounds of Table A1.

TABLE F45

Table F45 provides 352 compounds of formula (Ib) wherein $R^1$ is methyl; $R^2$ is cyano; $R^3$ is $CH_2.C.CH$; X is oxygen; Y is $NR^7$; $R^7$ is hydrogen; n is 0; and the values of $R^4$ match those of the correspondingly numbered compounds of Table A1.

TABLE F46

Table F46 provides 352 compounds of formula (Ib) wherein $R^1$ is ethyl; $R^2$ is hydrogen; $R^3$ is $CH_2.C.CH$; X is oxygen; Y is $NR^7$; $R^7$ is hydrogen; n is 0; and the values of $R^4$ match those of the correspondingly numbered compounds of Table A1.

TABLE F47

Table F47 provides 352 compounds of formula (Ib) wherein $R^1$ is ethyl; $R^2$ is fluoro; $R^3$ is $CH_2.C.CH$; X is oxygen; Y is $NR^7$; $R^7$ is hydrogen; n is 0; and the values of $R^4$ match those of the correspondingly numbered compounds of Table A1.

TABLE F48

Table F48 provides 352 compounds of formula (Ib) wherein $R^1$ is ethyl, $R^2$ is chloro; $R^3$ is $CH_2.C.CH$; X is oxygen; Y is $NR^7$; $R^7$ is hydrogen; n is 0; and the values of $R^4$ match those of the correspondingly numbered compounds of Table A1.

TABLE F49

Table F49 provides 352 compounds of formula (Ib) wherein $R^1$ is ethyl; $R^2$ is bromo; $R^3$ is $CH_2.C.CH$; X is oxygen; Y is $NR^7$; $R^7$ is hydrogen; n is 0; and the values of $R^4$ match those of the correspondingly numbered compounds of Table A1.

TABLE F50

Table F50 provides 352 compounds of formula (Ib) wherein $R^1$ is ethyl; $R^2$ is cyano; $R^3$ is $CH_2.C.CH$; X is oxygen; Y is $NR^7$; $R^7$ is hydrogen; n is 0; and the values of $R^4$ match those of the correspondingly numbered compounds of Table A1.

TABLE F51

Table F51 provides 352 compounds of formula (Ib) wherein $R^1$ is methyl; $R^2$ is hydrogen; $R^3$ is $CH_2.C.CH$; X is

TABLE F52

Table F52 provides 352 compounds of formula (Ib) wherein $R^1$ is methyl; $R^2$ is fluoro; $R^3$ is $CH_2C.CH$; X is oxygen; Y is $NR^7$; $R^7$ is methyl; n is 0; and the values of $R^4$ match those of the correspondingly numbered compounds of Table A1.

TABLE F53

Table F53 provides 352 compounds of formula (Ib) wherein $R^1$ is methyl; $R^2$ is chloro; $R^3$ is $CH_2C.CH$; X is oxygen; Y is $NR^7$; $R^7$ is methyl; n is 0; and the values of $R^4$ match those of the correspondingly numbered compounds of Table A1.

TABLE F54

Table F54 provides 352 compounds of formula (Ib) wherein $R^1$ is methyl; $R^2$ is bromo; $R^3$ is $CH_2C.CH$; X is oxygen; Y is $NR^7$; $R^7$ is methyl; n is 0; and the values of $R^4$ match those of the correspondingly numbered compounds of Table A1.

TABLE F55

Table F55 provides 352 compounds of formula (Ib) wherein $R^1$ is methyl; $R^2$ is cyano; $R^3$ is $CH_2C.CH$; X is oxygen; Y is $NR^7$; $R^7$ is methyl; n is 0; and the values of $R^4$ match those of the correspondingly numbered compounds of Table A1.

TABLE F56

Table F56 provides 352 compounds of formula (Ib) wherein $R^1$ is ethyl; $R^2$ is hydrogen; $R^3$ is $CH_2C.CH$; X is oxygen; Y is $NR^7$; $R^7$ is methyl; n is 0; and the values of $R^4$ match those of the correspondingly numbered compounds of Table A1.

TABLE F57

Table F57 provides 352 compounds of formula (Ib) wherein $R^1$ is ethyl; $R^2$ is fluoro; $R^3$ is $CH_2C.CH$; X is oxygen; Y is $NR^7$; $R^7$ is methyl; n is 0; and the values of $R^4$ match those of the correspondingly numbered compounds of Table A1.

TABLE F58

Table F58 provides 352 compounds of formula (Ib) wherein $R^1$ is ethyl; $R^2$ is chloro; $R^3$ is $CH_2C.CH$; X is oxygen; Y is $NR^7$; $R^7$ is methyl; n is 0; and the values of $R^4$ match those of the correspondingly numbered compounds of Table A1.

TABLE F59

Table F59 provides 352 compounds of formula (Ib) wherein $R^1$ is ethyl; $R^2$ is bromo; $R^3$ is $CH_2C.CH$; X is oxygen; Y is $NR^7$; $R^7$ is methyl; n is 0; and the values of $R^4$ match those of the correspondingly numbered compounds of Table A1.

TABLE F60

Table F60 provides 352 compounds of formula (Ib) wherein $R^1$ is ethyl; $R^2$ is cyano; $R^3$ is $CH_2C.CH$; X is oxygen; Y is $NR^7$; $R^7$ is methyl; n is 0; and the values of $R^4$ match those of the correspondingly numbered compounds of table A1.

TABLE F61

Table F61 provides 352 compounds of formula (Ia) wherein $R^1$ is methyl; $R^2$ is hydrogen; $R^3$ is $CH_2C.CH$; X is oxygen; Y is $NR^7$; $R^7$ is methyl; n is 0; and the values of $R^4$ match those of the correspondingly numbered compounds of Table A1.

TABLE F62

Table F62 provides 352 compounds of formula (Ia) wherein $R^1$ is methyl; $R^2$ is fluoro; $R^3$ is $CH_2C.CH$; X is oxygen; Y is $NR^7$; $R^7$ is methyl; n is 0; and the values of $R^4$ match those of the correspondingly numbered compounds of Table A1.

TABLE F63

Table F63 provides 352 compounds of formula (Ia) wherein $R^1$ is methyl; 2 is chloro; $R^3$ is $CH_2C.CH$; X is oxygen; Y is $NR^7$; $R^7$ is methyl; n is 0; and the values of $R^4$ match those of the correspondingly numbered compounds of Table A1.

TABLE F64

Table F64 provides 352 compounds of formula (Ia) wherein $R^1$ is methyl; $R^2$ is bromo; $R^3$ is $CH_2C.CH$; X is oxygen; Y is $NR^7$; $R^7$ is methyl; n is 0; and the values of $R^4$ match those of the correspondingly numbered compounds of Table A1.

TABLE F65

Table F65 provides 352 compounds of formula (Ib) wherein $R^1$ is methyl; $R^2$ is cyano; $R^3$ is $CH_2C.CH$; X is oxygen; Y is $NR^7$; $R^7$ is methyl; n is 0; and the values of $R^4$ match those of the correspondingly numbered compounds of Table A1.

TABLE F66

Table F66 provides 352 compounds of formula (Ia) wherein $R^1$ is ethyl; $R^2$ is hydrogen; $R^3$ is $CH_2C.CH$; X is oxygen; Y is $NR^7$; $R^7$ is methyl; n is 0; and the values of $R^4$ match those of the correspondingly numbered compounds of Table A1.

TABLE F67

Table F67 provides 352 compounds of formula (Ia) wherein $R^1$ is ethyl; $R^2$ is fluoro; $R^3$ is $CH_2C.CH$; X is oxygen; Y is $NR^7$; $R^7$ is methyl; n is 0; and the values of $R^4$ match those of the correspondingly numbered compounds of Table A1.

TABLE F68

Table F68 provides 352 compounds of formula (Ia) wherein $R^1$ is ethyl; $R^2$ is chloro; $R^3$ is $CH_2C.CH$; X is oxygen; Y is $NR^7$; $R^7$ is methyl; n is 0; and the value of $R^4$ match those of the correspondingly numbered compounds of Table A1.

TABLE F69

Table F69 provides 352 compounds of formula (Ia) wherein $R^1$ is ethyl; $R^2$ is bromo; $R^3$ is $CH_2C.CH$; X is oxygen; Y is NR$^7$; R$^7$ is methyl; n is 0; and the values of R$^4$ match those of the correspondingly numbered compounds of Table A1.

TABLE F70

Table F70 provides 352 compounds of formula (Ia) wherein R$^1$ is ethyl; R$^2$ is cyano; R$^3$ is CH$_2$C.CH; X is oxygen; Y is NR$^7$; R$^7$ is methyl; n is 0; and the values of R$^4$ match those of the correspondingly numbered compounds of Table A1.

TABLE G1

Table G1 provides 352 compounds of formula (Ia) wherein R$^1$ is methyl; R$^2$ is hydrogen; R$^3$ is CH$_2$CN; X and Y are each oxygen; n is 0; and the values of R$^4$ match those of the correspondingly numbered compounds of Table A1.

TABLE G2

Table G2 provides 352 compounds of formula (Ia) wherein R$^1$ is methyl; R$^2$ is fluoro; R$^3$ is CH$_2$CN; X and Y are each oxygen; n is 0; and the values of R$^4$ match those of the correspondingly numbered compounds of Table A1.

TABLE G3

Table G3 provides 352 compounds of formula (Ia) wherein R$^1$ is methyl; R$^2$ is chloro; R$^3$ is CH$_2$CN; X and Y are each oxygen; n is 0; and the values of R$^4$ match those of the correspondingly numbered compounds of Table A1.

TABLE G4

Table G4 provides 352 compounds of formula (Ia) wherein R$^1$ is methyl; R$^2$ is bromo; R$^3$ is CH$_2$CN; X and Y are each oxygen; n is 0; and the values of R$^4$ match those of the correspondingly numbered compounds of Table A1.

TABLE G5

Table G5 provides 352 compounds of formula (Ia) wherein R$^1$ is methyl; R$^2$ is cyano; R$^3$ is CH$_2$CN; X and Y are each oxygen; n is 0; and the values of R$^4$ match those of the correspondingly numbered compounds of Table A1.

TABLE G6

Table G6 provides 352 compounds of formula (Ia) wherein R$^1$ is ethyl; R$^2$ is hydrogen; R$^3$ is CH$_2$CN; X and Y are each oxygen; n is 0; and the values of R$^4$ match those of the correspondingly numbered compounds of Table A1.

TABLE G7

Table G7 provides 352 compounds of formula (Ia) wherein R$^1$ is ethyl; R$^2$ is fluoro; R$^3$ is CH$_2$CN; X and Y are each oxygen; n is 0; and the values of R$^4$ match those of the correspondingly numbered compounds of Table A1.

TABLE G8

Table G8 provides 352 compounds of formula (Ia) wherein R$^1$ is ethyl; R$^2$ is chloro; R$^3$ is CH$_2$CN; X and Y are each oxygen; n is 0; and the values of R$^4$ match those of the correspondingly numbered compounds of Table A1.

TABLE G9

Table G9 provides 352 compounds of formula (Ia) wherein R$^1$ is ethyl; R$^2$ is bromo; R$^3$ is CH$_2$CN; X and Y are each oxygen; n is 0; and the values of R$^4$ match those of the correspondingly numbered compounds of Table A1.

TABLE G10

Table G10 provides 352 compounds of formula (Ia) wherein R$^1$ is ethyl; R$^2$ is cyano; R$^3$ is CH$_2$CN; X and Y are each oxygen; n is 0; and the values of R$^4$ match those of the correspondingly numbered compounds of Table A1.

TABLE G11

Table G11 provides 352 compounds of formula (Ia) wherein R$^1$ is methyl; R$^2$ is hydrogen; R$^3$ is CH$_2$CN; X is oxygen; Y is sulphur; n is 0; and the values of R$^4$ match those of the correspondingly numbered compounds of Table A1.

TABLE G12

Table G12 provides 352 compounds of formula (Ia) wherein R$^1$ is methyl; R$^2$ is fluoro; R$^3$ is CH$_2$CN; X is oxygen; Y is sulphur; n is 0; and the values of R$^4$ match those of the correspondingly numbered compounds of Table A1.

TABLE G13

Table G13 provides 352 compounds of formula (Ia) wherein R$^1$ is methyl; R$^2$ is chloro; R$^3$ is CH$_2$CN; X is oxygen; Y is sulphur; n is 0; and the values of R$^4$ match those of the correspondingly numbered compounds of Table A1.

TABLE G14

Table G14 provides 352 compounds of formula (Ia) wherein R$^1$ is methyl; R$^2$ is bromo; R$^3$ is CH$_2$CN; X is oxygen; Y is sulphur; n is 0; and the values of R$^4$ match those of the correspondingly numbered compounds of Table A1.

TABLE G15

Table G15 provides 352 compounds of formula (Ia) wherein R$^1$ is methyl; R$^2$ is cyano; R$^3$ is CH$_2$CN; X is oxygen; Y is sulphur; n is 0; and the values of R$^4$ match those of the correspondingly numbered compounds of Table A1.

TABLE G16

Table G16 provides 352 compounds of formula (Ia) wherein R$^1$ is ethyl; R$^2$ is hydrogen; R$^3$ is CH$_2$CN; X is oxygen; Y is sulphur; n is 0; and the values of R$^4$ match those of the correspondingly numbered compounds of Table A1.

TABLE G17

Table G17 provides 352 compounds of formula (Ia) wherein R$^1$ is ethyl; R$^2$ is fluoro; R$^3$ is CH$_2$CN; X is oxygen; Y is sulphur; n is 0; and the values of R$^4$ match those of the correspondingly numbered compounds of Table A1.

TABLE G18

Table G18 provides 352 compounds of formula (Ia) wherein R$^1$ is ethyl; R$^2$ is chloro; R$^3$ is CH$_2$CN; X is oxygen; Y is sulphur; n is 0; and the values of R$^4$ match those of the correspondingly numbered compounds of Table A1.

TABLE G19

Table G19 provides 352 compounds of formula (Ia) wherein R$^1$ is ethyl; R$^2$ is bromo; R$^3$ is CH$_2$CN; X is oxygen; Y is sulphur; n is 0; and the values of $R^4$ match those of the correspondingly numbered compounds of Table A1.

TABLE G20

Table G20 provides 352 compounds of formula (Ia) wherein $R^1$ is ethyl; $R^2$ is cyano; $R^3$ is $CH_2CN$; X is oxygen; Y is sulphur; n is 0; and the values of $R^4$ match those of the correspondingly numbered compounds of Table A1.

TABLE G21

Table G21 provides 352 compounds of formula (Ib) wherein $R^1$ is methyl; $R^2$ is hydrogen; $R^3$ is $CH_2CN$; X and Y are each oxygen; n is 0; and the values of $R^4$ match those of the correspondingly numbered compounds of Table A1.

TABLE G22

Table G22 provides 352 compounds of formula (Ib) wherein $R^1$ is methyl; $R^2$ is fluoro; $R^3$ is $CH_2CN$; X and Y are each oxygen; n is 0; and the values of $R^4$ match those of the correspondingly numbered compounds of Table A1.

TABLE G23

Table G23 provides 352 compounds of formula (Ib) wherein $R^1$ is methyl; $R^2$ is chloro; $R^3$ is $CH_2CN$; X and Y are each oxygen; n is 0; and the values of $R^4$ match those of the correspondingly numbered compounds of Table A1.

TABLE G24

Table G24 provides 352 compounds of formula (Ib) wherein $R^1$ is methyl; $R^2$ is bromo; $R^3$ is $CH_2CN$; X and Y are each oxygen; n is 0; and the values of $R^4$ match those of the correspondingly numbered compounds of Table A1.

TABLE G25

Table G25 provides 352 compounds of formula (Ib) wherein $R^1$ is methyl; $R^2$ is cyano; $R^3$ is $CH_2CN$; X and Y are each oxygen; n is 0; and the values of $R^4$ match those of the correspondingly numbered compounds of Table A1.

TABLE G26

Table G26 provides 352 compounds of formula (Ib) wherein $R^1$ is ethyl; $R^2$ is hydrogen; $R^3$ is $CH_2CN$; X and Y are each oxygen; n is 0; and the values of $R^4$ match those of the correspondingly numbered compounds of Table A1.

TABLE G27

Table G27 provides 352 compounds of formula (Ib) wherein $R^1$ is ethyl; $R^2$ is fluoro; $R^3$ is $CH_2CN$; X and Y are each oxygen; n is 0; and the values of $R^4$ match those of the correspondingly numbered compounds of Table A1.

TABLE G28

Table G28 provides 352 compounds of formula (Ib) wherein $R^1$ is ethyl; $R^2$ is chloro; $R^3$ is $CH_2CN$; X and Y are each oxygen; n is 0; and the values of $R^4$ match those of the correspondingly numbered compounds of Table A1.

TABLE G29

Table G29 provides 352 compounds of formula (Ib) wherein $R^1$ is ethyl; $R^2$ is bromo; $R^3$ is $CH_2CN$; X and Y are each oxygen; n is 0; and the values of $R^4$ match those of the correspondingly numbered compounds of Table A1.

TABLE G30

Table G30 provides 352 compounds of formula (Ib) wherein $R^1$ is ethyl; $R^2$ is cyano; $R^3$ is $CH_2CN$; X and Y are each oxygen; n is 0; and the values of $R^4$ match those of the correspondingly numbered compounds of Table A1.

TABLE G31

Table G31 provides 352 compounds of formula (Ib) wherein $R^1$ is methyl; $R^2$ is hydrogen; $R^3$ is $CH_2CN$; X is oxygen; Y is sulphur; n is 0; and the values of $R^4$ match those of the correspondingly numbered compounds of Table A1.

TABLE G32

Table G32 provides 352 compounds of formula (Ib) wherein $R^1$ is methyl; $R^2$ is fluoro; $R^3$ is $CH_2CN$; X is oxygen; Y is sulphur; n is 0; and the values of $R^4$ match those of the correspondingly numbered compounds of Table A1.

TABLE G33

Table G33 provides 352 compounds of formula (Ib) wherein $R^1$ is methyl; $R^2$ is chloro; $R^3$ is $CH_2CN$; X is oxygen; Y is sulphur; n is 0; and the values of $R^4$ match those of the correspondingly numbered compounds of Table A1.

TABLE G34

Table G34 provides 352 compounds of formula (Ib) wherein $R^1$ is methyl; $R^2$ is bromo; $R^3$ is $CH_2CN$; X is oxygen; Y is sulphur; n is 0; and the values of $R^4$ match those of the correspondingly numbered compounds of Table A1.

TABLE G35

Table G35 provides 352 compounds of formula (Ib) wherein $R^1$ is methyl; $R^2$ is cyano; $R^3$ is $CH_2CN$; X is oxygen; Y is sulphur; n is 0; and the values of $R^4$ match those of the correspondingly numbered compounds of Table A1.

TABLE G36

Table G36 provides 352 compounds of formula (Ib) wherein $R^1$ is ethyl; $R^2$ is hydrogen; $R^3$ is $CH_2CN$; X is oxygen; Y is sulphur; n is 0; and the values of $R^4$ match those of the correspondingly numbered compounds of Table A1.

TABLE G37

Table G37 provides 352 compounds of formula (Ib) wherein $R^1$ is ethyl; $R^2$ is fluoro; $R^3$ is $CH_2CN$; X is oxygen; Y is sulphur; n is 0; and the values of $R^4$ match those of the correspondingly numbered compounds of Table A1.

TABLE G38

Table G38 provides 352 compounds of formula (Ib) wherein $R^1$ is ethyl; $R^2$ is chloro; $R^3$ is $CH_2CN$; X is oxygen; Y is sulphur; n is 0; and the values of $R^4$ match those of the correspondingly numbered compounds of Table A1.

TABLE G39

Table G39 provides 352 compounds of formula (Ib) wherein $R^1$ is ethyl; $R^2$ is bromo; $R^3$ is $CH_2CN$; X is oxygen; Y is sulphur; n is 0; and the values of $R^4$ match those of the correspondingly numbered compounds of Table A1.

TABLE G40

Table G40 provides 352 compounds of formula (Ib) wherein $R^1$ is ethyl; $R^2$ is cyano; $R^3$ is $CH_2CN$; X is oxygen; Y is sulphur; n is 0; and the values of $R^4$ match those of the correspondingly numbered compounds of Table A1.

TABLE G41

Table G41 provides 352 compounds of formula (Ib) wherein $R^1$ is methyl; $R^2$ is hydrogen; $R^3$ is $CH_2CN$; X is oxygen; Y is $NR^7$; $R^7$ is hydrogen; n is 0; and the values of $R^4$ match those of the correspondingly numbered compounds of Table A1.

TABLE G42

Table G42 provides 352 compounds of formula (Ib) wherein $R^1$ is methyl; $R^2$ is fluoro; $R^3$ is $CH_2CN$; X is oxygen; Y is $NR^7$; $R^7$ is hydrogen; n is 0; and the values of $R^4$ match those of the correspondingly numbered compounds of Table A1.

TABLE G43

Table G43 provides 352 compounds of formula (Ib) wherein $R^1$ is methyl; $R^2$ is chloro; $R^3$ is $CH_2CN$; X is oxygen; Y is is hydrogen; n is 0; and the values of $R^4$ match those of the correspondingly numbered compounds of Table A1.

TABLE G44

Table G44 provides 352 compounds of formula (Ib) wherein $R^1$ is methyl; $R^2$ is bromo; $R^3$ is $CH_2CN$; X is oxygen; Y is $NR^7$; $R^7$ is hydrogen; n is 0; and the values of $R^4$ match those of the correspondingly numbered compounds of Table A1.

TABLE G45

Table G45 provides 352 compounds of formula (Ib) wherein $R^1$ is methyl; $R^2$ is cyano; $R^3$ is $CH_2CN$; X is oxygen; Y is $NR^7$; $R^7$ is hydrogen; n is 0; and the values of $R^4$ match those of the correspondingly numbered compounds of Table A1.

TABLE G46

Table G46 provides 352 compounds of formula (Ib) wherein $R^1$ is ethyl; $R^2$ is hydrogen; $R^3$ is $CH_2CN$; X is oxygen; Y is $NR^7$; $R^7$ is hydrogen; n is 0; and the values of $R^4$ match those of the correspondingly numbered compounds of Table A1.

TABLE G47

Table G47 provides 352 compounds of formula (Ib) wherein $R^1$ is ethyl; $R^2$ is fluoro; $R^3$ is $CH_2CN$; X is oxygen; Y is $NR^7$; $R^7$ is hydrogen; n is 0; and the values of $R^4$ match those of the correspondingly numbered compounds of Table A1.

TABLE G48

Table G48 provides 352 compounds of formula (Ib) wherein $R^1$ is ethyl; $R^2$ is chloro; $R^3$ is $CH_2CN$; X is oxygen; Y is $NR^7$; $R^7$ is hydrogen; n is 0; and the values of $R^4$ match those of the correspondingly numbered compounds of Table A1.

TABLE G49

Table G49 provides 352 compounds of formula (Ib) wherein $R^1$ is ethyl; $R^2$ is bromo; $R^3$ is $CH_2CN$; X is oxygen; Y is $NR^7$; $R^7$ is hydrogen; n is 0; and the values of $R^4$ match those of the correspondingly numbered compounds of Table A1.

TABLE G50

Table G50 provides 352 compounds of formula (Ib) wherein $R^1$ is ethyl; $R^2$ is cyano; $R^3$ is $CH_2CN$; X is oxygen; Y is $NR^7$; $R^7$ is hydrogen; n is 0, and the values of $R^4$ match those of the correspondingly numbered compounds of Table A1.

TABLE G51

Table G51 provides 352 compounds of formula (Ib) wherein $R^1$ is methyl; $R^2$ is hydrogen; $R^3$ is $CH_2CN$; X is oxygen; Y is $NR^7$; $R^7$ is methyl; n is 0; and the values of $R^4$ match those of the correspondingly numbered compounds of Table A1.

TABLE G52

Table G52 provides 352 compounds of formula (Ib) wherein $R^1$ is methyl; $R^2$ is fluoro; $R^3$ is $CH_2CN$; X is oxygen; Y is $NR^7$; $R^7$ is methyl; n is 0; and the values of $R^4$ match those of the correspondingly numbered compounds of Table A1.

TABLE G53

Table G53 provides 352 compounds of formula (Ib) wherein $R^1$ is methyl; $R^2$ is chloro; $R^3$ is $CH_2CN$; X is oxygen; Y is $NR^7$; $R^7$ is methyl; n is 0; and the values of $R^4$ match those of the correspondingly numbered compounds of Table A1.

TABLE G54

Table G54 provides 352 compounds of formula (Ib) wherein $R^1$ is methyl; $R^2$ is bromo; $R^3$ is $CH_2CN$; X is oxygen; Y is $NR^7$; $R^7$ is methyl; n is 0; and the values of $R^4$ match those of the correspondingly numbered compounds of Table A1.

TABLE G55

Table G55 provides 352 compounds of formula (Ib) wherein $R^1$ is methyl; $R^2$ is cyano; $R^3$ is $CH_2CN$; X is oxygen; Y is $NR^7$; $R^7$ is methyl; n is 0; and the values of $R^4$ match those of the correspondingly numbered compounds of Table A1.

TABLE G56

Table G56 provides 352 compounds of formula (Ib) wherein $R^1$ is ethyl; $R^2$ is hydrogen; $R^3$ is $CH_2CN$; X is oxygen; Y is $NR^7$; $R^7$ is methyl; n is 0; and the values of $R^4$ match those of the correspondingly numbered compounds of Table A1.

TABLE G57

Table G57 provides 352 compounds of formula (Ib) wherein $R^1$ is ethyl; $R^2$ is fluoro; $R^3$ is $CH_2CN$; X is oxygen; Y is $NR^7$; $R^7$ is methyl; n is 0; and the values of $R^4$ match those of the correspondingly numbered compounds of Table A1.

TABLE G58

Table G58 provides 352 compounds of formula (Ib) wherein $R^1$ is ethyl; $R^2$ is chloro; $R^3$ is $CH_2CN$; X is oxygen;

Y is $NR^7$; $R^7$ is methyl; n is 0; and the values of $R^4$ match those of the correspondingly numbered compounds of Table A1.

TABLE G59

Table 59 provides 352 compounds of formula (Ib) wherein $R^1$ is ethyl; $R^2$ is bromo; $R^3$ is $CH_2CN$; X is oxygen; Y is $NR^7$; $R^7$ is methyl; n is 0; and the values of $R^4$ match those of the correspondingly numbered compounds of Table A1.

TABLE G60

Table G60 provides 352 compounds of formula (Ib) wherein $R^1$ is ethyl $R^2$ is cyano; $R^3$ is $CH_2CN$; X is oxygen; Y is $NR^7$; $R^7$ is methyl; n is 0; and the values of $R^4$ match those of the correspondingly numbered compounds of Table A1.

TABLE G61

Table G61 provides 352 compounds of formula (Ia) wherein $R^1$ is methyl; $R^2$ is hydrogen; $R^3$ is $CH_2CN$; X is oxygen; Y is $NR^7$; $R^7$ is methyl; n is 0; and the values of $R^4$ match those of the correspondingly numbered compounds of Table A1.

TABLE G62

Table G62 provides 352 compounds of formula (Ia) wherein $R^1$ is methyl; $R^2$ is fluoro; $R^3$ is $CH_2CN$; X is oxygen; Y is $NR^7$; $R^7$ is methyl; n is 0; and the values of $R^4$ match those of the correspondingly numbered compounds of Table A1.

TABLE G63

Table G63 provides 352 compounds of formula (Ia) wherein $R^1$ is methyl; $R^2$ is chloro; $R^3$ is $CH_2CN$; X is oxygen; Y is $NR^7$; $R^7$ is methyl; n is 0; and the values of $R^4$ match those of the correspondingly numbered compounds of Table A1.

TABLE G64

Table G64 provides 352 compounds of formula (Ia) wherein $R^1$ is methyl; $R^2$ is bromo; $R^3$ is $CH_2CN$; X is oxygen; Y is $NR^7$; $R^7$ is methyl; n is 0; and the values of $R^4$ match those of the correspondingly numbered compounds of Table A1.

TABLE G65

Table G65 provides 352 compounds of formula (Ib) wherein $R^1$ is methyl; $R^2$ is cyano; $R^3$ is CH2CN; X is oxygen; Y is $NR^7$; $R^7$ is methyl; n is 0; and the values of $R^4$ math those of the correspondingly numbered compounds of Table A1.

TABLE G66

Table G66 provides 352 compounds of formula (Ia) wherein $R^1$ is ethyl; $R^2$ is hydrogen; $R^3$ is $CH_2CN$; X is oxygen; Y is $NR^7$; $R^7$ is methyl; n is 0; and the values of $R^4$ match those of the correspondingly numbered compounds of Table A1.

TABLE G67

Table G67 provides 352 compounds of formula (Ia) wherein $R^1$ is ethyl; $R^2$ is fluoro; $R^3$ is $CH_2CN$; X is oxygen; Y is $NR^7$; $R^7$ is methyl; n is 0; and the values of $R^4$ match those of the correspondingly numbered compounds of Table A1.

TABLE G68

Table G68 provides 352 compounds of formula (Ia) wherein $R^1$ is ethyl; $R^2$ is chloro; $R^3$ is $CH_2CN$; X is oxygen; Y is $NR^7$; $R^7$ is methyl; n is 0; and the values of $R^4$ match those of the correspondingly numbered compounds of Table A1.

TABLE G69

Table G69 provides 352 compounds of formula (Ia) wherein $R^1$ is ethyl; $R^2$ is bromo; $R^3$ is $CH_2CN$; X is oxygen; Y is $NR^7$; $R^7$ is methyl; n is 0; and the values of $R^4$ match those of the correspondingly numbered compounds of Table A1.

TABLE G70

Table G70 provides 352 compounds of formula (Ia) wherein $R^1$ is ethyl; $R^2$ is cyano; $R^3$ is $CH_2CN$; X is oxygen; Y is $NR^7$; $R^7$ is methyl; n is 0; and the values of $R^4$ match those of the correspondingly numbered compounds of Table A1.

TABLE H1

Table H1 provides 352 compounds of formula (Ia) wherein $R^1$ is methyl; $R^2$ is hydrogen; $R^3$ is $CH_2CF_3$; X and Y are each oxygen; n is 0; and the values of $R^4$ match those of the correspondingly numbered compounds of Table A1.

TABLE H2

Table H2 provides 352 compounds of formula (Ia) wherein $R^1$ is methyl; $R^2$ is fluoro; $R^3$ is $CH_2CF_3$; X and Y are each oxygen; n is 0; and the values of $R^4$ match those of the correspondingly numbered compounds of Table A1.

TABLE H3

Table H3 provides 352 compounds of formula (Ia) wherein $R^1$ is methyl; $R^2$ is chloro; $R^3$ is $CH_2CF_3$; X and Y are each oxygen; n is 0; and the values of $R^4$ match those of the correspondingly numbered compound of Table A1.

TABLE H4

Table H4 provides 352 compounds of formula (Ia) wherein $R^1$ is methyl; $R^2$ is bromo; $R^3$ is $CH_2CF_3$; X and Y are each oxygen; n is 0; and the values of $R^4$ match those of the correspondingly numbered compounds of Table A1.

TABLE H5

Table H5 provides 352 compounds of formula (Ia) wherein $R^1$ is methyl; $R^2$ is cyano; $R^3$ is $CH_2CF_3$; X and Y are each oxygen; n is 0; and the values of $R^4$ match those of the correspondingly numbered compounds of Table A1.

TABLE H6

Table H6 provides 352 compounds of formula (Ia) wherein $R^1$ is ethyl; $R^2$ is hydrogen; $R^3$ is $CH_2CF_3$; X and Y are each oxygen; n is 0; and the values of $R^4$ match those of the correspondingly numbered compounds of Table A1.

TABLE H7

Table H7 provides 352 compounds of formula (Ia) wherein $R^1$ is ethyl; $R^2$ is fluoro; $R^3$ is $CH_2CF_3$; X and Y are

TABLE H8

Table H8 provides 352 compounds of formula (Ia) wherein $R^1$ is ethyl; $R^2$ is chloro; $R^3$ is $CH_2CF_3$; X and Y are each oxygen; n is 0; and the values of $R^4$ match those of the correspondingly numbered compounds of Table A1.

TABLE H9

Table H9 provides 352 compounds of formula (Ia) wherein $R^1$ is ethyl; $R^2$ is bromo; $R^3$ is $CH_2CF_3$; X and Y are each oxygen; n is 0; and the values of $R^4$ match those of the correspondingly numbered compounds of Table A1.

TABLE H10

Table H10 provides 352 compounds of formula (Ia) wherein $R^1$ is ethyl; $R^2$ is cyano; $R^3$ is $CH_2CF_3$; X and Y are each oxygen; n is 0; and the values of $R^4$ match those of the correspondingly numbered compounds of Table A1.

TABLE H11

Table H11 provides 352 compounds of formula (Ia) wherein $R^1$ is methyl; $R^2$ is hydrogen; $R^3$ is $CH_2CF_3$; X is oxygen; Y is sulphur; n is 0; and the values of $R^4$ match those of the correspondingly numbered compounds of Table A1.

TABLE H12

Table H12 provides 352 compounds of formula (Ia) wherein $R^1$ is methyl; $R^2$ is fluoro; $R^3$ is $CH_2CF_3$; X is oxygen; Y is sulphur; n is 0; and the values of $R^4$ match those of the correspondingly numbered compounds of Table A1.

TABLE H13

Table H13 provides 352 compounds of formula (Ia) wherein $R^1$ is methyl; $R^2$ is chloro; $R^3$ is $CH_2CF_3$; X is oxygen; Y is sulphur; n is 0; and the values of $R^4$ match those of the correspondingly numbered compounds of Table A1.

TABLE H14

Table H14 provides 352 compounds of formula (Ia) wherein $R^1$ is methyl; $R^2$ is bromo; $R^3$ is $CH_2CF_3$; X is oxygen; Y is sulphur; n is 0; and the values of $R^4$ match those of the correspondingly numbered compounds of Table A1.

TABLE H15

Table H15 provides 352 compounds of formula (Ia) wherein $R^1$ is methyl; $R^2$ is cyano; $R^3$ is $CH_2CF_3$; X is oxygen; Y is sulphur; n is 0; and the values of $R^4$ match those of the correspondingly numbered compounds of Table A1.

TABLE H16

Table H16 provides 352 compounds of formula (Ia) wherein $R^1$ is ethyl; $R^2$ is hydrogen; $R^3$ is $CH_2CF_3$; X is oxygen; Y is sulphur; n is 0; and the values of $R^4$ match those of the correspondingly numbered compounds of Table A1.

TABLE H17

Table H17 provides 352 compounds of formula (Ia) wherein $R^1$ is ethyl; $R^2$ is fluoro; $R^3$ is $CH_2CF_3$; X is oxygen; Y is sulphur; n is 0; and the values of $R^4$ match those of the correspondingly numbered compounds of Table A1.

TABLE H18

Table H18 provides 352 compounds of formula (Ia) wherein $R^1$ is ethyl; $R^2$ is chloro; $R^3$ is $CH_2CF_3$; X is oxygen; Y is sulphur; n is 0; and the values of $R^4$ match those of the correspondingly numbered compounds of Table A1.

TABLE H19

Table H19 provides 352 compounds of formula (Ia) wherein $R^1$ is ethyl; $R^2$ is bromo; $R^3$ is $CH_2CF_3$; X is oxygen; Y is sulphur; n is 0; and the values of $R^4$ match those of the correspondingly numbered compounds of Table A1.

TABLE H20

Table H20 provides 352 compounds of formula (Ia) wherein $R^1$ is ethyl; $R^2$ is cyano; $R^3$ is $CH_2CF_3$; X is oxygen; Y is sulphur; n is 0; and the values of $R^4$ match those of the correspondingly numbered compounds of Table A1.

TABLE H21

Table H21 provides 352 compounds of formula (Ib) wherein $R^1$ is methyl; $R^2$ is hydrogen; $R^3$ is $CH_2CF_3$; X and Y are each oxygen; n is 0; and the values of $R^4$ match those of the correspondingly numbered compounds of Table A1.

TABLE H22

Table H22 provides 352 compounds of formula (Ib) wherein $R^1$ is methyl; $R^2$ is fluoro; $R^3$ is $CH_2CF_3$; X and Y are each oxygen; n is 0; and the values of $R^4$ match those of the correspondingly numbered compounds of Table A1.

TABLE H23

Table H23 provides 352 compounds of formula (Ib) wherein $R^1$ is methyl; $R^2$ is chloro; $R^3$ is $CH_2CF_3$; X and Y are each oxygen; n is 0; and the values of $R^4$ match those of the correspondingly numbered compounds of Table A1.

TABLE H24

Table H24 provides 352 compounds of formula (Ib) wherein $R^1$ is methyl; $R^2$ is bromo; $R^3$ is $CH_2CF_3$; X and Y are each oxygen; n is 0; and the values of $R^4$ match those of the correspondingly numbered compounds of Table A1.

TABLE H25

Table H25 provides 352 compounds of formula (Ib) wherein $R^1$ is methyl; $R^2$ is cyano; $R^3$ is $CH_2CF_3$; X and Y are each oxygen; n is 0; and the values of $R^4$ match those of the correspondingly numbered compounds of Table A1.

TABLE H26

Table H26 provides 352 compounds of formula (Ib) wherein $R^1$ is ethyl; $R^2$ is hydrogen; $R^3$ is $CH_2CF_3$; X and Y are each oxygen; n is 0; and the values of $R^4$ match those of the correspondingly numbered compounds of Table A1.

TABLE H27

Table H27 provides 352 compounds of formula (Ib) wherein $R^1$ is ethyl; $R^2$ is fluoro; $R^3$ is $CH_2CF_3$; X and Y are each oxygen; n is 0; and the values of $R^4$ match those of the correspondingly numbered compounds of Table A1.

TABLE H28

Table H28 provides 352 compounds of formula (Ib) wherein $R^1$ is ethyl; $R^2$ is chloro; $R^3$ is $CH_2CF_3$; X and Y are each oxygen; n is 0; and the values of $R^4$ match those of the correspondingly numbered compounds of Table A1.

TABLE H29

Table H29 provides 352 compounds of formula (Ib) wherein $R^1$ is ethyl; $R^2$ is bromo; $R^3$ is $CH_2CF_3$; X and Y are each oxygen; n is 0; and the values of $R^4$ match those of the correspondingly numbered compounds of Table A1.

TABLE H30

Table H30 provides 352 compounds of formula (Ib) wherein $R^1$ is ethyl; $R^2$ is cyano; $R^3$ is $CH_2CF_3$; X and Y are each oxygen; n is 0, and the values of $R^4$ match those of the correspondingly numbered compounds of Table A1.

TABLE H31

Table H31 provides 352 compounds of formula (Ib) wherein $R^1$ is methyl; $R^2$ is hydrogen; $R^3$ is $CH_2CF_3$; X is oxygen; Y is sulphur; n is 0; and the values of $R^4$ match those of the correspondingly numbered compounds of Table A1.

TABLE H32

Table H32 provides 352 compounds of formula (Ib) wherein $R^1$ is methyl; $R^2$ is fluoro; $R^3$ is $CH_2CF_3$; X is oxygen; Y is sulphur; n is 0; and the values of $R^4$ match those of the correspondingly numbered compounds of Table A1.

TABLE H33

Table H33 provides 352 compounds of formula (Ib) wherein $R^1$ is methyl; $R^2$ is chloro; $R^3$ is $CH_2CF_3$; X is oxygen; Y is sulphur; n is 0; and the values of $R^4$ match those of the correspondingly numbered compounds of Table A1.

TABLE H34

Table H34 provides 352 compounds of formula (Ib) wherein $R^1$ is methyl; $R^2$ is bromo; $R^3$ is $CH_2CF_3$; X is oxygen; Y is sulphur; n is 0; and the values of $R^4$ match those of the correspondingly numbered compounds of Table A1.

TABLE H35

Table H35 provides 352 compounds of formula (b) wherein $R^1$ is methyl; $R^2$ is cyano; $R^3$ is $CH_2CF_3$; X is oxygen; Y is sulphur; n is 0; and the values of $R^4$ match those of the correspondingly numbered compounds of Table A1.

TABLE H36

Table H36 provides 352 compounds of formula (Ib) wherein $R^1$ is ethyl; $R^2$ is hydrogen; $R^3$ is $CH_2CF_3$; X is oxygen; Y is sulphur; n is 0; and the values of $R^4$ match those of the correspondingly numbered compounds of Table A1.

TABLE H37

Table H37 provides 352 compounds of formula (Ib) wherein $R^1$ is ethyl; $R^2$ is fluoro; $R^3$ is $CH_2CF_3$; X is oxygen; Y is sulphur; n is 0; and the values of $R^4$ match those of the correspondingly numbered compounds of Table A1.

TABLE H38

Table H38 provides 352 compounds of formula (Ib) wherein $R^1$ is ethyl; $R^2$ is chloro; $R^3$ is $CH_2CF_3$; X is oxygen; Y is sulphur; n is 0; and the values of $R^4$ match those of the correspondingly numbered compounds of Table A1.

TABLE H39

Table H39 provides 352 compounds of formula (Ib) wherein $R^1$ is ethyl; $R^2$ is bromo; $R^3$ is $CH_2CF_3$; X is oxygen; Y is sulphur; n is 0; and the values of $R^4$ match those of the correspondingly numbered compounds of Table A1.

TABLE H40

Table H40 provides 352 compounds of formula (Ib) wherein $R^1$ is ethyl; $R^2$ is cyano; $R^3$ is $CH_2CF_3$; X is oxygen; Y is sulphur; n is 0; and the values of $R^4$ match those of the correspondingly numbered compounds of Table A1.

TABLE H41

Table H41 provides 352 compounds of formula (Ib) wherein $R^1$ is methyl; $R^2$ is hydrogen; $R^3$ is $CH_2CF_3$; X is oxygen; Y is $NR^7$; $R^7$ is hydrogen; n is 0; and the values of $R^4$ match those of the correspondingly numbered compounds of Table A1.

TABLE H42

Table H42 provides 352 compounds of formula (Ib) wherein $R^1$ is methyl; $R^2$ is fluoro; $R^3$ is $CH_2CF_3$; X is oxygen; Y is $NR^7$; $R^7$ is hydrogen; n is 0; and the values of $R^4$ match those of the correspondingly numbered compounds of Table A1.

TABLE H43

Table H43 provides 352 compounds of formula (Ib) wherein $R^1$ is methyl; $R^2$ is chloro; $R^3$ is $CH_2CF_3$; X is oxygen; Y is $NR^7$; $R^7$ is hydrogen; n is 0; and the values of $R^4$ match those of the correspondingly numbered compounds of Table A1.

TABLE H44

Table H44 provides 352 compounds of formula (Ib) wherein $R^1$ is methyl; $R^2$ is bromo; $R^3$ is $CH_2CF_3$; X is oxygen; Y is $NR^7$; $R^7$ is hydrogen; n is 0; and the values of $R^4$ match those of the correspondingly numbered compounds of Table A1.

TABLE H45

Table H45 provides 352 compounds of formula (Ib) wherein $R^1$ is methyl; $R^2$ is cyano; $R^3$ is $CH_2CF_3$; X is oxygen; Y is $NR^7$; $R^7$ is hydrogen; n is 0; and the values of $R^4$ match those of the correspondingly numbered compounds of Table A1.

TABLE H46

Table H46 provides 352 compounds of formula (Ib) wherein $R^1$ is ethyl; $R^2$ is hydrogen; $R^3$ is $CH_2CF_3$; X is oxygen; Y is NR$^7$; R$^7$ is hydrogen; n is 0; and the values of R$^4$ match those of the correspondingly numbered compounds of Table A1.

TABLE H47

Table H47 provides 352 compounds of formula (Ib) wherein R$^1$ is ethyl; R$^2$ is fluoro; R$^3$ is CH$_2$CF$_3$; X is oxygen; Y is NR$^7$; R$^7$ is hydrogen; n is 0; and the values of R$^4$ match those of the correspondingly numbered compounds of Table A1.

TABLE H48

Table H48 provides 352 compounds of formula (Ib) wherein R$^1$ is ethyl; R$^2$ is chloro; R$^3$ is CH$_2$CF$_3$; X is oxygen; Y is NR$^7$; R$^7$ is hydrogen; n is 0; and the values of R$^4$ match those of the correspondingly numbered compounds of Table A1.

TABLE H49

Table H49 provides 352 compounds of formula (Ib) wherein R$^1$ is ethyl; R$^2$ is bromo; R$^3$ is CH$_2$CF$_3$; X is oxygen; Y is NR$^7$; R$^7$ is hydrogen; n is 0; and the values of R$^4$ match hose of the correspondingly numbered compounds of Table A1.

TABLE H50

Table H50 provides 352 compounds of formula (Ib) wherein R$^1$ is ethyl; R$^2$ is cyano; R$^3$ is CH$_2$CF$_3$; X is oxygen; Y is NR$^7$; R$^7$ is hydrogen; n is 0; and the values of R$^4$ match those of the correspondingly numbered compounds of Table A1.

TABLE H51

Table H51 provides 352 compounds of formula (Ib) wherein R$^1$ is methyl; R$^2$ is hydrogen; R$^3$ is CH$_2$CF$_3$; X is oxygen; Y is NR$^7$; R$^7$ is methyl; n is 0; and the values of R$^4$ match those of the correspondingly numbered compounds of Table A1.

TABLE H52

Table H52 provides 352 compounds of formula (Ib) wherein R$^1$ is methyl; R$^2$ is fluoro; R$^3$ is CH$_2$CF$_3$; X is oxygen; Y is NR$^7$; R$^7$ is methyl; n is 0; and the values of R$^4$ match those of the correspondingly numbered compounds of Table A1.

TABLE H53

Table H53 provides 352 compounds of formula (Ib) wherein R$^1$ is methyl; R$^2$ is chloro; R$^3$ is CH$_2$CF$_3$; X is oxygen; Y is NR$^7$; R$^7$ is methyl; n is 0; and the values of R$^4$ match those of the correspondingly numbered compounds of Table A1.

TABLE H54

Table H54 provides 352 compounds of formula (Ib) wherein R$^1$ is methyl; R$^2$ is bromo; R$^3$ is CH$_2$CF$_3$; X is oxygen; Y is NR$^7$; R$^7$ is methyl; n is 0; and the values of R$^4$ match those of the correspondingly numbered compounds of Table A1.

TABLE H55

Table H55 provides 352 compounds of formula (Ib) wherein R$^1$ is methyl; R$^2$ is cyano; R$^3$ is CH$_2$CF$_3$; X is oxygen; Y is NR$^7$; R$^7$ is methyl; n is 0; and the values of R$^4$ match those of the correspondingly numbered compounds of Table A1.

TABLE H56

Table H56 provides 352 compounds of formula (Ib) wherein R$^1$ is ethyl; R$^2$ is hydrogen; R$^3$ is CH$_2$CF$_3$; X is oxygen; Y is NR$^7$; R$^7$ is methyl; n is 0; and the values of R$^4$ match those of the correspondingly numbered compounds of Table A1.

TABLE H57

Table H57 provides 352 compounds of formula (Ib) wherein R$^1$ is ethyl; R$^2$ is fluoro; R$^3$ is CH$_2$CF$_3$; X is oxygen; Y is NR$^7$; R$^7$ is methyl; n is 0; and the values of R$^4$ match those of the correspondingly numbered compounds of Table A1.

TABLE H58

Table H58 provides 352 compounds of formula (Ib) wherein R$^1$ is ethyl; R$^2$ is chloro; R$^3$ is CH$_2$CF$_3$; X is oxygen; Y is NR$^7$; R$^7$ is methyl; n is 0; and the values of R$^4$ match tho of the correspondingly numbered compounds of Table A1.

TABLE H59

Table H59 provides 352 compounds of formula (Ib) wherein R$^1$ is ethyl; R$^2$ is bromo; R$^3$ is CH$_2$CF$_3$; X is oxygen; Y is NR$^7$; R$^7$ is methyl; n is 0; and the values of R$^4$ match those of the correspondingly numbered compounds of Table A1.

TABLE H60

Table H60 provides 352 compounds of formula (Ib) wherein R$^1$ is ethyl; R$^2$ is cyano; R$^3$ is CH$_2$CF$_3$; X is oxygen; Y is NR$^7$; R$^7$ is methyl; n is 0; and the values of R$^4$ match those of the correspondingly numbered compounds of Table A1.

TABLE H61

Table H61 provides 352 compounds of formula (Ia) wherein R$^1$ is methyl; R$^2$ is hydrogen; R$^3$ is CH$_2$CF$_3$; X is oxygen; Y is NR$^7$; R$^7$ is methyl; n is 0; and the values of R$^4$ match those of the correspondingly numbered compounds of Table A1.

TABLE H62

Table H62 provides 352 compounds of formula (Ia) wherein R$^1$ is methyl; R$^2$ is fluoro; R$^3$ is CH$_2$CF$_3$; X is oxygen; Y is NR$^7$; R$^7$ is methyl; n is 0; and the values of R$^4$ match those of the correspondingly numbered compounds of Table A1.

TABLE H63

Table H63 provides 352 compounds of formula (Ia) wherein R$^1$ is methyl; R$^2$ is chloro; R$^3$ is CH$_2$CF$_3$; X is oxygen; Y is NR$^7$; R$^7$ is methyl; n is 0; and the values of R$^4$ match those of the correspondingly numbered compounds of Table A1.

TABLE H64

Table H64 provides 352 compounds of formula (Ia) wherein R$^1$ is methyl; R$^2$ is bromo; R$^3$ is CH$_2$CF$_3$; X is oxygen; Y is $NR^7$; $R^7$ is methyl; n is 0; and the values of $R^4$ match those of the correspondingly numbered compounds of Table A1.

TABLE H65

Table H65 provides 352 compounds of formula (Ib) wherein $R^1$ is methyl; $R^2$ is cyano; $R^3$ is $CH_2CF_3$; X is oxygen; Y is $NR^7$; $R^7$ is methyl; n is 0; and the values of $R^4$ match those of the correspondingly numbered compounds of Table A1.

TABLE H66

Table H66 provides 352 compounds of formula (Ia) wherein $R^1$ is ethyl; $R^2$ is hydrogen; $R^3$ is $CH_2CF_3$; X is oxygen; Y is $NR^7$; $R^7$ is methyl; n is 0; and the values of $R^4$ match those of the correspondingly numbered compounds of Table A1.

TABLE H67

Table H67 provides 352 compounds of formula (Ia) wherein $R^1$ is ethyl; $R^2$ is fluoro; $R^3$ is $CH_2CF_3$; X is oxygen; Y is $NR^7$; $R^7$ is methyl; n is 0; and the values of $R^4$ match those of the correspondingly numbered compounds of Table A1.

TABLE H68

Table H68 provides 352 compounds of formula (Ia) wherein $R^1$ is ethyl; $R^2$ is chloro; $R^3$ is $CH_2CF_3$; X is oxygen; Y is $NR^7$; $R^7$ is methyl; n is 0; and the values of $R^4$ match those of the correspondingly numbered compounds of Table A1.

TABLE H69

Table H69 provides 352 compounds of formula (Ia) wherein $R^1$ is ethyl; $R^2$ is bromo; $R^3$ is $CH_2CF_3$; X is oxygen; Y is $NR^7$; $R^7$ is methyl; n is 0; and the values of $R^4$ match those of the correspondingly numbered compounds of Table A1.

TABLE H70

Table H70 provides 352 compounds of formula (Ia) wherein $R^1$ is ethyl; $R^2$ is cyano; $R^3$ is $CH_2CF_3$; X is oxygen; Y is $NR^7$; $R^7$ is methyl; n is 0; and the values of $R^4$ match those of the correspondingly numbered compounds of Table A1.

TABLE I1

Table I1 provides 352 compounds of formula (Ia) wherein $R^1$ is methyl; $R^2$ is hydrogen; $R^3$ is $CH_2CO_2CH_3$; X and Y are each oxygen; n is 0; and the values of $R^4$ match those of the correspondingly numbered compounds of Table A1.

TABLE I2

Table I2 provides 352 compounds of formula (Ia) wherein $R^1$ is methyl; $R^2$ is fluoro; $R^3$ is $CH_2CO_2CH_3$; X and Y are each oxygen; n is 0; and the values of $R^4$ match those of the correspondingly numbered compounds of Table A1.

TABLE I3

Table I3 provides 352 compounds of formula (Ia) wherein $R^1$ is methyl; $R^2$ is chloro; $R^3$ is $CH_2CO_2CH_3$; X and Y are each oxygen; n is 0; and the values of $R^4$ match those of the correspondingly numbered compound of Table A1.

TABLE I4

Table I4 provides 352 compounds of formula (Ia) wherein $R^1$ is methyl; $R^2$ is bromo; $R^3$ is $CH_2CO_2CH_3$; X and Y are each oxygen; n is 0; and the values of $R^4$ match those of the correspondingly numbered compounds of Table A1.

TABLE I5

Table I5 provides 352 compounds of formula (Ia) wherein $R^1$ is methyl; $R^2$ is cyano; $R^3$ is $CH_2CO_2CH_3$; X and Y are each oxygen; n is 0; and the values of $R^4$ match those of the correspondingly numbered compounds of Table A1.

TABLE I6

Table I6 provides 352 compounds of formula (Ia) wherein $R^1$ is ethyl; $R^2$ is hydrogen; $R^3$ is $CH_2CO_2CH_3$; X and Y are each oxygen; n is 0; and the values of $R^4$ match those of the correspondingly numbered compounds of Table A1.

TABLE I7

Table I7 provides 352 compounds of formula (Ia) wherein $R^1$ is ethyl; $R^2$ is fluoro; $R^3$ is $CH_2CO_2CH_3$; X and Y are each oxygen; n is 0; and the values of $R^4$ match those of the correspondingly numbered compounds of Table A1.

TABLE I8

Table I8 provides 352 compounds of formula (Ia) wherein $R^1$ is ethyl; $R^2$ is chloro; $R^3$ is $CH_2CO_2CH_3$; X and Y are each oxygen; n is 0; and the values of $R^4$ match those of the correspondingly numbered compounds of Table A1.

TABLE I9

Table I9 provides 352 compounds of formula (Ia) wherein $R^1$ is ethyl; $R^2$ is bromo; $R^3$ is $CH_2CO_2CH_3$; X and Y are each oxygen; n is 0; and the values of $R^4$ match those of the correspondingly numbered compounds of Table A1.

TABLE I10

Table I10 provides 352 compounds of formula (Ia) wherein $R^1$ is ethyl; $R^2$ is cyano; $R^3$ is $CH_2CO_2CH_3$; X and Y are each oxygen; n is 0; and the values of $R^4$ match those of the correspondingly numbered compounds of Table A1.

TABLE I11

Table I11 provides 352 compounds of formula (Ia) wherein $R^1$ is methyl; $R^2$ is hydrogen; $R^3$ is $CH_2CO_2CH_3$; X is oxygen; Y is sulphur; n is 0; and the values of $R^4$ match those of the correspondingly numbered compounds of Table A1.

TABLE I12

Table I12 provides 352 compounds of formula (Ia) wherein $R^1$ is methyl; $R^2$ is fluoro; $R^3$ is $CH_2CO_2CH_3$; X is oxygen; Y is sulphur; n is 0; and the values of $R^4$ match those of the correspondingly numbered compounds of Table A1.

TABLE I13

Table I13 provides 352 compounds of formula (Ia) wherein $R^1$ is methyl; $R^2$ is chloro; $R^3$ is $CH_2CO_2CH_3$; X is oxygen; Y is sulphur; n is 0; and the values of $R^4$ match those of the correspondingly numbered compounds of Table A1.

TABLE I14

Table I14 provides 352 compounds of formula (Ia) wherein $R^1$ is methyl; $R^2$ is bromo; $R^3$ is $CH_2CO_2CH_3$; X is oxygen; Y is sulphur; n is 0; and the values of $R^4$ match those of the correspondingly numbered compounds of Table A1.

TABLE I15

Table I15 provides 352 compounds of formula (Ia) wherein $R^1$ is methyl; $R^2$ is cyano; $R^3$ is $CH_2CO_2CH_3$; X is oxygen; Y is sulphur; n is 0, and the values of $R^4$ match those of the correspondingly numbered compounds of Table A1.

TABLE I16

Table I16 provides 352 compounds of formula (Ia) wherein $R^1$ is ethyl; $R^2$ is hydrogen; $R^3$ is $CH_2CO_2CH_3$; X is oxygen; Y is sulphur; n is 0; and the values of $R^4$ match those of the correspondingly numbered compounds of Table A1.

TABLE I17

Table I17 provides 352 compounds of formula (Ia) wherein $R^1$ is ethyl; $R^2$ is fluoro; $R^3$ is $CH_2CO_2CH_3$; X is oxygen; Y is sulphur; n is 0; and the values of $R^4$ match those of the correspondingly numbered compounds of Table A1.

TABLE I18

Table I18 provides 352 compounds of formula (Ia) wherein $R^1$ is ethyl; $R^2$ is chloro; $R^3$ is $CH_2CO_2CH_3$; X is oxygen; Y is sulphur; n is 0; and the values of $R^4$ match those of the correspondingly numbered compounds of Table A1.

TABLE I19

Table I19 provides 352 compounds of formula (Ia) wherein $R^1$ is ethyl; $R^2$ is bromo; $R^3$ is $CH_2CO_2CH_3$; X is oxygen; Y is sulphur; n is 0; and the values of $R^4$ match those of the correspondingly numbered compounds of Table A1.

TABLE I20

Table I20 provides 352 compounds of formula (Ia) wherein $R^1$ is ethyl; $R^2$ is cyano; $R^3$ is $CH_2CO_2CH_3$; X is oxygen; Y is sulphur; n is 0; and the values of $R^4$ match those of the correspondingly numbered compounds of Table A1.

TABLE I21

Table I21 provides 352 compounds of formula (Ib) wherein $R^1$ is methyl; $R^2$ is hydrogen; $R^3$ is $CH_2CO_2CH_3$; X and Y are each oxygen; n is 0; and the values of $R^4$ match those of the correspondingly numbered compounds of Table A1.

TABLE I22

Table I22 provides 352 compounds of formula (Ib) wherein $R^1$ is methyl; $R^2$ is fluoro; $R^3$ is $CH_2CO_2CH_3$; X and Y are each oxygen; n is 0; and the values of $R^4$ match those of the correspondingly numbered compounds of Table A1.

TABLE I23

Table I23 provides 352 compounds of formula (Ib) wherein $R^1$ is methyl; $R^2$ is chloro; $R^3$ is $CH_2CO_2CH_3$; X and Y are each oxygen; n is 0; and the values of $R^4$ match those of the correspondingly numbered compounds of Table A1.

TABLE I24

Table I24 provides 352 compounds of formula (Ib) wherein $R^1$ is methyl; $R^2$ is bromo; $R^3$ is $CH_2CO_2CH_3$; X and Y are each oxygen; n is 0; and the values of $R^4$ match those of the correspondingly numbered compounds of Table A1.

TABLE I25

Table I25 provides 352 compounds of formula (Ib) wherein $R^1$ is methyl; $R^2$ is cyano; $R^3$ is $CH_2CO_2CH_3$; X and Y are each oxygen; n is 0; and the values of $R^4$ match those of the correspondingly numbered compounds of Table A1.

TABLE I26

Table I26 provides 352 compounds of formula (Ib) wherein $R^1$ is ethyl; $R^2$ is hydrogen; $R^3$ is $CH_2CO_2CH_3$; X and Y are each oxygen; n is 0; and the values of $R^4$ match those of the correspondingly numbered compounds of Table A1.

TABLE I27

Table I27 provides 352 compounds of formula (Ib) wherein $R^1$ is ethyl; $R^2$ is fluoro; $R^3$ is $CH_2CO_2CH_3$; X and Y are each oxygen; n is 0; and the values of $R^4$ match those of the correspondingly numbered compounds of Table A1.

TABLE I28

Table I28 provides 352 compounds of formula (Ib) wherein $R^1$ is ethyl; $R^2$ is chloro; $R^3$ is $CH_2CO_2CH_3$; X and Y are each oxygen; n is 0; and the values of $R^4$ match those of the correspondingly numbered compounds of Table A1.

TABLE I29

Table I29 provides 352 compounds of formula (Ib) wherein $R^1$ is ethyl; $R^2$ is bromo; $R^3$ is $CH_2CO_2CH_3$; X and Y are each oxygen; n is 0; and the values of $R^4$ match those of the correspondingly numbered compounds of Table A1.

TABLE I30

Table I30 provides 352 compounds of formula (Ib) wherein $R^1$ is ethyl; $R^2$ is cyano, $R^3$ is $CH_2CO_2CH_3$; X and Y are each oxygen; n is 0; and the values of $R^4$ match those of the correspondingly numbered compounds of Table A1.

TABLE I31

Table I31 provides 352 compounds of formula (Ib) wherein $R^1$ is methyl; $R^2$ is hydrogen; $R^3$ is $CH_2CO_2CH_3$; X is oxygen; Y is sulphur; n is 0; and the values of $R^4$ match those of the correspondingly numbered compounds of Table A1.

TABLE I32

Table I32 provides 352 compounds of formula (Ib) wherein $R^1$ is methyl; $R^2$ is fluoro; $R^3$ is $CH_2CO_2CH_3$; X is oxygen; Y is sulphur; n is 0; and the values of $R^4$ match those of the correspondingly numbered compounds of Table A1.

TABLE I33

Table I33 provides 352 compounds of formula (Ib) wherein $R^1$ is methyl; $R^2$ is chloro; $R^3$ is $CH_2CO_2CH_3$; X is

TABLE I34

Table I34 provides 352 compounds of formula (Ib) wherein $R^1$ is methyl; $R^2$ is bromo; $R^3$ is $CH_2CO_2CH_3$; X is oxygen; Y is sulphur; n is 0; and the values of $R^4$ match those of the correspondingly numbered compounds of Table A1.

TABLE I35

Table I35 provides 352 compounds of formula (Ib) wherein $R^1$ is methyl; $R^2$ is cyano; $R^3$ is $CH_2CO_2CH_3$; X is oxygen; Y is sulphur; n is 0; and the values of $R^4$ match those of the correspondingly numbered compounds of Table A1.

TABLE I36

Table I36 provides 352 compounds of formula (Ib) wherein $R^1$ is ethyl; $R^2$ is hydrogen; $R^3$ is $CH_2CO_2CH_3$; X is oxygen; Y is sulphur; n is 0; and the values of $R^4$ match those of the correspondingly numbered compounds of Table A1.

TABLE I37

Table I37 provides 352 compounds of formula (Ib) wherein $R^1$ is ethyl; $R^2$ is fluoro; $R^3$ is $CH_2CO_2CH_3$; X is oxygen; Y is sulphur; n is 0; and the values of $R^4$ match those of the correspondingly numbered compounds of Table A1.

TABLE I38

Table I38 provides 352 compounds of formula (Ib) wherein $R^1$ is ethyl; $R^2$ is chloro; $R^3$ is $CH_2CO_2CH_3$; X is oxygen; Y is sulphur; n is 0; and the values of $R^4$ match those of the correspondingly numbered componds of Table A1.

TABLE I39

Table I39 provides 352 compounds of formula (Ib) wherein $R^1$ is ethyl; $R^2$ is bromo; $R^3$ is $CH_2CO_2CH_3$; X is oxygen; Y is sulphur; n is 0; and the values of $R^4$ match those of the correspondingly numbered compounds of Table A1.

TABLE I40

Table I40 provides 352 compounds of formula (Ib) wherein $R^1$ is ethyl; $R^2$ is cyano; $R^3$ is $CH_2CO_2CH_3$; X is oxygen; Y is sulphur; n is 0; and the values of $R^4$ match those of the correspondingly numbered compounds of Table A1.

TABLE I41

Table I41 provides 352 compounds of formula (Ib) wherein $R^1$ is methyl; $R^2$ is hydrogen; $R^3$ is $CH_2CO_2CH_3$; X is oxygen; Y is $NR^7$; $R^7$ is hydrogen; n is 0; and the values of $R^4$ match those of the correspondingly numbered compounds of Table A1.

TABLE I42

Table I42 provides 352 compounds of formula (Ib) wherein $R^1$ is methyl; $R^2$ is fluoro; $R^3$ is $CH_2CO_2CH_3$; X is oxygen; Y is $NR^7$; $R^7$ is hydrogen; n is 0; and the values of $R^4$ match those of the correspondingly numbered compounds of Table A1.

TABLE I43

Table I43 provides 352 compounds of formula (Ib) wherein $R^1$ is methyl; $R^2$ is chloro; $R^3$ is $CH_2CO_2CH_3$; X is oxygen; Y is $NR^7$; $R^7$ is hydrogen; n is 0; and the values of $R^4$ match those of the correspondingly numbered compounds of Table A1.

TABLE I44

Table I44 provides 352 compounds of formula (Ib) wherein $R^1$ is methyl; $R^2$ is bromo; $R^3$ is $CH_2CO_2CH_3$; X is oxygen; Y is $NR^7$; $R^7$ is hydrogen; n is 0; and the values of $R^4$ match those of the correspondingly numbered compounds of Table A1.

TABLE I45

Table I45 provides 352 compounds of formula (Ib) wherein $R^1$ is methyl; $R^2$ is cyano; $R^3$ is $CH_2CO_2CH_3$; X is oxygen; Y is $NR^7$; $R^7$ is hydrogen; n is 0; and the values of $R^4$ match those of the correspondingly numbered compounds of Table A1.

TABLE I46

Table I46 provides 352 compounds of formula (Ib) wherein $R^1$ is ethyl; $R^2$ is hydrogen; $R^3$ is $CH_2CO_2CH_3$; X is oxygen; Y is $NR^7$; $R^7$ is hydrogen; n is 0; and the values of $R^4$ match those of the correspondingly numbered compounds of Table A1.

TABLE I47

Table I47 provides 352 compounds of formula (Ib) wherein $R^1$ is ethyl; $R^2$ is fluoro; $R^3$ is $CH_2CO_2CH_3$; X is oxygen; Y is $NR^7$; $R^7$ is hydrogen; n is 0; and the values of $R^4$ match those of the correspondingly numbered compounds of Table A1.

TABLE I48

Table I48 provides 352 compounds of formula (Ib) wherein $R^1$ is ethyl; $R^2$ is chloro; $R^3$ is $CH_2CO_2CH_3$; X is oxygen; Y is $NR^7$; $R^7$ is hydrogen; n is 0; and the values of $R^4$ match those of the correspondingly numbered compounds of Table A1.

TABLE I49

Table I49 provides 352 compounds of formula (Ib) wherein $R^1$ is ethyl; $R^2$ is bromo; $R^3$ is $CH_2CO_2CH_3$; X is oxygen; Y is $NR^7$; $R^7$ is hydrogen; n is 0; and the values of $R^4$ match those of the correspondingly numbered compounds of Table A1.

TABLE I50

Table I50 provides 352 compounds of formula (Ib) wherein $R^1$ is ethyl; $R^2$ is cyano; $R^3$ is $CH_2CO_2CH_3$; X is oxygen; Y is $NR^7$; $R^7$ is hydrogen; n is 0; and the values of $R^4$ match those of the correspondingly numbered compounds of Table A1.

TABLE I51

Table I51 provides 352 compounds of formula (Ib) wherein $R^1$ is methyl; $R^2$ is hydrogen; $R^3$ is $CH_2CO_2CH_3$;

X is oxygen; Y is $NR^7$; $R^7$ is methyl; n is 0; and the values of $R^4$ match those of the correspondingly numbered compounds of Table A1.

TABLE I52

Table I52 provides 352 compounds of formula (Ib) wherein $R^1$ is methyl; $R^2$ is fluoro; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I53

Table I53 provides 352 compounds of formula (Ib) wherein $R^1$ is methyl; $R^2$ is chloro; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I54

Table I54 provides 352 compounds of formula (Ib) wherein $R^1$ is methyl; $R^2$ is bromo; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I55

Table I55 provides 352 compounds of formula (Ib) wherein $R^1$ is methyl; $R^2$ is cyano; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I56

Table I56 provides 352 compounds of formula (Ib) wherein $R^1$ is ethyl; $R^2$ is hydrogen; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I57

Table I57 provides 352 compounds of formula (Ib) wherein $R^1$ is ethyl; $R^2$ is fluoro; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I58

Table I58 provides 352 compounds of formula (Ib) wherein $R^1$ is ethyl; $R^2$ is chloro; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I59

Table I59 provides 352 compounds of formula (Ib) wherein $R^1$ is ethyl; $R^2$ is bromo; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I60

Table I60 provides 352 compounds of formula (Ib) wherein $R^1$ is ethyl; $R^2$ is cyano; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I61

Table I61 provides 352 compounds of formula (Ia) wherein $R^1$ is methyl; $R^2$ is hydrogen; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I62

Table I62 provides 352 compounds of formula (Ia) wherein $R^1$ is methyl; $R^2$ is fluoro; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I63

Table I63 provides 352 compounds of formula (Ia) wherein $R^1$ is methyl; $R^2$ is chloro; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I64

Table I64 provides 352 compounds of formula (Ia) wherein $R^1$ is methyl; $R^2$ is bromo; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I65

Table I65 provides 352 compounds of formula (Ib) wherein $R^1$ is methyl; $R^2$ is cyano; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I66

Table I66 provides 352 compounds of formula (Ia) wherein $R^1$ is ethyl; $R^2$ is hydrogen; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I67

Table I67 provides 352 compounds of formula (Ia) wherein $R^1$ is ethyl; $R^2$ is fluoro; $R^3$ is $CH_2CO_2CH_3$; X is oxygen; Y is $NR^7$; $R^7$ is methyl; n is 0; and the values of $R^4$ match those of the correspondingly numbered compounds of Table A1.

TABLE I68

Table I68 provides 352 compounds of formula (Ia) wherein $R^1$ is ethyl; $R^2$ is chloro; $R^3$ is $CH_2CO_2CH_3$; X is oxygen; Y is $NR^7$; $R^7$ is methyl; n is 0; and the values of $R^4$ match those of the correspondingly number compounds of Table A1.

TABLE I69

Table I69 provides 352 compounds of formula (Ia) wherein $R^1$ is ethyl; $R^2$ is bromo; $R^3$ is $CH_2CO_2CH_3$; X is oxygen; Y is NR$^7$; R$^7$ is methyl; n is 0; and the values of R$^4$ match those of the correspondingly numbered compounds of Table A1.

TABLE I70

Table I70 provides 352 compounds of formula (Ia) wherein R$^1$ is ethyl; R$^2$ is cyano; R$^3$ is CH$_2$CO$_2$CH$_3$; X is oxygen; Y is NR$^7$; R$^7$ is methyl; n is 0; and the values of R$^4$ watch those of the correspondingly numbered compounds of Table A1.

TABLE J1

Table J1 provides 352 compounds of formula (Ia) wherein R$^1$ is methyl; R$^2$ is hydrogen; R$^1$ is CH$_2$Ph; X and Y are each oxygen; n is 0; and the values of R$^4$ match those of the correspondingly numbered compounds of Table A1.

TABLE J2

Table J2 provides 352 compounds of formula (Ia) wherein R$^1$ is methyl; R$^2$ is fluoro; R$^3$ is CH$_2$Ph; X and Y are each oxygen; n is 0; and the values of R$^4$ match those of the correspondingly numbered compounds of Table A1.

TABLE J3

Table J3 provides 352 compounds of formula (Ia) wherein R$^1$ is methyl; R$^2$ is chloro; R$^3$ is CH$_2$Ph; X and Y are each oxygen; n is 0; and the values of R$^4$ match those of the correspondingly numbered compounds of Table A1.

TABLE J4

Table J4 provides 352 compounds of formula (Ia) wherein R$^1$ is methyl; R$^2$ is bromo; R$^3$ is CH$_2$Ph; X and Y are each oxygen; n is 0; and the values of R$^4$ match those of the correspondingly numbered compounds of Table A1.

TABLE J5

Table J5 provides 352 compounds of formula (Ia) wherein R$^1$ is methyl; R$^2$ is cyano; R$^3$ is CH$_2$Ph; X and Y are each oxygen; n is 0; and the values of R$^4$ match those of the correspondingly numbered compounds of Table A1.

TABLE J6

Table J6 provides 352 compounds of formula (Ia) wherein R$^1$ is ethyl; R$^2$ is hydrogen; R$^3$ is CH$_2$Ph; X and Y are each oxygen; n is 0; and the values of R$^4$ match those of the correspondingly numbered compounds of Table A1.

TABLE J7

Table J7 provides 352 compounds of formula (Ia) wherein R$^1$ is ethyl; R$^2$ is fluoro; R$^3$ is CH$_2$Ph; X and Y are each oxygen; n is 0; and the values of R$^4$ match those of the correspondingly numbered compounds of Table A1:.

TABLE J8

Table J8 provides 352 compounds of formula (Ia) wherein R$^1$ is ethyl; R$^2$ is chloro; R$^3$ is CH$_2$Ph; X and Y are each oxygen; n is 0; and the values of R$^4$ match those of the correspondingly numbered compounds of Table A1.

TABLE J9

Table J9 provides 352 compounds of formula (Ia) wherein R$^1$ is ethyl; R$^2$ is bromo; R$^3$ is CH$_2$Ph; X and Y are each oxygen; n is 0; and the values of R$^4$ match those of the correspondingly numbered compounds of Table A1.

TABLE J10

Table J10 provides 352 compounds of formula (Ia) wherein R$^1$ is ethyl; R$^2$ is cyano; R$^3$ is CH$_2$Ph; X and Y are each oxygen; n is 0; and the values of R$^4$ match those of the correspondingly numbered compounds of Table A1.

TABLE J11

Table J11 provides 352 compounds of formula (Ia) wherein R$^1$ is methyl; R$^2$ is hydrogen; R$^3$ is CH$_2$Ph; X is oxygen; Y is sulphur; n is 0; and the values of R$^4$ match those of the correspondingly numbered compounds of Table A1.

TABLE J12

Table J12 provides 352 compounds of formula (Ia) wherein R$^1$ is methyl; R$^2$ is fluoro; R$^3$ is CH$_2$Ph; X is oxygen; Y is sulphur; n is 0; and the values of R$^4$ match those of the correspondingly numbered compounds of Table A1.

TABLE J13

Table J13 provides 352 compounds of formula (Ia) wherein R$^1$ is methyl; R$^2$ is chloro; R$^3$ is CH$_2$Ph; X is oxygen; Y is sulphur; n is 0; and the values of R$^4$ match those of the correspondingly numbered compounds of Table A1.

TABLE J14

Table J14 provides 352 compounds of formula (Ia) wherein R$^1$ is methyl; R$^2$ is bromo; R$^3$ is CH$_2$Ph; X is oxygen; Y is sulphur; n is 0; and the values of R$^4$ match those of the correspondingly numbered compounds of Table A1.

TABLE J15

Table J15 provides 352 compounds of formula (Ia) wherein R$^1$ is methyl; R$^2$ is cyano; R$^3$ is CH$_2$Ph; X is oxygen; Y is sulphur; n is 0; and the values of R$^4$ match those of the correspondingly numbered compounds of Table A1.

TABLE J16

Table J16 provides 352 compounds of formula (Ia) wherein R$^1$ is ethyl; R$^2$ is hydrogen; R$^3$ is CH$_2$Ph; X is oxygen; Y is sulphur; n is 0; and the values of R$^4$ match those of the correspondingly numbered compounds of Table A1.

TABLE J17

Table J17 provides 352 compounds of formula (Ia) wherein R$^1$ is ethyl; R$^2$ is fluoro; R$^3$ is CH$_2$Ph; X is oxygen; Y is sulphur; n is 0; and the values of R$^4$ match those of the correspondingly numbered compounds of Table A1.

TABLE J18

Table J18 provides 352 compounds of formula (Ia) wherein R$^1$ is ethyl; R$^2$ is chloro; R$^3$ is CH$_2$Ph; X is oxygen; Y is sulphur; n is 0; and the values of R$^4$ match those of the correspondingly numbered compounds of Table A1.

TABLE J19

Table J19 provides 352 compounds of formula (Ia) wherein R$^1$ is ethyl; R$^2$ is bromo; R$^3$ is CH$_2$Ph; X is oxygen;

TABLE J20

Table J20 provides 352 compounds of formula (Ia) wherein $R^1$ is ethyl; $R^2$ is cyano; $R^3$ is $CH_2Ph$; X is oxygen; Y is sulphur; n is 0; and the values of $R^4$ match those of the correspondingly numbered compounds of Table A1.

TABLE J21

Table J21 provides 352 compounds of formula (Ib) wherein $R^1$ is methyl; $R^2$ is hydrogen; $R^3$ is $CH_2Ph$; X and Y are each oxygen; n is 0; and the values of $R^4$ match those of the correspondingly numbered compounds of Table A1.

TABLE J22

Table J22 provides 352 compounds of formula (Ib) wherein $R^1$ is methyl; $R^2$ is fluoro; $R^3$ is $CH_2Ph$; X and Y are each oxygen; n is 0; and the values of $R^4$ match those of the correspondingly numbered compounds of Table A1.

TABLE J23

Table J23 provides 352 compounds of formula (Ib) wherein $R^1$ is methyl; $R^2$ is chloro; $R^3$ is $CH_2Ph$; X and Y are each oxygen; n is 0; and the values of $R^4$ match those of the correspondingly numbered compounds of Table A1.

TABLE J24

Table J24 provides 352 compounds of formula (Ib) wherein $R^1$ is methyl; $R^2$ is bromo; $R^3$ is $CH_2Ph$; X and Y are each oxygen; n is 0; and the values of $R^4$ match those of the correspondingly numbered compounds of Table A1.

TABLE J25

Table J25 provides 352 compounds of formula (Ib) wherein $R^1$ is methyl; $R^2$ is cyano; $R^3$ is $CH_2Ph$; X and Y are each oxygen; n is 0; and the values of $R^4$ match those of the correspondingly numbered compounds of Table A1.

TABLE J26

Table J26 provides 352 compounds of formula (Ib) wherein $R^1$ is ethyl; $R^2$ is hydrogen; $R^3$ is $CH_2Ph$; X and Y are each oxygen; n is 0; and the values of $R^4$ match those of the correspondingly numbered compounds of Table A1.

TABLE J27

Table J27 provides 352 compounds of formula (Ib) wherein $R^1$ is ethyl; $R^2$ is fluoro; $R^3$ is $CH_2Ph$; X and Y are each oxygen; n is 0; and the values of $R^4$ match those of the correspondingly numbered compounds of Table A1.

TABLE J28

Table J28 provides 352 compounds of formula (Ib) wherein $R^1$ is ethyl; $R^2$ is chloro $R^3$ is $CH_2Ph$; X and Y are each oxygen; n is 0; and the values of $R^4$ match those of the correspondingly numbered compounds of Table A1.

TABLE J29

Table J29 provides 352 compounds of formula (Ib) wherein $R^1$ is ethyl; $R^2$ is bromo; $R^3$ is $CH_2Ph$; X and Y are each oxygen; n is 0; and the values of $R^4$ match those of the correspondingly numbered compounds of Table A1.

TABLE J30

Table J30 provides 352 compounds of formula (Ib) wherein $R^1$ is ethyl; $R^2$ is cyano; $R^3$ is $CH_2Ph$; X and Y are each oxygen; n is 0; and the values of $R^4$ match those of the correspondingly numbered compounds of Table A1.

TABLE J31

Table J31 provides 352 compounds of formula (Ib) wherein $R^1$ is methyl; $R^2$ is hydrogen; $R^3$ is $CH_2Ph$; X is oxygen; Y is sulphur; n is 0; and the values of $R^4$ match those of the correspondingly numbered compounds of Table A1.

TABLE J32

Table J32 provides 352 compounds of formula (Ib) wherein $R^1$ is methyl; $R^2$ is fluoro; $R^3$ is $CH_2Ph$; X is oxygen; Y is sulphur; n is 0; and the values of $R^4$ match those of the correspondingly numbered compounds of Table A1.

TABLE J33

Table J33 provides 352 compounds of formula (Ib) wherein $R^1$ is methyl; $R^2$ is chloro; $R^3$ is $CH_2Ph$; X is oxygen; Y is sulphur; n is 0; and the values of $R^4$ match those of the correspondingly numbered compounds of Table A1.

TABLE J34

Table J34 provides 352 compounds of formula (Ib) wherein $R^1$ is methyl; $R^2$ is bromo; $R^3$ is $CH_2Ph$; X is oxygen; Y is sulphur; n is 0; and the values of $R^4$ match those of the correspondingly numbered compounds of Table A1.

TABLE J35

Table J35 provides 352 compounds of formula (Ib) wherein $R^1$ is methyl; $R^2$ is cyano; $R^3$ is $CH_2Ph$; X is oxygen; Y is sulphur; n is 0; and the values of $R^4$ match those of the correspondingly numbered compounds of Table A1.

TABLE J36

Table J36 provides 352 compounds of formula (Ib) wherein $R^1$ is ethyl; $R^2$ is hydrogen; $R^3$ is CH X is oxygen; Y is sulphur; n is 0; and the values of $R^4$ math those of the correspondingly numbered compounds of Table A1.

TABLE J37

Table J37 provides 352 compounds of formula (Ib) wherein $R^1$ is ethyl; $R^2$ is fluoro; $R^3$ is $CH_2Ph$; X is oxygen; Y is sulphur; n is 0; and the values of $R^4$ match those of the correspondingly numbered compounds of Table A1.

TABLE J38

Table J38 provides 352 compounds of formula (Ib) wherein $R^1$ is ethyl; $R^2$ is chloro; $R^3$ is $CH_2Ph$; X is oxygen; Y is sulphur; n is 0; and the values of $R^4$ match those of the correspondingly numbered compounds of Table A1.

TABLE J39

Table J39 provides 352 compounds of formula (Ib) wherein $R^1$ is ethyl; $R^2$ is bromo; $R^3$ is $CH_2Ph$; X is oxygen;

Y is sulphur; n is 0; and the values of $R^4$ match those of the correspondingly numbered compounds of Table A1.

TABLE J40

Table J40 provides 352 compounds of formula (Ib) wherein $R^1$ is ethyl; $R^2$ is cyano; $R^3$ is $CH_2Ph$; X is oxygen; Y is sulphur; n is 0; and the values of $R^4$ match those of the correspondingly numbered compounds of Table A1.

TABLE J41

Table J41 provides 352 compounds of formula (Ib) wherein $R^1$ is methyl; $R^2$ is hydrogen; $R^3$ is $CH_2Ph$; X is oxygen; Y is $NR^7$; $R^7$ is hydrogen; n is 0; and the values of $R^4$ match those of the correspondingly numbered compounds of Table A1.

TABLE J42

Table J42 provides 352 compounds of formula (Ib) wherein $R^1$ is methyl; $R^2$ is fluoro; $R^3$ is $CH_2Ph$; X is oxygen; Y is $NR^7$; $R^7$ is hydrogen; n is 0; and the values of $R^4$ match those of the correspondingly numbered compounds of Table A1.

TABLE J43

Table J43 provides 352 compounds of formula (Ib) wherein $R^1$ is methyl; $R^2$ is chloro; $R^3$ is $CH_2Ph$; X is oxygen; Y is $NR^7$; $R^7$ is hydrogen; n is 0; and the values of $R^4$ match those of the correspondingly numbered compounds of Table A1.

TABLE J44

Table J44 provides 352 compounds of formula (Ib) wherein $R^1$ is methyl; $R^2$ is bromo; $R^3$ is $CH_2Ph$; X is oxygen; Y is $NR^7$; $R^7$ is hydrogen; n is 0; and the values of $R^4$ match those of the correspondingly numbered compounds of Table A1.

TABLE J45

Table J45 provides 352 compounds of formula (Ib) wherein $R^1$ is methyl; $R^2$ is cyano; $R^3$ is $CH_2Ph$; X is oxygen; Y is $NR^7$; $R^7$ is hydrogen; n is 0; and the values of $R^4$ match those of the correspondingly numbered compounds of Table A1.

TABLE J46

Table J46 provides 352 compounds of formula (Ib) wherein $R^1$ is ethyl; $R^2$ is hydrogen; $R^1$ is $CH_2Ph$; X is oxygen; Y is $NR^7$; $R^7$ is hydrogen; n is 0; and the values of $R^4$ match those of the correspondingly numbered compounds of Table A1.

TABLE J47

Table J47 provides 352 compounds of formula (Ib) wherein $R^1$ is ethyl; $R^2$ is fluoro; $R^3$ is $CH_2Ph$; X is oxygen; Y is $NR^7$; $R^7$ is hydrogen; n is 0; and the values of $R^4$ match those of the correspondingly numbered compounds of Table A1.

TABLE J48

Table J48 provides 352 compounds of formula (Ib) wherein $R^1$ is ethyl; $R^2$ is chloro; $R^3$ is $CH_2Ph$; X is oxygen; Y is $NR^7$; $R^7$ is hydrogen; n is 0; and the values of $R^4$ match those of the correspondingly numbered compounds of Table A1.

TABLE J49

Table J49 provides 352 compounds of formula (Ib) wherein $R^1$ is ethyl; $R^2$ is bromo; $R^3$ is $CH_2Ph$; X is oxygen; Y is $NR^7$; $R^7$ is hydrogen; n is 0; and the values of $R^4$ match those of the correspondingly numbered compounds of Table A1.

TABLE J50

Table J50 provides 352 compounds of formula (Ib) wherein $R^1$ is ethyl; $R^2$ is cyano, $R^3$ is $CH_2Ph$; X is oxygen; Y is $NR^7$; $R^7$ is hydrogen; n is 0; and the values of $R^4$ match those of the correspondingly numbered compounds of Table A1.

TABLE J51

Table J51 provides 352 compounds of formula (Ib) wherein $R^1$ is methyl; $R^2$ is hydrogen; $R^3$ is $CH_2Ph$; X is oxygen; Y is $NR^7$; $R^7$ is methyl; n is 0; and the values of $R^4$ match those of the correspondingly numbered compounds of Table A1.

TABLE J52

Table J52 provides 352 compounds of formula (Ib) wherein $R^1$ is methyl; $R^2$ is fluoro; $R^3$ is $CH_2Ph$; X is oxygen; Y is $NR^7$; $R^7$ is methyl; n is 0; and the values of $R^4$ match those of the correspondingly numbered compounds of Table A1.

TABLE J53

Table J53 provides 352 compounds of formula (Ib) wherein $R^1$ is methyl; $R^2$ is chloro; $R^3$ is $CH_2Ph$; X is oxygen; Y is $NR^7$; $R^7$ is methyl; n is 0; and the values of $R^4$ match those of the correspondingly numbered compounds of Table A1.

TABLE J54

Table J54 provides 352 compounds of formula (Ib) wherein $R^1$ is methyl; $R^2$ is bromo; $R^3$ is $CH_2Ph$; X is oxygen; Y is $NR^7$; $R^7$ is methyl; n is 0; and die values of $R^4$ match those of the correspondingly numbered compounds of Table A1.

TABLE J55

Table J55 provides 352 compounds of formula (Ib) wherein $R^1$ is methyl; $R^2$ is cyano; $R^3$ is $CH_2Ph$; X is oxygen; Y is $NR^7$; $R^7$ is methyl; n is 0; and the values of $R^4$ match those of the correspondingly numbered compounds of Table A1.

TABLE J56

Table J56 provides 352 compounds of formula (Ib) wherein $R^1$ is ethyl; $R^2$ is hydrogen; $R^3$ is $CH_2Ph$; X is oxygen; Y is $NR^7$; $R^7$ is methyl; n is 0; and the values of $R^4$ match those of the correspondingly numbered compounds of Table A1.

TABLE J57

Table J57 provides 352 compounds of formula (Ib) wherein $R^1$ is ethyl; $R^2$ is fluoro; $R^3$ is $CH_2Ph$; X is oxygen; Y is $NR^7$; $R^7$ is methyl; n is 0; and the values of $R^4$ match those of the correspondingly numbered compounds of Table A1.

TABLE J58

Table J58 provides 352 compounds of formula (Ib) wherein $R^1$ is ethyl; $R^2$ is chloro; $R^3$ is $CH_2Ph$; X is oxygen;

TABLE J59

Table J59 provides 352 compounds of formula (Ib) wherein $R^1$ is ethyl; $R^2$ is bromo; $R^3$ is $CH_2Ph$; X is oxygen; Y is $NR^7$; $R^7$ is methyl; n is 0; and the values of $R^4$ match those of the correspondingly numbered compounds of Table A1.

TABLE J60

Table J60 provides 352 compounds of formula (Ib) wherein $R^1$ is ethyl; $R^2$ is cyano; $R^3$ is $CH_2Ph$; X is oxygen; Y is $NR^7$; $R^7$ is methyl; n is 0; and the values of $R^4$ match those of the correspondingly numbered compounds of Table A1.

TABLE J61

Table J61 provides 352 compounds of formula (Ia) wherein $R^1$ is methyl; $R^2$ is hydrogen; $R^3$ is $CH_2Ph$; X is oxygen; Y is $NR^7$; $R^7$ is methyl; n is 0; and the values of $R^4$ match those of the correspondingly numbered compounds of Table A1.

TABLE J62

Table J62 provides 352 compounds of formula (Ia) wherein $R^1$ is methyl; $R^2$ is fluoro; $R^3$ is $CH_2Ph$; X is oxygen; Y is $NR^7$; $R^7$ is methyl; n is 0; and the values of $R^4$ match those of the correspondingly numbered compounds of Table A1.

TABLE J63

Table J63 provides 352 compounds of formula (Ia) wherein $R^1$ is methyl; $R^2$ is chloro; $R^3$ is $CH_2Ph$; X is oxygen; Y is $NR^7$; $R^7$ is methyl; n is 0; and the values of $R^4$ match those of the correspondingly numbered compounds of Table A1.

TABLE J64

Table J64 provides 352 compounds of formula (Ia) wherein $R^1$ is methyl; $R^2$ is bromo; $R^3$ is $CH_2Ph$; X is oxygen; Y is $NR^7$; $R^7$ is methyl; n is 0; and the values of $R^4$ match those of the correspondingly numbered compounds of Table A1.

TABLE J65

Table J65 provides 352 compounds of formula (Ib) wherein $R^1$ is methyl; $R^2$ is cyano; $R^3$ is $CH_2Ph$; X is oxygen; Y is $NR^7$; $R^7$ is methyl; n is 0; and the values of $R^4$ match those of the correspondingly numbered compounds of Table A1.

TABLE J66

Table J66 provides 352 compounds of formula (Ia) wherein $R^1$ is ethyl; $R^2$ is hydrogen $R^3$ is $CH_2Ph$; X is oxygen; Y is $NR^7$; $R^7$ is methyl; n is 0; and the values of $R^4$ match those of the correspondingly numbered compounds of Table A1.

TABLE J67

Table J67 provides 352 compounds of formula (Ia) wherein $R^1$ is ethyl; $R^2$ is fluoro; $R^3$ is $CH_2Ph$; X is oxygen; Y is $NR^7$; $R^7$ is methyl; n is 0; and the values of $R^4$ match those of the correspondingly numbered compounds of Table A1.

TABLE J68

Table J68 provides 352 compounds of formula (Ia) wherein $R^1$ is ethyl; $R^2$ is chloro; $R^3$ is $CH_2Ph$; X is oxygen; Y is $NR^7$; $R^7$ is methyl; n is 0; and the values of $R^4$ match those of the correspondingly numbered compounds of Table A1.

TABLE J69

Table J69 provides 352 compounds of formula (Ia) wherein $R^1$ is ethyl; $R^2$ is bromo; $R^3$ is $CH_2Ph$; X is oxygen; Y is $NR^7$; $R^7$ is methyl; n is 0; and the values of $R^4$ match those of the correspondingly numbered compounds of Table A1.

TABLE J70

Table J70 provides 352 compounds of formula (Ia) wherein $R^1$ is ethyl; $R^2$ is cyano; $R^3$ is $CH_2Ph$; X is oxygen; Y is $NR^7$; $R^7$ is methyl; n is 0; and the values of $R^4$ match those of the correspondingly numbered compounds of Table A1.

TABLE K1

Table K1 provides 352 compounds of formula (Ia) wherein $R^1$ is methyl; $R^2$ is hydrogen; $R^3$ is $CH_2OCH_3$; X and Y are each oxygen; n is 0; and the values of $R^4$ match those of the correspondingly numbered compounds of Table A1.

TABLE K2

Table K2 provides 352 compounds of formula (Ia) wherein $R^1$ is methyl; $R^2$ is fluoro; $R^3$ is $CH_2OCH_3$; X and Y are each oxygen; n is 0; and the values of $R^4$ match those of the correspondingly numbered compounds of Table A1.

TABLE K3

Table K3 provides 352 compounds of formula (Ia) wherein $R^1$ is methyl; $R^2$ is chloro; $R^3$ is $CH_2OCH_3$; X and Y are each oxygen; n is 0; and the values of $R^4$ match those of the correspondingly numbered compounds of Table A1.

TABLE K4

Table K4 provides 352 compound of formula (Ia) wherein $R^1$ is methyl; $R^2$ is bromo; $R^3$ is $CH_2OCH_3$; X and Y are each oxygen; n is 0; and the values of $R^4$ match those of the correspondingly numbered compounds of Table A1.

TABLE K5

Table K5 provides 352 compounds of formula (Ia) wherein $R^1$ is methyl; $R^2$ is cyano; $R^3$ is $CH_2OCH_3$; X and Y are each oxygen; n is 0; and the values of $R^4$ match those of the correspondingly numbered compounds of Table A1.

TABLE K6

Table K6 provides 352 compounds of formula (Ia) wherein $R^1$ is ethyl; $R^2$ is hydrogen; $R^3$ is $CH_2OCH_3$; X and Y are each oxygen; n is 0; and the values of $R^4$ match those of the correspondingly numbered compounds of Table A1.

TABLE K7

Table K7 provides 352 compounds of formula (Ia) wherein $R^1$ is ethyl; $R^2$ is fluoro; $R^3$ is $CH_2OCH_3$; X and Y are each oxygen; n is 0; and the values of $R^4$ match those of the correspondingly numbered compounds of Table A1.

TABLE K8

Table K8 provides 352 compounds of formula (Ia) wherein $R^1$ is ethyl; $R^2$ is chloro; $R^3$ is $CH_2OCH_3$; X and Y are each oxygen; n is 0; and the values of $R^4$ match those of the correspondingly numbered compounds of Table A1.

TABLE K9

Table K9 provides 352 compounds of formula (Ia) wherein $R^1$ is ethyl; $R^2$ is bromo; $R^3$ is $CH_2OCH_3$; X and Y are each oxygen; n is 0; and the values of $R^4$ match those of the correspondingly numbered compounds of Table A1.

TABLE K10

Table K10 provides 352 compounds of formula (Ia) wherein $R^1$ is ethyl; $R^2$ is cyano; $R^3$ is $CH_2OCH_3$; X and Y are each oxygen; n is 0; and the values of $R^4$ match those of the correspondingly numbered compounds of Table A1.

TABLE K11

Table K11 provides 352 compounds of formula (Ia) wherein $R^1$ is methyl; $R^2$ is hydrogen; $R^3$ is $CH_2OCH_3$; X is oxygen; Y is sulphur; n is 0; and the values of $R^4$ match those of the correspondingly numbered compounds of Table A1.

TABLE K12

Table K12 provides 352 compounds of formula (Ia) wherein $R^1$ is methyl; $R^2$ is fluoro; $R^3$ is $CH_2OCH_3$; X is oxygen; Y is sulphur; n is 0; and the values of $R^4$ match those of the correspondingly numbered compounds of Table A1.

TABLE K13

Table K13 provides 352 compounds of formula (Ia) wherein $R^1$ is methyl; $R^2$ is chloro; $R^3$ is $CH_2OCH_3$; X is oxygen; Y is sulphur; n is 0; and the values of $R^4$ match those of the correpondingly numbered compounds of Table A1.

TABLE K14

Table K14 provides 352 compounds of formula (Ia) wherein $R^1$ is methyl; $R^2$ is bromo; $R^3$ is $CH_2OCH_3$; X is oxygen; Y is sulphur; n is 0; and the values of $R^4$ match those of the correspondingly numbered compounds of Table A1.

TABLE K15

Table K15 provides 352 compounds of formula (Ia) wherein $R^1$ is methyl; $R^2$ is cyano; $R^3$ is $CH_2OCH_3$; X is oxygen; Y is sulphur; n is 0; and the values of $R^4$ match those of the correspondingly numbered compounds of Table A1.

TABLE K16

Table K16 provides 352 compounds of formula (Ia) wherein $R^1$ is ethyl; $R^2$ is hydrogen; $R^3$ is $CH_2OCH_3$; X is oxygen; Y is sulphur; n is 0; and the values of $R^4$ match those of the correspondingly numbered compounds of Table A1.

TABLE K17

Table K17 provides 352 compounds of formula (Ia) wherein $R^1$ is ethyl; $R^2$ is fluoro; $R^3$ is $CH_2OCH_3$; X is oxygen; Y is sulphur; n is 0; and the values of $R^4$ match those of the correspondingly numbered compounds of Table A1.

TABLE K18

Table K18 provides 352 compounds of formula (Ia) wherein $R^1$ is ethyl; $R^2$ is chloro; $R^3$ is $CH_2OCH_3$; X is oxygen; Y is sulphur; n is 0; and the values of $R^4$ match those of the correspondingly numbered compounds of Table A1.

TABLE K19

Table K19 provides 352 compounds of formula (Ia) wherein $R^1$ is ethyl; $R^2$ is bromo; $R^3$ is $CH_2OCH_3$; X is oxygen; Y is sulphur; n is 0; and the values of $R^4$ match those of the correspondingly numbered compounds of Table A1.

TABLE K20

Table K20 provides 352 compounds of formula (Ia) wherein $R^1$ is ethyl; $R^2$ is cyano; $R^3$ is $CH_2OCH_3$; X is oxygen; Y is sulphur; n is 0; and the values of $R^4$ match those of the correspondingly numbered compounds of Table A1.

TABLE K21

Table K21 provides 352 compounds of formula (Ib) wherein $R^1$ is methyl; $R^2$ is hydrogen; $R^3$ is $CH_2OCH_3$; X and Y are each oxygen; n is 0; and the values of $R^4$ match those of the correspondingly numbered compounds of Table A1.

TABLE K22

Table K22 provides 352 compounds of formula (Ib) wherein $R^1$ is methyl; $R^2$ is fluoro; $R^3$ is $CH_2OCH_3$; X and Y are each oxygen; n is 0; and the values of $R^4$ match those of the correspondingly numbered compounds of Table A1.

TABLE K23

Table K23 provides 352 compounds of formula (Ib) wherein $R^1$ is methyl; $R^2$ is chloro; $R^3$ is $CH_2OCH_3$; X and Y are each oxygen; n is 0; and the values of $R^4$ match those of the correspondingly numbered compounds of Table A1.

TABLE K24

Table K24 provides 352 compounds of formula (Ib) wherein $R^1$ is methyl; $R^2$ is bromo; $R^3$ is $CH_2OCH_3$; X and Y are each oxygen; n is 0; and the values of $R^4$ match those of the correspondingly numbered compounds of Table A1.

TABLE K25

Table K25 provides 352 compounds of formula (Ib) wherein $R^1$ is methyl; $R^2$ is cyano; $R^3$ is $CH_2OCH_3$; X and Y are each oxygen; n is 0; and the values of $R^4$ match those of the correspondingly numbered compounds of Table A1.

TABLE K26

Table K26 provides 352 compounds of formula (Ib) wherein $R^1$ is ethyl; $R^2$ is hydrogen; $R^3$ is $CH_2OCH_3$; X and Y are each oxygen; n is 0; and the values of $R^4$ match those of the correspondingly numbered compounds of Table A1.

TABLE K27

Table K27 provides 352 compounds of formula (Ib) wherein $R^1$ is ethyl; $R^2$ is fluoro; $R^3$ is $CH_2OCH_3$; X and Y

TABLE K28

Table K28 provides 352 compounds of formula (Ib) wherein $R^1$ is ethyl; $R^2$ is chloro; $R^3$ is $CH_2OCH_3$; X and Y are each oxygen; n is 0; and the values of $R^4$ match those of the correpondingly numbered compounds of Table A1.

TABLE K29

Table K29 provides 352 compounds of formula (Ib) wherein $R^1$ is ethyl; $R^2$ is bromo; $R^3$ is $CH_2OCH_3$; X and Y are each oxygen; n is 0; and the values of $R^4$ match those of the correspondingly numbered compounds of Table A1.

TABLE K30

Table K30 provides 352 compounds of formula (Ib) wherein $R^1$ is ethyl; $R^2$ is cyano; $R^3$ is $CH_2OCH_3$; X and Y are each oxygen; n is 0; and the values of $R^4$ match those of the correspondingly numbered compounds of Table A1.

TABLE K31

Table K31 provides 352 compounds of formula (Ib) wherein $R^1$ is methyl; $R^2$ is hydrogen; $R^3$ is $CH_2OCH_3$; X is oxygen; Y is sulphur; n is 0; and the values of $R^4$ match those of the correspondingly numbered compounds of Table A1.

TABLE K32

Table K32 provides 352 compounds of formula (Ib) wherein $R^1$ is methyl; $R^2$ is fluoro; $R^3$ is $CH_2OCH_3$; X is oxygen; Y is sulphur; n is 0; and the values of $R^4$ match those of the correspondingly numbered compounds of Table A1.

TABLE K33

Table K33 provides 352 compounds of formula (Ib) wherein $R^1$ is methyl; $R^2$ is chloro; $R^3$ is $CH_2OCH_3$; X is oxygen; Y is sulphur; n is 0; and the values of $R^4$ match those of the correspondingly numbered compounds of Table A1.

TABLE 34

Table K34 provides 352 compounds of formula (Ib) wherein in $R^1$ is methyl; $R^2$ is bromo; $R^3$ is $CH_2OCH_3$; X is oxygen; Y is sulphur; n is 0; and the values of $R^4$ match those of the correspondingly numbered compounds of Table A1.

TABLE K35

Table K35 provides 352 compounds of formula (Ib) wherein $R^1$ is methyl; $R^2$ is cyano; $R^3$ is $CH_2OCH_3$; X is oxygen; Y is sulphur; n is 0; and the values of $R^4$ match those of the correspondingly numbered compounds of Table A1.

TABLE K36

Table K36 provides 352 compounds of formula (Ib) wherein $R^1$ is ethyl; $R^2$ is hydrogen; $R^3$ is $CH_2OCH_3$; X is oxygen; Y is sulphur; n is 0; and the values of $R^4$ match those of the correspondingly numbered compounds of Table A1.

TABLE K37

Table K37 provides 352 compounds of formula (Ib) wherein $R^1$ is ethyl; $R^2$ is fluoro; $R^3$ is $CH_2OCH_3$; X is oxygen; Y is sulphur; n is 0; and the values of $R^4$ match those of the correspondingly numbered compounds of Table A1.

TABLE K38

Table K38 provides 352 compounds of formula (Ib) wherein $R^1$ is ethyl; $R^2$ is chloro; $R^3$ is $CH_2OCH_3$; X is oxygen; Y is sulphur; n is 0; and the values of $R^4$ match those of the correspondingly numbered compounds of Table A1.

TABLE K39

Table K39 provides 352 compounds of formula (Ib) wherein $R^1$ is ethyl; $R^2$ is bromo; $R^3$ is $CH_2OCH_3$; X is oxygen; Y is sulphur; n is 0; and the values of $R^4$ match those of the correspondingly numbered compounds of Table A1.

TABLE K40

Table K40 provides 352 compounds of formula (Ib) wherein $R^1$ is ethyl; $R^2$ is cyano; $R^3$ is $CH_2OCH_3$; X is oxygen; Y is sulphur; n is 0; and the values of $R^4$ match those of the correspondingly numbered compounds of Table A1.

TABLE K41

Table K41 provides 352 compounds of formula (Ib) wherein $R^1$ is methyl; $R^2$ is hydrogen; $R^3$ is $CH_2OCH_3$; X is oxygen; Y is $NR^7$; $R^7$ is hydrogen; n is 0; and the values of $R^4$ match those of the correspondingly numbered compounds of Table A1.

TABLE K42

Table K42 provides 352 compounds of formula (Ib) wherein $R^1$ is methyl; $R^2$ is fluoro; $R^3$ is $CH_2OCH_3$; X is oxygen; Y is $NR^7$; $R^7$ is hydrogen; n is 0; and the values of $R^4$ match those of the correspondingly numberd compounds of Table A1.

TABLE K43

Table K43 provides 352 compounds of formula (Ib) wherein $R^1$ is methyl; $R^2$ is chloro; $R^3$ is $CH_2OCH_3$; X is oxygen; Y is $NR^7$; $R^7$ is hydrogen; n is 0; and the values of $R^4$ match those of the correspondingly numbered compounds of Table A1.

TABLE K44

Table K44 provides 352 compounds of formula (Ib) wherein $R^1$ is methyl; $R^2$ is bromo; $R^3$ is $CH_2OCH_3$; X is oxygen; Y is $NR^7$; $R^7$ is hydrogen; n is 0; and the values of $R^4$ match those of the correspondingly numbered compounds of Table A1.

TABLE K45

Table K45 provides 352 compounds of formula (Ib) wherein $R^1$ is methyl; $R^2$ is cyano; $R^3$ is $CH_2OCH_3$; X is oxygen; Y is $NR^7$; $R^7$ is hydrogen; n is 0; and the values of $R^4$ match those of the correspondingly numbered compounds of Table A1.

TABLE K46

Table K46 provides 352 compounds of formula (Ib) wherein $R^1$ is ethyl; $R^2$ is hydrogen; $R^3$ is $CH_2OCH_3$; X is oxygen; Y is NR⁷; R⁷ is hydrogen; n is 0; and the values of R⁴ match those of the correspondingly numbered compounds of Table A1.

TABLE K47

Table K47 provides 352 compounds of formula (Ib) wherein R¹ is ethyl; R² is fluoro; R³ is CH₂OCH₃; X is oxygen; Y is NR⁷; R⁷ is hydrogen; n is 0; and the values of R⁴ match those of the correspondingly numbered compounds of Table A1.

TABLE K48

Table K48 provides 352 compound of formula (Ib) wherein R¹ is ethyl; R² is chloro; R³ is CH₂OCH₃; X is oxygen; Y is NR⁷; R⁷ is hydrogen; n is 0; and the values of R⁴ match those of the correspondingly numbered compounds of Table A1.

TABLE K49

Table K49 provides 352 compounds of formula (Ib) wherein R¹ is ethyl; R² is bromo; R³ is CH₂OCH₃; X is oxygen; Y is NR⁷; R⁷ is hydrogen; n is 0; and the values of R⁴ match those of the correspondingly numbered compounds of Table A1.

TABLE K50

Table K50 provides 352 compounds of formula (Ib) wherein R¹ is ethyl; R² is cyano; R³ is CH₂OCH₃; X is oxygen; Y is NR⁷; R⁷ is hydrogen; n is 0; and the values of R⁴ match those of the correspondingly numbered compounds of Table A1.

Table K51 provides 352 compounds of formula (Ib) wherein R¹ is methyl; R² is hydrogen; R³ is CH₂OCH₃; X is oxygen; Y is NR⁷; R⁷ is methyl; n is 0; and the values of R⁴ match those of the correspondingly numbered compounds of Table A1.

TABLE K52

Table K52 provides 352 compounds of formula (Ib) wherein R¹ is methyl; R² is fluoro; R³ is CH₂OCH₃; X is oxygen; Y is NR⁷; R⁷ is methyl; n is 0; and the values of R⁴ match those of the correspondingly numbered compounds of Table A1.

TABLE K53

Table K53 provides 352 compounds of formula (Ib) wherein R¹ is methyl; R² is chloro; R³ is CH₂OCH₃; X is oxygen; Y is NR⁷; R⁷ is methyl; n is 0; and the values of R⁴ match those of the correspondingly numbered compounds of Table A1.

TABLE K54

Table K54 provides 352 compounds of formula (Ib) wherein R¹ is methyl; R² is bromo; R³ is CH₂OCH₃; X is oxygen; Y is NR⁷; R⁷ is methyl; n is 0; and the values of R⁴ match those of the correspondingly numbered compounds of Table A1.

TABLE K55

Table K55 provides 352 compounds of formula (Ib) wherein R¹ is methyl; R² is cyano; R³ is CH₂OCH₃; X is oxygen; Y is NR⁷; R⁷ is methyl; n is 0; and the values of R⁴ match those of the correspondingly numbered compounds of Table A1.

TABLE K56

Table K56 provides 352 compounds of formula (Ib) wherein R¹ is ethyl; R² is hydrogen; R³ is CH₂OCH₃; X is oxygen; Y is NR⁷; R⁷ is methyl; n is 0; and the values of R⁴ match those of the correpondingly numbered compounds of Table A1.

TABLE K57

Table K57 provides 352 compounds of formula (Ib) wherein R¹ is ethyl; R² is fluoro; R³ is CH₂OCH₃; X is oxygen; Y is NR⁷; R⁷ is methyl; n is 0; and the values of R⁴ match those of the correspondingly numbered compounds of Table A1.

TABLE K58

Table K58 provides 352 compounds of formula (Ib) wherein R¹ is ethyl; R² is chloro; R³ is CH₂OCH₃; X is oxygen; Y is NR⁷; R⁷ is methyl; n is 0; and the values of R⁴ match those of the correspondingly numbered compounds of Table A1.

TABLE K59

Table K59 provides 352 compounds of formula (Ib) wherein R¹ is ethyl; R² is bromo; R³ is CH₂OCH₃; X is oxygen; Y is NR⁷; R⁷ is methyl; n is 0; and the values of R⁴ match those of the correspondingly numbered compounds of Table A1.

TABLE K60

Table K60 provides 352 compounds of formula (Ib) wherein R¹ is ethyl; R² is cyano; R³ is CH₂OCH₃; X is oxygen; Y is NR⁷; R⁷ is methyl; n is 0; and the values of R⁴ match those of the correspondingly numbered compounds of Table A1.

TABLE K61

Table K61 provides 352 compounds of formula (Ia) wherein R¹ is methyl; R² is hydrogen; R³ is CH₂OCH₃; X is oxygen; Y is NR⁷; R⁷ is methyl; n is 0; and the values of R⁴ match those of the correspondingly numbered compounds of Table A1.

TABLE K62

Table K62 provides 352 compounds of formula (Ia) wherein R¹ is methyl; R² is fluoro; R³ is CH₂OCH₃; X is oxygen; Y is NR⁷; R⁷ is methyl; n is 0; and the values of R⁴ match those of the correspondingly numbered compounds of Table A1.

TABLE K63

Table K63 provides 352 compounds of formula (Ia) wherein R¹ is methyl; R² is chloro; R³ is CH₂OCH₃; X is oxygen; Y is NR⁷; R⁷ is methyl; n is 0; and the values of R⁴ match those of the correspondingly numbered compounds of Table A1.

TABLE K64

Table K64 provides 352 compounds of formula (Ia) wherein R¹ is methyl; R² is bromo; R³ is CH₂OCH₃; X is oxygen; Y is NR⁷; R⁷ is methyl; n is 0; and the values of R⁴ match those of the correspondingly numbered compounds of Table A1.

TABLE K65

Table K65 provides 352 compounds of formula (Ib) wherein R¹ is methyl; R² is cyano; R³ is CH₂OCH₃; X is oxygen; Y is NR⁷; R⁷ is methyl; n is 0; and the values of R⁴ match those of the correpondingly numbered compounds of Table A1.

TABLE K66

Table K66 provides 352 compounds of formula (Ia) wherein R¹ is ethyl; R² is hydrogen; R³ is CH₂OCH₃; X is oxygen; Y is NR⁷; R⁷ is methyl; n is 0; and the values of R⁴ match those of the correspondingly numbered compounds of Table A1.

TABLE K67

Table K67 provides 352 compounds of formula (Ia) wherein R¹ is ethyl; R² is fluoro; R³ is CH₂OCH₃; X is oxygen; Y is NR⁷; R⁷ is methyl; n is 0; and the values of R⁴ match those of the correspondingly numbered compounds of Table A1.

TABLE K68

Table K68 provides 352 compounds of formula (Ia) wherein R¹ is ethyl; R² is chloro; R³ is CH₂OCH₃; X is oxygen; Y is NR⁷; R⁷ is methyl; n is 0; and the values of R⁴ match those of the correspondingly numbered compounds of Table A1.

TABLE K69

Table K69 provides 352 compounds of formula (Ia) wherein R¹ is ethyl; R² is bromo; R³ is CH₂OCH₃; X is oxygen; Y is NR⁷; R⁷ is methyl; n is 0; and the values of R⁴ match those of the correspondingly numbered compounds of Table A1.

TABLE K70

Table K70 provides 352 compounds of formula (Ia) wherein R¹ is ethyl; R² is cyano; R³ is CH₂OCH₃; X is oxygen; Y is NR⁷; R⁷ is methyl; n is 0; and the values of R⁴ match those of the correspondingly numbered compounds of Table A1.

TABLE L1

Table L1 provides 352 compounds of formula (Ia) wherein R¹ is methyl; R² is hydrogen; R³ is CH₂OCH₂CH₃; X and Y are each oxygen; n is 0; and the values of R⁴ match those of the correspondingly numbered compounds of Table A1.

TABLE L2

Table L2 provides 352 compounds of formula (Ia) wherein R¹ is methyl; R² is fluoro; R³ is CH₂OCH₂CH3; X and Y are each oxygen; n is 0; and the values of R⁴ match those of the correspondingly numbered compounds of Table A1.

TABLE L3

Table L3 provides 352 compounds of formula (Ia) wherein R¹ is methyl; R² is chloro; R³ is CH₂OCH₂CH₃; X and Y are each oxygen; n is 0; and the values of R⁴ match those of the correspondingly numbered compounds of Table A1.

TABLE L4

Table L4 provides 352 compounds of formula (Ia) wherein R¹ is methyl; R² is bromo; R³ is CH₂OCH₂CH₃; X and Y are each oxygen; n is 0; and the values of R⁴ match those of the correspondingly numbered compounds of Table A1.

TABLE L5

Table L5 provides 352 compounds of formula (Ia) wherein R¹ is methyl; R² is cyano; R³ is CH₂OCH₂CH₃; X and Y are each oxygen; n is 0; and the values of R⁴ match those of the correspondingly numbered compounds of Table A1.

TABLE L6

Table L6 provides 352 compounds of formula (Ia) wherein R¹ is ethyl; R² is hydrogen; R³ is CH₂OCH₂CH₃; X and Y are each oxygen; n is 0; and the values of R⁴ match those of the correspondingly numbered compounds of Table A1.

TABLE L7

Table L7 provides 352 compounds of formula (Ia) wherein R¹ is ethyl; R² is fluoro; R³ is CH₂OCH₂CH₃; X and Y are each oxygen; n is 0; and the values of R⁴ match those of the correspondingly numbered compounds of Table A1.

TABLE L8

Table L8 provides 352 compounds of formula (Ia) wherein R¹ is ethyl; R² is chloro; R² is CH₂OCH₂CH₃; X and Y are each oxygen; n is 0; and the values of R⁴ match those of the correspondingly numbered compounds of Table A1.

TABLE L9

Table L9 provides 352 compounds of formula (Ia) wherein R¹ is ethyl; R² is bromo; R³ is CH₂OCH₂CH₃; X and Y are each oxygen; n is 0; and the values of R⁴ match those of the correspondingly numbered compounds of Table A1.

TABLE L10

Table L10 provides 352 compounds of formula (Ia) wherein R¹ is ethyl; R² is cyano R³ is CH₂OCH₂CH₃; X and Y are each oxygen; n is 0; and the values of R⁴ match those of the correspondingly numbered compounds of Table A1.

TABLE L11

Table L11 provides 352 compounds of formula (Ia) Wherein R¹ is methyl; R² is hydrogen; R³ is CH₂OCH₂CH₃; X is oxygen; Y is sulphur; n is 0; and the values of R⁴ match those of the correspondingly numbered compounds of Table A1.

TABLE L12

Table L12 provides 352 compounds of formula (Ia) wherein R¹ is methyl; R² is fluoro; R³ is CH₂OCH₂CH₃; X is oxygen; Y is sulphur; n is 0; and the values of R⁴ match those of the correspondingly numbered compounds of Table A1.

TABLE L13

Table L13 provides 352 compounds of formula (Ia) wherein R¹ is methyl; R² is chloro; R³ is CH₂OCH₂CH₃; X is oxygen; Y is sulphur; n is 0; and the values of R⁴ match those of the correspondingly numbered compounds of Table A1.

TABLE L14

Table L14 provides 352 compounds of formula (Ia) wherein $R^1$ is methyl; $R^2$ is bromo; $R^3$ is $CH_2OCH_2CH_3$; X is oxygen; Y is sulphur; n is 0; and the values of $R^4$ match those of the correspondingly numbered compounds of Table A1.

TABLE L15

Table L15 provides 352 compounds of formula (Ia) wherein $R^1$ is methyl; $R^2$ is cyano; $R^3$ is $CH_2OCH_2CH_3$; X is oxygen; Y is sulphur; n is 0; and the values of $R^4$ match those of the correspondingly numbered compounds of Table A1.

TABLE L16

Table L16 provides 352 compounds of formula (Ia) wherein $R^1$ is ethyl; $R^2$ is hydrogen; $R^3$ is $CH_2OCH_2CH_3$; X is oxygen; Y; is sulphur; n is 0; and the values of $R^4$ match those of the correspondingly numbered compounds of Table A1.

TABLE L17

Table L17 provides 352 compounds of formula (Ia) wherein $R^1$ is ethyl; $R^2$ is fluoro; $R^3$ is $CH_2OCH_2CH_3$; X is oxygen; Y is sulphur; n is 0; and the values of $R^4$ match those of the correspondingly numbered compounds of Table A1.

TABLE L18

Table L18 provides 352 compounds of formula (Ia) wherein $R^1$ is ethyl; $R^2$ is chloro; $R^3$ is $CH_2OCH_2CH_3$; X is oxygen; Y is sulphur; n is 0; and the values of $R^4$ match those of the correspondingly numbered compounds of Table A1.

TABLE L19

Table L19 provides 352 compounds of formula (Ia) wherein $R^1$ is ethyl; $R^2$ is bromo; $R^3$ is $CH_2OCH_2CH_3$; X is oxygen; Y is sulphur; n is 0; and the values of $R^4$ match those of the correspondingly numbered compounds of Table A1.

TABLE L20

Table L20 provides 352 compounds of formula (Ia) wherein $R^1$ is ethyl; $R^2$ is cyano; $R^3$ is $CH_2OCH_2CH_3$; X is oxygen; Y is sulphur; n is 0; and the values of $R^4$ match those of the correspondingly numbered compounds of Table A1.

TABLE L21

Table L21 provides 352 compounds of formula (Ib) wherein $R^1$ is methyl; $R^2$ is hydrogen; $R^3$ is $CH_2OCH_2CH_3$; X and Y are each oxygen; n is 0; and the values of $R^4$ match those of the correspondingly numbered compounds of Table A1.

TABLE L22

Table L22 provides 352 compounds of formula (Ib) wherein $R^1$ is methyl; $R^2$ is fluoro; $R^3$ is $CH_2OCH_2CH_3$; X and Y are each oxygen; n is 0; and the values of $R^4$ match those of the correspondingly numbered compounds of Table A1.

TABLE L23

Table L23 provides 352 compounds of formula (Ib) wherein $R^1$ is methyl; $R^2$ is chloro; $R^3$ is $CH_2OCH_2CH_3$; X and Y are each oxygen; n is 0; and the values of $R^4$ match those of the correspondingly numbered compounds of Table A1.

TABLE L24

Table L24 provides 352 compounds of formula (Ib) wherein $R^1$ is methyl; $R^2$ is bromo; $R^3$ is $CH_2OCH_2CH_3$; X and Y are each oxygen; n is 0; and the values of $R^4$ match those of the correspondingly numbered compounds of Table A1.

TABLE L25

Table L25 provides 352 compounds of formula (Ib) wherein $R^1$ is methyl; $R^2$ is cyano; $R^3$ is $CH_2OCH_2CH_3$; X and Y are each oxygen; n is 0; and the values of $R^4$ match those of the correspondingly numbered compounds of Table A1.

TABLE L26

Table L26 provides 352 compounds of formula (Ib) wherein $R^1$ is ethyl; $R^2$ is hydrogen; $R^3$ is $CH_2OCH_2CH_3$; X and Y are each oxygen; n is 0; and the values of $R^4$ match those of the correspondingly numbered compounds of Table A1.

TABLE L27

Table L27 provides 352 compounds of formula (Ib) wherein $R^1$ is ethyl; $R^2$ is fluoro; $R^3$ is $CH_2OCH_2CH_3$; X and Y are each oxygen; n is 0; and the values of $R^4$ match those of the correspondingly numbered compounds of Table A1.

TABLE L28

Table L28 provides 352 compounds of formula (Ib) wherein $R^1$ is ethyl; $R^2$ is chloro; $R^3$ is $CH_2OCH_2CH_3$; X and Y are each oxygen; n is 0; and the values of $R^4$ match those of the correspondingly numbered compounds of Table A1.

TABLE L29

Table L29 provides 352 compounds of formula (Ib) wherein $R^1$ is ethyl; $R^2$ is bromo; $R^3$ is $CH_2OCH_2CH_3$; X and Y are each oxygen; n is 0; and the values of $R^4$ match those of the is correspondingly numbered compounds of Table A1.

TABLE L30

Table L30 provides 352 compounds of formula (Ib) wherein $R^1$ is ethyl; $R^2$ is cyano; $R^3$ is $CH_2OCH_2CH_3$; X and Y are each oxygen; n is 0; and the values of $R^4$ match those of the correspondingly numbered compounds of Table A1.

TABLE L31

Table L31 provides 352 compounds of formula (Ib) wherein $R^1$ is methyl; $R^2$ is hydrogen; $R^3$ is $CH_2OCH_2CH_3$; X is oxygen; Y is sulphur; n is 0; and the values of $R^4$ match those of the correspondingly numbered compounds of Table A1.

TABLE L32

Table L32 provides 352 compounds of formula (Ib) wherein $R^1$ is methyl; $R^2$ is fluoro; $R^3$ is $CH_2OCH_2CH_3$; X is oxygen; Y is sulphur; n is 0; and the values of $R^4$ match those of the correspondingly numbered compounds of Table A1.

TABLE L33

Table L33 provides 352 compounds of formula (Ib) wherein $R^1$ is methyl; $R^2$ is chloro; $R^3$ is $CH_2OCH_2CH_3$; X is oxygen; Y is sulphur; n is 0; and the values of $R^4$ match those of the correspondingly numbered compounds of Table A1.

TABLE L34

Table L34 provides 352 compounds of formula (Ib) wherein $R^1$ is methyl; $R^2$ is bromo; $R^3$ is $CH_2OCH_2CH_3$; X is oxygen; Y is sulphur; n is 0; and the values of $R^4$ match those of the correspondingly numbered compounds of Table A1.

TABLE L35

Table L35 provides 352 compounds of formula (Ib) wherein $R^1$ is methyl; $R^2$ is cyano; $R^3$ is $CH_2OCH_2CH_3$; X is oxygen; Y is sulphur; n is 0; and the values of $R^4$ match those of the correspondingly numbered compounds of Table A1.

TABLE L36

Table L36 provides 352 compounds of formula (Ib) wherein $R^1$ is ethyl; $R^2$ is hydrogen; $R^3$ is $CH_2OCH_2CH_3$; X is oxygen; Y is sulphur; n is 0; and the values of $R^4$ match those of the correspondingly numbered compounds of Table A1.

TABLE L37

Table L37 provides 352 compounds of formula (Ib) wherein $R^1$ is ethyl; $R^2$ is fluoro; $R^3$ is $CH_2OCH_2CH_3$; X is oxygen; Y is sulphur; n is 0; and the values of $R^4$ match those of the correspondingly numbered compounds of Table A1.

TABLE L38

Table L38 provides 352 compounds of formula (Ib) wherein $R^1$ is ethyl; $R^2$ is chloro; $R^3$ is $CH_2OCH_2CH_3$; X is oxygen; Y is sulphur; n is 0; and the values of $R^4$ match those of the correspondingly numbered compounds of Table A1.

TABLE L39

Table L39 provides 352 compounds of formula (Ib) wherein $R^1$ is ethyl; $R^2$ is bromo; $R^3$ is $CH_2OCH_2CH_3$; X is oxygen; Y is sulphur; n is 0; and the values of $R^4$ match those of the correpondingly numbered compounds of Table A1.

TABLE L40

Table L40 provides 352 compounds of formula (Ib) wherein $R^1$ is ethyl; $R^2$ is cyano; $R^3$ is $CH_2OCH_2CH_3$; X is oxygen; Y is sulphur; n is 0; and the values of $R^4$ match those of the correspondingly numbered compounds of Table A1.

TABLE L41

Table L41 provides 352 compounds of formula (Ib) wherein $R^1$ is methyl; $R^2$ is hydrogen; $R^3$ is $CH_2OCH_2CH_3$; X is oxygen; Y is $NR^7$; $R^7$ is hydrogen; n is 0; and the values of $R^4$ match those of the correspondingly numbered compounds of Table A1.

TABLE LA42

Table L42 provides 352 compounds of formula (Ib) wherein $R^1$ is methyl; $R^2$ is fluoro; $R^3$ is $CH_2OCH_2CH_3$; X is oxygen; Y is $NR^7$; $R^7$ is hydrogen; n is 0; and the values of $R^4$ match those of the correspondingly numbered compounds of Table A1.

TABLE L43

Table L43 provides 352 compounds of formula (Ib) wherein $R^1$ is methyl; $R^2$ is chloro; $R^3$ is $CH_2OCH_2CH_3$; X is oxygen; Y is $NR^7$; $R^7$ is hydrogen; n is 0; and the values of $R^4$ match those of the correspondingly numbered compounds of Table A1.

TABLE L44

Table L44 provides 352 compounds of formula (Ib) wherein $R^1$ is methyl; $R^2$ is bromo; $R^3$ is $CH_2OCH_2CH_3$; X is oxygen; Y is $NR^7$; $R^7$ is hydrogen; n is 0; and the values of $R^4$ match those of the correspondingly numbered compounds of Table A1.

TABLE L45

Table L45 provides 352 compounds of formula (Ib) wherein $R^1$ is methyl; $R^2$ is cyano; $R^3$ is $CH_2OCH_2CH_3$; X is oxygen; Y is $NR^7$; $R^7$ is hydrogen; n is 0; and the values of $R^4$ match those of the correspondingly numbered compounds of Table A1.

TABLE L46

Table L46 provides 352 compounds of formula (Ib) wherein $R^1$ is ethyl; $R^2$ is hydrogen; $R^3$ is $CH_2OCH_2CH_3$; X is oxygen; Y is $NR^7$; $R^7$ is hydrogen; n is 0; and the values of $R^4$ match those of the correspondingly numbered compounds of Table A1.

TABLE L47

Table L47 provides 352 compounds of formula (Ib) wherein $R^1$ is ethyl; $R^2$ is fluoro; $R^3$ is $CH_2OCH_2CH_3$; X is oxygen; Y is $NR^7$; $R^7$ is hydrogen; n is 0; and the values of $R^4$ match those of the correspondingly numbered compounds of Table A1.

TABLE L48

Table L48 provides 352 compounds of formula (Ib) wherein $R^1$ is ethyl; $R^2$ is chloro; $R^3$ is $CH_2OCH_2CH_3$; X is oxygen; Y is $NR^7$; $R^7$ is hydrogen; n is 0; and the values of $R^4$ match those of the correspondingly numbered compounds of Table A1.

TABLE L49

Table L49 provides 352 compounds of formula (Ib) wherein $R^1$ is ethyl; $R^2$ is bromo; $R^3$ is $CH_2OCH_2CH_3$; X is oxygen; Y is $NR^7$; $R^7$ is hydrogen; n is 0; and the values of $R^4$ match those of the correspondingly numbered compounds of Table A1.

TABLE L50

Table L50 provides 352 compounds of formula (Ib) wherein $R^1$ is ethyl; $R^2$ is cyano; $R^3$ is $CH_2OCH_2CH_3$; X is oxygen; Y is NR$^7$; R$^7$ is hydrogen; n is 0; and the values of R$^4$ match those of the correspondingly numbered compounds of Table A1.

TABLE L51

Table L51 provides 352 compounds of formula (Ib) wherein R$^1$ is methyl; R$^2$ is hydrogen; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L52

Table L52 provides 352 compounds of formula (Ib) wherein R$^1$ is methyl; R$^2$ is fluoro; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L53

Table L53 provides 352 compounds of formula (Ib) wherein R$^1$ is methyl; R$^2$ is chloro; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L54

Table L54 provides 352 compounds of formula (Ib) wherein R$^1$ is methyl; R$^2$ is bromo; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L55

Table L55 provides 352 compounds of formula (Ib) wherein R$^1$ is methyl; R$^2$ is cyano; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L56

Table L56 provides 352 compounds of formula (Ib) wherein R$^1$ is ethyl; R$^2$ is hydrogen; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L57

Table L57 provides 352 compounds of formula (Ib) wherein R$^1$ is ethyl; R$^2$ is fluoro; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L58

Table L58 provides 352 compounds of formula (Ib) wherein R$^1$ is ethyl; R$^2$ is chloro; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L59

Table L59 provides 352 compounds of formula (Ib) wherein R$^1$ is ethyl; R$^2$ is bromo; R$^3$ is CH$_2$OCH$_2$CH$_3$; X is oxygen; Y is NR$^7$; R$^7$ is methyl n is 0; and the values of R$^4$ match those of the correspondingly numbered compounds of Table A1.

TABLE L60

Table L60 provides 352 compounds of formula (Ib) wherein R$^1$ is ethyl; R$^2$ is cyano; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L61

Table L61 provides 352 compounds of formula (Ia) wherein R$^1$ is methyl; R$^2$ is hydrogen; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L62

Table L62 provides 352 compounds of formula (Ia) wherein R$^1$ is methyl; R$^2$ is fluoro; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLED L63

Table L63 provides 352 compounds of formula (Ia) wherein R$^1$ is methyl; R$^2$ is chloro; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L64

Table L64 provides 352 compounds of formula (Ia) wherein R$^1$ is methyl; R$^2$ is bromo; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L65

Table L65 provides 352 compounds of formula (Ib) wherein R$^1$ is methyl; R$^2$ is cyano; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L66

Table L66 provides 352 compounds of formula (Ia) wherein R$^1$ is ethyl; R$^2$ is hydrogen; R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L67

Table L67 provides 352 compounds of formula (Ia) wherein R$^1$ is ethyl; R$^2$ is fluoro; is R$^3$ is CH$_2$OCH$_2$CH$_3$; X is oxygen; Y is NR$^7$; R$^7$ is methyl; n is 0; and the values of R$^4$ match those of the correspondingly numbered compounds of Table A1.

TABLE L68

Table L68 provides 352 compounds of formula (Ia) wherein R$^1$ is ethyl; R$^2$ is chloro; R$^3$ is CH$_2$OCH$_2$CH$_3$; X is oxygen; Y is $NR^7$; $R^7$ is methyl; n is 0; and the values of $R^4$ match those of the correspondingly numbered compounds of Table A1.

TABLE L69

Table L69 provides 352 compounds of formula (Ia) wherein $R^1$ is ethyl; $R^2$ is bromo; $R^3$ is $CH_2OCH_2CH_3$; X is oxygen; Y is $NR^7$; $R^7$ is methyl; n is 0; and the values of $R^4$ match those of the correspondingly numbered compounds of Table A1.

TABLE L70

Table L70 provides 352 compounds of formula (Ia) wherein $R^1$ is ethyl; $R^2$ is cyano; $R^3$ is $CH_2OCH_2CH_3$; X is oxygen; Y is $NR^7$; $R^7$ is methyl; n is 0; and the values of $R^4$ match those of the correspondingly numbered compounds of Table A1.

TABLE M1

Table M1 provides 352 compounds of formula (Ia) wherein $R^1$ is methyl; $R^2$ is hydrogen; $R^3$ is $CH_2OCH_2CH_2OCH_3$; X and Y are each oxygen; n is 0; and the values of $R^4$ match those of the correspondingly numbered compounds of Table A1.

TABLE M2

Table M2 provides 352 compounds of formula (Ia) wherein $R^1$ is methyl; $R^2$ is fluoro; $R^3$ is $CH_2OCH_2CH_2OCH_3$; X and Y are each oxygen; n is 0; and the values of $R^4$ match those of the correspondingly numbered compounds of Table A1.

TABLE M3

Table M3 provides 352 compounds of formula (Ia) wherein $R^1$ is methyl; $R^2$ is chloro; $R^3$ is $CH_2OCH_2CH_2OCH_3$; X and Y are each oxygen; n is 0; and the values of $R^4$ match those of the correspondingly numbered compounds of Table A1.

TABLE M4

Table M4 provides 352 compounds of formula (Ia) wherein $R^1$ is methyl; $R^2$ is bromo; $R^3$ is $CH_2OCH_2CH_2OCH_3$; X and Y are each oxygen; n is 0; and the values of $R^4$ match those of the correspondingly numbered compounds of Table A1.

TABLE M5

Table M5 provides 352 compounds of formula (Ia) wherein $R^1$ is methyl; $R^2$ is cyano; $R^3$ is $CH_2OCH_2CH_2OCH_3$; X and Y are each oxygen; n is 0; and the values of $R^4$ match those of the correspondingly numbered compounds of Table A1.

TABLE M6

Table M6 provides 352 compounds of formula (Ia) wherein $R^1$ is ethyl; $R^2$ is hydrogen; $R^3$ is $CH_2OCH_2CH_2OCH_3$; X and Y are each oxygen; n is 0; and the values of $R^4$ match those of the correspondingly numbered compounds of Table A1.

TABLE M7

Table M7 provides 352 compounds of formula (Ia) wherein $R^1$ is ethyl; $R^2$ is fluoro; $R^3$ is $CH_2OCH_2CH_2OCH_3$; X and Y are each oxygen; n is 0; and the values of $R^4$ of the correspondingly numbered compounds of Table A1.

TABLE M8

Table M8 provides 352 compounds of formula (Ia) wherein $R^1$ is ethyl; $R^2$ is chloro; $R^3$ is $CH_2OCH_2CH_2OCH_3$; X and Y are each oxygen; n is 0; and the values of $R^4$ match those of the correspondingly numbered compounds of Table A1.

TABLE M9

Table M9 provides 352 compounds of formula (Ia) wherein $R^1$ is ethyl; $R^2$ is bromo; $R^3$ is $CH_2OCH_2CH_2OCH_3$; X and Y are each oxygen; n is 0; and the values of $R^4$ match those of the correspondingly numbered compounds of Table A1.

TABLE M10

Table M10 provides 352 compounds of formula (Ia) wherein $R^1$ is ethyl; $R^2$ is cyano; $R^3$ is $CH_2OCH_2CH_2OCH_3$; X and Y are each oxygen; n is 0; and the values of $R^4$ match those of the correspondingly numbered compounds of Table A1.

TABLE M11

Table M11 provides 352 compounds of formula (Ia) wherein $R^1$ is methyl; $R^2$ is hydrogen; $R^3$ is $CH_2OCH_2CH_2OCH_3$; X is oxygen; Y is sulphur; n is 0; and the values of $R^4$ match those of the correspondingly numbered compounds of Table A1.

TABLE M12

Table M12 provides 352 compounds of formula (Ia) wherein $R^1$ is methyl; $R^2$ is fluoro; $R^3$ is $CH_2OCH_2CH_2OCH_3$; X is oxygen; Y is sulphur; n is 0; and the values of $R^4$ match those of the correspondingly numbered compounds of Table A1.

TABLE M13

Table M13 provides 352 compounds of formula (Ia) wherein $R^1$ is methyl; $R^2$ is chloro; $R^3$ is $CH_2OCH_2CH_2OCH_3$; X is oxygen; Y is sulphur; n is 0; and the values of $R^4$ match those of the correspondingly numbered compounds of Table A1.

TABLE M14

Table M14 provides 352 compounds of formula (Ia) wherein $R^1$ is methyl; $R^2$ is bromo; $R^3$ is $CH_2OCH_2CH_2OCH_3$; X is oxygen; Y is sulphur; n is 0; and the values of $R^4$ match those of the correspondingly numbered compounds of Table A1.

TABLE M15

Table M15 provides 352 compounds of formula (Ia) wherein $R^1$ is methyl; $R^2$ is cyano; $R^3$ is $CH_2OCH_2CH_2OCH_3$; X is oxygen; Y is sulphur; n is 0; and the values of $R^4$ match those of the correspondingly numbered compounds of Table A1.

TABLE M16

Table M16 provides 352 compounds of formula (Ia) wherein $R^1$ is ethyl; $R^2$ is hydrogen; $R^3$ is $CH_2OCH_2CH_2OCH_3$; X is oxygen; Y is sulphur; n is 0; and

TABLE M17

Table M17 provides 352 compounds of formula (Ia) wherein $R^1$ is ethyl; $R^2$ is fluoro; $R^3$ is $CH_2OCH_2CH_2OCH_3$; X is oxygen; Y is sulphur; n is 0; and the values of $R^4$ match those of the correspondingly numbered compounds of Table A1.

TABLE M18

Table M18 provides 352 compounds of formula (Ia) wherein $R^1$ is ethyl; $R^2$ is chloro; $R^3$ is $CH_2OCH_2CH_2OCH_3$; X is oxygen; Y is sulphur; n is 0; and the values of $R^4$ match those of the correspondingly numbered compounds of Table A1.

TABLE M19

Table M19 provides 352 compounds of formula (Ia) wherein $R^1$ is ethyl; $R^2$ is bromo; $R^3$ is $CH_2OCH_2CH_2OCH_3$; X is oxygen; Y is sulphur; n is 0; and the values of $R^4$ match those of the correspondingly numbered compounds of Table A1.

TABLE M20

Table M20 provides 352 compounds of formula (Ia) wherein $R^1$ is ethyl; $R^2$ is cyano; $R^3$ is $CH_2OCH_2CH_2OCH_3$; X is oxygen; Y is sulphur; n is 0; and the values of $R^4$ match those of the correspondingly numbered compounds of Table A1.

TABLE M21

Table M21 provides 352 compounds of formula (Ib) wherein $R^1$ is methyl; $R^2$ is hydrogen; $R^3$ is $CH_2OCH_2CH_2OCH_3$; X and Y are each oxygen; n is 0; and the values of $R^4$ match those of the correspondingly numbered compounds of Table A1.

TABLE M22

Table M22 provides 352 compounds of formula (Ib) wherein $R^1$ is methyl; $R^2$ is fluoro; $R^3$ is $CH_2OCH_2CH_2OCH_3$; X and Y are each oxygen; n is 0; and the values of $R^4$ match those of the correspondingly numbered compounds of Table A1.

TABLE M23

Table N23 provides 352 compounds of formula (Ib) wherein $R^1$ is methyl; $R^2$ is chloro; $R^3$ is $CH_2OCH_2CH_2OCH_3$; X and Y are each oxygen; n is 0; and the values of $R^4$ match those of the correspondingly numbered compounds of Table A1.

TABLE M24

Table M24 provides 352 compounds of formula (Ib) wherein $R^1$ is methyl; $R^2$ is bromo; $R^3$ is $CH_2OCH_2CH_2OCH_3$; X and Y are each oxygen; n is 0; and the values of $R^4$ match those of the correspondingly numbered compounds of Table A1.

TABLE M25

Table M25 provides 352 compounds of formula (Ib) wherein $R^1$ is methyl; $R^2$ is cyano; $R^3$ is $CH_2OCH_2CH_2OCH_3$; X and Y are each oxygen; n is 0; and the values of $R^4$ match those of the correspondingly numbered compounds of Table A1.

TABLE M26

Table M26 provides 352 compounds of formula (Ib) wherein $R^1$ is ethyl; $R^2$ is hydrogen; $R^3$ is $CH_2OCH_2CH_2OCH_3$; X and Y are each oxygen; n is 0; and the values of $R^4$ match those of the correspondingly numbered compounds of Table A1.

TABLE M27

Table M27 provides 352 compounds of formula (Ib) wherein $R^1$ is ethyl; $R^2$ is fluoro; $R^3$ is $CH_2OCH_2CH_2OCH_3$; X and Y are each oxygen; n is 0; and the values of $R^4$ match those of the correspondingly numbered compounds of Table A1.

TABLE M28

Table M28 provides 352 compounds of formula (Ib) wherein $R^1$ is ethyl; $R^2$ is chloro; $R^3$ is $CH_2OCH_2CH_2OCH_3$; X and Y are each oxygen; n is 0; and the values of $R^4$ match those of the correpondingly numbered compounds of Table A1.

TABLE M29

Table M29 provides 352 compounds of formula (Ib) wherein $R^1$ is ethyl; $R^2$ is bromo; $R^3$ is $CH_2OCH_2CH_2OCH_3$; X and Y are each oxygen; n is 0; and the values of $R^4$ match those of the correspondingly numbered compounds of Table A1.

TABLE M30

Table M30 provides 352 compounds of formula (Ib) wherein $R^1$ is ethyl; $R^2$ is cyano; is $CH_2OCH_2CH_2OCH_3$; X and Y are each oxygen; n is 0; and the values of $R^4$ match those of the correspondingly numbered compounds of Table A1.

TABLE M31

Table M31 provides 352 compounds of formula (Ib) wherein $R^1$ is methyl; $R^2$ is hydrogen; $R^3$ is $CH_2OCH_2CH_2OCH_3$; X is oxygen; Y is sulphur; n is 0; and the values of $R^4$ match those of the correspondingly numbered compounds of Table A1.

TABLE M32

Table M32 provides 352 compounds of formula (Ib) wherein $R^1$ is methyl; $R^2$ is fluoro; $R^3$ is $CH_2OCH_2CH_2OCH_3$; X is oxygen; Y is sulphur; n is 0; and the values of $R^4$ match those of the correspondingly numbered compounds of Table A 1.

TABLE M33

Table M33 provides 352 compounds of formula (Ib) wherein $R^1$ is methyl; $R^2$ is chloro; $R^3$ is $CH_2OCH_2CH_2OCH_3$; X is oxygen; Y is sulphur; n is 0; and the values of $R^4$ match those of the correspondingly numbered compounds of Table A1.

TABLE M34

Table M34 provides 352 compounds of formula (Ib) wherein $R^1$ is methyl; $R^2$ is bromo; $R^3$ is $CH_2OCH_2CH_2OCH_3$; X is oxygen; Y is sulphur; n is 0; and

TABLE M35

Table M35 provides 352 compounds of formula (Ib) wherein $R^1$ is methyl; $R^2$ is cyano; $R^3$ is $CH_2OCH_2CH_2OCH_3$; X is oxygen; Y is sulphur; n is 0; and the values of $R^4$ match those of the correspondingly numbered compounds of Table A1.

TABLE M36

Table M36 provides 352 compounds of formula (Ib) wherein $R^1$ is ethyl; $R^2$ is hydrogen; $R^3$ is $CH_2OCH_2CH_2OCH_3$; X is oxygen; Y is sulphur; n is 0; and the values of $R^4$ match those of the correspondingly numbered compounds of Table A1.

TABLE M37

Table M37 provides 352 compounds of formula (Ib) wherein $R^1$ is ethyl; $R^2$ is fluoro; $R^3$ is $CH_2OCH_2CH_2OCH_3$; X is oxygen; Y is sulphur; n is 0; and the values of $R^4$ match those of the correspondingly numbered compounds of Table A1.

TABLE M38

Table M38 provides 352 compounds of formula (Ib) wherein $R^1$ is ethyl; $R^2$ is chloro; $R^3$ is $CH_2OCH_2CH_2OCH_3$; X is oxygen; Y is sulphur; n is 0; and the values of $R^4$ match those of the correspondingly numbered compounds of Table A1.

TABLE M39

Table M39 provides 352 compounds of formula (Ib) wherein $R^1$ is ethyl; $R^2$ is bromo; $R^3$ is $CH_2OCH_2CH_2OCH_3$; X is oxygen; Y is sulphur; n is 0; and the values of $R^4$ match those of the correspondingly numbered compounds of Table A1.

TABLE M40

Table M40 provides 352 compounds of formula (Ib) wherein $R^1$ is ethyl; $R^2$ is cyano; $R^3$ is $CH_2OCH_2CH_2OCH_3$; X is oxygen; Y is sulphur; n is 0; and the values of $R^4$ match those of the correspondingly numbered compounds of Table A1.

TABLE M41

Table M41 provides 352 compounds of formula (Ib) wherein $R^1$ is methyl; $R^2$ is hydrogen; $R^3$ is $CH_2OCH_2CH_2OCH_3$; X is oxygen; Y is $NR^7$; $R^7$ is hydrogen; n is 0; and the values of $R^4$ match those of the correspondingly numbered compounds of Table A1.

TABLE M42

Table M42 provides 352 compounds of formula (Ib) wherein $R^1$ is methyl; $R^2$ is fluoro; $R^3$ is $CH_2OCH_2CH_2OCH_3$; X is oxygen; Y is $NR^7$; $R^7$ is hydrogen; n is 0; and the values of $R^4$ match those of the correspondingly numbered compounds of Table A1.

TABLE M43

Table M43 provides 352 compounds of formula (Ib) wherein $R^1$ is methyl; $R^2$ is chloro; $R^3$ is $CH_2OCH_2CH_2OCH_3$; X is oxygen; Y is $NR^7$; $R^7$ is hydrogen; n is 0; and the values of $R^4$ match those of the correspondingly numbered compounds of Table A1.

TABLE M44

Table M44 provides 352 compounds of formula (Ib) wherein $R^1$ is methyl; $R^2$ is bromo; $R^3$ is $CH_2OCH_2CH_2OCH_3$; X is oxygen; Y is $NR^7$; $R^7$ is hydrogen; n is 0; and the values of $R^4$ match those of the correspondingly numbered compounds of Table A1.

TABLE M45

Table M45 provides 352 compounds of formula (Ib) wherein $R^1$ is methyl; $R^2$ is cyano; $R^3$ is $CH_2OCH_2CH_2OCH_3$; X is oxygen; Y is $NR^7$; $R^7$ is hydrogen; n is 0; and the values of $R^4$ match those of the correspondingly numbered compounds of Table A1.

TABLE M46

Table M46 provides 352 compounds of formula (Ib) wherein $R^1$ is ethyl; $R^2$ is hydrogen; $R^3$ is $CH_2OCH_2CH_2OCH_3$; X is oxygen; Y is $NR^7$; $R^7$ is hydrogen; n is 0; and the values of $R^4$ match those of the correspondingly numbered compounds of Table A1.

TABLE M47

Table M47 provides 352 compounds of formula (Ib) wherein $R^1$ is ethyl; $R^2$ is fluoro; $R^3$ is $CH_2OCH_2CH_2OCH_3$; X is oxygen; Y is $NR^7$; $R^7$ is hydrogen; n is 0; and the values of $R^4$ match those of the correspondingly numbered compounds of Table A1.

TABLE M48

Table M48 provides 352 compounds of formula (Ib) wherein $R^1$ is ethyl; $R^2$ is chloro; $R^3$ is $CH_2OCH_2CH_2OCH_3$; X is oxygen; Y is $NR^7$; $R^7$ is hydrogen; n is 0; and the values of $R^4$ match those of the correspondingly numbered compounds of Table A1.

TABLE M49

Table M49 provides 352 compounds of formula (Ib) wherein $R^1$ is ethyl; $R^2$ is bromo; $R^3$ is $CH_2OCH_2CH_2OCH_3$; X is oxygen; Y is $NR^7$; $R^7$ is hydrogen; n is 0; and the values of $R^4$ match those of the correspondingly numbered compounds of Table A1.

TABLE M50

Table M50 provides 352 compounds of formula (Ib) wherein $R^1$ is ethyl; $R^2$ is cyano; $R^3$ is $CH_2OCH_2CH_2OCH_3$; X is oxygen; Y is $NR^7$; $R^7$ is hydrogen; n is 0; and the values of $R^4$ match those of the correspondingly numbered compounds of Table A1.

TABLE M51

Table M51 provides 352 compounds of formula (Ib) wherein $R^1$ is methyl; $R^2$ is hydrogen; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M52

Table M52 provides 352 compounds of formula (Ib) wherein $R^1$ is methyl; $R^2$ is fluoro; $R^3$ is $CH_2OCH_2CH_2OCH_3$; X is oxygen; Y is $NR^7$; $R^7$ is methyl;

n is 0; and the values of $R^4$ match those of the correspondingly numbered compounds of Table A1.

TABLE M53

Table M53 provides 352 compounds of formula (Ib) wherein $R^1$ is methyl; $R^2$ is chloro; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M54

Table M54 provides 352 compounds of formula (Ib) wherein $R^1$ is methyl; $R^2$ is bromo; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M55

Table M55 provides 352 compounds of formula (Ib) wherein $R^1$ is methyl; $R^2$ is cyano; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M56

Table M56 provides 352 compounds of formula (Ib) wherein $R^1$ is ethyl; $R^2$ is hydrogen; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M57

Table M57 provides 352 compounds of formula (Ib): wherein $R^1$ is ethyl; $R^2$ is fluoro; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M58

Table M58 provides 352 compounds of formula (Ib) wherein $R^1$ is ethyl; $R^2$ is chloro; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M59

Table M59 provides 352 compounds of formula (Ib) wherein $R^1$ is ethyl; $R^2$ is bromo; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M60

Table M60 provides 352 compounds of formula (Ib) wherein $R^1$ is ethyl; $R^2$ is cyano; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M61

Table M61 provides 352 compounds of formula (Ia) wherein $R^1$ is methyl; $R^2$ is hydrogen; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M62

Table M62 provides 352 compounds of formula (Ia) wherein $R^1$ is methyl; $R^2$ is fluoro; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M63

Table M63 provides 352 compounds of formula (Ia) wherein $R^1$ is methyl; $R^2$ is chloro; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M64

Table M64 provides 352 compounds of formula (Ia) wherein $R^1$ is methyl; $R^2$ is bromo; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M65

Table M65 provides 352 compounds of formula (Ib) wherein $R^1$ is methyl; $R^2$ is cyano; $R^3$ is $CH_2OCH_2CH_2CH_3$; X is oxygen; Y is $NR^7$; $R^7$ is methyl; n is 0; and the values of $R^4$ match those of the correspondingly numbered compounds of Table A1.

TABLE M66

Table M66 provides 352 compounds of formula (Ia) wherein $R^1$ is ethyl; $R^2$ is hydrogen; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M67

Table M67 provides 352 compounds of formula (Ia) wherein $R^1$ is ethyl; $R^2$ is fluoro; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M68

Table M68 provides 352 compounds of formula (Ia) wherein $R^1$ is ethyl; $R^2$ is chloro; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M69

Table M69 provides 352 compounds of formula (Ia) wherein $R^1$ is ethyl; $R^2$ is bromo; $R^3$ is $CH_2OCH_2CH_2OCH_3$; X is oxygen; Y is $NR^7$; $R^7$ is methyl; n is 0; and the values of $R^4$ match those of the correspondingly numbered compounds of Table A1.

TABLE M70

Table M70 provides 352 compounds of formula (Ia) wherein $R^1$ is ethyl; $R^2$ is cyano; $R^3$ is $CH_2OCH_2CH_2OCH_3$; X is oxygen; Y is $NR^7$; $R^7$ is methyl; n is 0; and the values of R⁴ match those of the correspondingly numbered compounds of Table A1.

TABLE N1

Table N1 provides 352 compounds of formula (Ia) wherein $R^1$ is methyl; $R^2$ is hydrogen; $R^3$ is $CH(CH_3)_2$; X and Y are each oxygen; n is 0; and the values of $R^4$ match those of the correspondingly numbered compounds of Table A1.

TABLE N2

Table N2 provides 352 compounds of formula (Ia) wherein $R^1$ is methyl; $R^2$ is fluoro; is $CH(CH_3)_2$; X and Y are each oxygen; n is 0; and the values of $R^4$ match those of the correspondingly numbered compounds of Table A1.

TABLE N3

Table N3 provides 352 compounds of formula (Ia) wherein $R^1$ is methyl; $R^2$ is chloro; $R^3$ is $CH(CH_3)_2$; X and Y are each oxygen; n is 0; and the values of $R^4$ match those of the correspondingly numbered compounds of Table A1.

TABLE N4

Table N4 provides 352 compounds of formula (Ia) wherein $R^1$ is methyl; $R^2$ is bromo; $R^3$ is $CH(CH_3)_2$; X and Y are each oxygen; n is 0; and the values of $R^4$ match those of the correspondingly numbered compounds of Table A1.

TABLE N5

Table N5 provides 352 compounds of formula (Ia) wherein $R^1$ is methyl; $R^2$ is cyano; $R^3$ is $CH(CH_3)_2$; X and Y are each oxygen; n is 0; and the values of $R^4$ match those of the correspondingly numbered compounds of Table A1.

TABLE N6

Table N6 provides 352 compounds of formula (Ia) wherein $R^1$ is ethyl; $R^2$ is hydrogen; $R^3$ is $CH(CH_3)_2$; X and Y are each oxygen; n is 0; and the values of $R^4$ match those of the correspondingly numbered compounds of Table A1.

TABLE N7

Table N7 provides 352 compounds of formula (Ia) wherein $R^1$ is ethyl; $R^2$ is fluoro; $R^3$ is $CH(CH_3)_2$; X and Y are each oxygen; n is 0; and the values of $R^4$ match those of the correspondingly numbered compounds of Table A1.

TABLE N8

Table N8 provides 352 compounds of formula (Ia) wherein $R^1$ is ethyl; $R^2$ is chloro; $R^3$ is $CH(CH_3)_2$; X and Y are each oxygen; n is 0; and the values of $R^4$ match those of the correspondingly numbered compounds of Table A1.

TABLE N9

Table N9 provides 352 compounds of formula (Ia) wherein $R^1$ is ethyl; $R^2$ is bromo; $R^3$ is $CH(CH_3)_2$; X and Y are each oxygen; n is 0; and the values of $R^4$ match those of the correspondingly numbered compounds of Table A1.

TABLE N10

Table N10 provides 352 compounds of formula (Ia) wherein $R^1$ is ethyl; $R^2$ is cyano; $R^3$ is $CH(CH_3)_2$; X and Y are each oxygen; n is 0; and the values of $R^4$ match those of the correspondingly numbered compounds of Table A1.

TABLE N11

Table N11 provides 352 compounds of formula (Ia) wherein $R^1$ is methyl; $R^2$ is hydrogen; $R^3$ is $CH(CH_3)_2$; X is oxygen; Y is sulphur; n is 0; and the values of $R^4$ match those of the correspondingly numbered compounds of Table A1.

TABLE N12

Table N12 provides 352 compounds of formula (Ia) wherein $R^1$ is methyl; $R^2$ is fluoro; $R^3$ is $CH(CH_3)_2$; X is oxygen; Y is sulphur; n is 0; and the values of $R^4$ match those of the correspondingly numbered compounds of Table A1.

TABLE N13

Table N13 provides 352 compounds of formula (Ia) wherein $R^1$ is methyl; $R^2$ is chloro; $R^3$ is $CH(CH_3)_2$; X is oxygen; Y is sulphur; n is 0; and the values of $R^4$ match those of the correspondingly numbered compounds of Table A1.

TABLE 14

Table N14 provides 352 compounds of formula (Ia) wherein $R^1$ is methyl; $R^2$ is bromo; $R^3$ is $CH(CH_3)_2$; X is oxygen; Y is sulphur; n is 0; and the values of $R^4$ match those of the correspondingly numbered compounds of Table A1.

TABLE N15

Table N15 provides 352 compounds of formula (Ia) wherein $R^1$ is methyl; $R^2$ is cyano; $R^3$ is $CH(CH_3)_2$; X is oxygen; Y is sulphur; n is 0; and the values of $R^4$ match those of the correspondingly numbered compounds of Table A1.

TABLE N16

Table N16 provides 352 compounds of formula (Ia) wherein $R^1$ is ethyl; $R^2$ is hydrogen; $R^3$ is $CH(CH_3)_2$; X is oxygen; Y is sulphur; n is 0; and the values of $R^4$ match those of the correspondingly numbered compounds of Table A1.

TABLE N17

Table N17 provides 352 compounds of formula (Ia) wherein $R^1$ is ethyl; $R^2$ is fluoro; is $R^3$ is $CH(CH_3)_2$; X is oxygen; Y is sulphur; n is 0; and the values of $R^4$ match those of the correspondingly numbered compounds of Table A1.

TABLE N18

Table N18 provides 352 compounds of formula (Ia) wherein $R^1$ is ethyl; $R^2$ is chloro; $R^3$ is $CH(CH_3)_2$; X is oxygen; Y is sulphur; n is 0; and the values of $R^4$ match those of the correspondingly numbered compounds of Table A1.

TABLE N19

Table N19 provides 352 compounds of formula (Ia) wherein $R^1$ is ethyl; $R^2$ is bromo; $R^3$ is $CH(CH_3)_2$; X is oxygen; Y is sulphur; n is 0; and the values of $R^4$ match those of the correspondingly numbered compounds of Table A1.

TABLE N20

Table N20 provides 352 compounds of formula (Ia) wherein $R^1$ is ethyl; $R^2$ is cyano; $R^3$ is $CH(CH_3)_2$; X is oxygen; Y is sulphur; n is 0; and the values of $R^4$ match those of the correspondingly numbered compounds of Table A1.

TABLE N21

Table N21 provides 352 compounds of formula (Ib) wherein $R^1$ is methyl; $R^2$ is hydrogen; $R^3$ is $CH(CH_3)_2$; X and Y are each oxygen; n is 0; and the values of $R^4$ match those of the correspondingly numbered compounds of Table A1.

TABLE N22

Table N22 provides 352 compounds of formula (Ib) wherein $R^1$ is methyl; $R^2$ is fluoro; $R^3$ is $CH(CH_3)_2$; X and Y are each oxygen; n is 0; and the values of $R^4$ match those of the correspondingly numbered compounds of Table A1.

TABLE N23

Table N23 provides 352 compounds of formula (Ib) wherein $R^1$ is methyl; $R^2$ is chloro; $R^3$ is $CH(CH_3)_2$; X and Y are each oxygen; n is 0; and the values of $R^4$ match those of the correspondingly numbered compounds of Table A1.

TABLE N24

Table N24 provides 352 compounds of formula (Ib) wherein $R^1$ is methyl; $R^2$ is bromo; $R^3$ is $CH(CH_3)_2$; X and Y are each oxygen; n is 0; and the values of $R^4$ match those of the correspondingly numbered compounds of Table A1.

TABLE N25

Table N25 provides 352 compounds of formula (Ib) wherein $R^1$ is methyl; $R^2$ is cyano; $R^3$ is $CH(CH_3)_2$; X and Y are each oxygen; n is 0; and the values of $R^4$ match those of the correspondingly numbered compounds of Table A1.

TABLE N26

Table N26 provides 352 compounds of formula (Ib) wherein $R^1$ is ethyl; $R^2$ is hydrogen; $R^3$ is $CH(CH_3)_2$; X and Y are each oxygen; n is 0; and the values of $R^4$ match those of the correspondingly numbered compounds of Table A1.

TABLE N27

Table N27 provides 352 compounds of formula (Ib) wherein $R^1$ is ethyl; $R^2$ is fluoro; $R^3$ is $CH(CH_3)_2$; X and Y are each oxygen; n is 0; and the values of $R^4$ match those of the correspondingly numbered compounds of Table A1.

TABLE N28

Table N28 provides 352 compounds of formula (Ib) wherein $R^1$ is ethyl; $R^2$ is chloro; $R^3$ is $CH(CH_3)_2$; X and Y are each oxygen; n is 0; and the values of $R^4$ match those of the correspondingly numbered compounds of Table A1.

TABLE N29

Table N29 provides 352 compounds of formula (Ib) wherein $R^1$ is ethyl; $R^2$ is bromo; $R^3$ is $CH(CH_3)_2$; X and Y are each oxygen; n is 0; and the values of $R^4$ match those of the correspondingly numbered compounds of Table A1.

TABLE N30

Table N30 provides 352 compounds of formula (Ib) wherein $R^1$ is ethyl; $R^2$ is cyano; $R^3$ is $CH(CH_3)_2$; X and Y are each oxygen; n is 0; and the values of $R^4$ match those of the correspondingly numbered compounds of Table A1.

TABLE N31

Table N31 provides 352 compounds of formula (Ib) wherein $R^1$ is methyl; $R^2$ is hydrogen; $R^3$ is $CH(CH_3)_2$; X is oxygen; Y is sulphur; n is 0; and the values of $R^4$ match those of the correspondingly numbered compounds of Table A1.

TABLE N32

Table N32 provides 352 compounds of formula (Ib) wherein $R^1$ is methyl; $R^2$ is is fluoro; $R^3$ is $CH(CH_3)_2$; X is oxygen; Y is sulphur; n is 0; and the values of $R^4$ match those of the correspondingly numbered compounds of Table A1.

TABLE N33

Table N33 provides 352 compounds of formula (Ib) wherein $R^1$ is methyl; $R^2$ is chloro; $R^3$ is $CH(CH_3)_2$; X is oxygen; Y is sulphur; n is 0; and the values of $R^4$ match those of the correspondingly numbered compounds of Table A1.

TABLE N34

Table N34 provides 352 compounds of formula (Ib) wherein $R^1$ is methyl; $R^2$ is bromo; $R^3$ is $CH(CH_3)_2$; X is oxygen; Y is sulphur; n is 0; and the values of $R^4$ match those of the correspondingly numbered compounds of Table A1.

TABLE N35

Table N35 provides 352 compounds of formula (Ib) wherein $R^1$ is methyl; $R^2$ is cyano; $R^3$ is $CH(CH_3)_2$; X is oxygen; Y is sulphur; n is 0; and the values of $R^4$ match those of the correspondingly numbered compounds of Table A1.

TABLE N36

Table N36 provides 352 compounds of formula (Ib) wherein $R^1$ is ethyl; $R^2$ is hydrogen; $R^3$ is $CH(CH_3)_2$; X is oxygen; Y is sulphur; n is 0; and the values of $R^4$ match those of the correspondingly numbered compounds of Table A1.

TABLE N37

Table N37 provides 352 compounds of formula (Ib) wherein $R^1$ is ethyl; $R^2$ is fluoro; $R^3$ is $CH(CH_3)_2$; X is oxygen; Y is sulphur; n is 0; and the values of $R^4$ match those of the correspondingly numbered compounds of Table A1.

TABLE N38

Table N38 provides 352 compounds of formula (Ib) wherein $R^1$ is ethyl; $R^2$ is chloro; $R^3$ is $CH(CH_3)_2$; X is oxygen; Y is sulphur; n is 0; and the values of $R^4$ match those of the correspondingly numbered compounds of Table A1.

TABLE N39

Table N39 provides 352 compounds of formula (Ib) wherein $R^1$ is ethyl; $R^2$ is bromo; $R^3$ is $CH(CH_3)_2$; X is oxygen; Y is sulphur; n is 0; and the values of $R^4$ match those of the is correspondingly numbered compounds of Table A1.

TABLE N40

Table N40 provides 352 compounds of formula (Ib) wherein $R^1$ is ethyl; $R^2$ is cyano; $R^3$ is $CH(CH_3)_2$; X is oxygen; Y is sulphur; n is 0; and the values of $R^4$ match those of the correspondingly numbered compounds of Table A1.

TABLE N41

Table N41 provides 352 compounds of formula (Ib) wherein $R^1$ is methyl; $R^2$ is hydrogen; $R^3$ is $CH(CH_3)_2$; X is oxygen; Y is $NR^7$; $R^7$ is hydrogen; n is 0; and the values of $R^4$ match those of the correspondingly numbered compounds of Table A1.

TABLE N42

Table N42 provides 352 compounds of formula (Ib) wherein $R^1$ is methyl; $R^2$ is fluoro; $R^3$ is $CH(CH_3)_2$; X is, oxygen; Y is $NR^7$; $R^7$ is hydrogen; n is 0; and the values of $R^4$ match those of the correspondingly numbered compounds of Table A1.

TABLE N43

Table N43 provides 352 compounds of formula (Ib) wherein $R^1$ is methyl; $R^2$ is chloro; $R^3$ is $CH(CH_3)_2$; X is oxygen; Y is $NR^7$; $R^7$ is hydrogen; n is 0; and the values of $R^4$ match those of the correspondingly numbered compounds of Table A1.

TABLE N44

Table N44 provides 352 compounds of formula (Ib) wherein $R^1$ is methyl; $R^2$ is bromo; $R^3$ is $CH(CH_3)_2$; X is oxygen; Y is $NR^7$; $R^7$ is hydrogen; n is 0; and the values of $R^4$ match those of the correspondingly numbered compounds of Table A1.

TABLE N45

Table N45 provides 352 compounds of formula (Ib) wherein $R^1$ is methyl; $R^2$ is cyano; $R^3$ is $CH(CH_3)_2$; X is oxygen; Y is $NR^7$; $R^7$ is hydrogen; n is 0; and the values of $R^4$ match those of the correspondingly numbered compounds of Table A1.

TABLE N46

Table N46 provides 352 compounds of formula (Ib) wherein $R^1$ is ethyl; $R^2$ is hydrogen; $R^3$ is $CH(CH_3)_2$; X is oxygen; Y is $NR^7$; $R^7$ is hydrogen; n is 0; and the values of $R^4$ match those of the correspondingly numbered compounds of Table A1.

TABLE N47

Table N47 provides 352 compounds of formula (Ib) wherein $R^1$ is ethyl; $R^2$ is fluoro; $R^3$ is $CH(CH_3)_2$; X is oxygen; Y is $NR^7$; $R^7$ is hydrogen; n is 0; and the values of $R^4$ those of the correspondingly numbered compounds of Table A1.

TABLE N48

Table N48 provides 352 compounds of formula (Ib) wherein $R^1$ is ethyl; $R^2$ is chloro; $R^3$ is $CH(CH_3)_2$; X is oxygen; Y is $NR^7$; $R^7$ is hydrogen; n is 0; and the values of $R^4$ match those of the correspondingly numbered compounds of Table A1.

TABLE N49

Table N49 provides 352 compounds of formula (Ib) wherein $R^1$ is ethyl; $R^2$ is bromo; $R^3$ is $CH(CH_3)_2$; X is oxygen; Y is $NR^7$; $R^7$ is hydrogen; n is 0; and the values of $R^4$ match those of the correspondingly numbered compounds of Table A1.

TABLE N50

Table N50 provides 352 compounds of formula (Ib) wherein $R^1$ is ethyl; $R^2$ is cyano; $R^3$ is $CH(CH_3)_2$; X is oxygen; Y is $NR^7$; $R^7$ is hydrogen; n is 0; and the values of $R^4$ match those of the correspondingly numbered compounds of Table A1.

TABLE N51

Table N51 provides 352 compounds of formula (Ib) wherein $R^1$ is methyl; $R^2$ is hydrogen; $R^3$ is $CH(CH_3)_2$; X is oxygen; Y is $NR^7$; $R^7$ is methyl; n is 0; and the values of $R^4$ match those of the correspondingly numbered compounds of Table A1.

TABLE N52

Table N52 provides 352 compounds of formula (Ib) wherein $R^1$ is methyl; $R^2$ is fluoro; $R^3$ is $CH(CH_3)_2$; X is oxygen; Y is $NR^7$; $R^7$ is methyl; n is 0; and the values of $R^4$ match those of the correspondingly numbered compounds of Table A1.

TABLE N53

Table N53 provides 352 compounds of formula (Ib) wherein $R^1$ is methyl; $R^2$ is chloro; $R^3$ is $CH(CH_3)_2$; X is oxygen; Y is $NR^7$; $R^7$ is methyl; n is 0; and the values of $R^4$ match those of the correspondingly numbered compounds of Table A1.

TABLE N54

Table N54 provides 352 compounds of formula (Ib) wherein $R^1$ is methyl; $R^2$ is bromo; $R^3$ is $CH(CH_3)_2$; X is oxygen; Y is $NR^7$; $R^7$ is methyl; n is 0; and the values of $R^4$ match those of the correspondingly numbered compounds of Table A1.

TABLE N55

Table N55 provides 352 compounds of formula (Ib) wherein $R^1$ is methyl; $R^2$ is cyano; $R^3$ is $CH(CH_3)_2$; X is oxygen; Y is $NR^7$; $R^7$ is methyl; n is 0; and the values of $R^4$ match those of the correspondingly numbered compounds of Table A1.

TABLE N56

Table N56 provides 352 compounds of formula (Ib) wherein $R^1$ is ethyl; $R^2$ is hydrogen; $R^3$ is $CH(CH_3)_2$; X is oxygen; Y is $NR^7$; $R^7$ is methyl; n is 0; and the values of $R^4$ match those of the correspondingly numbered compounds of Table A1.

TABLE N57

Table N57 provides 352 compounds of formula (Ib) wherein $R^1$ is ethyl; $R^2$ is fluoro; $R^3$ is $CH(CH_3)_2$; X is oxygen; Y is $NR^7$; $R^7$ is methyl; n is 0; and the values of $R^4$ match those of the correspondingly numbered compounds of Table A1.

TABLE N58

Table N58 provides 352 compounds of formula (Ib) wherein $R^1$ is ethyl; $R^2$ is chloro; $R^3$ is $CH(CH_3)_2$; X is oxygen; Y is NR$^7$; R$^7$ is methyl; n is 0; and the values of R$^4$ match those of the correspondingly numbered compounds of Table A1.

TABLE N59

Table N59 provides 352 compounds of formula (Ib) wherein R$^1$ is ethyl; R$^2$ is bromo; R$^3$ is CH(CH$_3$)$_2$; X is oxygen; Y is NR$^7$; R$^7$ is methyl; n is 0; and the values of R$^4$ match those of the correspondingly numbered compounds of Table A1.

TABLE N60

Table N60 provides 352 compounds of formula (Ib) wherein R$^1$ is ethyl; R$^2$ is cyano; R$^3$ is CH(CH$_3$)$_2$; X is oxygen; Y is NR$^7$; R$^7$ is methyl; n is 0; and the values of R$^4$ match those of the correspondingly numbered compounds of Table A1.

TABLE N61

Table N61 provides 352 compounds of formula (Ia) wherein R$^1$ is methyl; R$^2$ is hydrogen; R$^3$ is CH(CH$_3$)$_2$; X is oxygen; Y is NR$^7$; R$^7$ is methyl; n is 0; and the values of R$^4$ match those of the correspondingly numbered compounds of Table A1.

TABLE N62

Table N62 provides 352 compounds of formula (Ia) wherein R$^1$ is methyl; R$^2$ is is fluoro; R$^3$ is CH(CH$_3$)$_2$; X is oxygen; Y is NR$^7$; R$^7$ is methyl; n is 0; and the values of R$^4$ match those of the correspondingly numbered compounds of Table A1.

TABLE N63

Table N63 provides 352 compounds of formula (Ia) wherein R$^1$ is methyl; R$^2$ is chloro; R$^3$ is CH(CH$_3$)$_2$; X is oxygen; Y is NR$^7$; R$^7$ is methyl; n is 0; and the values of R$^4$ match those of the correspondingly numbered compounds of Table A1.

TABLE N64

Table N64 provides 352 compounds of formula (Ia) wherein R$^1$ is methyl; R$^2$ is bromo; R$^3$ is CH(CH$_3$)$_2$; X is oxygen; Y is NR$^7$; R$^7$ is methyl; n is 0; and the values of R$^4$ match those of the correspondingly numbered compounds of Table A1.

TABLE N65

Table N65 provides 352 compounds of formula (Ib) wherein R$^1$ is methyl; R$^2$ is cyano; R$^3$ is CH(CH$_3$)$_2$; X is oxygen; Y is NR$^7$; R$^7$ is methyl; n is 0; and the values of R$^4$ match those of the correspondingly numbered compounds of Table A1.

TABLE N66

Table N66 provides 352 compounds of formula (Ia) wherein R$^1$ is ethyl; R$^2$ is hydrogen; R$^3$ is CH(CH$_3$)$_2$; X is oxygen; Y is NR$^7$; R$^7$ is methyl; n is 0; and the values of R$^4$ match those of the correspondingly numbered compounds of Table A1.

TABLE N67

Table N67 provides 352 compounds of formula (Ia) wherein R$^1$ is ethyl; R$^2$ is fluoro; R$^3$ is CH(CH$_3$)$_2$; X is oxygen; Y is NR$^7$; R$^7$ is methyl; n is 0; and the values of R$^4$ match those of the correspondingly numbered compounds of Table A1.

TABLE N68

Table N68 provides 352 compounds of formula (Ia) wherein R$^1$ is ethyl; R$^2$ is chloro; R$^3$ is CH(CH$_3$)$_2$; X is oxygen; Y is NR$^7$; R$^7$ is methyl; n is 0; and the values of R$^4$ match of the correspondingly numbered compounds of Table A1.

TABLE N69

Table N69 provides 352 compounds of formula (Ia) wherein R$^1$ is ethyl; R$^2$ is bromo; R$^3$ is CH(CH$_3$)$_2$; X is oxygen; Y is NR$^7$; R$^7$ is methyl; n is 0; and the values of R$^4$ match those of the correspondingly numbered compounds of Table A1.

TABLE N70

Table N70 provides 352 compounds of formula (Ia) wherein R$^1$ is ethyl; R$^2$ is cyano; R$^3$ is CH(CH$_3$)$_2$; X is oxygen; Y is NR$^7$; R$^7$ is methyl; n is 0; and the values of R$^4$ match those of the correspondingly numbered compounds of Table A1.

TABLE O1

Table O1 provides 352 compounds of formula (Ia) wherein R$^1$ is methyl; R$^2$ is hydrogen; R$^3$ is CO$_2$CH$_3$; X and Y are each oxygen; n is 0; and the values of R$^4$ match those of the correspondingly numbered compounds of Table A1.

TABLE O2

Table O2 provides 352 compounds of formula (Ia) wherein R$^1$ is methyl; R$^2$ is fluoro; R$^3$ is CO$_2$CH$_3$; X and Y are each oxygen; n is 0; and the values of R$^4$ match those of the correspondingly numbered compounds of Table A1.

TABLE O3

Table O3 provides 352 compounds of formula (Ia) wherein R$^1$ is methyl; R$^2$ is chloro; R$^3$ is CO$_2$CH$_3$; X and Y are each oxygen; n is 0; and the values of R$^4$ match those of the correspondingly numbered compounds of Table A1.

TABLE O4

Table O4 provides 352 compounds of formula (Ia) wherein R$^1$ is methyl; R$^2$ is bromo; R$^3$ is CO$_2$CH$_3$; X and Y are each oxygen; n is 0; and the values of R$^4$ match those of the correspondingly numbered compounds of Table A1.

TABLE O5

Table O5 provides 352 compounds of formula (Ia) wherein R$^1$ is methyl; R$^2$ is cyano; R$^3$ is CO$_2$CH$_3$; X and Y are each oxygen; n is 0; and the values of R$^4$ match those of the correspondingly numbered compounds of Table A1.

TABLE O6

Table O6 provides 352 compounds of formula (Ia) wherein R$^1$ is ethyl; R$^2$ is hydrogen; R$^3$ is CO$_2$CH$_3$; X and Y are each oxygen; n is 0; and the values of R$^4$ match those of the correspondingly numbered compounds of Table A1.

TABLE O7

Table O7 provides 352 compounds of formula (Ia) wherein R$^1$ is ethyl; R$^2$ is fluoro; R$^3$ is CO$_2$CH$_3$; X and Y are

TABLE O8

Table O8 provides 352 compounds of formula (Ia) wherein $R^1$ is ethyl; $R^2$ is chloro; $R^3$ is $CO_2CH_3$; X and Y are each oxygen; n is 0; and the values of $R^4$ match those of the correspondingly numbered compounds of Table A1.

TABLE O9

Table O9 provides 352 compounds of formula (Ia) wherein $R^1$ is ethyl; $R^2$ is bromo; $R^3$ is $CO_2CH_3$; X and Y are each oxygen; n is 0; and the values of $R^4$ match those of the correspondingly numbered compounds of Table A1.

TABLE O10

Table O10 provides 352 compounds of formula (Ia) wherein $R^1$ is ethyl; $R^2$ is cyano; $R^3$ is $CO_2CH_3$; X and Y are each oxygen; n is 0; and the values of $R^4$ match those of the correspondingly numbered compounds of Table A1.

TABLE O11

Table O11 provides 352 compounds of formula (Ia) wherein $R^1$ is methyl; $R^2$ is hydrogen; $R^3$ is $CO_2CH_3$; X is oxygen; Y is sulphur; n is 0; and the values of $R^4$ match those of the correspondingly numbered compounds of Table A1.

TABLE O12

Table O12 provides 352 compounds of formula (Ia) wherein $R^1$ is methyl; $R^2$ is fluoro; $R^3$ is $CO_2CH_3$; X is oxygen; Y is sulphur; n is 0; and the values of $R^4$ match those of the correspondingly numbered compounds of Table A1.

TABLE O13

Table O13 provides 352 compounds of formula (Ia) wherein $R^1$ is methyl; $R^2$ is chloro; $R^3$ is $CO_2CH_3$; X is oxygen; Y is sulphur; n is 0; and the values of $R^4$ match those of the correspondingly numbered compounds of Table A1.

TABLE O14

Table O14 provides 352 compounds of formula (Ia) wherein $R^1$ is methyl; $R^2$ is bromo; $R^3$ is $CO_2CH_3$; X is oxygen; Y is sulphur; n is 0; and the values of $R^4$ match those of the correspondingly numbered compounds of Table A1.

TABLE O15

Table O15 provides 352 compounds of formula (Ia) wherein $R^1$ is methyl; $R^2$ is cyano; $R^3$ is $CO_2CH_3$; X is oxygen; Y is sulphur; n is 0; and the values of $R^4$ match those of the correspondingly numbered compounds of Table A1.

TABLE O16

Table O16 provides 352 compounds of formula (Ia) wherein $R^1$ is ethyl; $R^2$ is hydrogen; $R^3$ is $CO_2CH_3$; X is oxygen; Y is sulphur; n is 0; and the values of $R^4$ match those of the correspondingly numbered compounds of Table A1.

TABLE O17

Table O17 provides 352 compounds of formula (Ia) wherein $R^1$ is ethyl; $R^2$ is fluoro; $R^3$ is $CO_2CH_3$; X is oxygen; Y is sulphur; n is 0; and the values of $R^4$ match those of the correspondingly numbered compounds of Table A1.

TABLE O18

Table O18 provides 352 compounds of formula (Ia) wherein $R^1$ is ethyl; $R^2$ is chloro; $R^3$ is $CO_2CH_3$; X is oxygen; Y is sulphur; n is 0; and the values of $R^4$ match those of the correspondingly numbered compounds of Table A1.

TABLE O19

Table O19 provides 352 compounds of formula (Ia) wherein $R^1$ is ethyl; $R^2$ is bromo; $R^3$ is $CO_2CH_3$; X is oxygen; Y is sulphur; n is 0; and the values of $R^4$ match those of the correspondingly numbered compounds of Table A1.

TABLE O20

Table O20 provides 352 compounds of formula (Ia) wherein $R^1$ is ethyl; $R^2$ is cyano; $R^3$ is $CO_2CH_3$; X is oxygen; Y is sulphur; n is 0; and the values of $R^4$ match those of the correspondingly numbered compounds of Table A1.

TABLE O21

Table O21 provides 352 compounds of formula (Ib) wherein $R^1$ is methyl; $R^2$ is hydrogen; $R^3$ is $CO_2CH_3$; X and Y are each oxygen; n is 0; and the values of $R^4$ match those of the correspondingly numbered compounds of Table A1.

TABLE O22

Table O22 provides 352 compounds of formula (Ib) wherein $R^1$ is methyl; $R^2$ is fluoro; $R^3$ is $CO_2CH_3$; X and Y are each oxygen; n is 0; and the values of $R^4$ match those of the correspondingly numbered compounds of Table A1.

TABLE O23

Table O23 provides 352 compounds of formula (Ib) wherein $R^1$ is methyl; $R^2$ is chloro; $R^3$ is $CO_2CH_3$; X and Y are each oxygen; n is 0; and the values of $R^4$ match those of the correspondingly numbered compounds of Table A1.

TABLE O24

Table O24 provides 352 compounds of formula (Ib) wherein $R^1$ is methyl; $R^2$ is bromo; $R^3$ is $CO_2CH_3$; X and Y are each oxygen; n is 0; and the values of $R^4$ match those of the correspondingly numbered compounds of Table A1.

TABLE O25

Table O25 provides 352 compounds of formula (Ib) wherein $R^1$ is methyl; $R^2$ is cyano; $R^3$ is $CO_2CH_3$; X and Y are each oxygen; n is 0; and the values of $R^4$ match those of the correspondingly numbered compounds of Table A1.

TABLE O26

Table O26 provides 352 compounds of formula (Ib) wherein $R^1$ is ethyl; $R^2$ is hydrogen; $R^3$ is $CO_2CH_3$; X and Y are each oxygen; n is 0; and the values of $R^4$ match those of the correspondingly numbered compounds of Table A1.

TABLE O27

Table O27 provides 352 compounds of formula (Ib) wherein $R^1$ is ethyl; $R^2$ is fluoro; $R^3$ is $CO_2CH_3$; X and Y are each oxygen; n is 0; and the values of $R^4$ match those of the correspondingly numbered compounds of Table A1.

TABLE O28

Table O28 provides 352 compounds of formula (Ib) wherein $R^1$ is ethyl; $R^2$ is chloro; $R^3$ is $CO_2CH_3$; X and Y are each oxygen; n is 0; and the values of $R^4$ match those of the correspondingly numbered compounds of Table A1.

TABLE O29

Table O29 provides 352 compounds of formula (Ib) wherein $R^1$ is ethyl; $R^2$ is bromo; $R^3$ is $CO_2CH_3$; X and Y are each oxygen; n is 0; and the values of $R^4$ match those of the correspondingly numbered compounds of Table A1.

TABLE O30

Table O30 provides 352 compounds of formula (Ib) wherein $R^1$ is ethyl; $R^2$ is cyano; $R^3$ is $CO_2CH_3$; X and Y are each oxygen; n is 0; and the values of $R^4$ match those of the correspondingly numbered compounds of Table A1.

TABLE O31

Table O31 provides 352 compounds of formula (Ib) wherein $R^1$ is methyl; $R^2$ is hydrogen; $R^3$ is $CO_2CH_3$; X is oxygen; Y is sulphur; n is 0; and the values of $R^4$ match those of the correspondingly numbered compounds of Table A1.

TABLE O32

Table O32 provides 352 compounds of formula (Ib) wherein $R^1$ is methyl; $R^2$ is fluoro; $R^3$ is $CO_2CH_3$; X is oxygen; Y is sulphur; n is 0; and the values of $R^4$ match those of the correspondingly numbered compounds of Table A1.

TABLE O33

Table O33 provides 352 compounds of formula (Ib) wherein $R^1$ is methyl; $R^2$ is chloro; $R^3$ is $CO_2CH_3$; X is oxygen; Y is sulphur; n is 0; and the values of $R^4$ match those of the correspondingly numbered compounds of Table A1.

TABLE O34

Table O34 provides 352 compounds of formula (Ib) wherein $R^1$ is methyl; $R^2$ is bromo; $R^3$ is $CO_2CH_3$; X is oxygen; Y is sulphur; n is 0; and the values of $R^4$ match those of the correspondingly numbered compounds of Table A1.

TABLE O35

Table O35 provides 352 compounds of formula (Ib) wherein $R^1$ is methyl; $R^2$ is cyano; $R^3$ is $CO_2CH_3$; X is oxygen; Y is sulphur; n is 0; and the values of $R^4$ match those of the correspondingly numbered compounds of Table A1.

TABLE O36

Table O36 provides 352 compounds of formula (Ib) wherein $R^1$ is ethyl; $R^2$ is hydrogen; $R^3$ is $CO_2CH_3$; X is oxygen; Y is sulphur; n is 0; and the values of $R^4$ match those of the correspondingly numbered compounds of Table A1.

TABLE O37

Table O37 provides 352 compounds of formula (Ib) wherein $R^1$ is ethyl; $R^2$ is fluoro; $R^3$ is $CO_2CH_3$; X is oxygen; Y is sulphur; n is 0; and the values of $R^4$ match those of the correspondingly numbered compounds of Table A1.

TABLE O38

Table O38 provides 352 compounds of formula (Ib) wherein $R^1$ is ethyl; $R^2$ is chloro; $R^3$ is $CO_2CH_3$; X is oxygen; Y is sulphur; n is 0; and the values of $R^4$ match those of the correspondingly numbered compounds of Table A1.

TABLE O39

Table O39 provides 352 compounds of formula (Ib) wherein $R^1$ is ethyl; $R^2$ is bromo; $R^3$ is $CO_2CH_3$; X is oxygen; Y is sulphur; n is 0; and the values of $R^4$ match those of the correspondingly numbered compounds of Table A1.

TABLE O40

Table O40 provides 352 compounds of formula (Ib) wherein $R^1$ is ethyl; $R^2$ is cyano; $R^3$ is $CO_2CH_3$; X is oxygen; Y is sulphur; n is 0; and the values of $R^4$ match those of the correspondingly numbered compounds of Table A1.

TABLE O41

Table O41 provides 352 compounds of formula (Ib) wherein $R^1$ is methyl; $R^2$ is hydrogen; $R^3$ is $CO_2CH_3$; X is oxygen; Y is $NR^7$; $R^7$ is hydrogen; n is 0; and the values of $R^4$ match those of the correspondingly numbered compounds of Table A1.

TABLE O42

Table O42 provides 352 compounds of formula (Ib) wherein $R^1$ is methyl; $R^2$ is fluoro; $R^3$ is $CO_2CH_3$; X is oxygen; Y is $NR^7$; $R^7$ is hydrogen; n is 0; and the values of $R^4$ match those of the correspondingly numbered compounds of Table A1.

TABLE O43

Table O43 provides 352 compounds of formula (Ib) wherein $R^1$ is methyl; $R^2$ is chloro; $R^3$ is $CO_2CH_3$; X is oxygen; Y is $NR^7$; $R^7$ is hydrogen; n is 0; and the values of $R^4$ match those of the correspondingly numbered compounds of Table A1.

TABLE O44

Table O44 provides 352 compounds of formula (Ib) wherein $R^1$ is methyl; $R^2$ is bromo; $R^3$ is $CO_2CH_3$; X is oxygen; Y is $NR^7$; $R^7$ is hydrogen; n is 0; and the values of $R^4$ match those of the correspondingly numbered compounds of Table A1.

TABLE O45

Table O45 provides 352 compounds of formula (Ib) wherein $R^1$ is methyl; $R^2$ is cyano; $R^3$ is $CO_2CH_3$; X is oxygen; Y is $NR^7$; $R^7$ is hydrogen; n is 0; and the values of $R^4$ match those of the correspondingly numbered compounds of Table A1.

TABLE O46

Table O46 provides 352 compounds of formula (Ib) wherein $R^1$ is ethyl; $R^2$ is hydrogen; R is $CO_2CH_3$; X is oxygen; Y is $NR^7$; $R^7$ is hydrogen; n is 0; and the values of $R^4$ match those of the correspondingly numbered compounds of Table A1.

TABLE O47

Table O47 provides 352 compounds of formula (Ib) wherein $R^1$ is ethyl; $R^2$ is fluoro; $R^3$ is $CO_2CH_3$; X is oxygen; Y is $NR^7$; $R^7$ is hydrogen; n is 0; and the values of $R^4$ match those of the correspondingly numbered compounds of Table A1.

TABLE O48

Table O48 provides 352 compounds of formula (Ib) wherein $R^1$ is ethyl; $R^2$ is chloro; $R^3$ is $CO_2CH_3$; X is oxygen; Y is $NR^7$; $R^7$ is hydrogen; n is 0; and the values of $R^4$ match those of the correspondingly numbered compounds of Table A1.

TABLE O49

Table O49 provides 352 compounds of formula (Ib) wherein $R^1$ is ethyl; $R^2$ is bromo; $R^3$ is $CO_2CH_3$; X is oxygen; Y is $NR^7$; $R^7$ is hydrogen; n is 0; and the values of $R^4$ match those of the correspondingly numbered compounds of Table A1.

TABLE O50

Table O50 provides 352 compounds of formula (Ib) wherein $R^1$ is ethyl; $R^2$ is cyano; $R^3$ is $CO_2CH_3$; X is oxygen; Y is $NR^7$; $R^7$ is hydrogen; n is 0; and the values of $R^4$ match those of the correspondingly numbered compounds of Table A1.

TABLE O51

Table O51 provides 352 compounds of formula (Ib) wherein $R^1$ is methyl; $R^2$ is hydrogen; $R^3$ is $CO_2CH_3$; X is oxygen; Y is $NR^7$; $R^7$ is methyl; n is 0; and the values of $R^4$ match those of the correspondingly numbered compounds of Table A1.

TABLE O52

Table O52 provides 352 compounds of formula (Ib) wherein $R^1$ is methyl; $R^2$ is fluoro; $R^3$ is $CO_2CH_3$; X is oxygen; Y is $NR^7$; $R^7$ is methyl; n is 0; and the values of $R^4$ match those of the correspondingly numbered compounds of Table A1.

TABLE O53

Table O53 provides 352 compounds of formula (Ib) wherein $R^1$ is methyl; $R^2$ is chloro; $R^3$ is $CO_2CH_3$; X is oxygen; Y is $NR^7$; $R^7$ is methyl; n is 0; and the values of $R^4$ match those of the correspondingly numbered compounds of Table A1.

TABLE O54

Table O54 provides 352 compounds of formula (Ib) wherein $R^1$ is methyl; $R^2$ is bromo; $R^3$ is $CO_2CH_3$; X is oxygen; Y is $NR^7$; $R^7$ is methyl; n is 0; and the values of $R^4$ match those of the correspondingly numbered compounds of Table A1.

TABLE O55

Table O55 provides 352 compounds of formula (Ib) wherein $R^1$ is methyl; $R^2$ is cyano; $R^3$ is $CO_2CH_3$; X is oxygen; Y is $NR^7$; $R^7$ is methyl; n is 0; and the values of $R^4$ match those of the correspondingly numbered compounds of Table A1.

TABLE O56

Table O56 provides 352 compounds of formula (Ib) wherein $R^1$ is ethyl; $R^2$ is hydrogen; $R^3$ is $CO_2CH_3$; X is oxygen; Y is $NR^7$; $R^7$ is methyl; n is 0; and the values of $R^4$ match those of the correspondingly numbered compounds of Table A1.

TABLE O57

Table O57 provides 352 compounds of formula (Ib) wherein $R^1$ is ethyl; $R^2$ is fluoro; $R^3$ is $CO_2CH_3$; X is oxygen; Y is $NR^7$; $R^7$ is methyl; n is 0; and the values of $R^4$ match those of the correspondingly numbered compounds of Table A1.

TABLE O58

Table O58 provides 352 compounds of formula (Ib) wherein $R^1$ is ethyl; $R^2$ is chloro; $R^3$ is $CO_2CH_3$; X is oxygen; Y is $NR^7$; $R^7$ is methyl; n is 0; and the values of $R^4$ match those of the correspondingly numbered compounds of Table A1.

TABLE O59

Table O59 provides 352 compounds of formula (Ib) wherein $R^1$ is ethyl; $R^2$ is bromo; $R^3$ is $CO_2CH_3$; X is oxygen; Y is $NR^7$; $R^7$ is methyl; n is 0; and the values of $R^4$ match those of the correspondingly numbered compounds of Table A1.

TABLE O60

Table O60 provides 352 compounds of formula (Ib) wherein $R^1$ is ethyl; $R^2$ is cyano; $R^3$ is $CO_2CH_3$; X is oxygen; Y is $NR^7$; $R^7$ is methyl; n is 0; and the values of $R^4$ match those of the correspondingly numbered compounds of Table A1.

TABLE O61

Table O61 provides 352 compounds of formula (Ia) wherein $R^1$ is methyl; $R^2$ is hydrogen; $R^3$ is $CO_2CH_3$; X is oxygen; Y is $NR^7$; $R^7$ is methyl; n is 0; and the values of $R^4$ match those of the correspondingly numbered compounds of Table A1.

TABLE O62

Table O62 provides 352 compounds of formula (Ia) wherein $R^1$ is methyl; $R^2$ is fluoro; $R^3$ is $CO_2CH_3$; X is oxygen; Y is $NR^7$; $R^7$ is methyl; n is 0; and the values of $R^4$ match those of the correspondingly numbered compounds of Table A1.

TABLE O63

Table O63 provides 352 compounds of formula (Ia) wherein $R^1$ is methyl; $R^2$ is chloro; $R^3$ is $CO_2CH_3$; X is oxygen; Y is $NR^7$; $R^7$ is methyl; n is 0; and the values of $R^4$ match those of the correspondingly numbered compounds of Table A1.

TABLE O64

Table O64 provides 352 compounds of formula (Ia) wherein $R^1$ is methyl; $R^2$ is bromo; $R^3$ is $CO_2CH_3$; X is oxygen; Y is NR⁷; R⁷ is methyl; n is 0; and the values of R⁴ match those of the correspondingly numbered compounds of Table A1.

TABLE O65

Table O65 provides 352 compounds of formula (Ib) wherein $R^1$ is methyl; $R^2$ is cyano; $R^3$ is $CO_2CH_3$; X is oxygen; Y is $NR^7$; $R^7$ is methyl; n is 0; and the values of $R^4$ match those of the correspondingly numbered compounds of Table A1.

TABLE O66

Table O66 provides 352 compounds of formula (Ia) wherein $R^1$ is ethyl; $R^2$ is hydrogen; $R^3$ is $CO_2CH_3$; X is oxygen; Y is $NR^7$; $R^7$ is methyl; n is 0; and the values of $R^4$ match those of the correspondingly numbered compounds of Table A1.

TABLE O67

Table O67 provides 352 compounds of formula (Ia) wherein $R^1$ is ethyl; $R^2$ is fluoro; $R^3$ is $CO_2CH_3$; X is oxygen; Y is $NR^7$; $R^7$ is methyl; n is 0; and the values of $R^4$ match those of the correspondingly numbered compounds of Table A1.

TABLE O68

Table O68 provides 352 compounds of formula (Ia) wherein $R^1$ is ethyl; $R^2$ is chloro; $R^3$ is $CO_2CH_3$; X is oxygen; Y is $NR^7$; $R^7$ is methyl; n is 0; and the values of $R^4$ match those of the correspondingly numbered compounds of Table A1.

TABLE O69

Table O69 provides 352 compounds of formula (Ia) wherein $R^1$ is ethyl; $R^2$ is bromo; $R^3$ is $CO_2CH_3$; X is oxygen; Y is $NR^7$; $R^7$ is methyl; n is 0; and the values of $R^4$ match those of the correspondingly numbered compounds of Table A1.

TABLE O70

Table O70 provides 352 compounds of formula (Ia) wherein $R^1$ is ethyl; $R^2$ is cyano; $R^3$ is $CO_2CH_3$; X is oxygen; Y is $NR^7$; $R^7$ is methyl; n is 0; and the values of $R^4$ match those of the correspondingly numbered compounds of Table A1.

TABLE P1

Table P1 provides 352 compounds of formula (Ia) wherein $R^1$ is methyl; $R^2$ is hydrogen; $R^3$ is $CO_2CH_2CH_3$; X and Y are each oxygen; n is 0; and the values of $R^4$ match those of the correspondingly numbered compounds of Table A1.

TABLE P2

Table P2 provides 352 compounds of formula (Ia) wherein $R^1$ is methyl; $R^2$ is fluoro; $R^3$ is $CO_2CH_2CH_3$; X and Y are each oxygen; n is 0; and the values of $R^4$ match those of the correspondingly numbered compounds of Table A1.

TABLE P3

Table P3 provides 352 compounds of formula (Ia) wherein $R^1$ is methyl; $R^2$ is chloro; $R^3$ is $CO_2CH_2CH_3$; X and Y are each oxygen; n is 0; and the values of $R^4$ match those of the correspondingly numbered compounds of Table A1.

TABLE P4

Table P4 provides 352 compounds of formula (Ia) wherein $R^1$ is methyl; $R^2$ is bromo; $R^3$ is $CO_2CH_2CH_3$; X and Y are each oxygen; n is 0; and the values of $R^4$ match those of the correspondingly numbered compounds of Table A1.

TABLE P5

Table P5 provides 352 compounds of formula (Ia) wherein $R^1$ is methyl; $R^2$ is cyano; $R^3$ is $CO_2CH_2CH_3$; X and Y are each oxygen; n is 0; and the values of $R^4$ match those of the correspondingly numbered compounds of Table A1.

TABLE P6

Table P6 provides 352 compounds of formula (Ia) wherein $R^1$ is ethyl; $R^2$ is hydrogen; $R^3$ is $CO_2CH_2CH_3$; X and Y are:each oxygen; n is 0; and the values of $R^4$ match those of the correspondingly numbered compounds of Table A1.

TABLE P7

Table P7 provides 352 compounds of formula (Ia) wherein $R^1$ is ethyl; $R^2$ is fluoro; $R^3$ is $CO_2CH_2CH_3$; X and Y are each oxygen; n is 0; and the values of $R^4$ match those of the correspondingly numbered compounds of Table A1.

TABLE P8

Table P8 provides 352 compounds of formula (Ia) wherein $R^1$ is ethyl; $R^2$ is chloro; $R^3$ is $CO_2CH_2CH_3$; X and Y are each oxygen; n is 0; and the values of $R^4$ match those of the correspondingly numbered compounds of Table A1.

TABLE P9

Table P9 provides 352 compounds of formula (Ia) wherein $R^1$ is ethyl; $R^2$ is bromo; $R^3$ is $CO_2CH_2CH_3$; X and Y are each oxygen; n is 0; and the values of $R^4$ match those of the correspondingly numbered compounds of Table A1.

TABLE P10

Table P10 provides 352 compounds of formula (Ia) wherein $R^1$ is ethyl; $R^2$ is cyano; $R^3$ is $CO_2CH_2CH_3$; X and Y are each oxygen; n is 0; and the values of $R^4$ match those of the correspondingly numbered compounds of Table A1.

TABLE P11

Table P11 provides 352 compounds of formula (Ia) wherein $R^1$ is methyl; $R^2$ is hydrogen; $R^3$ is $CO_2CH_2CH_3$; X is oxygen; Y is sulphur; n is 0; and the values of $R^4$ match those of the correspondingly numbered compounds of Table A1.

TABLE P12

Table P12 provides 352 compounds of formula (Ia) wherein $R^1$ is methyl; $R^2$ is fluoro; $R^3$ is $CO_2CH_2CH_3$; X is oxygen; Y is sulphur; n is 0; and the values of $R^4$ match those of the correspondingly numbered compounds of Table A1.

TABLE P13

Table P13 provides 352 compounds of formula (Ia) wherein $R^1$ is methyl; $R^2$ is chloro; $R^3$ is $CO_2CH_2CH_3$; X is oxygen; Y is sulphur; n is 0; and the values of $R^4$ match those of the correspondingly numbered compounds of Table A1.

TABLE P14

Table P14 provides 352 compounds of formula (Ia) wherein $R^1$ is methyl; $R^2$ is bromo; $R^3$ is $CO_2CH_2CH_3$; X is oxygen; Y is sulphur; n is 0; and the values of $R^4$ match those of the correspondingly numbered compounds of Table A1.

TABLE P15

Table P15 provides 352 compounds of formula (Ia) wherein $R^1$ is methyl; $R^2$ is cyano; $R^3$ is $CO_2CH_2CH_3$; X is oxygen; Y is sulphur; n is 0; and the values of $R^4$ match those of the correspondingly numbered compounds of Table A1.

TABLE P16

Table P16 provides 352 compounds of formula (Ia) wherein $R^1$ is ethyl; $R^2$ is hydrogen; $R^3$ is $CO_2CH_2CH_3$; X is oxygen; Y is sulphur; n is 0; and the values of $R^4$ match those of the correspondingly numbered compounds of Table A1.

TABLE P17

Table P17 provides 352 compounds of formula (Ia) wherein $R^1$ is ethyl; $R^2$ is fluoro; $R^3$ is $CO_2CH_2CH_3$; X is oxygen; Y is sulphur; n is 0; and the values of $R^4$ match those of the correspondingly numbered compounds of Table A1.

TABLE P18

Table P18 provides 352 compounds of formula (Ia) wherein $R^1$ is ethyl; $R^2$ is chloro; $R^3$ is $CO_2CH_2CH_3$; X is oxygen; Y is sulphur; n is 0; and the values of $R^4$ match those of the correspondingly numbered compounds of Table A1.

TABLE P19

Table P19 provides 352 compounds of formula (Ia) wherein $R^1$ is ethyl; $R^2$ is bromo; $R^3$ is $CO_2CH_2CH_3$; X is oxygen; Y is sulphur; n is 0; and the values of $R^4$ match those of the correspondingly numbered compounds of Table A1.

TABLE P20

Table P20 provides 352 compounds of formula (Ia) wherein $R^1$ is ethyl; $R^2$ is cyano; $R^3$ is $CO_2CH_2CH_3$; X is oxygen; Y is sulphur; n is 0; and the values of $R^4$ match those of the correspondingly numbered compounds of Table A1.

TABLE P21

Table P21 provides 352 compounds of formula (Ib) wherein $R^1$ is methyl; $R^2$ is hydrogen; $R^3$ is $CO_2CH_2CH_3$; X and Y are each oxygen; n is 0; and the values of $R^4$ match those of the correspondingly numbered compounds of Table A1.

TABLE P22

Table P22 provides 352 compounds of formula (Ib) wherein $R^1$ is methyl; $R^2$ is fluoro; $R^3$ is $CO_2CH_2CH_3$; X and Y are each oxygen; n is 0; and the values of $R^4$ match those of the correspondingly numbered compounds of Table A1.

TABLE P23

Table P23 provides 352 compounds of formula (Ib) wherein $R^1$ is methyl; $R^2$ is chloro; $R^3$ is $CO_2CH_2CH_3$; X and Y are each oxygen; n is 0; and the values of $R^4$ match those of the correspondingly numbered compounds of Table A1.

TABLE P24

Table P24 provides 352 compounds of formula (Ib) wherein $R^1$ is methyl; $R^2$ is bromo; $R^3$ is $CO_2CH_2CH_3$; X and Y are each oxygen; n is 0; and the values of $R^4$ match those of the correspondingly numbered compounds of Table A1.

TABLE P25

Table P25 provides 352 compounds of formula (Ib) wherein $R^1$ is methyl; $R^2$ is cyano; $R^3$ is $CO_2CH_2CH_3$; X and Y are each oxygen; n is 0; and the values of $R^4$ match those of the correspondingly numbered compounds of Table A1.

TABLE P26

Table P26 provides 352 compounds of formula (Ib) wherein $R^1$ is ethyl; $R^2$ is hydrogen; $R^3$ is $CO_2CH_2CH_3$; X and Y are each oxygen; n is 0; and the values of $R^4$ match those of the correspondingly numbered compounds of Table A1.

TABLE P27

Table P27 provides 352 compounds of formula (Ib) wherein $R^1$ is ethyl; $R^2$ is fluoro; $R^3$ is $CO_2CH_2CH_3$; X and Y are each oxygen; n is 0; and the values of $R^4$ match those of the correspondingly numbered compounds of Table A1.

TABLE P28

Table P28 provides 352 compounds of formula (Ib) wherein $R^1$ is ethyl; $R^2$ is chloro; $R^3$ is $CO_2CH_2CH_3$; X and Y are each oxygen; n is 0; and the values of $R^4$ match those of the correspondingly numbered compounds of Table A1.

TABLE P29

Table P29 provides 352 compounds of formula (Ib) wherein $R^1$ is ethyl; $R^2$ is bromo; $R^3$ is $CO_2CH_2CH_3$; X and Y are each oxygen; n is 0; and the values of $R^4$ match those of the correspondingly numbered compounds of Table A1.

TABLE P30

Table P30 provides 352 compounds of formula (Ib) wherein $R^1$ is ethyl; $R^2$ is cyano; $R^3$ is $CO_2CH_2CH_3$; X and Y are each oxygen; n is 0; and the values of $R^4$ match those of the correspondingly numbered compounds of Table A1.

TABLE P31

Table P31 provides 352 compounds of formula (Ib) wherein $R^1$ is methyl; $R^2$ is hydrogen; $R^3$ is $CO_2CH_2CH_3$; X is oxygen; Y is sulphur; n is 0; and the values of $R^4$ match those of the correspondingly numbered compounds of Table A1.

TABLE P32

Table P32 provides 352 compounds of formula (Ib) wherein $R^1$ is methyl; $R^2$ is fluoro; $R^3$ is $CO_2CH_2CH_3$; X is oxygen; Y is sulphur; n is 0; and the values of $R^4$ match those of the correspondingly numbered compounds of Table A1.

TABLE P33

Table P33 provides 352 compounds of formula (Ib) wherein $R^1$ is methyl; $R^2$ is chloro; $R^3$ is $CO_2CH_2CH_3$; X is oxygen; Y is sulphur; n is 0; and the values of $R^4$ match those of the correspondingly numbered compounds of Table A1.

TABLE P34

Table P34 provides 352 compounds of formula (Ib) wherein $R^1$ is methyl; $R^2$ is bromo; $R^3$ is $CO_2CH_2CH_3$; X is oxygen; Y is sulphur; n is 0; and the values of $R^4$ match those of the correspondingly numbered compounds of Table A1.

TABLE P35

Table P35 provides 352 compounds of formula (Ib) wherein $R^1$ is methyl; $R^2$ is cyano; $R^3$ is $CO_2CH_2CH_3$; X is oxygen; Y is sulphur; n is 0; and the values of $R^4$ match those of the correspondingly numbered compounds of Table A1.

TABLE P36

Table P36 provides 352 compounds of formula (Ib) wherein $R^1$ is ethyl; $R^2$ is hydrogen; $R^3$ is $CO_2CH_2CH_3$; X is oxygen; Y is sulphur; n is 0; and the values of $R^4$ match those of the correspondingly numbered compounds of Table A1.

TABLE P37

Table P37 provides 352 compounds of formula (Ib) wherein $R^1$ is ethyl; $R^2$ is fluoro; $R^3$ is $CO_2CH_2CH_3$; X is oxygen; Y is sulphur; n is 0; and the values of $R^4$ match those of the correspondingly numbered compounds of Table A1.

TABLE P38

Table P38 provides 352 compounds of formula (Ib) wherein $R^1$ is ethyl; $R^2$ is chloro; $R^3$ is $CO_2CH_2CH_3$; X is oxygen; Y is sulphur; n is 0; and the values of $R^4$ match those of the correspondingly numbered compounds of Table A1.

TABLE P39

Table P39 provides 352 compounds of formula (Ib) wherein $R^1$ is ethyl; $R^2$ is bromo; $R^3$ is $CO_2CH_2CH_3$; X is oxygen; Y is sulphur; n is 0; and the values of $R^4$ match those of the correspondingly numbered compounds of Table A1.

TABLE P40

Table P40 provides 352 compounds of formula (Ib) wherein $R^1$ is ethyl; $R^2$ is cyano; $R^3$ is $CO_2CH_2CH_3$; X is oxygen; Y is sulphur; n is 0; and the values of $R^4$ match those of the correspondingly numbered compounds of Table A1.

TABLE P41

Table P41 provides 352 compounds of formula (Ib) wherein $R^1$ is methyl; $R^2$ is hydrogen; $R^3$ is $CO_2CH_2CH_3$; X is oxygen; Y is $NR^7$; $R^7$ is hydrogen; n is 0; and the values of $R^4$ match those of the correspondingly numbered compounds of Table A1.

TABLE P42

Table P42 provides 352 compounds of formula (Ib) wherein $R^1$ is methyl; $R^2$ is fluoro; $R^3$ is $CO_2CH_2CH_3$; X is oxygen; Y is $NR^7$; $R^7$ is hydrogen; n is 0; and the values of $R^4$ match those of the correspondingly numbered compounds of Table A1.

TABLE P43

Table P43 provides 352 compounds of formula (Ib) wherein $R^1$ is methyl; $R^2$ is chloro; $R^3$ is $CO_2CH_2CH_3$; X is oxygen; Y is $NR^7$; $R^7$ is hydrogen; n is 0; and the values of $R^4$ match those of the correspondingly numbered compounds of Table A1.

TABLE P44

Table P44 provides 352 compounds of formula (Ib) wherein $R^1$ is methyl; $R^2$ is bromo; $R^3$ is $CO_2CH_2CH_3$; X is oxygen; Y is $NR^7$; $R^7$ is hydrogen; n is 0; and the values of $R^4$ match those of the correspondingly numbered compounds of Table A1.

TABLE P45

Table P45 provides 352 compounds of formula (Ib) wherein $R^1$ is methyl; $R^2$ is cyano; $R^3$ is $CO_2CH_2CH_3$; X is oxygen; Y is $NR^7$; $R^7$ is hydrogen; n is 0; and the values of $R^4$ match those of the correspondingly numbered compounds of Table A1.

TABLE P46

Table P46 provides 352 compounds of formula (Ib) wherein $R^1$ is ethyl; $R^2$ is hydrogen; $R^3$ is $CO_2CH_2CH_3$; X is oxygen; Y is $NR^7$; $R^7$ is hydrogen; n is 0; and the values of $R^4$ match those of the correspondingly numbered compounds of Table A1.

TABLE P47

Table P47 provides 352 compounds of formula (Ib) wherein $R^1$ is ethyl; $R^2$ is fluoro; $R^3$ is $CO_2CH_2CH_3$; X is oxygen; Y is $NR^7$; $R^7$ is hydrogen; n is 0; and the values of $R^4$ match those of the correspondingly numbered compounds of Table A1.

TABLE P48

Table P48 provides 352 compounds of formula (Ib) wherein $R^1$ is ethyl; $R^2$ is chloro; $R^3$ is $CO_2CH_2CH_3$; X is oxygen; Y is $NR^7$; $R^7$ is hydrogen; n is 0; and the values of $R^4$ match those of the correspondingly numbered compounds of Table A1.

TABLE P49

Table P49 provides 352 compounds of formula (Ib) wherein $R^1$ is ethyl; $R^2$ is bromo; $R^3$ is $CO_2CH_2CH_3$; X is oxygen; Y is $NR^7$; $R^7$ is hydrogen; n is 0; and the values of $R^4$ match those of the correspondingly numbered compounds of Table A1.

TABLE P50

Table P50 provides 352 compounds of formula (Ib) wherein $R^1$ is ethyl; $R^2$ is cyano; $R^3$ is $CO_2CH_2CH_3$; X is oxygen; Y is $NR^7$; $R^7$ is hydrogen; n is 0; and the values of $R^4$ match those of the correspondingly numbered compounds of Table A1.

TABLE P51

Table P51 provides 352 compounds of formula (Ib) wherein $R^1$ is methyl; $R^2$ is hydrogen; $R^3$ is $CO_2CH_2CH_3$; X is oxygen; Y is $NR^7$; $R^7$ is methyl; n is 0; and he values of $R^4$ match those of the correspondingly numbered compounds of Table A1.

TABLE P52

Table P52 provides 352 compounds of formula (Ib) wherein $R^1$ is methyl; $R^2$ is fluoro; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P53

Table P53 provides 352 compounds of formula (Ib) wherein $R^1$ is methyl; $R^2$ is chloro; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P54

Table P54 provides 352 compounds of formula (Ib) wherein $R^1$ is methyl; $R^2$ is bromo; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P55

Table P55 provides 352 compounds of formula (Ib) wherein $R^1$ is methyl; $R^2$ is cyano; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P56

Table P56 provides 352 compounds of formula (Ib) wherein $R^1$ is ethyl; $R^2$ is hydrogen; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P57

Table P57 provides 352 compounds of formula (Ib) wherein $R^1$ is ethyl; $R^2$ is fluoro; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P58

Table P58 provides 352 compounds of formula (Ib) wherein $R^1$ is ethyl; $R^2$ is chloro; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P59

Table P59 provides 352 compounds of formula (Ib) wherein $R^1$ is ethyl; $R^2$ is bromo; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P60

Table P60 provides 352 compounds of formula (Ib) wherein $R^1$ is ethyl; $R^2$ is cyano; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P61

Table P61 provides 352 compounds of formula (Ia) wherein $R^1$ is methyl; $R^2$ is hydrogen; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P62

Table P62 provides 352 compounds of formula (Ia) wherein $R^1$ is methyl; $R^2$ is fluoro; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P63

Table P63 provides 352 compounds of formula (Ia) wherein $R^1$ is methyl; $R^2$ is chloro; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P64

Table P64 provides 352 compounds of formula (Ia) wherein $R^1$ is methyl; $R^2$ is bromo; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P65

Table P65 provides 352 compounds of formula (Ib) wherein $R^1$ is methyl; $R^2$ is cyano; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P66

Table P66 provides 352 compounds of formula (Ia) wherein $R^1$ is ethyl; $R^2$ is hydrogen; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P67

Table P67 provides 352 compounds of formula (Ia) wherein $R^1$ is ethyl; $R^2$ is fluoro; $R^3$ is $CO_2CH_2CH_3$; X is oxygen; Y is $NR^7$; $R^7$ is methyl; n is 0; and the values of $R^4$ match those of the correspondingly numbered compounds of Table A1.

TABLE P68

Table P68 provides 352 compounds of formula (Ia) wherein $R^1$ is ethyl; $R^2$ is chloro; $R^3$ is $CO_2CH_2CH_3$; X is oxygen; Y is NR$^7$; R$^7$ is methyl; n is 0; and the values of R$^4$ match those of the correspondingly numbered compounds of Table A1.

TABLE P69

Table P69 provides 352 compounds of formula (Ia) wherein R$^1$ is ethyl; R$^2$ is bromo; R$^3$ is CO$_2$CH$_2$CH$_3$; X is oxygen; Y is NR$^7$; R$^7$ is methyl; n is 0; and the values of R$^4$ match those of the correspondingly numbered compounds of Table A1.

TABLE P70

Table P70 provides 352 compounds of formula (Ia) wherein R$^1$ is ethyl; R$^2$ is cyano; R$^3$ is CO$_2$CH$_2$CH$_3$; X is oxygen; Y is NR$^7$; R$^7$ is methyl; n is 0; and the values of R$^4$ match those of the correspondingly numbered compounds of Table A1.

TABLE Q1

Table Q1 provides 352 compounds of formula (Ia) wherein R$^1$ is methyl; R$^2$ is hydrogen; R$^2$ is CON(CH$_3$)$_2$; X and Y are each oxygen; n is 0; and the values of R$^4$ match those of the correspondingly numbered compounds of Table A1.

TABLE Q2

Table Q2 provides 352 compounds of formula (Ia) wherein R$^1$ is methyl; R$^2$ is fluoro; R$^3$ is CON(CH$_3$)$_2$; X and Y are each oxygen; n is 0; and the values of R$^4$ match those of the correspondingly numbered compounds of Table A1.

TABLE Q3

Table Q3 provides 352 compounds of formula (Ia) wherein R$^1$ is methyl; R$^2$ is chloro; R$^3$ is CON(CH$_3$)$_2$; X and Y are each oxygen; n is 0; and :the values of R$^4$ match those of the correspondingly numbered compounds of Table A1.

TABLE Q4

Table Q4 provides 352 compounds of formula (Ia) wherein R$^1$ is methyl; R$^2$ is bromo; R$^3$ is CON(CH$_3$)$_2$; X and Y are each oxygen; n is 0; and the values of R$^4$ match those of the correspondingly numbered compounds of Table A1.

TABLE Q5

Table Q5 provides 352 compounds of formula (Ia) wherein R$^1$ is methyl; R$^2$ is cyano; R$^3$ is CON(CH$_3$)$_2$; X and Y are each oxygen; n is 0; and the values of R$^4$ match those of the correspondingly numbered compounds of Table A1.

TABLE Q6

Table Q6 provides 352 compounds of formula (Ia) wherein R$^1$ is ethyl; R$^2$ is hydrogen; R$^3$ is CON(CH$_3$)$_2$; X and Y are each oxygen; n is 0; and the values of R$^4$ match those of the correspondingly numbered compounds of Table A1.

TABLE Q7

Table Q7 provides 352 compounds of formula (Ia) wherein R$^1$ is ethyl; R$^2$ is fluoro; R$^3$ is CON(CH$_3$)$_2$; X and Y are each oxygen; n is 0; and the values of R$^4$ match those of the correspondingly numbered compounds of Table A1.

TABLE Q8

Table Q8 provides 352 compounds of formula (Ia) wherein R$^1$ is ethyl; R$^2$ is chloro; R$^3$ is CON(CH$_3$)$_2$; X and Y are each oxygen; n is 0; and the values of R$^4$ match those of the correspondingly numbered compounds of Table A1.

TABLE Q9

Table Q9 provides 352 compounds of formula (Ia) wherein R$^1$ is ethyl; R$^2$ is bromo; R$^3$ is CON(CH$_3$)$_2$; X and Y are each oxygen; n is 0; and the values of R$^4$ match those of the correspondingly numbered compounds of Table A1.

TABLE Q10

Table Q10 provides 352 compounds of formula (Ia) wherein R$^1$ is ethyl; R$^2$ is cyano; R$^3$ is CON(CH$_3$)$_2$; X and Y are each oxygen; n is 0; and the values of R$^4$ match those of the correspondingly numbered compounds of Table A1.

TABLE Q11

Table Q11 provides 352 compounds of formula (Ia) wherein R$^1$ is methyl; R$^2$ is hydrogen; R$^3$ is CON(CH$_3$)$_2$; X is oxygen; Y is sulphur; n is 0; and the values of R$^4$ match those of the correspondingly numbered compounds of Table A1.

TABLE Q12

Table Q12 provides 352 compounds of formula (Ia) wherein R$^1$ is methyl; R$^2$ is fluoro; R$^3$ is CON(CH$_3$)$_2$; X is oxygen; Y is sulphur; n is 0; and the values of R$^4$ match those of the correspondingly numbered compounds of Table A1.

TABLE Q13

Table Q13 provides 352 compounds of formula (Ia) wherein R$^1$ is methyl; R$^2$ is chloro; R$^3$ is CON(CH$_3$)$_2$; X is oxygen; Y is sulphur; n is 0; and the values of R$^4$ match those of the correspondingly numbered compounds of Table A1.

TABLE 14

Table Q14 provides 352 compounds of formula (Ia) wherein R$^1$ is methyl; R$^2$ is bromo; R$^3$ is CON(CH$_3$)$_2$; X is oxygen; Y is sulphur; n is 0; and the values of R$^4$ match those of the correspondingly numbered compounds of Table A1.

TABLE Q15

Table Q15 provides 352 compounds of formula (Ia) wherein R$^1$ is methyl; R$^2$ is cyano; R$^3$ is CON(CH$_3$)$_2$; X is oxygen; Y is sulphur; n is 0; and the values of R$^4$ match those of the correspondingly numbered compounds of Table A1.

TABLE Q16

Table Q16 provides 352 compounds of formula (Ia) wherein R$^1$ is ethyl; R$^2$ is hydrogen; R$^2$ is CON(CH$_3$)$_2$; X is oxygen; Y is sulphur; n is 0; and the values of R$^4$ match those of the correspondingly numbered compounds of Table A1.

TABLE Q17

Table Q17 provides 352 compounds of formula (Ia) wherein R$^1$ is ethyl; R$^2$ is fluoro; R$^3$ is CON(CH$_3$)$_2$; X is oxygen; Y is sulphur; n is 0; and the values of R$^4$ match those of the correspondingly numbered compounds of Table A1.

TABLE Q18

Table Q18 provides 352 compounds of formula (Ia) wherein $R^1$ is ethyl; $R^2$ is chloro; $R^3$ is $CON(CH_3)_2$; X is oxygen; Y is sulphur; n is 0; and the values of $R^4$ match those of the correspondingly numbered compounds of Table A1.

TABLE Q19

Table Q19 provides 352 compounds of formula (Ia) wherein $R^1$ is ethyl; $R^2$ is bromo; $R^3$ is $CON(CH_3)_2$; X is oxygen; Y is sulphur; n is 0; and the values of $R^4$ match those of the correspondingly numbered compounds of Table A1.

TABLE Q20

Table Q20 provides 352 compounds of formula (Ia) wherein $R^1$ is ethyl; $R^2$ is cyano; $R^3$ is $CON(CH_3)_2$; X is oxygen; Y is sulphur; n is 0; and the values of $R^4$ match those of the correspondingly numbered compounds of Table A1.

TABLE Q21

Table Q21 provides 352 compounds of formula (Ib) wherein $R^1$ is methyl; $R^2$ is hydrogen; $R^3$ is $CON(CH_3)_2$; X and Y are each oxygen; n is 0; and the values of $R^4$ match those of the correspondingly numbered compounds of Table A1.

TABLE Q22

Table Q22 provides 352 compounds of formula (Ib) wherein $R^1$ is methyl; $R^2$ is fluoro; $R^3$ is $CON(CH_3)_2$; X and Y are each oxygen; n is 0; and the values of $R^4$ match those of the correspondingly numbered compounds of Table A1.

TABLE Q23

Table Q23 provides 352 compounds of formula (Ib) wherein $R^1$ is methyl; $R^2$ is chloro; $R^3$ is $CON(CH_3)_2$; X and Y are each oxygen; n is 0; and the values of $R^4$ match those of the correspondingly numbered compounds of Table A1.

TABLE Q24

Table Q24 provides 352 compounds of formula (Ib) wherein $R^1$ is methyl; $R^2$ is bromo; $R^3$ is $CON(CH_3)_2$; X and Y are each oxygen; n is 0; and the values of $R^4$ match those of the correspondingly numbered compounds of Table A1.

TABLE Q25

Table Q25 provides 352 compounds of formula (Ib) wherein $R^1$ is methyl; $R^2$ is cyano; $R^3$ is $CON(CH_3)_2$; X and Y are each oxygen; n is 0; and the values of $R^4$ match those of the correspondingly numbered compounds of Table A1.

TABLE Q26

Table Q26 provides 352 compounds of formula (Ib) wherein $R^1$ is ethyl; $R^2$ is hydrogen; $R^3$ is $CON(CH_3)_2$; X and Y are each oxygen; n is 0; and the values of $R^4$ match those of the correspondingly numbered compounds of Table A1.

TABLE Q27

Table Q27 provides 352 compounds of formula (Ib) wherein $R^1$ is ethyl; $R^2$ is fluoro; $R^3$ is $CON(CH_3)_2$; X and Y are each oxygen; n is 0; and the values of $R^4$ match those of the correspondingly numbered compounds of Table A1.

TABLE Q28

Table Q28 provides 352 compounds of formula (Ib) wherein $R^1$ is ethyl; $R^2$ is chloro; $R^3$ is $CON(CH_3)_2$; X and Y are each oxygen; n is 0; and the values of $R^4$ match those of the correspondingly numbered compounds of Table A1.

TABLE Q29

Table Q29 provides 352 compounds of formula (Ib) wherein $R^1$ is ethyl; $R^2$ is bromo; $R^3$ is $CON(CH_3)_2$; X and Y are each oxygen; n is 0; and the values of $R^4$ match those of the correspondingly numbered compounds of Table A1.

TABLE Q30

Table Q30 provides 352 compounds of formula (Ib) wherein $R^1$ is ethyl; $R^2$ is cyano; $R^3$ is $CON(CH_3)_2$; X and Y are each oxygen; n is 0; and the values of $R^4$ match those of the correspondingly numbered compounds of Table A1.

TABLE Q31

Table Q31 provides 352 compounds of formula (Ib) wherein $R^1$ is methyl; $R^2$ is hydrogen; $R^3$ is $CON(CH_3)_2$; X is oxygen; Y is sulphur; n is 0; and the values of $R^4$ match those of the correspondingly numbered compounds of Table A1.

TABLE Q32

Table Q32 provides 352 compounds of formula (Ib) wherein $R^1$ is methyl; $R^2$ is fluoro; $R^3$ is $CON(CH_3)_2$; X is oxygen; Y is sulphur; n is 0; and the values of $R^4$ match of the correspondingly numbered compounds of Table A1.

TABLE Q33

Table Q33 provides 352 compounds of formula (Ib) wherein $R^1$ is methyl; $R^2$ is chloro; $R^3$ is $CON(CH_3)_2$; X is oxygen; Y is sulphur; n is 0; and the values of $R^4$ match those of the correspondingly numbered compounds of Table A1.

TABLE Q34

Table Q34 provides 352 compounds of formula (Ib) wherein $R^1$ is methyl; $R^2$ is bromo; $R^3$ is $CON(CH_3)_2$; X is oxygen; Y is sulphur; n is 0; and the values of $R^4$ match those of the correspondingly numbered compounds of Table A1.

TABLE Q35

Table Q35 provides 352 compounds of formula (Ib) wherein $R^1$ is methyl; $R^2$ is cyano; $R^3$ is $CON(CH_3)_2$; X is oxygen; Y is sulphur; n is 0; and the values of $R^4$ match those of the correspondingly numbered compounds of Table A1.

TABLE Q36

Table Q36 provides 352 compounds of formula (Ib) wherein $R^1$ is ethyl; $R^2$ is hydrogen; $R^3$ is $CON(CH_3)_2$; X is oxygen; Y is sulphur; n is 0; and the values of $R^4$ match those of the correspondingly numbered compounds of Table A1.

TABLE Q37

Table Q37 provides 352 compounds of formula (Ib) wherein $R^1$ is ethyl; $R^2$ is fluoro; $R^3$ is $CON(CH_3)_2$; X is oxygen; Y is sulphur; n is 0; and the values of $R^4$ match those of the correspondingly numbered compounds of Table A1.

TABLE Q38

Table Q38 provides 352 compounds of formula (Ib) wherein $R^1$ is ethyl; $R^2$ is chloro; $R^3$ is $CON(CH_3)_2$; X is oxygen; Y is sulphur; n is 0; and the values of $R^4$ match those of the correspondingly numbered compounds of Table A1.

TABLE Q39

Table Q39 provides 352 compounds of formula (Ib) wherein $R^1$ is ethyl; $R^2$ is bromo; $R^3$ is $CON(CH_3)_2$; X is oxygen; Y is sulphur; n is 0; and the values of $R^4$ match those of the correspondingly numbered compounds of Table A1.

TABLE Q40

Table Q40 provides 352 compounds of formula (Ib) wherein $R^1$ is ethyl; $R^2$ is cyano; $R^3$ is $CON(CH_3)_2$; X is oxygen; Y is sulphur; n is 0; and the values of $R^4$ match those of the correspondingly numbered compounds of Table A1.

TABLE Q41

Table Q41 provides 352 compounds of formula (Ib) wherein $R^1$ is methyl; $R^2$ is hydrogen; $R^3$ is $CON(CH_3)_2$; X is oxygen; Y is $NR^7$; $R^7$ is hydrogen; n is 0; and the values of $R^4$ match those of the correspondingly numbered compounds of Table A1.

TABLE Q42

Table Q42 provides 352 compounds of formula (Ib) wherein $R^1$ is methyl; $R^2$ is fluoro; $R^3$ is $CON(CH_3)_2$; X is oxygen; Y is $NR^7$; $R^7$ is hydrogen; n is 0; and the values of $R^4$ match those of the correspondingly numbered compounds of Table A1.

TABLE Q43

Table Q43 provides 352 compounds of formula (Ib) wherein $R^1$ is methyl; $R^2$ is chloro; $R^3$ is $CON(CH_3)_2$; X is oxygen; Y is $NR^7$; $R^7$ is hydrogen; n is 0; and the values of $R^4$ match those of the correspondingly numbered compounds of Table A1.

TABLE Q44

Table Q44 provides 352 compounds of formula (Ib) wherein $R^1$ is methyl; $R^2$ is bromo; $R^3$ is $CON(CH_3)_2$; X is oxygen; Y is $NR^7$; $R^7$ is hydrogen; n is 0; and the values of $R^4$ match those of the correspondingly numbered compounds of Table A1.

TABLE Q45

Table Q45 provides 352 compounds of formula (Ib) wherein $R^1$ is methyl; $R^2$ is cyano; $R^3$ is $CON(CH_3)_2$; X is oxygen; Y is $NR^7$; $R^7$ is hydrogen; n is 0; and the values of $R^4$ match those of the correspondingly numbered compounds of Table A1.

TABLE Q46

Table Q46 provides 352 compounds of formula (Ib) wherein $R^1$ is ethyl; $R^2$ is hydrogen; $R^3$ is $CON(CH_3)_2$; X is oxygen; Y is $NR^7$; $R^7$ is hydrogen; n is 0; and the values of $R^4$ match those of the correspondingly numbered compounds of Table A1.

TABLE Q47

Table Q47 provides 352 compounds of formula (Ib) wherein $R^1$ is ethyl; $R^2$ is fluoro; $R^3$ is $CON(CH_3)_2$; X is oxygen; Y is $NR^7$; $R^7$ is hydrogen; n is 0; and the values of $R^4$ match those of the correspondingly numbered compounds of Table A1.

TABLE Q48

Table Q48 provides 352 compounds of formula (Ib) wherein $R^1$ is ethyl; $R^2$ is chloro; $R^3$ is $CON(CH_3)_2$; X is oxygen; Y is $NR^7$; $R^7$ is hydrogen; n is 0; and the values of $R^4$ match those of the correspondingly numbered compounds of Table A1.

TABLE Q49

Table Q49 provides 352 compounds of formula (Ib) wherein $R^1$ is ethyl; $R^2$ is bromo; $R^3$ is $CON(CH_3)_2$; X is oxygen; Y is $NR^7$; $R^7$ is hydrogen; n is 0; and the values of $R^4$ match those of the correspondingly numbered compounds of Table A1.

TABLE Q50

Table Q50 provides 352 compounds of formula (Ib) wherein $R^1$ is ethyl; $R^2$ is cyano; $R^3$ is $CON(CH_3)_2$; X is oxygen; Y is $NR^7$; $R^7$ is hydrogen; n is 0; and the values of $R^4$ match those of the correspondingly numbered compounds of Table A1.

TABLE Q51

Table Q51 provides 352 compounds of formula (Ib) wherein $R^1$ is methyl; $R^2$ is hydrogen; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q52

Table Q52 provides 352 compounds of formula (Ib) wherein $R^1$ is methyl; $R^2$ is fluoro; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q53

Table Q53 provides 352 compounds of formula (Ib) wherein $R^1$ is methyl; $R^2$ is chloro; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q54

Table Q54 provides 352 compounds of formula (Ib) wherein $R^1$ is methyl; $R^2$ is bromo; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q55

Table Q55 provides 352 compounds of formula (Ib) wherein $R^1$ is methyl; $R^2$ is cyano; $R^3$ is $CON(CH_3)_2$; X is

TABLE Q56

Table Q56 provides 352 compounds of formula (Ib) wherein $R^1$ is ethyl; $R^2$ is hydrogen; $R^2$ is $CON(CH_3)_2$; X is oxygen; Y is $NR^7$; $R^7$ is methyl; n is 0; and the values of $R^4$ match those of the correspondingly numbered compounds of Table A1.

TABLE Q57

Table Q57 provides 352 compounds of formula (Ib) wherein $R^1$ is ethyl; $R^2$ is fluoro; $R^7$ is $CON(CH_3)_2$; X is oxygen; Y is $NR^7$; $R^7$ is methyl; n is 0; and the values of $R^4$ match those of the correspondingly numbered compounds of Table A1

TABLE Q58

Table Q58 provides 352 compounds of formula (Ib) wherein $R^1$ is ethyl; $R^2$ is chloro; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q59

Table Q59 provides 352 compounds of formula (Ib) wherein $R^1$ is ethyl; $R^2$ is bromo; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q60

Table Q60 provides 352 compounds of formula (Ib) wherein $R^1$ is ethyl; $R^2$ is cyano; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q61

Table Q61 provides 352 compounds of formula (Ia) wherein $R^1$ is methyl; $R^2$ is hydrogen; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q62

Table Q62 provides 352 compounds of formula (Ia) wherein $R^1$ is methyl; $R^2$ is fluoro; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q63

Table Q63 provides 352 compounds of formula (Ia) wherein $R^1$ is methyl; $R^2$ is chloro; $R^2$ is $CON(CH_3)_2$; X is oxygen; Y is $NR^7$; $R^7$ is methyl; n is 0; and the values of $R^4$ match those of the correspondingly numbered compounds of Table A1.

TABLE Q64

Table Q64 provides 352 compounds of formula (Ia) wherein $R^1$ is methyl; $R^2$ is bromo; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q65

Table Q65 provides 352 compounds of formula (Ib) wherein $R^1$ is methyl; $R^2$ is cyano; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q66

Table Q66 provides 352 compounds of formula (Ia) wherein $R^1$ is ethyl; $R^2$ is hydrogen; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q67

Table Q67 provides 352 compounds of formula (Ia) wherein $R^1$ is ethyl; $R^2$ is fluoro; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q68

Table Q68 provides 352 compounds of formula (Ia) wherein $R^1$ is ethyl; $R^2$ is chloro; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q69

Table Q69 provides 352 compounds of formula (Ia) wherein $R^1$ is ethyl; $R^2$ is bromo; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE Q70

Table Q70 provides 352 compounds of formula (Ia) wherein $R^1$ is ethyl; $R^2$ is cyano; $R^3$ is $CON(CH_3)_2$; X is oxygen; Y is $NR^7$; $R^7$ is methyl; n is 0; and the values of $R^4$ match those of the correspondingly numbered compounds of Table A1.

TABLE R1

Table R1 provides 352 compounds of formula (Ia) wherein $R^1$ is methyl; $R^2$ is hydrogen; $R^3$ is $CONHCH_3$; X and Y are each oxygen; n is 0; and the values of $R^4$ match those of the correspondingly numbered compounds of Table A1.

TABLE R2

Table R2 provides 352 compounds of formula (Ia) wherein $R^1$ is methyl; $R^2$ is fluoro; $R^3$ is $CONHCH_3$; X and Y are each oxygen; n is 0; and the values of $R^4$ match those of the correspondingly numbered compounds of Table A1.

TABLE R3

Table R3 provides 352 compounds of formula (Ia) wherein $R^1$ is methyl; $R^2$ is chloro; $R^3$ is $CONHCH_3$; X and Y are each oxygen; n is 0; and the values of $R^4$ match those of the correspondingly numbered compounds of Table A1.

TABLE R4

Table R4 provides 352 compounds of formula (Ia) wherein $R^1$ is methyl; $R^2$ is bromo; $R^3$ is CONHCH$_3$; X and Y are each oxygen; n is 0; and the values of $R^4$ match those of the correspondingly numbered compounds of Table A1.

TABLE R5

Table R5 provides 352 compounds of formula (Ia) wherein $R^1$ is methyl; $R^2$ is cyano; $R^3$ is CONHCH$_3$; X and Y are each oxygen; n is 0; and the values of $R^4$ match those of the correspondingly numbered compounds of Table A1.

TABLE R6

Table R6 provides 352 compounds of formula (Ia) wherein $R^1$ is ethyl; $R^2$ is hydrogen; $R^3$ is CONHCH$_3$; X and Y are each oxygen; n is 0; and the values of $R^4$ match those of the correspondingly numbered compounds of Table A1.

TABLE R7

Table R7 provides 352 compounds of formula (Ia) wherein $R^1$ is ethyl; $R^2$ is fluoro; $R^3$ is CONHCH$_3$; X and Y are each oxygen; n is 0; and the values of $R^4$ match those of the correspondingly numbered compounds of Table A1.

TABLE R8

Table R8 provides 352 compounds of formula (Ia) wherein $R^1$ is ethyl; $R^2$ is chloro; $R^3$ is CONHCH$_3$; X and Y are each oxygen; n is 0; and the values of $R^4$ match those of the correspondingly numbered compounds of Table A1.

TABLE R9

Table R9 provides 352 compounds of formula (Ia) wherein $R^1$ is ethyl; $R^2$ is bromo; $R^3$ is CONHCH$_3$; X and Y are each oxygen; n is 0; and the values of $R^4$ match those of the correspondingly numbered compounds of Table A1.

TABLE R10

Table R10 provides 352 compounds of formula (Ia) wherein $R^1$ is ethyl; $R^2$ is cyano; $R^3$ is CONHCH$_3$; X and Y are each oxygen; n is 0; and the values of $R^4$ match those of the correspondingly numbered compounds of Table A1.

TABLE R11

Table R11 provides 352 compounds of formula (Ia) wherein $R^1$ is methyl; $R^2$ is hydrogen; $R^3$ is CONHCH$_3$; X is oxygen; Y is sulphur; n is 0; and the values of $R^4$ match those of the correspondingly numbered compounds of Table A1.

TABLE R12

Table R12 provides 352 compounds of formula (Ia) wherein $R^1$ is methyl; $R^2$ is fluoro; $R^3$ is CONHCH$_3$; X is oxygen; Y is sulphur; n is 0; and the values of $R^4$ match those of the correspondingly numbered compounds of Table A1.

TABLE R13

Table R13 provides 352 compounds of formula (Ia) wherein $R^1$ is methyl; $R^2$ is chloro; $R^3$ is CONHCH$_3$; X is oxygen; Y is sulphur; n is 0; and the values of $R^4$ match those of the correspondingly numbered compounds of Table A1.

TABLE R14

Table R14 provides 352 compounds of formula (Ia) wherein $R^1$ is methyl; $R^2$ is bromo; $R^3$ is CONHCH$_3$; X is oxygen; Y is sulphur; n is 0; and the values of $R^4$ match those is of the correspondingly numbered compounds of Table A1.

TABLE R15

Table R15 provides 352 compounds of formula (Ia) wherein $R^1$ is methyl; $R^2$ is cyano; $R^3$ is CONHCH$_3$; X is oxygen; Y is sulphur; n is 0; and the values of $R^4$ match those of the correspondingly numbered compounds of Table A1.

TABLE R16

Table R16 provides 352 compounds of formula (Ia) wherein $R^1$ is ethyl; $R^2$ is hydrogen; $R^3$ is CONHCH$_3$; X is oxygen; Y is sulphur; n is 0; and the values of $R^4$ match those of the correspondingly numbered compounds of Table A1.

TABLE R17

Table R17 provides 352 compounds of formula (Ia) wherein $R^1$ is ethyl; $R^2$ is fluoro; $R^3$ is CONHCH$_3$; X is oxygen; Y is sulphur; n is 0; and the values of $R^4$ match those of the correspondingly numbered compounds of Table A1.

TABLE R18

Table R18 provides 352 compounds of formula (Ia) wherein $R^1$ is ethyl; $R^2$ is chloro; $R^3$ is CONHCH$_3$; X is oxygen; Y is sulphur; n is 0; and the values of $R^4$ match those of the correspondingly numbered compounds of Table A1.

TABLE R19

Table R19 provides 352 compounds of formula (Ia) wherein $R^1$ is ethyl; $R^2$ is bromo; $R^3$ is CONHCH$_3$; X is oxygen; Y is sulphur; n is 0; and the values of $R^4$ match those of the correspondingly numbered compounds of Table A1.

TABLE R20

Table R20 provides 352 compounds of formula (Ia) wherein $R^1$ is ethyl; $R^2$ is cyano; $R^3$ is CONHCH$_3$; X is oxygen; Y is sulphur; n is 0; and the values of $R^4$ match those of the correspondingly numbered compounds of Table A1.

TABLE R21

Table R21 provides 352 compounds of formula (Ib) wherein $R^1$ is methyl; $R^2$ is hydrogen; $R^3$ is CONHCH$_3$; X and Y are each oxygen; n is 0; and the values of $R^4$ match those of the correspondingly numbered compounds of Table A1.

TABLE R22

Table R22 provides 352 compounds of formula (Ib) wherein $R^1$ is methyl; $R^2$ is fluoro; $R^3$ is CONHCH$_3$; X and Y are each oxygen; n is 0; and the values of $R^4$ match those of the correspondingly numbered compounds of Table A1.

TABLE R23

Table R23 provides 352 compounds of formula (Ib) wherein $R^1$ is methyl; $R^2$ is chloro; $R^3$ is CONHCH$_3$; X and

TABLE R24

Table R24 provides 352 compounds of formula (Ib) wherein $R^1$ is methyl; $R^2$ is bromo; $R^3$ is CONHCH$_3$; X and Y are each oxygen; n is 0; and the values of $R^4$ match those of the correspondingly numbered compounds of Table A1.

TABLE R25

Table R25 provides 352 compounds of formula (Ib) wherein $R^1$ is methyl; $R^2$ is cyano; $R^3$ is CONHCH$_3$; X and Y are each oxygen; n is 0; and the values of $R^4$ match those of the correspondingly numbered compounds of Table A1.

TABLE R26

Table R26 provides 352 compounds of formula (Ib) wherein $R^1$ is ethyl; $R^2$ is hydrogen; $R^3$ is CONHCH$_3$; X and Y are each oxygen; n is 0; and the values of $R^4$ match those of the correspondingly numbered compounds of Table A1.

TABLE R27

Table R27 provides 352 compounds of formula (Ib) wherein $R^1$ is ethyl; $R^2$ is fluoro; $R^3$ is CONHCH$_3$; X and Y are each oxygen; n is 0; and the values of $R^4$ match those of the correspondingly numbered compounds of Table A1.

TABLE R28

Table R28 provides 352 compounds of formula (Ib) wherein $R^1$ is ethyl; $R^2$ is chloro; $R^3$ is CONHCH$_3$; X and Y are each oxygen; n is 0; and the values of $R^4$ match those of the correspondingly numbered compounds of Table A1.

TABLE R29

Table R29 provides 352 compounds of formula (Ib) wherein $R^1$ is ethyl; $R^2$ is bromo; $R^3$ is CONHCH$_3$; X and Y are each oxygen; n is 0; and the values of $R^4$ match those of the correspondingly numbered compounds of Table A1.

TABLE R30

Table R30 provides 352 compounds of formula (Ib) wherein $R^1$ is ethyl; $R^2$ is cyano; $R^3$ is CONHCH$_3$; X and Y are each oxygen; n is 0; and the values of $R^4$ match those of the correspondingly numbered compounds of Table A1.

TABLE R31

Table R31 provides 352 compounds of formula (Ib) wherein $R^1$ is methyl; $R^2$ is hydrogen; $R^3$ is CONHCH$_3$; X is oxygen; Y is sulphur; n is 0; and the values of $R^4$ match those of the correspondingly numbered compounds of Table A1.

TABLE R32

Table R32 provides 352 compounds of formula (Ib) wherein $R^1$ is methyl; $R^2$ is fluoro; $R^3$ is CONHCH$_3$; X is oxygen; Y is sulphur; n is 0; and the values of $R^4$ match those of the correspondingly numbered compounds of Table A1.

TABLE R33

Table R33 provides 352 compounds of formula (Ib) wherein $R^1$ is methyl; $R^2$ is chloro; $R^3$ is CONHCH$_3$; X is oxygen; Y is sulphur; n is 0; and the values of $R^4$ match those of the correspondingly numbered compounds of Table A1.

TABLE R34

Table R34 provides 352 compounds of formula (Ib) wherein $R^1$ is methyl; $R^2$ is bromo; $R^3$ is CONHCH$_3$; X is oxygen; Y is sulphur; n is 0; and the values of $R^4$ match those of the correspondingly numbered compounds of Table A1.

TABLE R35

Table R35 provides 352 compounds of formula (Ib) wherein $R^1$ is methyl; $R^2$ is cyano; $R^3$ is CONHCH$_3$; X is oxygen; Y is sulphur; n is 0; and the values of $R^4$ match those of the correspondingly numbered compounds of Table A1.

TABLE R36

Table R36 provides 352 compounds of formula (Ib) wherein $R^1$ is ethyl; $R^2$ is hydrogen; $R^3$ is CONHCH$_3$; X is oxygen; Y is sulphur; n is 0; and the values of $R^4$ match those of the correspondingly numbered compounds of Table A1.

TABLE R37

Table R37 provides 352 compounds of formula (Ib) wherein $R^1$ is ethyl; $R^2$ is fluoro; is $R^3$ is CONHCH$_3$; X is oxygen; Y is sulphur; n is 0; and the values of $R^4$ match those of the correspondingly numbered compounds of Table A1.

TABLE R38

Table R38 provides 352 compounds of formula (Ib) wherein $R^1$ is ethyl; $R^2$ is chloro; $R^3$ is CONHCH$_3$; X is oxygen; Y is sulphur; n is 0; and the values of $R^4$ match those of the correspondingly numbered compounds of Table A1.

TABLE R39

Table R39 provides 352 compounds of formula (Ib) wherein $R^1$ is ethyl; $R^2$ is bromo; $R^3$ is CONHCH$_3$; X is oxygen; Y is sulphur; n is 0; and the values of $R^4$ match those of the correspondingly numbered compounds of Table A1.

TABLE R40

Table R40 provides 352 compounds of formula (Ib) wherein $R^1$ is ethyl; $R^2$ is cyano; $R^3$ is CONHCH$_3$; X is oxygen; Y is sulphur; n is 0; and the values of $R^4$ match those of the correspondingly numbered compounds of Table A1.

TABLE R41

Table R41 provides 352 compounds of formula (Ib) wherein $R^1$ is methyl; $R^2$ is hydrogen; $R^3$ is CONHCH$_3$; X is oxygen; Y is NR$^7$; $R^7$ is hydrogen; n is 0; and the values of $R^4$ match those of the correspondingly numbered compounds of Table A1.

TABLE R42

Table R42 provides 352 compounds of formula (Ib) wherein $R^1$ is methyl; $R^2$ is fluoro; $R^3$ is CONHCH$_3$; X is oxygen; Y is NR$^7$; R$^7$ is hydrogen; n is 0; and the values of R$^4$ match those of the correspondingly numbered compounds of Table A1.

TABLE R43

Table R43 provides 352 compounds of formula (Ib) wherein R$^1$ is methyl; R$^2$ is chloro; R$^3$ is CONHCH$_3$; X is oxygen; Y is NR$^7$; R$^7$ is hydrogen; n is 0; and the values of R$^4$ match those of the correspondingly numbered compounds of Table A1.

TABLE R44

Table R44 provides 352 compounds of formula (Ib) wherein R$^1$ is methyl; R$^2$ is bromo; R$^3$ is CONHCH$_3$; X is oxygen; Y is NR$^7$; R$^7$ is hydrogen; n is 0; and he values of R$^4$ match those of the correspondingly numbered compounds of Table A1.

TABLE R45

Table R45 provides 352 compounds of formula (Ib) wherein R$^1$ is methyl; R$^2$ is cyano; R$^3$ is CONHCH$_3$; X is oxygen; Y is NR$^7$; R$^7$ is hydrogen; n is 0; and the values of R$^4$ match those of the correspondingly numbered compounds of Table A1.

TABLE R46

Table R46 provides 352 compounds of formula (Ib) wherein R$^1$ is ethyl; R$^2$ is hydrogen; R$^3$ is CONHCH$_3$; X is oxygen; Y is NR$^7$; R$^7$ is hydrogen; n is 0; and the values of R$^4$ match those of the correspondingly numbered compounds of Table A1.

TABLE R47

Table R47 provides 352 compounds of formula (Ib) wherein R$^1$ is ethyl; R$^2$ is fluoro; R$^3$ is CONHCH$_3$; X is oxygen; Y is NR$^7$; R$^7$ is hydrogen; n is 0; and the values of R$^4$ match those of the correspondingly numbered compounds of Table A1.

TABLE R48

Table R48 provides 352 compounds of formula (Ib) wherein R$^1$ is ethyl; R$^2$ is chloro; R$^3$ is CONHCH$_3$; X is oxygen; Y is NR$^7$; R$^7$ is hydrogen; n is 0; and the values of R$^4$ match those of the correspondingly numbered compounds of Table A1.

TABLE R49

Table R49 provides 352 compounds of formula (Ib) wherein R$^1$ is ethyl; R$^2$ is bromo; R$^3$ is CONHCH$_3$; X is oxygen; Y is NR$^7$; R$^7$ is hydrogen; n is 0; and the values of R$^4$ match those of the correspondingly numbered compounds of Table A1.

TABLE R50

Table R50 provides 352 compounds of formula (Ib) wherein R$^1$ is ethyl; R$^2$ is cyano; R$^3$ is CONHCH$_3$; X is oxygen; Y is NR$^7$; R$^7$ is hydrogen; n is 0; and the values of R$^4$ match those of the correspondingly numbered compounds of Table A1.

TABLE R51

Table R51 provides 352 compounds of formula (Ib) wherein R$^1$ is methyl; R$^2$ is hydrogen; R$^3$ is CONHCH$_3$; X is oxygen; Y is NR$^7$; R$^7$ is methyl; n is 0; and the values of R$^4$ match those of the correspondingly numbered compounds of Table A1.

TABLE R52

Table R52 provides 352 compounds of formula (Ib) wherein R$^1$ is methyl; R$^2$ is is fluoro; R$^3$ is CONHCH$_3$; X is oxygen; Y is NR$^7$; R$^7$ is methyl; n is 0; and the values of R$^4$ match those of the correspondingly numbered compounds of Table A1.

TABLE R53

Table R53 provides 352 compounds of formula (Ib) wherein R$^1$ is methyl; R$^2$ is chloro; R$^3$ is CONHCH$_3$; X is oxygen; Y is NR$^7$; R$^7$ is methyl; n is 0; and the values of R$^4$ match those of the correspondingly numbered compounds of Table A1.

TABLE R54

Table R54 provides 352 compounds of formula (Ib) wherein R$^1$ is methyl; R$^2$ is bromo; R$^3$ is CONHCH$_3$; X is oxygen; Y is NR$^7$; R$^7$ is methyl; n is 0; and the values of R$^4$ match those of the correspondingly numbered compounds of Table A1.

TABLE R55

Table R55 provides 352 compounds of formula (Ib) wherein R$^1$ is methyl; R$^2$ is cyano; R$^3$ is CONHCH$_3$; X is oxygen; Y is NR$^7$; R$^7$ is methyl; n is 0; and the values of R$^4$ match those of the correspondingly numbered compounds of Table A1.

TABLE R56

Table R56 provides 352 compounds of formula (Ib) wherein R$^1$ is ethyl; R$^2$ is hydrogen; R$^3$ is CONHCH$_3$; X is oxygen; Y is NR$^7$; R$^7$ is methyl; n is 0; and the values of R$^4$ match those of the correspondingly numbered compounds of Table A1.

TABLE R57

Table R57 provides 352 compounds of formula (Ib) wherein R$^1$ is ethyl; R$^2$ is fluoro; R$^3$ is CONHCH$_3$; X is oxygen; Y is NR$^7$; R$^7$ is methyl; n is 0; and the values of R$^4$ match those of the correspondingly numbered compounds of Table A1.

TABLE R58

Table R58 provides 352 compounds of formula (Ib) wherein R$^1$ is ethyl; R$^2$ is chloro; R$^3$ is CONHCH$_3$; X is oxygen; Y is NR$^7$; R$^7$ is methyl; n is 0; and the values of R$^4$ match those of the correspondingly numbered compounds of Table A1.

TABLE R59

Table R59 provides 352 compounds of formula (Ib) wherein R$^1$ is ethyl; R$^2$ is bromo; R$^3$ is CONHCH$_3$; X is oxygen; Y is NR$^7$; R$^7$ is methyl; n is 0; and the values of R$^4$ match those of the correspondingly numbered compounds of Table A1.

TABLE R60

Table R60 provides 352 compounds of formula (Ib) wherein R$^1$ is ethyl; R$^2$ is cyano; R$^3$ is CONHCH$_3$; X is oxygen; Y is NR$^7$; R$^7$ is methyl; n is 0; and the values of R$^4$ match those of the correspondingly numbered compounds of Table A1.

TABLE R61

Table R61 provides 352 compounds of formula (Ia) wherein R$^1$ is methyl; R$^2$ is hydrogen; R$^3$ is CONHCH$_3$; X is oxygen; Y is NR$^7$; R$^7$ is methyl; n is 0; and the values of R$^4$ match those of the correspondingly numbered compounds of Table A1.

TABLE R62

Table R62 provides 352 compounds of formula (Ia) wherein R$^1$ is methyl; R$^2$ is fluoro; R$^3$ is CONHCH$_3$; X is oxygen; Y is NR$^7$; R$^7$ is methyl; n is 0; and the values of R$^4$ match those of the correspondingly numbered compounds of Table A1.

TABLE R63

Table R63 provides 352 compounds of formula (Ia) wherein R$^1$ is methyl; R$^2$ is chloro; R$^3$ is CONHCH$_3$; X is oxygen; Y is NR$^7$; R$^7$ is methyl; n is 0; and the values of R$^4$ match those of the correspondingly numbered compounds of Table A1.

TABLE R64

Table R64 provides 352 compounds of formula (Ia) wherein R$^1$ is methyl; R$^2$ is bromo; R$^3$ is CONHCH$_3$; X is oxygen; Y is NR$^7$; R$^7$ is methyl; n is 0; and the values of R$^4$ match those of the correspondingly numbered compounds of Table A1.

TABLE R65

Table R65 provides 352 compounds of formula (Ib) wherein R$^1$ is methyl; R$^2$ is cyano; R$^3$ is CONHCH$_3$; X is oxygen; Y is NR$^7$; R$^7$ is methyl; n is 0; and the values of R$^4$ match those of the correspondingly numbered compounds of Table A1.

TABLE R66

Table R66 provides 352 compounds of formula (Ia) wherein R$^1$ is ethyl; R$^2$ is hydrogen; R$^3$ is CONHCH$_3$; X is oxygen; Y is NR$^7$; R$^7$ is methyl; n is 0; and the values of R$^4$ match those of the correspondingly numbered compounds of Table A1.

TABLE R67

Table R$^{67}$ provides 352 compounds of formula (Ia) wherein R$^1$ is ethyl; R$^2$ is fluoro; R$^3$ is CONHCH$_3$; X is oxygen; Y is NR$^7$; R$^7$ is methyl; n is 0; and the values of R$^4$ match those of the correspondingly numbered compounds of Table A1.

TABLE R68

Table R68 provides 352 compounds of formula (Ia) wherein R$^1$ is ethyl; R$^2$ is chloro; R$^3$ is CONHCH$_3$; X is oxygen; Y is NR$^7$; R$^7$ is methyl; n is 0; and the values of R$^4$ match those of the correspondingly numbered.compounds of Table A1.

TABLE R69

Table R69 provides 352 compounds of formula (Ia) wherein R$^1$ is ethyl; R$^2$ is bromo; R$^3$ is CONHCH$_3$; X is oxygen; Y is NR$^7$; R$^7$ is methyl; n is 0; and the values of R$^4$ match those of the correspondingly numbered compounds of Table A1.

TABLE R70

Table R70 provides 352 compounds of formula (Ia) wherein R$^1$ is ethyl; R$^2$ is cyano; R$^3$ is CONHCH$_3$; X is oxygen; Y is NR$^7$; R$^7$ is methyl; n is 0; and the values of R$^4$ match those of the correspondingly numbered compounds of Table A1.

TABLE S1

Table S1 provides 352 compounds of formula (Ia) wherein R$^1$ is methyl; R$^2$ is hydrogen; R$^3$ is CH$_2$SCH$_3$; X and Y are each oxygen; n is 0; and the values of R$^4$ match those of the correspondingly numbered compounds of Table A1.

TABLE S2

Table S2 provides 352 compounds of formula (Ia) wherein R$^1$ is methyl; R$^2$ is fluoro; R$^3$ is CH$_2$SCH$_3$; X and Y are each oxygen; n is 0; and the values of R$^4$ match those of the correspondingly numbered compounds of Table A1.

TABLE S3

Table S3 provides 352 compounds of formula (Ia) wherein R$^1$ is methyl; R$^2$ is chloro; R$^3$ is CH$_2$SCH$_3$; X and Y are each oxygen; n is 0; and the values of R$^4$ match those of the correspondingly numbered compounds of Table A1.

TABLE S4

Table S4 provides 352 compounds of formula (Ia) wherein R$^1$ is methyl; R$^2$ is bromo; R$^3$ is CH$_2$SCH$_3$; X and Y are each oxygen; n is 0; and the values of R$^4$ match those of the correspondingly numbered compounds of Table A1.

TABLE S5

Table S5 provides 352 compounds of formula (Ia) wherein R$^1$ is methyl; R$^2$ is cyano; R$^3$ is CH$_2$SCH$_3$; X and Y are each oxygen; n is 0; and the values of R$^4$ match those of the correspondingly numbered compounds of Table A1.

TABLE S6

Table S6 provides 352 compounds of formula (Ia) wherein R$^1$ is ethyl; R$^2$ is hydrogen; R$^3$ is CH$_2$SCH$_3$; X and Y are each oxygen; n is 0; and the values of R$^4$ match those of the correspondingly numbered compounds of Table A1.

TABLE S7

Table S7 provides 352 compounds of formula (Ia) wherein R$^1$ is ethyl; R$^2$ is fluoro; R$^3$ is CH$_2$SCH$_3$; X and Y are each oxygen; n is 0; and the values of R$^4$ match those of the correspondingly numbered compounds of Table A1.

TABLE S8

Table S8 provides 352 compounds of formula (Ia) wherein R$^1$ is ethyl; R$^2$ is chloro; R$^3$ is CH$_2$SCH$_3$; X and Y are each oxygen; n is 0; and the values of R$^4$ match those of the correspondingly numbered compounds of Table A1.

TABLE S9

Table S9 provides 352 compounds of formula (Ia) wherein R$^1$ is ethyl; R$^2$ is bromo; R$^3$ is CH$_2$SCH$_3$; X and Y

TABLE S10

Table S10 provides 352 compounds of formula (Ia) wherein $R^1$ is ethyl; $R^2$ is cyano; $R^3$ is $CH_2SCH_3$; X and Y are each oxygen; n is 0; and the values of $R^4$ match those of the correspondingly numbered compounds of Table A1.

TABLE S11

Table S11 provides 352 compounds of formula (Ia) wherein $R^1$ is methyl; $R^2$ is hydrogen; $R^3$ is $CH_2SCH_3$; X is oxygen; Y is sulphur; n is 0; and the values of $R^4$ match those of the correspondingly numbered compounds of Table A1.

TABLE S12

Table S12 provides 352 compounds of formula (Ia) wherein $R^1$ is methyl; $R^2$ is fluoro; $R^3$ is $CH_2SCH_3$; X is oxygen; Y is sulphur; n is 0; and the values of $R^4$ match those of the correspondingly numbered compounds of Table A1.

TABLE S13

Table S13 provides 352 compounds of formula (Ia) wherein $R^1$ is methyl; $R^2$ is chloro; $R^3$ is $CH_2SCH_3$; X is oxygen; Y is sulphur; n is 0; and the values of $R^4$ match those of the correspondingly numbered compounds of Table A1.

TABLE S14

Table S14 provides 352 compounds of formula (Ia) wherein $R^1$ is methyl; $R^2$ is bromo; $R^3$ is $CH_2SCH_3$; X is oxygen; Y is sulphur; n is 0; and the values of $R^4$ match those of the correspondingly numbered compounds of Table A1.

TABLE S15

Table S15 provides 352 compounds of formula (Ia) wherein $R^1$ is methyl; $R^2$ is cyano; $R^3$ is $CH_2SCH_3$; X is oxygen; Y is sulphur; n is 0; and the values of $R^4$ match those of the correspondingly numbered compounds of Table A1.

TABLE S16

Table S16 provides 352 compounds of formula (Ia) wherein $R^1$ is ethyl; $R^2$ is hydrogen; $R^3$ is $CH_2SCH_3$; X is oxygen; Y is sulphur; n is 0; and the values of $R^4$ match those of the correspondingly numbered compounds of Table A1.

TABLE S17

Table S17 provides 352 compounds of formula (Ia) wherein $R^1$ is ethyl; $R^2$ is fluoro; $R^3$ is $CH_2SCH_3$; X is oxygen; Y is sulphur; n is 0; and the values of $R^4$ match those of the correspondingly numbered compounds of Table A1.

TABLE S18

Table S18 provides 352 compounds of formula (Ia) wherein $R^1$ is ethyl; $R^2$ is chloro; $R^3$ is $CH_2SCH_3$; X is oxygen; Y is sulphur; n is 0; and the values of $R^4$ match those of the correspondingly numbered compounds of Table A1.

TABLE S19

Table S19 provides 352 compounds of formula (Ia) wherein $R^1$ is ethyl; $R^2$ is bromo; $R^3$ is $CH_2SCH_3$; X is oxygen; Y is sulphur; n is 0; and the values of $R^4$ match those of the correspondingly numbered compounds of Table A1.

TABLE S20

Table S20 provides 352 compounds of formula (Ia) wherein $R^1$ is ethyl; $R^2$ is cyano; $R^3$ is $CH_2SCH_3$; X is oxygen; Y is sulphur; n is 0; and the values of $R^4$ match those of the correspondingly numbered compounds of Table A1.

TABLE S21

Table S21 provides 352 compounds of formula (Ib) wherein $R^1$ is methyl; $R^2$ is hydrogen; $R^3$ is $CH_2SCH_3$; X and Y are each oxygen; n is 0; and the values of $R^4$ match those of the correspondingly numbered compounds of Table A1.

TABLE S22

Table S22 provides 352 compounds of formula (Ib) wherein $R^1$ is methyl; $R^2$ is fluoro; $R^3$ is $CH_2SCH_3$; X and Y are each oxygen; n is 0; and the values of $R^4$ match those of the correspondingly numbered compounds of Table A1.

TABLE S23

Table S23 provides 352 compounds of formula (Ib) wherein $R^1$ is methyl; $R^2$ is chloro; $R^3$ is $CH_2SCH_3$; X and Y are each oxygen; n is 0; and the values of $R^4$ match those of the correspondingly numbered compounds of Table A1.

TABLE S24

Table S24 provides 352 compounds of formula (Ib) wherein $R^1$ is methyl; $R^2$ is bromo; $R^3$ is $CH_2SCH_3$; X and Y are each oxygen; n is 0; and the values of $R^4$ match those of the correspondingly numbered compounds of Table A1.

TABLE S25

Table S25 provides 352 compounds of formula (Ib) wherein $R^1$ is methyl; $R^2$ is cyano; $R^3$ is $CH_2SCH_3$; X and Y are each oxygen; n is 0; and the values of $R^4$ match those of the correspondingly numbered compounds of Table A1.

TABLE S26

Table S26 provides 352 compounds of formula (Ib) wherein $R^1$ is ethyl; $R^2$ is hydrogen; $R^3$ is $CH_2SCH_3$; X and Y are each oxygen; n is 0; and the values of $R^4$ match those of the correspondingly numbered compounds of Table A1.

TABLE S27

Table S27 provides 352 compounds of formula (Ib) wherein $R^1$ is ethyl; $R^2$ is fluoro; $R^3$ is $CH_2SCH_3$; X and Y are each oxygen; n is 0; and the values of $R^4$ match those of the correspondingly numbered compounds of Table A1.

TABLE S28

Table S28 provides 352 compounds of formula (Ib) wherein $R^1$ is ethyl; $R^2$ is chloro; $R^3$ is $CH_2SCH_3$; X and Y are each oxygen; n is 0; and the values of $R^4$ match those of the correspondingly numbered compounds of Table A1.

TABLE S29

Table S29 provides 352 compounds of formula (Ib) wherein $R^1$ is ethyl; $R^2$ is bromo; $R^3$ is $CH_2SCH_3$; X and Y are each oxygen; n is 0; and the values of $R^4$ match those of the correspondingly numbered compounds of Table A1.

TABLE S30

Table S30 provides 352 compounds of formula (Ib) wherein $R^1$ is ethyl; $R^2$ is cyano; $R^3$ is $CH_2SCH_3$; X and Y are each oxygen; n is 0; and the values of $R^4$ match those of the correspondingly numbered compounds of Table A1.

TABLE S31

Table S31 provides 352 compounds of formula (Ib) wherein $R^1$ is methyl; $R^2$ is hydrogen; $R^3$ is $CH_2SCH_3$; X is oxygen; Y is sulphur; n is 0; and the values of $R^4$ match those of the correspondingly numbered compounds of Table A1.

TABLE S32

Table S32 provides 352 compounds of formula (Ib) wherein $R^1$ is methyl; $R^2$ is fluoro; $R^3$ is $CH_2SCH_3$; X is oxygen; Y is sulphur; n is 0; and the values of $R^4$ match those of the correspondingly numbered compounds of Table A1.

TABLE S33

Table S33 provides 352 compounds of formula (Ib) wherein $R^1$ is methyl; $R^2$ is chloro; $R^3$ is $CH_2SCH_3$; X is oxygen; Y is sulphur; n is 0; and the values of $R^4$ match those of the correspondingly numbered compounds of Table A1.

TABLE S34

Table S34 provides 352 compounds of formula (Ib) wherein $R^1$ is methyl; $R^2$ is bromo; $R^3$ is $CH_2SCH_3$; X is oxygen; Y is sulphur; n is 0; and the values of $R^4$ match those of the correspondingly numbered compounds of Table A1.

TABLE S35

Table S35 provides 352 compounds of formula (Ib) wherein $R^1$ is methyl; $R^2$ is cyano; $R^3$ is $CH_2SCH_3$; X is oxygen; Y is sulphur; n is 0; and the values of $R^4$ match those of the correspondingly numbered compounds of Table A1.

TABLE S36

Table S36 provides 352 compounds of formula (Ib) wherein $R^1$ is ethyl; $R^2$ is hydrogen; $R^3$ is $CH_2SCH_3$; X is oxygen; Y is sulphur; n is 0; and the values of $R^4$ match those of the correspondingly numbered compounds of Table A1.

TABLE S37

Table S37 provides 352 compounds of formula (Ib) wherein $R^1$ is ethyl; $R^2$ is fluoro; $R^3$ is $CH_2SCH_3$; X is oxygen; Y is sulphur; n is 0; and the values of $R^4$ match those of the correspondingly numbered compounds of Table A1.

TABLE S38

Table S38 provides 352 compounds of formula (Ib) wherein $R^1$ is ethyl; $R^2$ is chloro; $R^3$ is $CH_2SCH_3$; X is oxygen; Y is sulphur; n is 0; and the values of $R^4$ match those of the correspondingly numbered compounds of Table A1.

TABLE S39

Table S39 provides 352 compounds of formula (Ib) wherein $R^1$ is ethyl; $R^2$ is bromo; $R^3$ is $CH_2SCH_3$; X is oxygen; Y is sulphur; n is 0; and the values of $R^4$ match those of the correspondingly numbered compounds of Table A1.

TABLE S40

Table S40 provides 352 compounds of formula (Ib) wherein $R^1$ is ethyl; $R^2$ is cyano; $R^3$ is $CH_2SCH_3$; X is oxygen; Y is sulphur; n is 0; and the values of $R^4$ match those of the correspondingly numbered compounds of Table A1.

TABLE S41

Table S41 provides 352 compounds of formula (Ib) wherein $R^1$ is methyl; $R^2$ is hydrogen; $R^3$ is $CH_2SCH_3$; X is oxygen; Y is $NR^7$; $R^7$ is hydrogen; n is 0; and the values of $R^4$ match those of the correspondingly numbered compounds of Table A1.

TABLE S42

Table S42 provides 352 compounds of formula (Ib) wherein $R^1$ is methyl; $R^2$ is fluoro; $R^3$ is $CH_2SCH_3$; X is oxygen; Y is $NR^7$; $R^7$ is hydrogen; n is 0; and the values of $R^4$ match those of the correspondingly numbered compounds of Table A1.

TABLE S43

Table S43 provides 352 compounds of formula (Ib) wherein $R^1$ is methyl; $R^2$ is chloro; $R^3$ is $CH_2SCH_3$; X is oxygen; Y is $NR^7$; $R^7$ is hydrogen; n is 0; and the values of $R^4$ match those of the correspondingly numbered compounds of Table A1.

TABLE S44

Table S44 provides 352 compounds of formula (Ib) wherein $R^1$ is methyl; $R^2$ is bromo; $R^3$ is $CH_2SCH_3$; X is oxygen; Y is $NR^7$; $R^7$ is hydrogen; n is 0; and the values of $R^4$ match those of the correspondingly numbered compounds of Table A1.

TABLE S45

Table S45 provides 352 compounds of formula (Ib) wherein $R^1$ is methyl; $R^2$ is cyano; $R^3$ is $CH_2SCH_3$; X is oxygen; Y is $NR^7$; $R^7$ is hydrogen; n is 0; and the values of $R^4$ match those of the correspondingly numbered compounds of Table A1.

TABLE S46

Table S46 provides 352 compounds of formula (Ib) wherein $R^1$ is ethyl; $R^2$ is hydrogen; $R^3$ is $CH_2SCH_3$; X is oxygen; Y is $NR^7$; $R^7$ is hydrogen; n is 0; and the values of $R^4$ match those of the correspondingly numbered compounds of Table A1.

TABLE S47

Table S47 provides 352 compounds of formula (Ib) wherein $R^1$ is ethyl; $R^2$ is fluoro; $R^3$ is $CH_2SCH_3$; X is oxygen; Y is $NR^7$; $R^7$ is hydrogen; n is 0; and the values of $R^4$ match those of the correspondingly numbered compounds of Table A1.

TABLE S48

Table S48 provides 352 compounds of formula (Ib) wherein $R^1$ is ethyl; $R^2$ is chloro; $R^3$ is $CH_2SCH_3$; X is oxygen; Y is $NR^7$; $R^7$ is hydrogen; n is 0; and the values of $R^4$ match those of the correspondingly numbered compounds of Table A1.

TABLE S49

Table S49 provides 352 compounds of formula (Ib) wherein $R^1$ is ethyl; $R^2$ is bromo; $R^3$ is $CH_2SCH_3$; X is oxygen; Y is $NR^7$; $R^7$ is hydrogen; n is 0; and the values of $R^4$ match those of the correspondingly numbered compounds of Table A1.

TABLE S50

Table S50 provides 352 compounds of formula (Ib) wherein $R^1$ is ethyl; $R^2$ is cyano; $R^3$ is $CH_2SCH_3$; X is oxygen; Y is $NR^7$; $R^7$ is hydrogen; n is 0; and the values of $R^4$ match those of the correspondingly numbered compounds of Table A1.

TABLE S51

Table S51 provides 352 compounds of formula (Ib) wherein $R^1$ is methyl; $R^2$ is hydrogen; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S52

Table S52 provides 352 compounds of formula (Ib) wherein $R^1$ is methyl; $R^2$ is fluoro; $R^2$ is $CH_2SCH_3$; X is oxygen; Y is $NR^7$; $R^7$ is methyl; n is 0; and the values of $R^4$ match those of the correspondingly numbered compounds of Table A1.

TABLE S53

Table S53 provides 352 compounds of formula (Ib) wherein $R^1$ is methyl; $R^2$ is chloro; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S54

Table S54 provides 352 compounds of formula (Ib) wherein $R^1$ is methyl; $R^2$ is bromo; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S55

Table S55 provides 352 compounds of formula (Ib) wherein $R^1$ is methyl; $R^2$ is cyano; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S56

Table S56 provides 352 compounds of formula (Ib) wherein $R^1$ is ethyl; $R^2$ is hydrogen; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S57

Table S57 provides 352 compounds of formula (Ib) wherein $R^1$ is ethyl; $R^2$ is fluoro; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S58

Table S58 provides 352 compounds of formula (Ib) wherein $R^1$ is ethyl; $R^2$ is chloro; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S59

Table S59 provides 352 compounds of formula (Ib) wherein $R^1$ is ethyl; $R^2$ is bromo; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S60

Table S60 provides 352 compounds of formula (Ib) wherein $R^1$ is ethyl; $R^2$ is cyano; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S61

Table S61 provides 352 compounds of formula (Ia) wherein $R^1$ is methyl; $R^2$ is hydrogen; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S62

Table S62 provides 352 compounds of formula (Ia) wherein $R^1$ is methyl; $R^2$ is fluoro; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S63

Table S63 provides 352 compounds of formula (Ia) wherein $R^1$ is methyl; $R^2$ is chloro; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S64

Table S64 provides 352 compounds of formula (Ia) wherein $R^1$ is methyl; $R^2$ is bromo; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S65

Table S65 provides 352 compounds of formula (Ib) wherein $R^1$ is methyl; $R^2$ is cyano; $R^3$ is $CH_2SCH_3$; X is

TABLE S66

Table S66 provides 352 compounds of formula (Ia) wherein $R^1$ is ethyl; $R^2$ is hydrogen; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S67

Table S67 provides 352 compounds of formula (Ia) wherein $R^1$ is ethyl; $R^2$ is fluoro; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S68

Table S68 provides 352 compounds of formula (Ia) wherein $R^1$ is ethyl; $R^2$ is chloro; $R^1$ is $CH_2SCH_3$; X is oxygen; Y is $NR^7$; $R^7$ is methyl; n is 0; and the values of $R^4$ match those of the correspondingly numbered compounds of Table A1.

TABLE S69

Table S69 provides 352 compounds of formula (Ia) wherein $R^1$ is ethyl; $R^2$ is bromo; $R^3$ is $CH_2SCH_3$; X is oxygen; Y is $NR^7$; $R^7$ is methyl; n is 0; and the values of $R^4$ match those of the correspondingly numbered compounds of Table A1.

TABLE S70

Table S70 provides 352 compounds of formula (Ia) wherein $R^1$ is ethyl; $R^2$ is cyano; $R^3$ is $CH_2SCH_3$; X is oxygen; Y is $NR^7$; $R^7$ is methyl; n is 0; and the values of $R^4$ match those of the correspondingly numbered compounds of Table A1.

TABLE T1

Table T1 provides 352 compounds of formula (Ia) wherein $R^1$ is methyl; $R^2$ is hydrogen; $R^3$ is $SCH_3$; X and Y are each oxygen; n is 0; and the values of $R^4$ match those of the correspondingly numbered compounds of Table A1.

TABLE T2

Table T2 provides 352 compounds of formula (Ia) wherein $R^1$ is methyl; $R^2$ is fluoro; $R^3$ is $SCH_3$; X and Y are each oxygen; n is 0; and the values of $R^4$ match those of the correspondingly numbered compounds of Table A1.

TABLE T3

Table T3 provides 352 compounds of formula (Ia) wherein $R^1$ is methyl; $R^2$ is chloro; $R^3$ is $SCH_3$; X and Y are each oxygen; n is 0; and the values of $R^4$ match those of the correspondingly numbered compound of Table A1.

TABLE T4

Table T4 provides 352 compounds of formula (Ia) wherein $R^1$ is methyl; $R^2$ is bromo; $R^3$ is $SCH_3$; X and Y are each oxygen; n is 0; and the values of $R^4$ match those of the correspondingly numbered compounds of Table A1.

TABLE T5

Table T5 provides 352 compounds of formula (Ia) wherein $R^1$ is methyl; $R^2$ is cyano; $R^3$ is $SCH_3$; X and Y are each oxygen; n is 0; and the values of $R^4$ match those of the correspondingly numbered compounds of Table A1.

TABLE T6

Table T6 provides 352 compounds of formula (Ia) wherein $R^1$ is ethyl; $R^2$ is hydrogen; $R^3$ is $SCH_3$; X and Y are each oxygen; n is 0; and the values of $R^4$ match those of the correspondingly numbered compounds of Table A1.

TABLE T7

Table T7 provides 352 compounds of formula (Ia) wherein $R^1$ is ethyl; $R^2$ is fluoro; $R^3$ is $SCH_3$; X and Y are each oxygen; n is 0; and the values of $R^4$ match those of the correspondingly numbered compounds of Table A1.

TABLE T8

Table T8 provides 352 compounds of formula (Ia) wherein $R^1$ is ethyl; $R^2$ is chloro; $R^3$ is $SCH_3$; X and Y are each oxygen; n is 0; and the values of $R^4$ match those of the correspondingly numbered compounds of Table A1.

TABLE T9

Table T9 provides 352 compounds of formula (Ia) wherein $R^1$ is ethyl; $R^2$ is bromo; $R^3$ is $SCH_3$; X and Y are each oxygen; n is 0; and the values of $R^4$ match those of the correspondingly numbered compounds of Table A1.

TABLE T10

Table T10 provides 352 compounds of formula (Ia) wherein $R^1$ is ethyl; $R^2$ is cyano; $R^3$ is $SCH_3$; X and Y are each oxygen; n is 0; and the values of $R^4$ match those of the correspondingly numbered compounds of Table A1.

TABLE T11

Table T11 provides 352 compounds of formula (Ia) wherein $R^1$ is methyl; $R^2$ is hydrogen; $R^3$ is $SCH_3$; X is oxygen; Y is sulphur; n is 0; and the values of $R^4$ match those of the correspondingly numbered compounds of Table A1.

TABLE T12

Table T12 provides 352 compounds of formula (Ia) wherein $R^1$ is methyl; $R^2$ is fluoro; $R^3$ is $SCH_3$; X is oxygen; Y is sulphur; n is 0; and the values of $R^4$ match those of the correspondingly numbered compounds of Table A1.

TABLE T13

Table T13 provides 352 compounds of formula (Ia) wherein $R^1$ is methyl; $R^2$ is chloro; $R^3$ is $SCH_3$; X is oxygen; Y is sulphur; n is 0; and the values of $R^4$ match those of the correspondingly numbered compounds of Table A1.

TABLE T14

Table T14 provides 352 compounds of formula (Ia) wherein $R^1$ is methyl; $R^2$ is bromo; $R^3$ is $SCH_3$; X is oxygen; Y is sulphur; n is 0; and the values of $R^4$ match those of the correspondingly numbered compounds of Table A1.

TABLE T15

Table T15 provides 352 compounds of formula (Ia) wherein $R^1$ is methyl; $R^2$ is cyano; $R^3$ is $SCH_3$; X is oxygen; Y is sulphur; n is 0; and the values of $R^4$ match those of the correspondingly numbered compounds of Table A1.

TABLE T16

Table T16 provides 352 compounds of formula (Ia) wherein $R^1$ is ethyl; $R^2$ is hydrogen; $R^3$ is $SCH_3$; X is oxygen; Y is sulphur; n is 0; and the values of $R^4$ match those of the correspondingly numbered compounds of Table A1.

TABLE T17

Table T17 provides 352 compounds of formula (Ia) wherein $R^1$ is ethyl; $R^2$ is fluoro; $R^3$ is $SCH_3$; X is oxygen; Y is sulphur; n is 0; and the values of $R^4$ match those of the correspondingly numbered compounds of Table A1.

TABLE T18

Table T18 provides 352 compounds of formula (Ia) wherein $R^1$ is ethyl; $R^2$ is chloro; $R^3$ is $SCH_3$; X is oxygen; Y is sulphur; n is 0; and the values of $R^4$ match those of the correspondingly numbered compounds of Table A1.

TABLE T19

Table T19 provides 352 compounds of formula (Ia) wherein $R^1$ is ethyl; $R^2$ is bromo; $R^3$ is $SCH_3$; X is oxygen; Y is sulphur; n is 0; and the values of $R^4$ match those of the correspondingly numbered compounds of Table A1.

TABLE T20

Table T20 provides 352 compounds of formula (Ia) wherein $R^1$ is ethyl; $R^2$ is cyano; $R^3$ is $SCH_3$; X is oxygen; Y is sulphur; n is 0; and the values of $R^4$ match those of the correspondingly numbered compounds of Table A1.

TABLE T21

Table T21 provides 352 compounds of formula (Ib) wherein $R^1$ is methyl; $R^2$ is hydrogen; $R^3$ is $SCH_3$; X and Y are each oxygen; n is 0; and the values of $R^4$ match those of the correspondingly numbered compounds of Table A1.

TABLE T22

Table T22 provides 352 compounds of formula (Ib) wherein $R^1$ is methyl; $R^2$ is fluoro; $R^3$ is $SCH_3$; X and Y are each oxygen; n is 0; and the values of $R^4$ match those of the correspondingly numbered compounds of Table A1.

TABLE T23

Table T13 provides 352 compounds of formula (Ib) wherein $R^1$ is methyl; $R^2$ is chloro; $R^3$ is $SCH_3$; X and Y are each oxygen; n is 0; and the values of $R^4$ match those of the correspondingly numbered compounds of Table A1.

TABLE T24

Table T24 provides 352 compounds of formula (Ib) wherein $R^1$ is methyl; $R^2$ is bromo; $R^3$ is $SCH_3$; X and Y are each oxygen; n is 0; and the values of $R^4$ match those of the correspondingly numbered compounds of Table A1.

TABLE T25

Table T25 provides 352 compounds of formula (Ib) wherein $R^1$ is methyl; $R^2$ is cyano; $R^3$ is $SCH_3$; X and Y are each oxygen; n is 0; and the values of $R^4$ match those of the correspondingly numbered compounds of Table A1.

TABLE T26

Table T26 provides 352 compounds of formula (Ib) wherein $R^1$ is ethyl; $R^2$ is hydrogen; $R^3$ is $SCH_3$; X and Y are each oxygen; n is 0; and the values $R^4$ match those of the correspondingly numbered compounds of Table A1.

TABLE T27

Table T27 provides 352 compounds of formula (Ib) wherein $R^1$ is ethyl; $R^2$ is fluoro; $R^3$ is $SCH_3$; X and Y are each oxygen; n is 0; and the values of $R^4$ match those of the correspondingly numbered compounds of Table A1.

TABLE T28

Table T28 provides 352 compounds of formula (Ib) wherein $R^1$ is ethyl; $R^2$ is chloro; $R^3$ is $SCH_3$; X and Y are each oxygen; n is 0; and the values of $R^4$ match those of the correspondingly numbered compounds of Table A1.

TABLE T29

Table T29 provides 352 compounds of formula (Ib) wherein $R^1$ is ethyl; $R^2$ is bromo; $R^3$ is $SCH_3$; X and Y are each oxygen; n is 0; and the values of $R^4$ match those of the correspondingly numbered compounds of Table A1.

TABLE T30

Table T30 provides 352 compounds of formula (Ib) wherein $R^1$ is ethyl; $R^2$ is cyano; $R^3$ is $SCH_3$; X and Y are each oxygen; n is 0; and the values of $R^4$ match those of the correspondingly numbered compounds of Table A1.

TABLE T31

Table T31 provides 352 compounds of formula (Ib) wherein $R^1$ is methyl; $R^2$ is hydrogen; $R^3$ is $SCH_3$; X is oxygen; Y is sulphur; n is 0; and the values of $R^4$ match those of the correspondingly numbered compounds of Table A1.

TABLE T32

Table T32 provides 352 compounds of formula (Ib) wherein $R^1$ is methyl; $R^2$ is fluoro; $R^3$ is $SCH_3$; X is oxygen; Y is sulphur; n is 0; and the values of $R^4$ match those of the correspondingly numbered compounds of Table A1.

TABLE T33

Table T33 provides 352 compounds of formula (Ib) wherein $R^1$ is methyl; $R^2$ is chloro; $R^3$ is $SCH_3$; X is oxygen; Y is sulphur; n is 0; and the values of $R^4$ match those of he correspondingly numbered compounds of Table A1.

TABLET34

Table T34 provides 352 compounds formula (Ib) wherein $R^1$ is methyl; $R^2$ is bromo; $R^3$ is $SCH_3$; X is oxygen; Y is sulphur; n is 0; and the values of $R^4$ match those of the correspondingly numbered compounds of Table A1.

TABLE T35

Table T35 provides 352 compounds of formula (Ib) wherein $R^1$ is methyl; $R^2$ is cyano; $R^3$ is $SCH_3$; X is oxygen; Y is sulphur; n is 0; and the values of $R^4$ match those of the correspondingly numbered compounds of Table A1.

TABLE T36

Table T36 provides 352 compounds of formula (Ib) wherein $R^1$ is ethyl; $R^2$ is hydrogen; $R^3$ is $SCH_3$; X is oxygen; Y is sulphur; n is 0; and the values of $R^4$ match those of the correspondingly numbered compounds of Table A1.

TABLE T37

Table T37 provides 352 compounds of formula (Ib) wherein $R^1$ is ethyl; $R^2$ is fluoro; $R^3$ is $SCH_3$; X is oxygen; Y is sulphur; n is 0; and the values of $R^4$ match those of the correspondingly numbered compounds of Table A1.

TABLE T38

Table T38 provides 352 compounds of formula (Ib) wherein $R^1$ is ethyl; $R^2$ is chloro; $R^3$ is $SCH_3$; X is oxygen; Y is sulphur; n is 0; and the values of $R^4$ match those of the correspondingly numbered compounds of Table A1.

TABLE T39

Table T39 provides 352 compounds of formula (Ib) wherein $R^1$ is ethyl; $R^2$ is bromo; $R^3$ is $SCH_3$; X is oxygen; Y is sulphur; n is 0; and the values of $R^4$ match those of the correspondingly numbered compounds of Table A1.

TABLE T40

Table T40 provides 352 compounds of formula (Ib) wherein $R^1$ is ethyl; $R^2$ is cyano; $R^3$ is $SCH_3$; X is oxygen; Y is sulphur; n is 0; and the values of $R^4$ match those of the correspondingly numbered compounds of Table A1.

TABLE T41

Table T41 provides 352 compounds of formula (Ib) wherein $R^1$ is methyl; $R^2$ is hydrogen; $R^3$ is $SCH_3$; X is oxygen; Y is $NR^7$; $R^7$ is hydrogen; n is 0; and the values of $R^4$ match those of the correspondingly numbered compounds of Table A1.

TABLE T42

Table T42 provides 352 compounds of formula (Ib) wherein $R^1$ is methyl; $R^2$ is fluoro; $R^3$ is $SCH_3$; X is oxygen; Y is $NR^7$; $R^7$ is hydrogen; n is 0; and the values of $R^4$ match those of the correspondingly numbered compounds of Table A1.

TABLE T43

Table T43 provides 352 compounds of formula (Ib) wherein $R^1$ is methyl; $R^2$ is chloro; $R^3$ is $SCH_3$; X is oxygen; Y is $NR^7$; $R^7$ is hydrogen; n is 0; and the values of $R^4$ match those of the correspondingly numbered compounds of Table A1.

TABLE T44

Table T44 provides 352 compounds of formula (Ib) wherein $R^1$ is methyl; $R^2$ is bromo; $R^3$ is $SCH_3$; X is oxygen; Y is $NR^7$; $R^7$ is hydrogen; n is 0; and the values of $R^4$ match those of the correspondingly numbered compounds of Table A1.

TABLE T45

Table T45 provides 352 compounds of formula (Ib) wherein $R^1$ is methyl; $R^2$ is cyano; $R^3$ is $SCH_3$; X is oxygen; Y is $NR^7$; $R^7$ is hydrogen; n is 0; and the values of $R^4$ match those of the correspondingly numbered compounds of Table A1.

TABLE T46

Table T46 provides 352 compounds of formula (Ib) wherein $R^1$ is ethyl; $R^2$ is hydrogen; $R^3$ is $SCH_3$; X is oxygen; Y is $NR^7$; $R^7$ is hydrogen; n is 0; and the values of $R^4$ match those of the correspondingly numbered compounds of Table A1.

TABLE T47

Table T47 provides 352 compounds of formula (Ib) wherein $R^1$ is ethyl; $R^2$ is fluoro; $R^3$ is $SCH_3$; X is oxygen; Y is $NR^7$; $R^7$ is hydrogen; n is 0; and the values of $R^4$ match those of the correspondingly numbered compounds of Table A1.

TABLE T48

Table T48 provides 352 compounds of formula (Ib) wherein $R^1$ is ethyl; $R^2$ is chloro; $R^3$ is $SCH_3$; X is oxygen; Y is $NR^7$; $R^7$ is hydrogen; n is 0; and the values of $R^4$ match those of the correspondingly numbered compounds of Table A1.

TABLE T49

Table T49 provides 352 compounds of formula (Ib) wherein $R^1$ is ethyl; $R^2$ is bromo; $R^3$ is $SCH_3$; X is oxygen; Y is $NR^7$; $R^7$ is hydrogen; n is 0; and the values of $R^4$ match those of the correspondingly numbered compounds of Table A1.

TABLE T50

Table T50 provides 352 compounds of formula (Ib) wherein $R^1$ is ethyl; $R^2$ is cyano; $R^3$ is $SCH_3$; X is oxygen; Y is $NR^7$; $R^7$ is hydrogen; n is 0; and the values of $R^4$ match those of the correspondingly numbered compounds of Table A1.

TABLE T51

Table T51 provides 352 compounds of formula (Ib) wherein $R^1$ is methyl; $R^2$ is hydrogen; $R^3$ is $SCH_3$; X is oxygen; Y is $NR^7$; $R^7$ is methyl; n is 0; and the values of $R^4$ match those of the correspondingly numbered compounds of Table A1.

TABLE T52

Table T52 provides 352 compounds of formula (Ib) wherein $R^1$ is methyl; $R^2$ is fluoro; $R^3$ is $SCH_3$; X is oxygen; Y is $NR^7$; $R^7$ is methyl; n is 0; and the values of $R^4$ match those of the correspondingly numbered compounds of Table A1.

TABLE T53

Table T53 provides 352 compounds of formula (Ib) wherein $R^1$ is methyl; $R^2$ is chloro; $R^3$ is $SCH_3$; X is oxygen; Y is $NR^7$; $R^7$ is methyl; n is 0; and the values of $R^4$ match those of the correspondingly numbered compounds of Table A1.

TABLE T54

Table T54 provides 352 compounds of formula (Ib) wherein $R^1$ is methyl; $R^2$ is bromo; $R^3$ is $SCH_3$; X is oxygen; Y is $NR^7$; $R^7$ is methyl; n is 0; and the values of $R^4$ match those of the correspondingly numbered compounds of Table A1.

TABLE T55

Table T55 provides 352 compounds of formula (Ib) wherein $R^1$ is methyl; $R^2$ is cyano; $R^3$ is $SCH_3$; X is oxygen;

Y is $NR^7$; $R^7$ is methyl; n is 0; and the values of $R^4$ match those of the correspondingly numbered compounds of Table A1.

TABLE T56

Table T56 provides 352 compounds of formula (Ib) wherein $R^1$ is ethyl; $R^2$ is hydrogen; $R^3$ is $SCH_3$; X is oxygen; Y is $NR^7$; $R^7$ is methyl; n is 0; and the values of $R^4$ match those of the correspondingly numbered compounds of Table A1.

TABLE T57

Table T57 provides 352 compounds of formula (Ib) wherein $R^1$ is ethyl; $R^2$ is fluoro; $R^3$ is $SCH_3$; X is oxygen; Y is $NR^7$; $R^7$ is methyl; n is 0; and the values of $R^4$ match those of the correspondingly numbered compounds of Table A1.

TABLE T58

Table T58 provides 352 compounds of formula (Ib) wherein $R^1$ is ethyl; $R^2$ is chloro; $R^3$ is $SCH_3$; X is oxygen; Y is $NR^7$; $R^7$ is methyl; n is 0; and the values of $R^4$ match those of the correspondingly numbered compounds of Table A1.

TABLE T59

Table T59 provides 352 compounds of formula (Ib) wherein $R^1$ is ethyl; $R^2$ is bromo; $R^3$ is $SCH_3$; X is oxygen; Y is $NR^7$; $R^7$ is methyl; n is 0; and the values of $R^4$ match those of the correspondingly numbered compounds of Table A1.

TABLE T60

Table T60 provides 352 compounds of formula (Ib) wherein $R^1$ is ethyl; $R^2$ is cyano; $R^3$ is $SCH_3$; X is oxygen; Y is $NR^7$; $R^7$ is methyl; n is 0; and the values of $R^4$ match those of the correspondingly numbered compounds of Table A1.

TABLE T61

Table T61 provides 352 compounds of formula (Ia) wherein $R^1$ is methyl; $R^2$ is hydrogen; $R^3$ is $SCH_3$; X is oxygen; Y is $NR^7$; $R^7$ is methyl; n is 0; and the values of $R^4$ match those of the correspondingly numbered compounds of Table A1.

TABLE T62

Table T62 provides 352 compounds of formula (Ia) wherein $R^1$ is methyl; $R^2$ is fluoro; $R^3$ is $SCH_3$; X is oxygen; Y is $NR^7$; $R^7$ is methyl; n is 0; and the values of $R^4$ match those of the correspondingly numbered compounds of Table A1.

TABLE T63

Table T63 provides 352 compounds of formula (Ia) wherein $R^1$ is methyl; $R^2$ is chloro; $R^3$ is $SCH_3$; X is oxygen; Y is $NR^7$; $R^7$ is methyl; n is 0; and the values of $R^4$ match those of the correspondingly numbered compounds of Table A1.

TABLE T64

Table T64 provides 352 compounds of formula (Ia) wherein $R^1$ is methyl; $R^2$ is bromo; $R^3$ is $SCH_3$; X is oxygen; Y is $NR^7$; $R^7$ is methyl; n is 0; and the values of $R^4$ match those of the correspondingly numbered compounds of Table A1.

TABLE T65

Table T65 provides 352 compounds of formula (Ib) wherein $R^1$ is methyl; $R^2$ is cyano; $R^3$ is $SCH_3$; X is oxygen; Y is $NR^7$; $R^7$ is methyl; n is 0; and the values of $R^4$ match those of the correspondingly numbered compounds of Table A1.

TABLE T66

Table T66 provides 352 compounds of formula (Ia) wherein $R^1$ is ethyl; $R^2$ is hydrogen; $R^3$ is $SCH_3$; X is oxygen; Y is $NR^7$; $R^7$ is methyl; n is 0; and the values of $R^4$ match those of the correspondingly numbered compounds of Table A1.

TABLE T67

Table T67 provides 352 compounds of formula (Ia) wherein $R^1$ is ethyl; $R^2$ is fluoro; $R^3$ is $SCH_3$; X is oxygen; Y is $NR^7$; $R^7$ is methyl; n is 0; and the values of $R^4$ match those of the correspondingly numbered compounds of Table A1.

TABLE T68

Table T68 provides 352 compounds of formula (Ia) wherein $R^1$ is ethyl; $R^2$ is chloro; $R^3$ is $SCH_3$; X is oxygen; Y is $NR^7$; $R^7$ is methyl; n is 0; and the values of $R^4$ match those of the correspondingly numbered compounds of Table A1.

TABLE T69

Table T69 provides 352 compounds of formula (Ia) wherein $R^1$ is ethyl; $R^2$ is bromo; $R^3$ is $SCH_3$; X is oxygen; Y is $NR^7$; $R^7$ is methyl; n is 0; and the values of $R^4$ match those of the correspondingly numbered compounds of Table A1.

TABLE T70

Table T70 provides 352 compounds of formula (Ia) wherein $R^1$ is ethyl; $R^2$ is cyano; $R^3$ is $SCH_3$; X is oxygen; Y is $NR^7$; $R^7$ is methyl; n is 0; and the values of $R^4$ match those of the correspondingly numbered compounds of Table A1.

TABLE U1

Table U1 provides 352 compounds of formula (Ia) wherein $R^1$ is methyl; $R^2$ is hydrogen; $R^3$ is SPh; X and Y are each oxygen; n is 0; and the values of $R^4$ match those of the correspondingly numbered compounds of Table A1.

TABLE U2

Table U2 provides 352 compounds of formula (Ia) wherein $R^1$ is methyl; $R^2$ is fluoro; $R^3$ is SPh; X and Y are each oxygen; n is 0; and the values of $R^4$ match those of the correspondingly numbered compounds of Table A1.

TABLE U3

Table U3 provides 352 compounds of formula (Ia) wherein $R^1$ is methyl; $R^2$ is chloro; $R^3$ is SPh; X and Y are each oxygen; n is 0; and the values of $R^4$ match those of the correspondingly numbered compounds of Table A1.

TABLE U4

Table U4 provides 352 compounds of formula (Ia) wherein $R^1$ is methyl; $R^2$ is bromo; $R^3$ is SPh; X and Y are each oxygen; n is 0; and the values of $R^4$ match those of the correspondingly numbered compounds of Table A1.

TABLE U5

Table U5 provides 352 compounds of formula (Ia) wherein $R^1$ is methyl; $R^2$ is cyano; $R^3$ is SPh; X and Y are each oxygen; n is 0; and the values of $R^4$ match those of the correspondingly numbered compounds of Table A1.

TABLE U6

Table U6 provides 352 compounds of formula (Ia) wherein $R^1$ is ethyl; $R^2$ is hydrogen; $R^3$ is SPh; X and Y are each oxygen; n is 0; and the values of $R^4$ match those of the correspondingly numbered compounds of Table A1.

TABLE U7

Table U7 provides 352 compounds of formula (Ia) wherein $R^1$ is ethyl; $R^2$ is fluoro; $R^3$ is SPh; X and Y are each oxygen; n is 0; and the values of $R^4$ match those of the correspondingly numbered compounds of Table A1.

TABLE U8

Table U8 provides 352 compounds of formula (Ia) wherein $R^1$ is ethyl; $R^2$ is chloro; $R^3$ is SPh; X and Y are each oxygen; n is 0; and the values of $R^4$ match those of the correspondingly numbered compounds of Table A1.

TABLE U9

Table U9 provides 352 compounds of formula (Ia) wherein $R^1$ is ethyl; $R^2$ is bromo; $R^3$ is SPh; X and Y are each oxygen; n is 0; and the values of $R^4$ match those of the correspondingly numbered compounds of Table A1.

TABLE U10

Table U10 provides 352 compounds of formula (Ia) wherein $R^1$ is ethyl; $R^2$ is cyano; $R^3$ is SPh; X and Y are each oxygen; n is 0; and the values of $R^4$ match those of the correspondingly numbered compounds of Table A1.

TABLE U11

Table U11 provides 352 compounds of formula (Ia) wherein $R^1$ is methyl; $R^2$ is hydrogen; $R^3$ is SPh; X is oxygen; Y is sulphur; n is 0; and the values of $R^4$ match those of the correspondingly numbered compounds of Table A1.

TABLE U12

Table U12 provides 352 compounds of formula (Ia) wherein $R^1$ is methyl; $R^2$ is fluoro; $R^3$ is SPh; X is oxygen; Y is sulphur; n is 0; and the values of $R^4$ match those of the correspondingly numbered compounds of Table A1.

TABLE U13

Table U13 provides 352 compounds of formula (Ia) wherein $R^1$ is methyl; $R^2$ is chloro; $R^3$ is SPh; X is oxygen; Y is sulphur; n is 0; and the values of $R^4$ match those of the correspondingly numbered compounds of Table A1.

TABLE U14

Table U14 provides 352 compounds of formula (Ia) wherein $R^1$ is methyl; $R^2$ is bromo; $R^3$ is SPh; X is oxygen; Y is sulphur; n is 0; and the values of $R^4$ match those of the correspondingly numbered compounds of Table A1.

TABLE U15

Table U15 provides 352 compounds of formula (Ia) wherein $R^1$ is methyl; $R^2$ is cyano; $R^3$ is SPh; X is oxygen; Y is sulphur; n is 0; and the values of $R^4$ match those of the correspondingly numbered compounds of Table A1.

TABLE U16

Table U16 provides 352 compounds of formula (Ia) wherein $R^1$ is ethyl; $R^2$ is hydrogen; $R^3$ is SPh; X is oxygen; Y is sulphur; n is 0; and the values of $R^4$ match those of the correspondingly numbered compounds of Table A1.

TABLE U17

Table U17 provides 352 compounds of formula (Ia) wherein $R^1$ is ethyl; $R^2$ is fluoro; $R^3$ is SPh; X is oxygen; Y is sulphur; n is 0; and the values of $R^4$ match those of the correspondingly numbered compounds of Table A1.

TABLE U18

Table U18 provides 352 compounds of formula (Ia) wherein $R^1$ is ethyl; $R^2$ is chloro; $R^3$ is SPh; X is oxygen; Y is sulphur; n is 0; and the values of $R^4$ match those of the correspondingly numbered compounds of Table A1.

TABLE U19

Table U19 provides 352 compounds of formula (Ia) wherein $R^1$ is ethyl; $R^2$ is bromo; $R^3$ is SPh; X is oxygen; Y is sulphur; n is 0; and the values of $R^4$ match those of the correspondingly numbered compounds of Table A1.

TABLE U20

Table U20 provides 352 compounds of formula (Ia) wherein $R^1$ is ethyl; $R^2$ is cyano; $R^3$ is SPh; X is oxygen; Y is sulphur; n is 0; and the values of $R^4$ match those of the correspondingly numbered compounds of Table A1.

TABLE U21

Table U21 provides 352 compounds of formula (Ib) wherein $R^1$ is methyl; $R^2$ is hydrogen; $R^3$ is SPh; X and Y are each oxygen; n is 0; and the values of $R^4$ match those of the correspondingly numbered compounds of Table A1.

TABLE U22

Table U22 provides 352 compounds of formula (Ib) wherein $R^1$ is methyl; $R^2$ is fluoro; $R^3$ is SPh; X and Y are each oxygen; n is 0; and the values of $R^4$ match those of the correspondingly numbered compounds of Table A1.

TABLE U23

Table U23 provides 352 compounds of formula (Ib) wherein $R^1$ is methyl; $R^2$ is chloro; $R^3$ is SPh; X and Y are each oxygen; n is 0; and the values of $R^4$ match those of the correspondingly numbered compounds of Table A1.

TABLE U24

Table U24 provides 352 compounds of formula (Ib) wherein $R^1$ is methyl; $R^2$ is bromo; $R^3$ is SPh; X and Y are each oxygen; n is 0; and the values of $R^4$ match those of the correspondingly numbered compounds of Table A1.

TABLE U25

Table U25 provides 352 compounds of formula (Ib) wherein $R^1$ is methyl; $R^2$ is cyano; $R^3$ is SPh; X and Y are each oxygen; n is 0; and the values of $R^4$ match those of the correspondingly numbered compounds of Table A1.

TABLE U26

Table U26 provides 352 compounds of formula (Ib) wherein $R^1$ is ethyl; $R^2$ is hydrogen; $R^3$ is SPh; X and Y are each oxygen; n is 0; and the values of $R^4$ match those of the correspondingly numbered compounds of Table A1.

TABLE U27

Table U27 provides 352 compounds of formula (Ib) wherein $R^1$ is ethyl; $R^2$ is fluoro; $R^3$ is SPh; X and Y are each oxygen; n is 0; and the values of $R^4$ match those of the correspondingly numbered compounds of Table A1.

TABLE U28

Table U28 provides 352 compounds of formula (Ib) wherein $R^1$ is ethyl; $R^2$ is chloro; $R^3$ is SPh; X and Y are each oxygen; n is 0; and the values of $R^4$ match those of the correspondingly numbered compounds of Table A1.

TABLE U29

Table U29 provides 352 compounds of formula (Ib) wherein $R^1$ is ethyl; $R^2$ is bromo; $R^3$ is SPh; X and Y are each oxygen; n is 0; and the values of $R^4$ match those of the correspondingly numbered compounds of Table A1.

TABLE U30

Table U30 provides 352 compounds of formula (Ib) wherein $R^1$ is ethyl; $R^2$ is cyano; $R^3$ is SPh; X and Y are each oxygen; n is 0; and the values of $R^4$ match those of the correspondingly numbered compounds of Table A1.

TABLE U31

Table U31 provides 352 compounds of formula (Ib) wherein $R^1$ is methyl; $R^2$ is hydrogen; $R^3$ is SPh; X is oxygen; Y is sulphur; n is 0; and the values of $R^4$ match those of the correspondingly numbered compounds of Table A1.

TABLE U32

Table U32 provides 352 compounds of formula (Ib) wherein $R^1$ is methyl; $R^2$ is fluoro; $R^3$ is SPh; X is oxygen; Y is sulphur; n is 0; and the values of $R^4$ match those of the correspondingly numbered compounds of Table A1.

TABLE U33

Table U33 provides 352 compounds of formula (Ib) wherein $R^1$ is methyl; $R^2$ is chloro; $R^3$ is SPh; X is oxygen; Y is sulphur; n is 0; and the values of $R^4$ match those of the correspondingly numbered compounds of Table A1.

TABLE U34

Table U34 provides 352 compounds of formula (Ib) wherein $R^1$ is methyl; $R^2$ is bromo; $R^3$ is SPh; X is oxygen; Y is sulphur; n is 0; and the values of $R^4$ match those of the correspondingly numbered compounds of Table A1.

TABLE U35

Table U35 provides 352 compounds of formula (Ib) wherein $R^1$ is methyl; $R^2$ is cyano; $R^3$ is SPh; X is oxygen; Y is sulphur; n is 0; and the values of $R^4$ match those of the correspondingly numbered compounds of Table A1.

TABLE U36

Table U36 provides 352 compounds of formula (Ib) wherein $R^1$ is ethyl; $R^2$ is hydrogen; $R^3$ is SPh; X is oxygen; Y is sulphur; n is 0; and the values of $R^4$ match those of the correspondingly numbered compounds of Table A1.

TABLE U37

Table U37 provides 352 compounds of formula (Ib) wherein $R^1$ is ethyl; $R^2$ is fluoro; $R^3$ is SPh; X is oxygen; Y is sulphur; n is 0; and the values of $^4$ match those of the correspondingly numbered compounds of Table A1.

TABLE U38

Table U38 provides 352 compounds of formula (Ib) wherein $R^1$ is ethyl; $R^2$ is chloro; $R^3$ is SPh; X is oxygen; Y is sulphur; n is 0; and the values of $R^4$ match those of the correspondingly numbered compounds of Table A1.

tableu39

Table U39 provides 352 compounds of formula (Ib) wherein $R^1$ is ethyl; $R^2$ is bromo; $R^3$ is SPh; X is oxygen; Y is sulphur; n is 0; and the values of $R^4$ match those of the correspondingly numbered compounds of Table A1.

TABLE U40

Table U40 provides 352 compounds of formula (Ib) wherein $R^1$ is ethyl; $R^2$ is cyano; $R^3$ is SPh; X is oxygen; Y is sulphur; n is 0; and the values of $R^4$ match those of the correspondingly numbered compounds of Table A1.

TABLE U41

Table U41 provides 352 compounds of formula (Ib) wherein $R^1$ is methyl; $R^2$ is hydrogen; $R^3$ is SPh; X is oxygen; Y is $NR^7$; $R^7$ is hydrogen; n is 0; and the values of $R^4$ match those of the correspondingly numbered compounds of Table A1.

TABLE U42

Table U42 provides 352 compounds of formula (Ib) wherein $R^1$ is methyl; $R^2$ is fluoro; $R^3$ is SPh; X is oxygen; Y is $NR^7$; $R^7$ is hydrogen; n is 0; and the values of $R^4$ match those of the correspondingly numbered compounds of Table A1.

TABLE U43

Table U43 provides 352 compounds of formula (Ib) wherein $R^1$ is methyl; $R^2$ is chloro; $R^3$ is SPh; X is oxygen; Y is $NR^7$; $R^7$ is hydrogen; n is 0; and the values of $R^4$ match those of the correspondingly numbered compounds of Table A1.

TABLE U44

Table U44 provides 352 compounds of formula (Ib) wherein $R^1$ is methyl; $R^2$ is bromo; $R^3$ is SPh; X is oxygen; Y is $NR^7$; $R^7$ is hydrogen; n is 0; and the values of $R^4$ match those of the correspondingly numbered compounds of Table A1.

TABLE U45

Table U45 provides 352 compounds of formula (Ib) wherein $R^1$ is methyl; $R^2$ is cyano; $R^3$ is SPh; X is oxygen;

Y is NR$^7$; R$^7$ is hydrogen; n is 0; and the values of R$^4$ match those of the correspondingly numbered compounds of Table A1.

TABLE U46

Table U46 provides 352 compounds of formula (Ib) wherein R$^1$ is ethyl; R$^2$ is hydrogen; R$^3$ is SPh, X is oxygen; Y is NR$^7$; R$^7$ is hydrogen; n is 0; and the values of R$^4$ match those of the correspondingly numbered compounds of Table A1.

TABLE U47

Table U47 provides 352 compounds of formula (Ib) wherein R$^1$ is ethyl; R$^2$ is fluoro; R$^3$ is SPh; X is oxygen; Y is NR$^7$; R$^7$ is hydrogen; n is 0; and the values of R$^4$ match those of the correspondingly numbered compounds of Table A1.

TABLE U48

Table U48 provides 352 compounds of formula (Ib) wherein R$^1$ is ethyl; R$^2$ is chloro; R$^3$ is SPh; X is oxygen; Y is NR$^7$; R$^7$ is hydrogen; n is 0; and the values of R$^4$ match those of the correspondingly numbered compounds of Table A1.

TABLE U49

Table U49 provides 352 compounds of formula (Ib) wherein R$^1$ is ethyl; R$^2$ is bromo; R$^3$ is SPh; X is oxygen; Y is NR$^7$; R$^7$ is hydrogen; n is 0; and the values of R$^4$ match those of the correspondingly numbered compounds of Table A1.

TABLE U50

Table U50 provides 352 compounds of formula (Ib) wherein R$^1$ is ethyl; R$^2$ is cyano; R$^3$ is SPh; X is oxygen; Y is NR$^7$; R$^7$ is hydrogen; n is 0; and the values of R$^4$ match those of the correspondingly numbered compounds of Table A1.

TABLE U51

Table U51 provides 352 compounds of formula (Ib) wherein R$^1$ is methyl; R$^2$ is hydrogen; R$^3$ is SPh; X is oxygen; Y is NR$^7$; R$^7$ is methyl; n is 0; and the values of R$^4$ match those of the correspondingly numbered compounds of Table A1.

TABLE U52

Table U52 provides 352 compounds of formula (Ib) wherein R$^1$ is methyl; R$^2$ is fluoro; R$^3$ is SPh; X is oxygen; Y is NR$^7$; R$^7$ is methyl; n is 0; and the values of R$^4$ match those of the correspondingly numbered compounds of Table A1.

TABLE U53

Table U53 provides 352 compounds of formula (Ib) wherein R$^1$ is methyl; R$^2$ is chloro; R$^3$ is SPh; X is oxygen; Y is NR$^7$; R$^7$ is methyl; n is 0; and the values of R$^4$ match those of the correspondingly numbered compounds of Table A1.

TABLE U54

Table U54 provides 352 compounds of formula (Ib) wherein R$^1$ is methyl; R$^2$ is bromo; R$^3$ is SPh; X is oxygen; Y is NR$^7$; R$^7$ is methyl; n is 0; and the values of R$^4$ match those of the correspondingly numbered compounds of Table A1.

TABLE U55

Table U55 provides 352 compounds of formula (Ib) wherein R$^1$ is methyl; R$^2$ is cyano; R$^3$ is SPh; X is oxygen; Y is NR$^7$; R$^7$ is methyl; n is 0; and the values of R$^4$ match those of the correspondingly numbered compounds of Table A1.

TABLE U56

Table U56 provides 352 compounds of formula (Ib) wherein R$^1$ is ethyl; R$^2$ is hydrogen; R$^3$ is SPh; X is oxygen; Y is NR$^7$; R$^7$ is methyl; n is 0; and the values of R$^4$ match those of the correspondingly numbered compounds of Table A1.

TABLE U57

Table U57 provides 352 compounds of formula (Ib) wherein R$^1$ is ethyl; R$^2$ is fluoro; R$^3$ is SPh; X is oxygen; Y is NR$^7$; R$^7$ is methyl; n is 0; and the values of R$^4$ match those of the correspondingly numbered compounds of Table A1.

TABLE U58

Table U58 provides 352 compounds of formula (Ib) wherein R$^1$ is ethyl; R$^2$ is chloro; R$^3$ is SPh; X is oxygen; Y is NR$^7$; R$^7$ is methyl; n is 0; and the values of R$^4$ match those of the correspondingly numbered compounds of Table A1.

TABLE U59

Table U59 provides 352 compounds of formula (Ib) wherein R$^1$ is ethyl; R$^2$ is bromo; R$^3$ is SPh; X is oxygen; Y is NR$^7$; R$^7$ is methyl; n is 0; and the values of R$^4$ match those of the correspondingly numbered compounds of Table A1.

TABLE U60

Table U60 provides 352 compounds of formula (Ib) wherein R$^1$ is ethyl; R$^2$ is cyano; R$^3$ is SPh; X is oxygen; Y is NR$^7$; R$^7$ is methyl; n is 0; and the values of R$^4$ match those of the correspondingly numbered compounds of Table A1.

TABLE U61

Table U61 provides 352 compounds of formula (Ia) wherein R$^1$ is methyl; R$^2$ is hydrogen; R$^3$ is SPh; X is oxygen; Y is NR$^7$; R$^7$ is methyl; n is 0; and the values of R$^4$ match those of the correspondingly numbered compounds of Table A1.

TABLE U62

Table U62 provides 352 compounds of formula (Ia) wherein R$^1$ is methyl; R$^2$ is fluoro; R$^3$ is SPh; X is oxygen; Y is NR$^7$; R$^7$ is methyl; n is 0; and the values of R$^4$ match those of the correspondingly numbered compounds of Table A1.

TABLE U63

Table U63 provides 352 compounds of formula (Ia) wherein R$^1$ is methyl; R$^2$ is chloro; R$^3$ is SPh, X is oxygen; Y is NR$^7$; R$^7$ is methyl; n is 0; and the values of R$^4$ match those of the correspondingly numbered compounds of Table A1.

TABLE U64

Table U64 provides 352 compounds of formula (Ia) wherein $R^1$ is methyl; $R^2$ is bromo; $R^3$ is SPh; X is oxygen; Y is $NR^7$; $R^7$ is methyl; n is 0; and the values of $R^4$ match those of the correspondingly numbered compounds of Table A1.

TABLE U65

Table U65 provides 352 compounds of formula (Ib) wherein $R^1$ is methyl; $R^2$ is cyano; $R^3$ is SPh; X is oxygen; Y is $NR^7$; $R^7$ is methyl; n is 0; and the values of $R^4$ match those of the correspondingly numbered compounds of Table A1.

TABLE U66

Table U66 provides 352 compounds of formula (Ia) wherein $R^1$ is ethyl; $R^2$ is hydrogen; $R^3$ is SPh, X is oxygen; Y is $NR^7$; $R^7$ is methyl; n is 0; and the values of $R^4$ match those of the correspondingly numbered compounds of Table A1.

TABLE U67

Table U67 provides 352 compounds of formula (Ia) wherein $R^1$ is ethyl; $R^2$ is fluoro; $R^3$ is SPh; X is oxygen; Y is $NR^7$; $R^7$ is methyl; n is 0; and the values of $R^4$ match those of the correspondingly numbered compounds of Table A1.

TABLE U68

Table U68 provides 352 compounds of formula (Ia) wherein $R^1$ is ethyl; $R^2$ is chloro; $R^3$ is SPh; X is oxygen; Y is $NR^7$; $R^7$ is methyl; n is 0; and the values of $R^4$ match those of the correspondingly numbered compounds of Table A1.

TABLE U69

Table U69 provides 352 compounds of formula (Ia) wherein $R^1$ is ethyl; $R^2$ is bromo; $R^3$ is SPh; X is oxygen; Y is $NR^4$; $R^7$ is methyl; n is 0; and the values of $R^4$ match those of the correspondingly numbered compounds of Table A1.

TABLE U70

Table U70 provides 352 compounds of formula (Ia) wherein $R^1$ is ethyl; $R^2$ is cyano; $R^3$ is SPh; X is oxygen; Y is $NR^7$; $R^4$ is methyl; n is 0; and the values of $R^4$ match those of the correspondingly numbered compounds of Table A1.

TABLE V1

Table V1 provides 352 compounds of formula (Ia) wherein $R^1$ is methyl; $R^2$ is hydrogen; $R^3$ is hydrogen; X is sulphur; Y is oxygen; n is 0; and the values of $R^4$ match those of the correspondingly numbered compounds of Table A1.

TABLE V2

Table V2 provides 352 compounds of formula (Ia) wherein $R^1$ is methyl; $R^2$ is fluoro; $R^3$ is hydrogen; X is sulphur; Y is oxygen; n is 0; and the values of $R^4$ match those of the correspondingly numbered compounds of Table A1.

TABLE V3

Table V3 provides 352 compounds of formula (Ia) wherein $R^1$ is methyl; $R^2$ is chloro; $R^3$ is hydrogen; X is sulphur; Y is oxygen; n is 0; and the values of $R^4$ match those of the correspondingly numbered compounds of Table A1.

TABLE V4

Table V4 provides 352 compounds of formula (Ia) wherein $R^1$ is methyl; $R^2$ is bromo; $R^3$ is hydrogen; X is sulphur; Y is oxygen; n is 0; and the values of $R^4$ match those of the correspondingly numbered compounds of Table A1.

TABLE V5

Table V5 provides 352 compounds of formula (Ia) wherein $R^1$ is methyl; $R^2$ is cyano; $R^3$ is hydrogen; X is sulphur; Y is oxygen; n is 0; and the values of $R^4$ match those of the correspondingly numbered compounds of Table A1.

TABLE V6

Table V6 provides 352 compounds of formula (Ia) wherein $R^1$ is ethyl; $R^2$ is hydrogen; $R^3$ is hydrogen; X is sulphur; Y is oxygen; n is 0; and.the values of $R^4$ match those of the correspondingly numbered compounds of Table A1.

TABLE V7

Table V7 provides 352 compounds of formula (Ia) wherein $R^1$ is ethyl; $R^2$ is fluoro; $R^3$ is hydrogen; X is sulphur; Y is oxygen; n is 0; and the values of $R^4$ match those of the correspondingly numbered compounds of Table A1.

TABLE V8

Table V8 provides 352 compounds of formula (Ia) wherein $R^1$ is ethyl; $R^2$ is chloro; $R^3$ is hydrogen; X is sulphur; Y is oxygen; n is 0; and the values of $R^4$ match those of the correspondingly numbered compounds of Table A1.

TABLE V9

Table V9 provides 352 compounds of formula (Ia) wherein $R^1$ is ethyl; $R^2$ is bromo; $R^3$ is hydrogen; X is sulphur; Y is oxygen; n is 0; and the values of $R^4$ match those of the correspondingly numbered compounds of Table A1.

TABLE V10

Table V10 provides 352 compounds of formula (Ia) wherein $R^1$ is ethyl; $R^2$ is cyano; $R^3$ is hydrogen; X is sulphur; Y is oxygen; n is 0; and the values of $R^4$ match those of the correspondingly numbered compounds of Table A1.

TABLE V11

Table V11 provides 352 compounds of formula (Ia) wherein $R^1$ is methyl; $R^2$ is hydrogen; $R^3$ is hydrogen; X is sulphur; Y is sulphur; n is 0; and the values of $R^4$ match those of the correspondingly numbered compounds of Table A1.

TABLE V12

Table V12 provides 352 compounds of formula (Ia) wherein $R^1$ is methyl; $R^2$ is fluoro; $R^3$ is hydrogen; X is

TABLE V13

Table V13 provides 352 compound of formula (Ia) wherein $R^1$ is methyl; $R^2$ is chloro; $R^3$ is hydrogen; X is sulphur; Y is sulphur; n is 0; and the values of $R^4$ match those of the correspondingly numbered compounds of Table A1.

TABLE V14

Table V14 provides 352 compounds of formula (Ia) wherein $R^1$ is methyl; $R^2$ is bromo; $R^3$ is hydrogen; X is sulphur; Y is sulphur; n is 0; and the values of $R^4$ match those of the correspondingly numbered compounds of Table A1.

TABLE V15

Table V15 provides 352 compounds of formula (Ia) wherein $R^1$ is methyl; $R^2$ is cyano; $R^3$ is hydrogen; X is sulphur; Y is sulphur; n is 0; and the values of $R^4$ match those of the correspondingly numbered compounds of Table A1.

TABLE V16

Table V16 provides 352 compounds of formula (Ia) wherein $R^1$ is ethyl; $R^2$ is hydrogen; $R^3$ is hydrogen; X is sulphur; Y is sulphur; n is 0; and the values of $R^4$ match those of the correspondingly numbered compounds of Table A1.

TABLE V17

Table V17 provides 352 compounds of formula (Ia) wherein $R^1$ is ethyl; $R^2$ is fluoro; $R^3$ is hydrogen; X is sulphur; Y is sulphur; n is 0; and the values of $R^4$ match those of the correspondingly numbered compounds of Table A1.

TABLE V18

Table V18 provides 352 compounds of formula (Ia) wherein $R^1$ is ethyl; $R^2$ is chloro; $R^3$ is hydrogen; X is sulphur; Y is sulphur; n is 0; and the values of $R^4$ match those of the correspondingly numbered compounds of Table A1.

TABLE V19

Table V19 provides 352 compounds of formula (Ia) wherein $R^1$ is ethyl; $R^2$ is bromo; $R^3$ is hydrogen; X is sulphur; Y is sulphur; n is 0; and the values of $R^4$ match those of the correspondingly numbered compounds of Table A1.

TABLE V20

Table V20 provides 352 compounds of formula (Ia) wherein $R^1$ is ethyl; $R^2$ is cyano; $R^3$ is hydrogen; X is sulphur; Y is sulphur; n is 0; and the values of $R^4$ match those of the correspondingly numbered compounds of Table A1.

The following abbreviations are used throughout this description:

| | |
|---|---|
| mp = melting point | ppm = parts per million |
| s = singlet | b = broad |
| d = doublet | dd = doublet of doublets |
| t = triplet | q = quartet |
| m = multiplet | $J_{AB}$ = coupling constant between atom A and atom B |

Table W shows selected melting point and selected NMR data, all with $CDCl_3$ as the solvent (unless otherwise stated; if a mixture of solvents is present, this is indicated as, for example, ($CDCl_3/d_6$-DMSO)), (no attempt is made to list all characterising data in all cases) for compounds of Tables A1, A3, A4, A5, A8, A13, A23, A43, B3, C3, D3, E3, F3, H3, K3, L3, M3, N3 and V3.

TABLE W

| Compound No (Table No) | Melting point (/° C.) | NMR proton shifts (/ppm) ($CDCl_3$ unless otherwise stated.) |
|---|---|---|
| 15 (A1) | 130–131 | 2.3(s, 3H); 2.8(s, 2H); 3.9(s, 2H); 6.5(s, 1H); 7.25(dd, 1H); 7.5(d, 1H); 7.6(d, 1H); 8.9(b, 1H). |
| 1 (A3) | 164–165 | 2.4(s, 3H); 4.0(s, 2H); 7.4(dd, 1H); 7.65(d, 1H); 7.8 (d, 1H); 8.1(b, 1H); 8.15(s, 1H). |
| 2 (A3) | 161–163 | 2.35(s, 3H); 2.7(s, 3H); 3.9(s, 2H); 7.3(m, 1H); 7.5(d, 1H); 7.6(d, 1H); 8.05(b, 1H). |
| 3 (A3) | 169–171 | 1.45(t, 3H); 2.35(s, 3H); 3.0(q, 2H); 4.0(s, 2H); 7.25(dd, 1H); 7.5(d, 1H); 7.6(d, 1H); 8.1(b, 1H). |
| 4 (A3) | 153–155 | 1.05(t, 3H); 1.9(m, 2H); 2.35(s, 3H); 3.95(t, 2H), 4.0(s, 2H); 7.35(dd, 1H). |
| 5 (A3) | 146–147 | 0.98(t, 3H); 1.5(m, 2H); 1.9(m, 2H); 2.4(s, 3H); 2.95(t, 2H); 4.0(s, 2H); 7.3(dd, 1H); 7.5 (d, 1H); 7.65(d, 1H); 8.05(b, 1H) |
| 8 (A3) | 167–168 | 1.45(d, 6H); 2.35(s, 3H); 3.25(m, 1H); 3.95(s, 2H); 7.25(dd, 1H); 7.5(d, 1H); 7.6(d, 1H); 8.1 (b, 1H). |
| 9 (A3) | 144–145 | 1.5(s, 9H); 2.35(s, 3H); 4.0(s, 2H);, 7.3(dd, 1H); 7.55(d, 1H); 7.65(d, 1H); 8.1(b, 1H). |
| 10 (A3) | 136–137 | 0.95(t, 3H); 1.45(d, 3H); 1.9(m, 2H); 2.4(s, 3H); 3.1(m, 1H); 4.0(s, 2H); 7.3(dd, 1H); 7.55: (d, 1H): 7.65(s, 1H); 8.1(b, 1H). |
| 12 (A3) | 84–86 | 0.9(t, 3H); 1.4(m, 2H); 1.45(d, 3H); 1.7(m, 1H); 1.9(m, 1H); 2.4(s, 3H); 3.15(m, 1H); 4.0(s, 2H); 7.3(dd, 1H); 7.5(d, 1H); 7.65.(d, 1H) 8.2(b, 1H). |
| 13 (A3) | 127–129 | 0.9(m, 6H); 1.85(m, 4H); 2.35(s, 3H); 2.9(m, 1H); 4.0(s, 2H); 7.25(dd, 1H), 7.55(d, 1H); 7.65(d, H); 8.15(b, 1H). |

TABLE W-continued

| Compound No (Table No) | Melting point (/° C.) | NMR proton shifts (/ppm) (CDCl₃ unless otherwise stated.) |
|---|---|---|
| 14 (A3) | 118–119 | 1.05(d, 6H), 2.3(m, 1H); 2.4(s, 3H); 2.8(d, 2H); 3.95(s, 2H); 7.25(dd, 1H) 7.5(d, 1H); 7.6(d, 1H); 8.1(b, 1H); |
| 15 (A3) | 144–145 | 1.1(s, 9H); 2.35(s, 3H); 2.85(s, 2H); 3.95(s, 2H); 7.2,5(dd, 1H); 1.55(d, 1H) 7.65(d, 1H); 8.1(b, 1H). |
| 21 (A3) | 193–194 | 1.25 (m, 4H) 2.2(m, 1H); 2.35(s, 3H); 4.0(s, 2H); 72(dd, 1H); 7.5(d, 1H); 7.55(d, 1H); 8.1(b, 1H). |
| 28 (A3) | 158–159 | 1.8(m, 4H); 2.1(m, 4H); 2.4(s, 3H); 3.4(m, 1H); 4.0(s, 3H); 7.25(dd, 1H); 7.5(d, 1H); 7.6(d, 1H); 8.1(b, 1H). |
| 35 (A3) | 144–146 | 1.4(m, 3H); 1.7(m, 3H); 1.9(m, 2H); 22(m, 2H); 2.4(s, 3H); 3.0(m, 1H); 4.0(s, 2H); 7.3(dd, 1H); 7.5(d, 1H); 7.6(d, 1H); 8.1(b, 1H). |
| 36 (A3) | 140–141 | 1.2(s, 3H); 1.3(m, 2H); 1.55(m, 4H); 2.15(m, 2H); 2.3(m, 2H); 2A(s, 3H); 4.0(5,2H); 7.3(dd, 1H); 7.5(d, 1H); 7.65(d, 1H); 8.15(b, 1H). |
| 41 (A3) | 165–167 | 0.35(m, 2H); 0.65(m, 2H); 125(m, 1H); 2.4(s, 3H); 2.9(d, 2H); 4.0(s, 2H); 7.3(dd, 1H); 7.55(d, 1H); 7.65(d, 1H); 8.1(b, 1H). |
| 42 (A3) | 118–119 | 1.3(m, 2H); 1.7(m, 4H); 1.9(m, 2H); 2.4(s, 3H); 2.5(m, 1H); 2.95(d, 2H); 4.0(s, 2H); 7.3(dd, 1H); 7.5(d, 1H); 7.6(d, 1H); 8.1(b, 1H). |
| 45 (43) | 176–178 | 2.05(m, 3H); 2.35(s, 3H); 4.0(s, 2H); 6.5(dd, 1H); 7.1(m, 1H); 7.3(dd, 1H); 7.5(d, 1H); 7.65(dd, 1H); 8.1(b, 1H). |
| 46 (A3) | 145–147 | 2.05(s, 3H); 2.35(s, 3H); 2.36(s, 3H); 4.0(s, 2H); 6.25(m, 1H); 725(dd, 1H); 7.5(d, 1H); 7.65(d, 1H); 8.1(b, 1H). |
| 47 (A3) | 151–152 | 1.95(dd, 3H); 2.2(d, 3H); 2.35(s, 3H); 3.95(s, 2H); 7.0(m, 1H); 7.25(dd, 1H); 7.5(d, 1H); 7.65(d, 1H); 8.05(b, 1H). |
| 63 (A3) | 209–210 | (CDCl₃/d₆-DMSO): 2.35(s, 3H); 4.05(s, 2H); 7.2(d, 1H); 7.4(dd, 1H); 7.55(d, 1H); 7.8(m, 4H); 8.3(d, 2H). |
| 73 (A3) | 146–147 | 2.4(s, 3H); 4.0(s, 2H); 5.6(d, 2H, $J_{HF}$ = 7 Hz); 7.4(dd, 1H); 7.6(d, 1H); 7.75(d, 1H); 8.1(b, 1H). |
| 75 (A3) | 187–188 | 2.4(s, 3H); 4.0(s, 2H); 7.5(dd, 1H); 7.7(d, 1H); 7.85(d, 1H); 8.1(b, 1H). |
| 79 (A3) | 128–129 | 2.4(s, 1H); 4.0(5,2H); 6.3(m, 1H); 7.5(dd, 1H); 7.7(d, 1H); 7.85(d, 1H); 8.15(b, 1H). |
| 80 (A3) | 141–142 | 2A(s, 3H); 4.05(s, 2H); 7.55(dd, 1H); 7.7(d, 1H); 7.9(d, 1H); 8.15(b, 1H). |
| 86 (A3) |  | 2.4(s, 3H); 4.0(s, 3H); 7.5(dd, 1H); 7.7(d, 1H); 7.9(d, 1H); 8.2(b, 1H). |
| 93 (A3) | 183–185 | 2.05(d, 3H); 2.4(s, 3H); 4.0(s, 2H); 5.25(q, 1H), 7.4(dd, 1H); 7.6(d, 1H); 7.7(d, 1H); 8.1(b, 1H). |
| 95 (A3) | 163–164 | 1.1(t, 3H); 2.4(m, 2H); 2.4(s, 3H); 4.0(s, 2H); 5.0(t, 1H); 7.4(dd, 1H); 7,6(d, 1H); 7.7(dd, 1H); 8.1(b, 1H). |
| 98 (A3) | 130–131 | 1.6(s, 6H) 2.35(s 3H); 3.9(s, 2H); 4.0(s, 2H); 7.3(dd, 1H); 7.6(d, 1H) 7.7(d, 1H); 8.1(b, 1H). |
| 103 (A3) | 165–167 | 2.4(s, 3H), 4.0(s, 2H); 7.5(dd, 1H); 7.7(d, 1H); 7.8(d, 1H); 8.1(b, 1H) |
| 113 (A3) | 192–194 | 2.4(s, 3H); 4.0(s, 2H); 4.15(s, 2H); 7.4(dd, 1H); 7.6(d, 1H); 7.7(dd, 1H); 8.1(b, 1H). |
| 115 (A3) | 165–166 | 1.9(d, 3H); 2.4(s, 3H); 4.0(s, 2H); 4:3(q, 1H); 7A(dd, 1H); 7.6(d, 1H); 7.7(d, 1H); 8.1(b, 1H). |
| 130 (A3) | 124–125 | 2.35(s, 3H); 3.55(s, 3H); 4.0(s, 2H); 4.75(s, 2H); 7.35(dd, 1H); 7.6(d, 1H); 7.7(d, 1H); 8.1(b, 1H) |
| 140 (A3) | 126–129 | 2.4(s, 3H); 4.0(s, 2H); 5.35(s, 2H); 7.05(m, 3H); 7.35(m, 3H); 7.6(d, 1H); 7.7(d, 1H); 8.13(b, 1H) |
| 172 (A3) | 123–124 | 2.2(s, 3H); 2.4(s, 3H); 3.05(m, 2H); 3.3(m, 2H); 4.0(s, 3H); 7.3(dd, 1H); 7.55(d, 1H); 7.65(d, 1H); 8.1(b, 1H). |
| 173 (A3) | 163–164 | 2.4(s, 3H); 4.0(s, 2H); 4.3(s, 2H); 7.3(m, 4H); 7.45(m, 2H); 7.55(d, 1H); 7.6(d, 1H); 8.1(b, 1H). |
| 174 (A3) | 147–148 | 2.4(s, 3H); 4.0(s, 2H); 7.35(dd, 1H); 7.55(d, 1H); 7.65(d, 1H); 8.1(b, 1H). |
| 180 (A3) | 151–153 | 1.3(t, 3H); 2.35(s, 3H); 3.2(s, 3H); 3.6(q, 2H), 3.9(s, 3H); 6.9(dd, 1H); 7.25(m, 2H); 8.1(b, 1H). |
| 183 (A3) | 181–183 | 1.5(s, 9H); 2.35(s, 3H); 3.9(s, 2H); 5.0(b, 1H); 6.95(dd, 1H); 7.25(s, 1H); 7.3(dd, 1H); 8.1(b, 1H). |
| 191 (A3) | 172–173 | 2.4(s, 3H); 3.7(m, 4H); 3.85(m, 4H); 3.9(s, 2H); 7.0(dd, 1H); 7.3(m, 2H); 8.1(b, 1H). |
| 203 (A3) | 151–152 | 2.4(s, 3H); 3.95(s, 2H); 4.2(s, 3H); 7.15(dd, 1H); 7.4(d, 1H); 7.45(d, 1H); 8.05(b, 1H). |
| 204 (A3) | 130–131 | 1.5(t, 3H); 2.4(s, 3H); 3.95(s, 2H); 4.6(q, 2H); 7.1(dd, 1H); 7.4(m, 2H); 8.05(b, 1H). |
| 206 (A3) | 158–159 | 1.5(d, 6H); 2.4(s, 3H); 3.9(s, 2H); 5.3(m, 1H); 7.1(dd, 1H); 7.38(d, 1H); 7.4(d, 1H); 8.1(b, 1H). |
| 220 (A3) | 152–154 | 2.4(s, 3H); 2.8(s, 3H); 3.95(s, 2H); 7.2(dd, 1H); 7.5(d, 1H); 7.55(d, 1H); 8.05(b, 1H). |
| 221 (A3) | 148–149 | 1.5(t, 3H); 2.4(s, 3H); 3.35(q, 2H); 3.95(s, 2H); 7.2(dd, 1H); 7.5(d, 1H); 7.6(dd, 1H); 8.05(b, 1H). |

TABLE W-continued

| Compound No (Table No) | Melting point (/° C.) | NMR proton shifts (/ppm) (CDCl₃ unless otherwise stated.) |
|---|---|---|
| 223 (A3) | 113–115 | 1.5(d, 6H); 2.35(s, 3H); 3.9(s, 2H); 4.05(m, 1H); 7.2(dd, 1H); 7.45(d, 1H); 7.65(d, 1H); 8.1(b, 1H). |
| 224 (A3) | 101–102 | 1.2(s, 9H); 2.4(s, 3H); 3.95(s, 2H); 7.25(dd, 1H); 7.5(d, 1H); 7.6(d, 1H); 8.1(b, 1H). |
| 228(A3) | 203–205 | 2.25(s, 3H); 4.0(s, 2H); 4.45(s, 2H); 7.3(dd, 1H); 7.6(b, 2H); 11.75(s, 1H). |
| 229 (A3) | 149–150 | 2.4(s, 3H); 3.8(s, 3H); 4.0(s, 2H); 4.15(s, 2H); 7.2(dd, 1H); 7.5(d, 1H); 7.55(d, 1H); 8.05(b, 1H). |
| 239 (A3) | 201–202 | 2.35(s, 3H); 4.0(s, 2H); 4.4(s, 2H); 7.3(dd, 1.H); 7.55(d, 1H); 7.6(d, 1H); 8.1(b,1H). |
| 244 (A3) | 196–197 | 2.4 (s, 3H); 4:.0(s, 2H); 4.7(s, 2H); 7.3(dd, 1H); 7.55(d, 1H); 7.6(d, 1H); 7.65(s, 2H); 8.05(b, 1H). |
| 246 (A3) | 75–77 | 2.4(s, 3H); 3.95(s, 2H); 5.8(s, 1H); 7.3(m, 11H); 7.5(d, 1H); 7.7(d, 1H); 8.3(b, 1H): |
| 247 (A3) | 114–115 | 2.4(s, 3H); 325(m, 4H); 4.0(s, 2H); 7.25(m, 6H); 7.5(d, 1H); 7.65(d, 1H); 8.1(b,1H) |
| 248 (A3) | 208–209 | 2.4(s, 3H); 4.0(s, 2H); 7.3(dd, 1H); 7.5(m, 3H); 7.6(d, 1H); 7.7(d, 1H); 8.15(b, 1H); 8.25(m, 2H). |
| 252 (A3) | 152–153 | 1.35(s, 9H); 2.35(s, 3H); 4.0(s, 2H); 7.3(dd, 1H); 7.55(d, 2H); 7.6(d, 1H); 7.7(d, 1H); 8.1(b, 1H); 8.2(d, 2H). |
| 253 (A3) | 175–176 | 2.4(s, 3H); 4.0(s, 2H); 7.45(m, 3H); 7.6(dd, 1H); 7.7(d, 1H); 7.8(d, 1H); 8.1(b, H); 8.2(m, 1H). |
| 257(A3) | 189–191 | 2.4(s, 3H); 4.0(s, 2H); 7.4(m, 2H); 7.6(d, 1H); 7.65(dd, 1H); 7.8(d, 1H); 8.1(b, 1H); 8.15(d, 1H). |
| 261 (A3) | 216–217 | 2.4(s, 3H); 4.0(s, 2H); 7.4(dd, 1H); 7.5(m, 1H); 7.65(d, 1H); 7.75(d, 1H); 8.1(b, 1H); 8.15(d, 2H). |
| 267 (A3) | | 2.4(s, 3H); 4.05(s, 2H); 7.45(dd, 1H); 7.7(d, 1H); 7.85(d, 1H); 8.1(b, 1H); 8.8(m, 1H); 8.45(m, 2H). |
| 272 (A3) | 212–214 | (CDCl₃/ d₆-DMSO): 2.4(s, 3H); 4.1(s, 2H); 7.3(m, 2H); 7.4(dd, 1H); 7.55(m, 1H); 7.6(d, 1H); 7.8(d, 1H); 8.1(m, 1H); 10.4(b, 1H). |
| 278 (A3) | | 2.4(s, 3H); 4.05(s, 2H); 7.15(m, 2H); 7.4(dd, 1H); 7.5(m, 1H); 7.7(d, 1H); 7.85(d, 1H); 8.12 (b, 1H). |
| 287 (A3) | 215–216 | 2.4(s, 3H); 4.05(s, 2H); 7.45(dd, 1H); 7.7(d, 1H); 7.85(d, 1H); 8.1(b, 1H). |
| 305 (A3) | 184–185 | 2.4(s, 3H); 3.95(s, 3H); 4.0(s, 2H); 7.1(m, 1H); 7.35(m, 1H); 7.45(t, 1H); 7.65(d, 1H); 7.75(d, 1H); 7.8(m, 1H); 7.85(m, 1H); 8.1(b, 1H). |
| 307 (A3) | 211–212 | 2.4(s, 3H); 3.9(s, 3H); 4.0(s, 2H); 7.05(m, 2H); 7.3(dd, 1H); 7.6(d, 1H); 7.2(d, 1H); 8.1(b, 1H); 8.2(m, 2H). |
| 329 (A3) | 255–256 | 2.4(s, 3H); 3.95(s, 3H); 4.0(s, 2H); 7.4(dd, 1H); 7.65(d, 1H); 7.75(d, 1H); 8.1(b, 1H); 82(d, 2H); 8.3(d, 2H). |
| 330 (A3) | 181–183 | 2.4(s, 3H); 4.0(s, 2H); 7.2(m, 1H); 7.3(dd, 1H); 7.6(m, 2H); 7.7(d, 1H); 7.9(m, 1H); 8.1(b, 1H). |
| 331 (A3) | 193–194 | 2.4(s, 3H); 4.0(s, 2H); 7.1(d, 1H); 7.35(dd, 1H); 7.53(d, 1H); 7.65(d, 1H); 7.75(d, 1H); 8.1(b, 1H). |
| 334 (A3) | 143–144 | 2.4(s, 3H); 4.0(s, 2H); 4.5(s, 2H); 7.0(m, 1H); 7.05(m, 1H); 7.25(m, 1H); 7.3(dd, 1H); 7.55(d, 1H); 7.65(d, 1H); 8.1(b, 1H). |
| 339 (A3) | 245 | (CDCl₃/d₆-DMSO): 2.4(s, 3H); 4.i(s, 2H); 7.45(dd, 1H); 7.6(d, 1H); 7.8(d, 1H); 8.1(m, 2H); 8.8(m, 2H); 10.6(b, 1H). |
| 343 (A3) | 183–184 | 2.4(s, 3H); 4.0(s, 2H); 7.4(dd, 1H); 7.45(m, 1H); 7.7(d, 1H); 7.8(d, 1H); 8.1(b, 1H); 8.5(m, 1H); 8.6(m, 1H). |
| 349 (A3) | 171–173 | 2.4(s, 3H); 4.05(s, 2H); 7.15(d, 1H); 7.5(dd, 1H); 7.7(d, 1H); 7.8(d, 1H); 8.2(b, 1H); 8.5(d, 1H). |
| 351 (A3) | | (CDC₃/d₆-DMSO): 2.25(s, 3H); 3.9(s, 2H); 6.95(m, 2H); 7.15(d, 1H); 11.55(s, 1H). |
| 352 (A3) | | (CDCl₃/d₆-DMSO): 2.4(s, 3H); 3.95(s, 2H); 7.2(m, 3H), 10.9.(s, 1H); 13.4(s, 1H). |
| 2 (A4) | 156–157 | 2.4(s, 3H); 2.7(s, 3H); 4.0(s, 2H); 7.25(dd, 1H); 7.5(d, 1H), 7.6(d, 1H); 8.1(b, 1H). |
| 15 (A4) | 115–117 | 1.1(s, 9H); 2.45(s, 3H); 2.9(s, 2H); 4.1(s, 2H), 7.35(dd, 1H) 7.55(d, 1H); 7.7(d, 1H); 8.75(b, 1H). |
| 2 (A5) | 213–214 | 2.5(s, 3H); 2.65(s, 3H); 4.0(s, 2H); 7.3(dd, 1H); 7.5(d, 1H) 7.6(d, 1H); 9.7(b, 1H); |
| 15 (A5) | 134–135 | 1.1(s, 9H); 2.5(s, 3H); 2.8(s, 2H); 4.0(s, 2H); 7.3(dd, 1H); 7.5(d, 1H); 7.65(d, 1H); 9.8(b, 1H). |
| 2 (A8) | 165–167 | 125(t, 3H); 2.7(s, 3H); 2.7(q, 2H); 4.0(s, 2H); 7.25(dd, 1H); 7.5(d, 1H);7.6(d, 1H); 8.1(b, 81H). |
| 15 (A8) | 126–127 | 1.1(s, 9H); 1.3(t, 3H); 2.7(q, 2H); 2.8(s, 2H); 4.0(s, 2H); 7.3(dd, 1H); 7.5(d, 1H); 7.65(d, 1H); 8.1(b, 1H). |
| 2 (A13) | 160–164 | 2.35(s, 3H); 2.85(s, 3H); 4.0(s, 2H); 7.35(dd, 1H); 7.9(m, 2H); 8.15(s, 1H). |
| 4 (A13) | gum | 1.1(t, 3H); 1.95(m, 2H); 2.4(s, 3H); 3.1(t, 2H); 4.0(s, 2H); 7.3.5(dd, 1H); 7.85(d, 1.H); 7.9(d, 1H); 8.3(b, 1H). |
| 8 (A13) | 134–136 | 1.5(d, 6H); 2.35(s, 3H); 3.5(m, 1H); 4.0(s, 2H); 7.35(dd, 1H); 7.85(m, 2H); 8.25(b, 1H). |

TABLE W-continued

| Compound No (Table No) | Melting point (/° C.) | NMR proton shifts (/ppm) (CDCl₃ unless otherwise stated.) |
|---|---|---|
| 9 (A13) | gum | 1.5(s, 9H); 2.35(s, 3H); 4.0(s, 2H); 735(dd, 1H); 7.9(d, 1H); 7.95(s, 1H); 8.15(b, 1H). |
| 15 (A13) | gum | 1.1(s, 9H); 2.35(s, 3H); 2.95(t, 2H); 4.0(s, 2H); 7.35(dd, 1H); 7.85(d, 1H); 7.95(d, 1H); 8.25(b, 1H). |
| 2 (A23) | 170–172 | 2.4(s, 3H); 2.65(s, 3H); 4.0(s, 2H); 7.25(dd, 1H); 7.5(d, 1H); 7.70(b, 1H) 8.1(s, 1H). |
| 4 (A23) | 95–97 | 1.05(t, 3H); 1.95(m, 2H); 2.4(s, 3H); 2.95(t, 2H); 4.0(s, 2H); 7.35(m, 1H); 7.5(s, 1H); 7.7(d, 1H); 8.2(b, 1H). |
| 15 (A23) | gum | 1.05(s, 9H); 2.4(s, 3H); 2.8(s, 2H); 4.0(s, 2H); 7.25(d, 1H); 7.5(b, 1H); 7.7(d, 1H); 8.45(b, 1H). |
| 2 (A43) | | (CDCl₃/d₆-DMSO): 2.3(s, 3H); 2.6(s, 3H); 4.0(s, 2H); 7.15(d, 1H); 7.5(m, 2H); 9.3(b, 1H). |
| 4 (A43) | | (CDCl₃/d₆-DMSO): 1.0(t, 3H); 1.8(m, 2H);. 2.4(s, 2H); 2.9(t, 2H); 4.0(s, 2H); 7.2(dd, 1H); 7.5(d, 1H); 7.6(d, 1H). |
| 9 (A43) | | (CDCl₃/d₆-DMSO): 1.6(s, 9H); 2.4(s, 2H); 4.0(s, 2H); 7.2(dd, 1H); 7.55(b, 2H). |
| 15 (A43) | | (CDCl₃/d₆-DMSO): 1.1(s, 9H); 2.4(s, 3H); 2.8(s, 2H); 3.8(s, 2H); 7.2(dd, 1H); 7.5(b, 1H); 7.6(b, 1H). |
| 248 (A43) | | (CDCl₃/d₆-DMSO): 2.3(s, 3H); 3.9(s, 2H); 7.1(dd, 1H); 7.45(m, 4H); 7.55(m, 1H); 8.1(m, 2H); 8.75(b, 1H). |
| 2 (B3) | 97–98 | 2.5(s, 3H); 2.6(s, 3H); 3.3(b, 3H); 3.7(b, 2H); 7.05(b, 1H);. 7.35(b, 2H). |
| 4 (B3) | 75–76 | 1.05(t, 3H); 1.9(m, 2H); 2.5(s, 3H); 2.9(t, 2H); 3.25(b, 3H); 3.65(b, 2H); 7.05(b, 1H); 7.4(b, 2H). |
| 15 (B3) | 80–90 | (d₆-DMSO): 1.0(s, 9H); 2.3(s, 3H); 2.75(s, 2H); 3.4(s;3H); 3.85(s, 2H); 7.1 (dd, 1H); 7.4(b, 1H); 7.5(d, 1H). |
| 2 (C3) | gum | 1.15(t, 3H); 2.5(s, 3H); 2.6(s, 3H); 3.6(b, 2H); 3.8(b, 2H); 7.05(b, 1H); 7.35(b, 2H) |
| 4 (C3) | gum | 1.0(t, 3H); 1.2(t, 3H); 1.9(m, 2H); 2.5(s, 3H); 2.9(t, 2H); 3.6(b, 2H); 3.8(b, 2H); 7.05(b, 1H); 7.4(b, 2H). |
| 15 (C3) | 53–54 | 1.05(s, 9H); 1.2(t, 3H); 2.5(s, 3H); 2.8(s, 2H); 3.6(b, 2H); 3.75(b, 2H); 7.05(b, 1H); 7.4(b, 2H). |
| 2 (D3) | gum | 0.9(s, 3H); 1.6(m, 2H); 2.5(s, 3H); 2.6(s, 3H); 3.6(b, 2H); 3.7(b, 2H); 7.05(b, 1H); 7.35(b, 2H). |
| 4 (D3) | gwn | 0.9(t, 3H); 1.05(t, 3H); 1.55(m, 2H); 1.9(m, 2H); 2.5(s, 3H); 2.9(t, 2H); 3.6(b, 2H); 3.7(b, 2H); 7.05(b, 1H); 7.35(b, 2H). |
| 15 (D3) | gum | 0.9(t, 3H); 1.05(s, 9H); 1.55(m, 2H); 2.5(s, 3H); 2.8(s, 3H); 3.65(m, 4H); 7.05(b, 1H); 7.35(b, 2H). |
| 2 (E3) | gum | 2.5(s, 3H); 2.6(s, 3H); 3.65(b, 2H); 4.3(b, 2H);. 5.2(b, 2H); 5.8(b, 1H); 7.05(b, 1H); 7.35(b, 2H). |
| 4 (E3) | gum | 1.05(t, 3H); 1.9(m, 2H); 2.5(s, 3H); 2.9(t, 2H); 3.65(b, 2H); 4.3(b, 2H); 5.2(b, 2H); 5.8(b, 1H); 7.05(b, 1H); 7.4(b, 2H). |
| 15 (E3) | gum | 1.1(s, 9H); 2.5(s, 3H); 2.8(s, 2H); 3.7(b, 2H); 4.3(b, 2H); 5.2(b, 2H); 5.8(b, 1H); 7.05(b, 1H); 7.4(b, 2H). |
| 2 (F3) | gum | 2.3(b, 1H); 2.5(s, 3H); 2.6(s, 3H); 3.65(b, 2H); 4.5(b, 2H); 7.05(b, 2H); 7.35(b, 2H). |
| 4 (F3) | gwn | 1.05(t, 3H); 1.9(m, 2H); 2.3(b, 1H); 2.5(s, 3H); 2.9(t, 2H); 3.65(b, 2H); 4.5(b, 2H); 7.05(b, 1H); 7.4(b, 2H). |
| 15 (F3) | gum | 1.05(s, 9H); 2.3(b, 1H); 2.5(s, 3H); 2.8(s, 2H); 3.65(b, 2H); 4.5(b, 2H); 7.05(b, 1H); 7.4(b, 2H). |
| 15 (H3) | 93–95 | 1.05(s, 9H); 2.5(s, 3H); 2.8(s, 2H); 3.7(s, 2H); 4.3(b, 2H); 7.0(dd, 1H); 7.3(b, 1H); 7.4(b, 1H). |
| 2 (K3) | gum | 2.5(s, 3H); 2.6(s, 3H); 3.4(s, 3H); 3.5(m, 2H); 3.7(b, 2H); 3.75(m, 2H); 5.15(b, 2H); 7.05(b, 1H); 7.4(b, 2H). |
| 4 (K3) | gum | 1.05(t, 3H); 1.9(m, 2H); 2.5(s, 3H); 2.9(t, 2H); 3.35(s, 3H); 3.5(m, 2H); 3.7(b, 2H); 3.75(m, 2H); 5.15(b, 2H); 7.05(b, 1H); 7.4(b, 2H). |
| 15 (K3) | gum | 1.05(s, 9H); 2.5(s, 3H); 2.8(s, 2H); 3.35(s, 3H); 3.5(m, 2H); 3.7(b, 2H); 3.75(m, 2H); 5.15(b, 2H); 7.05(b, 1H); 7.4(b, 2H). |
| 2 (L3) | gum | 1.2(t, 3H); 2.5(s, 3H); 2.6(s, 3H); 3.6(q, 2H); 3.7(b, 2H); 5.1(b, 2H); 7.05(b, 1H); 7.4(b, 2H). |
| 4 (L3) | gum | 1.05(t, 3H); 1.2(t, 3H); 1.9(m, 2H); 2.5(s, 3H); 2.9(t, 2H); 3.6(q, 2H); 3.7(b, 2H); 5.1(b, 2H); 7.05(b, 1H); 7.4(b, 2H). |
| 15 (L3) | gum | 1.05(s, 9H); 1.2(t, 3H); 2.5(s, 3H);.2.8(s, 2H); 3.6(q, 2H); 3.7(b, 2H); 5.1(b, 2H); 7.05(b, 1H); 7.4(b, 2H). |
| 2 (M3) | gum | 2.5(s, 3H); 2.6(s, 3H); 3.4(s, 3H); 3.5(m, 2H); 3.7(b, 2H); 3.75(m, 2H); 5.15(b, 2H); 7.05(b, 1H); 7.4(b, 2H). |
| 4 (M3) | gum | 1.05(t, 3H); 1.9(m, 2H); 2.5(s, 3H); 2.9(t, 2H); 3.35(s, 3H); 3.5(m, 2H); 3.7(b, 2H); 3.15(m, 2H); 5.15(b, 2H); 7.0(b, 1H); 7.4(b, 2H). |
| 15 (M3) | gwn | 1.05(s, 9H); 2.5(s, 3H); 2.8(s, 2H); 3.35(s, 3H); 3.5(m, 2H); 3.7(b, 2H); 3.75(m, 2H); 5.15(b, 2H); 7.05(b, 1H); 7.4(b, 2H). |
| 15 (N3) | 80–81 | 1.0(b, 3H); 1.05(s, 9H); 1.2(b, 3H); 2.5(s, 3H); 2.8(s, 2H); 3.55(b, 2H); 5.0(m, 1H); 7.05(b, 1H); 7.4(m, 2H). |

TABLE W-continued

| Compound No (Table No) | Melting point (/° C.) | NMR proton shifts (/ppm) (CDCl₃ unless otherwise stated.) |
|---|---|---|
| 15 (V3) | 160–161 | 1.1(s, 9H); 2.4(s, 3H); 2.85(s, 2H); 4.4(s, 2H); 7.3(dd, 1H); 7.6(d, 1H); 7.7(d, 1H); 9.3(b, 1H). |

A compound of formula (I) may be prepared by acylating a compound of formula (II) with a compound of formula (III), preferably in the presence of a known coupling agent such as 1,3-dicyclohexylcarbodiimide, 1,3-diisopropylcarbodiimide or 1-(3-dimetyloamopropyl)-3-ethylcarbodimide. Altemnatively a compound of formula (III) may first be converted to an acid chloride, anhydride or chloroformate suitable for reaction with an amine to form an amide; such procedures are well known and are described, for example, in J. March, Advanced Organic Chemistry, Third Edition, John Wiley and Sons, New York, 1985, pages 370–376 and references therein.

Compounds of formula (II) are either known compounds or may be prepared from commercially available stating materials by methods described in the literature (see, for example, C. Oliver Kappe, Robert Flammang, and Curt Wentrup, Heterocycles, Vol. 37, No. 3, 1615, (1994); A. Adam and R. Slack, J. Chem, Soc., 3061, (1959); and Ronald E Hackler, Kenneth W. Burow, Jr., Sylvester V. Kaster and David I. Wickiser, J. Heterocyclic Chem, 26, 1575, (1989)).

A compound of formula (III) may be prepared by hydrolysis of the corresponding compound of formula (IV) (wherein R is preferably $C_{1-6}$ alkyl) by a method known in the art. A compound of formula (IV) may be hydrolysed under neutral, basic or acidic conditions; the reaction conditions are chosen such that substituent $R^4$ is unchanged during the hydrolysis reaction. Compounds of formula (IV) capable of ready hydrolysis under different conditions are known in the literature and suitable compounds of formula (IV) may be selected, for example, by reference to Theodora W. Greene, Protective Groups in Organic Synthesis, Chapter 5, John Wiley and Sons, New York, 1981.

A compound of formula (IV) may be prepared from a compound of formula (V) under conditions described in the literature (see, for example, David W. Dunwell, Delme Evans, Terence A. Hicks, J. Med. Chem., 1975, Vol. 18, No. 1, 53; Abdou O. Abdelhamid, Cyril Parkanyi, S. M. Khaledur Rashid and Winston D. Lloyd, J. Heterocyclic Chem., 25, 403, (1988); Teruyuki Kondo, Sungbong Yang, Keun-Tae Huh, Masanobu Kobayashi, Shinju Kotachi and Yoshihisa Watanabe, Chemistry Letters, 1275–1278, 1991; Dale L. Boger, J. Org. Chem., 43, No 11, 2296, 1978). The substituent $R^4$ may be an atom or group which itself may be converted into other functional groups; procedures are known in the literature for such transformations involving benzoxazoles and benzothiazoles (for example, Lazer, Edward S., Adams, Julian; Miao, Clara K.; Farina, Peter, Eur. Pat. Appl. EP0535521). Alternatively $R^4$ may contain atoms or groups which may be replaced by other moieties under known conditions.

A compound of formula (V) may be prepared by reduction of a compound of formula (VI) and such procedures are known in the art (see, for example, J. March, Advanced Organic Chemistry, Third Edition, John Wiley and Sons, New York, 1985, and references therein). A compound of formula (VI), wherein Y is oxygen, may be prepared by the nitration of a compound of formula (VII) under known conditions. A compound of formula (VI), wherein Y is sulfur, may be prepared from a compound of formula (VI), wherein Y is oxygen, using conditions similar to those described by J. Scheigetz, R. Zamboni and B. Roy, Synth. Commun., 25 (1995) (18), pages 2791–2806. A compound of formula (VI), wherein Y is nitrogen, may be prepared from a compound of formula (VII) by a sequence of acylation, nitration and deacylation; using conditions known in the art.

Compounds of formula (VII) are either commercially available compounds or may be made from commercially available materials by known methods.

Alternatively, a compound of formula (I) may be prepared by treating a compound of formula (VIII) with, for example, an acid in the presence of a coupling reagent, an orthoester, acid chloride, hydroxyimoyl chloride or an alcohol in the presence of a ruthenium catalyst as described previously for the preparation of a compound of formula (IV).

A compound of formula (VIII) may be obtained by reduction of a compound of formula (IX), itself obtained from a compound of formula (X) using the procedures described above for the transformation of a compound of formula (VII) to a compound of formula (V).

A compound of formula (X) may be prepared by reacting a compound of formula (VII) with a compound of formula (II) in a manner analogous to that-described above for the transformation of a compound of formula (m) to a compound of formula (I).

Alternatively, a compound of formula (X), wherein Y is oxygen, may be obtained by reacting a compound of formula (XI), wherein Y is oxygen, with a suitable reagent such as boron tribromide, hydriodic acid or another suitable reagent, as described by Theodora W. Greene, Protective Groups in Organic Synthesis, Chapter 1, John Wiley and Sons, New York, 1981.

A compound of formula (XI), wherein Y is oxygen, may be prepared by coupling a compound of formula (II) with a compound of formula (XII), wherein Y is oxygen, in a manner analogous to the described above for the formation of a compound of formula (III) to a compound of formula (I).

Compounds of formula (XII), wherein Y is oxygen, are known compounds.

An alternative method for preparing a compound of formula (IV), wherein Y is sulfur, involves the cyclisation of a a compound of formula (XIII) wherein Z is a halogen (such as fluorine, chlorine or bromine) as described, for example, in Comprehensive Heterocyclic Chemistry, Volume 6, Ed. Katritzky and Rees, Pergamon Press, 1984. A compound of formula (XIII) may be prepared by reacting a compound of formula (XIV) with 2,4-bis(4-methoxyphenyl)-1,3-dithia-2,4-diphosphetane-2,4-disulfide (Lawesson's reagent) or phophorus pentasulfide in a solvent such as toluene. A compound of formula (XIV) may be derived from a compound of formula (XIV) by nitration followed by reduction of the resultant nitrohalobenzene compound and subsequent acylation of the resultant aminohalobenzene compound, using procedures well known to those skilled in the art.

Compounds of formula (XV) are commercially available or may be made from commercially available materials using known methods.

A compound of formula (III), wherein n is zero, may also be prepared by halogenation of a compound of formula (XVI) followed by displacement of the resultant compound of formula (XVII) (where Hal is chloro or bromo) with cyanide. Hydrolysis of the resultant compound of formula (XVIII) gives a compound of formula (III).

Treatment of a compound of formula (I), wherein $R^3$ is hydrogen, with an alkylating or acylating agent, optionally in the presence of a base and a phase transfer catalyst, provides a compound of formula (I), wherein $R^3$ is an alkyl or acyl group. Examples of suitable alkylating agents include, but are not restricted to, alkyl halides (such as methyl iodide) and alkyl sulfates (such as dimethylsulfate). Suitable acylating agents include anhydrides (such as acetic anhydride), acid chlorides (such as acetyl chloride or benzoyl chloride) and chloroformates (such as ethyl chloroformate). Suitable bases include organic bases (such as triethylamine or pyridine), alkali metal alkoxides (such as potassium tert-butoxide) and inorganic bases (such as sodium hydride of sodium hydroxide). Suitable phase transfer catalysts may be selected by reference, to the literature (see, for example, J. March, Advanced Organic Chemistry, Third Edition, John Wiley and Sons, New York, 1985, pages 320–322 and references therein).

A compound of formula (I), wherein X is sulphur; may be prepared by reacting a compound of formula (I), wherein X is oxygen, with 2,4-bis(4-methoxyphenyl)-1,3-dithia-2,4-diphosphetane-2,4-disufide (Lawesson's reagent) or phophorus pentasulfide in a solvent such as toluene.

The compounds of formula (I) can be used to combat and control infestations of insect pests such as Lepidoptera, Diptera, Hemiptem, Thysanoptera, Orthoptera, Dictyoptera, Coleoptera, Siphonaptera, Hymenoptera and Isoptera and also other invertebrate pests, for example, acarine, nematode and mollusc pests. Insects, acaines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (rips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panoychis citri* (citrus red mite), *Tetranychus urticae* (two-spotted spider mite), *Tetranychus cinnabarinus* (carmine spider mite), *Phyllocoptruta oleivora* (citrus rust mite,), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (bloweflies), *Blattella germanica* (cookroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotemitidae (for example *Coptotermes formosanus, Reticulitermes flavipes, R speratu, R. virginicus, R. hesperus*, and *R. santonensis*) and the Termitidae (for example *Globitermes sulphureus*), *Solenopsis geminata* (fire ant), *Monomorium pharaonis* (phamoh's ant), *Damalinia*. spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The compounds of formula (I) are also active fungicides and may be used to control one or more of the following pathogens: *Pyricularia oryzae* (Magnaporthe grisea) on rice and wheat and other Pyricularia spp. on other hosts; *Puccinia recondita, Puccinia striiformis* and other rusts on wheat, *Puccinia hordei, Puccinia striiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Erysiphe graminis* (powdery mildew) on barley, wheat, rye and turf and other powdery mildews on various hosts, such as *Sphaerotheca macularis* on hops, *Sphaerotheca fuliginea* on cucurbits (for example cucumber), *Leveillula taurica* on tomatoes, aubergine and green pepper, *Podosphaera leucotricha* on apples and *Uncinula necator* on vines; Cochliobolus spp., Helminthosporium spp., Drechslera spp. (Pyrenophora spp.), Rhynchosporium spp., *Mycosphaerella graminicola* (Septoria tritici) and *Phaeosphaeria nodorum* (*Stagonospora nodorum* or *Septoria nodorum*), *Pseudocercosporella herpotrichoides* and *Gaeumannomyces graminis* on cereals (for example wheat, barley rye), turf and other hosts; *Cercospora arachidicola* and *Cercosporidium personatum* on peanuts and other Cercospora spp. on other hosts, for example sugar beet, bananas, soya beans and rice; *Botrytis cinerea* (grey mould) on tomatoes, strawberries, vegetables, vines and other hosts and other Botrytis spp. on other hosts; Alternaria spp. on vegetables (for example carrots), oil-seed rape, apples, tomatoes, cereals (for example wheat) and other hosts; Venturia spp. (including *Venturia inaequalis* (scab)) on apples, pears, stone fruit, tree nuts and other hosts; Ciadosporium spp. on a range of hosts including cereals (for example wheat) and tomatoes; Monilinia spp. on stone fruit, tree nuts and other hosts; Didymella spp. on tomatoes, turf, wheat and other hosts; Phoma spp. on oil-seed rape, turfs rice, potatoes, wheat and other hosts; Aspergillzus spp. and Aureobasidium spp. on wheat, lumber and other hosts; Ascochyta spp. on peas, wht barley and other hosts, Stemphylium spp. (Pleospora spp.) on apples, pears, onions and other hosts; summer diseases (for example bitter rot (*Glomerella cingulata*), black rot or frogeye leaf spot (*Botryosphaeria obtusa*), Brooks hit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; other downy mildews, such as *Bremia lactucae* on lettuce, *Peronospora* spp. on soybeans, tobacco, onions and other hosts, *Pseudoperonospora humuli* on hops and *Pseudoperonospora cubensis* on cucurbits; *Pythium* spp. (including *Pythium ultimum*) on turf and other hosts; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and turf and other *Rhizoctonia* spp. on various hosts such as wheat and barley, peanuts, vegetables, cotton and turf; *Sclerotinia* spp. on turf, peanuts, oil-seed rape and other hosts; *Sclerotium* spp. on turf, peanuts and other hosts; *Gibberella fujikuroi* on rice; Colletotrichum spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp., *Typhula* spp., *Microdochium nivale*, *Ustilago* spp., *Urocystis* spp., *Tilletia* spp. and *Claviceps pupurpea* on a variety of hosts but particularly wheat, barley, turf and maize; *Ramularia* spp. on sugar beet and other hosts; post-harvest diseases particularly of fruit (for example *Penicillium digitatum, Penicillium, italicum* and *Trichoderma viride* on oranges, *Colletotrichum musae* and *Gloeosporium musarum* on bananas and *Botrytis cinerea* on grapes; other pathogens on vines notably *Eutypa lata, Guignardia bidwellii, Phellinus igniarus, Phomopsis viticola, Pseudopeziza tracheiphila* and *Stereum hirsutum*; other pathogens on trees (for example *Lophodermium seditiosum*) or lumber, notably *Cephaloascus fragrans*, *Ceratocystis* spp., *Ophiostoma piceae*, *Penicillium* spp., *Trichoderma pseudokoningii, Trichoderma viride, Trichoderma harzianum, Aspergillus niger, Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

A compound of formula (I) May move acropetally, basipetally or locally in plant tissue to be active against one or more fungi. Moreover, a compound of formula (I) may be volatile enough to be active in the vapour phase against one or more fungi on the plant.

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest, and a method of combating and controlling fungi which comprises applying a fungicidally effective amount of a compound of formula (I), or a composition containing a compound of formula (I), to a plant, to a seed of a plant, to the locus of the plant or seed or to soil. The compounds of formula (I) are preferably used against insects, acarines, nematodes or fungi.

The term "plant" as used herein includes seedlings, bushes and trees. Furthermore, the fungicidal method of the invention includes protectant, curative, systemic, eradicant and antisporulant treatments.

As fungicides, the compounds of formula (I) are preferably used for agricultural, horticultural and turfgrass purposes in the form of a composition.

In order to apply a compound of formula (I) as an insecticide, acaricidi, nematicide or molluscicide to a pest, a locus of pest, or to a plant susceptible to attack by a pest, or, as a fungicide to a plant, to a seed of a plant, to the locus of the plant or seed or to soil, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that tall compositions (both solid and liquid formulations) comprise, by weight, 0.0001 to 95%, more preferably 1 to 85%, for example 5 to 60%, of a compound of formula (I). The composition is generally used for the control of pests or fungi such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal, molluscicidal or fungicidal composition comprising an insecticidally, acaricidally, nematicidally, molluscicidally or fungicidally effective amount of a compound of formula (I) and a suitable carrier or diluent therefor. The composition is preferably an insecticidal, acaricidal, nematicidal or fungicidal composition.

In a still further aspect the invention provides a method of combating and controlling pests or fungi at a locus which comprises treating the pests or fungi or the locus of the pests or fungi with an insecticidally, acaricidally, nematicidally, molluscicidally or fungicidally effective amount of a composition comprising a compound of formula (I). The compounds of formula (I) are preferably used against insects, acarines, nematodes or fungi.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphurl lime, flours, talc and other organic and inorganic solid carriers) and mechanically grinding the mixture to a fine powder.

Soluble powders (SP) can be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) can be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) can be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzes or alkylnhthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$–$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity-measurements) and may be suitable for mixing water-soluble and oil-soluble pesticides in the same-formulation. An ME is suitable for dilution into water, either remaining as a microemulsion or forming a conventional oil-in-water emulsion.

Suspension concentrates (SC) may comprise aqueous or non-aqueous suspensions of finely divided insoluble so lid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Altatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dipersed in a suitable medium (for example water or a water miscible liquid, such as n-propanol) to provide compositions for use in non-pressurised, hand-actuated spray pumps.

A compound of formula (I) can be mixed in the dry state with a pyrotechnic mixture to form a composition suitable for generating, in an enclosed space, a smoke containing the compound.

Capsule suspensions (CS) can be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reactiin or by a coacervation procedure. The compositions may provide for controlled release of the compound of formula (I) and they can be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible-powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosucc inmates, paraffin or olefine sulphontes, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene-oxide; block polymers (comprising ethylene oxide and propylene oxide); alkano-lamides; simple esters (for example fatty acid polyethylene glycol esters); amine oxides (for example lauryl dimethyl amine oxide), and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) can be applied by any of the known means of applying pesticidal or fungicidal compounds. For example, it can be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it can be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which reman homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) can be used in mixtures with fertilizers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser a compound of formula (I).

The compositions of this invention may contain other compounds having biological activity, for example micro-nutrients or compounds having similar or complementary fungicidal activity or which possess plant growth regulating, herbicidal, insecticidal, nematicidal or acaricidal activity.

By including another fungicide, the resulting composition can have a broader spectrum of activity or a greater level of intrinsic activity than the compound of formula (I) alone. Further the other fungicide can have a synergistic effect on the fungicidal activity of the compound of formula (I).

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermetrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxin, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr, or q) Pymetrozine.

In addition to the major chemical classes of pesticide listed above, other pesticides having particular targets may be employed in the composition, if appropriate for the intended utility of the composition For instance, selective insecticides for particular crops, for example stemborer specific insectides (such as cartap) or hopper specific insecticides (such as buprofezin) for use in rice can be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fuingicidal compounds which may be included-in the composition of the invention are (E)-N-methyl-2-[2-(2,5-dimethylphenoxymethyl)phenyl]-2-methoxy-iminoacetamide (SSF-129), 4-bromo-2-cyano-N,N,-dimethyl-6-trifluoromethyl-benzimidazole-1-sulphonamide, α-[N-(3-chloro-2,6-xylyl)-2-methoxy-acetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-cloro-1-ethyl-1-methyl-2-oxopropyl-4-methylbenzamide (RH-7281, zoxamide), N-allyl-4,5,-dimethyl-2-trimethylsilyltiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, aniazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinan, fludioxonil, flumetover, fluoroimide, fluquinconazole, flusilazole, flutolanil, flutriafol, folpet fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxin-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl oxasulfuron, oxolinic acid, oxpoconazole, oxycarboxin, perfurazoate, penconazole, pencycuron, phenazin oxide, phosetyl-Al, phosphorus acids, phthalide, picoxystrobin (ZA1963), polyoxin D, polyram, probenazole, procholoraz, procymidone, propamocarb, propiconazole, propineb, propionic acid, pyrazophos, pyrifenox, pyrimethanil, pyroquilon, pyroxyfur, pyrrlonitrin quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-thiocyanomethylthio) benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

In a further aspect, the present invention provides a method of combating and controlling fungi comprising applying to a plant, to a seed of a plant, to the locus of the plant or seed or to the soil a fungicidally effective amount of either a first active ingredient, which is a compound of formula (I) or a composition, containing a first active ingredient which is a compound of formula (I); and a second active ingredient which is azoxystrobin, picoxystobin, kresoxim-methyl, trifloxystrobin, metominostrobin or SSF129; wherein the weight ratio of the first active ingredient to the second active ingredient is in the range from 5000:1 to 1:10, preferably in the range from 3000:1 to 1:1, the relative amounts of the first and second active ingredients being such as to produce a synergistic effect.

It is preferred that the first active ingredient is a compound as hereinbefore defined (such as a compound of Table A3).

It is preferred that the second active ingredient is azoxystrobin.

It is preferred that the fungi are fungal infections of plants caused by Plasmopara spp. (especially *Plasmopara viticola*), Septoria spp. (especially *Septoria nodorum*), or Rhizoctonia spp. (especially *Rhizoctonia solani*).

In a further aspect, the present invention provides a method of combating and controlling fungal infections of plants caused by Plasmopara spp. or Rhizoctonia spp., the method comprising applying to a plant, to a seed of a plant, to the locus of the plant or seed or to the soil a fungicidally effective amount of either a first active ingredient, which is a compound of formula (I) or a composition, containing a first active ingredient which is a compound of formula (I); and a second active ingredient which is fluazinam, wherein the weight ratio of the first active ingredient to the second active ingredient is in the range from 500:1 to 1:10, preferably in the range from 100:1 to 1:5, the relative amounts of the first and second active ingredients being such as to produce a synergistic effect.

It is preferred that the first active ingredient is a compound as hereinbefore defined (such as a compound of Table A3).

It is preferred that the fungal infections are those caused by Plasmopara viticola or Rhizoctonia solani.

In a further aspect, the present invention provides a method of combating and controlling fungal infections of plants caused by Plasmopara spp., the method comprising applying to a plant, to a seed of a plan, to the locus of the plant or seed or to the soil a fungicidally effective amount of either a first active ingredient, which is a compound of formula (I) or a composition, containing a first active ingredient which is a compound of formula (I); and a second active ingredient which is fenamidone or famoxadone; wherein the weight ratio of the first active ingredient to the second active ingredient is in the range from 10:1 to 1:10, preferably in the ratio 1:1, the relative amounts of the first and second active ingredients being such as to produce a synergistic effect.

It is preferred that the first active ingredient is a compound as hereinbefore defined (such as a compound of Table A3).

It is preferred that the second active ingredient is fenamidone.

It is preferred that the fungal infections are those caused by Plasmopara viticola.

The compounds of formula (I) can be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which can be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active Ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples, in which the ingredients below are referred to by their Registered Trade Marks and have the following compositions.

| Registered Trade Mark | Composition |
| --- | --- |
| SYNPERONIC NP8 } SYNPERONIC NP13 } | Nonylphenol-ethylene oxide condensate |
| SYNPERONIC A7 | Synthetic primary alcohol-ethylene oxide condensate |
| AROMASOL H | Alkylbenzene solvent |
| SOLVESSO 200 | Inert organic diluent |
| KELTROL | Polysaccharide |
| PROXEL | Bactericide |

EXAMPLE 1

This Example illustrates the preparation of Compound 4 (Table A3).

Step 1

Methyl 4-hydroxyphenylacetate (49.8 g, 0.3 mol) was dissolved in glacial acetic acid (500 ml) and the resultant solution was cooled to below 15° C. Concentrated nitric acid (40 ml) was added slowly and the reaction mixture was sired until completion and then poured onto a mixture of ice and water. The precipitated solid was filtered, washed with ice cold water and dried to give methyl 4-hydroxy-3-nitrophenylacetate (51.2 g) as a yellow solid.

$^1$H NMR (CDCl$_3$) δ: 3.65 (s, 2H); 3.75 (s, 3H); 7.15 (d, 1H); 7.5 (dd, 1H); 8.0 (d, 1H); 10.5 (s, 1H) ppm.

Step 2

Methyl 4-hydroxy-3-nitrophenylacetate (52.2 g, 0.247 mol) was dissolved in methanol (400 ml) and the resultant solution was then hydrogenated at 5 bar over a 5% w/w palladium on carbon catalyst. The catalyst was removed by filtration and the filtrate was evaporated in vacuo. Trituration with hexane gave methyl 3-amino-4-hydroxyphenylacetate (43.4 g).

$^1$H NMR (CDCl$_3$) δ: 3.45 (s, 2H); 3.65 (s, 3H); 6.5 (dd, 1H); 6.6 (d, 1H); 6.7 (d, 1H) ppm.

Step 3

The product from Step 2 (5.43 g, 0.03 mol), triethylamine (3.27 g, 0.033 mol) and pyridinium para-toluenesulfonate (2.01 g, 0.008 mol) were stirred together in xylene (250 ml). n-Butyryl chloride (3.96 g, 0.033 mol) was-added dropwise at room temperature and once the addition was complete stirring was continued for 30 minutes. The mixture was heated to reflux for 17 hours, then cooled to room temperature, diluted with ethyl acetate and washed with water and brine sequentially. The organic solution was dried over anhydrous magnesium sulfate, filtered and the filtrate was evaporated in vacuo. The residue was further purified by flash column chromatography on silica gel, eluting with a 2:1 mixture of hexane: ethyl acetate, to give methyl (2-propyl-5-benzoxazolyl)acetate (4.2 g) as a pale orange liquid.

$^1$H NMR (CDCl$_3$) δ: 1.05 (t, 3H); 1.9 (m, 2H); 2.9 (t, 2H); 3.7 (s, 3H); 3.75 (s, 2H); 7.2 (m, 1H); 7.4 (d, 1H); 7.65 (d, 1H) ppm.

Step 4

The product from Step 3 (4.0 g, 0.01 72 mol) was dissolved in methanol (30 ml) and potassium hydroxide flakes (1.06 g, 0.0188 mol) were added. The mixture was heated at reflux for 2 hours, then cooled and the solvent was evaporated in vacuo. The residue was taken up in water and extracted with diethyl ether. The aqueous phase was collected, acidified to pH1 with dilute aqueous hydrochloric acid and extracted with ethyl acetate. The organic extract was washed with brine, dried over anhydrous magnesium sulfate, filtered and the filtrate was evaporated in vacuo to afford (2-propyl-5-benzoxazolyl)acetic acid (2.9 g) as an off-white solid, mp. 67–68° C.

¹H NMR (CDCl₃) δ: 1.0 (t, 3H); 1.9 (m, 2H); 2.9 (t, 2H); 3.75 (s, 2H); 7.2 (dd, 1H); 7.4 (d, 1H); 7.6 (d, 1H) ppm.

Step 5

The acid prepared in Step 4 (0.876 g, 0.004 mol) was suspended in dichloromethane (10 ml) and one drop of N,N-diethylformamide and oxalyl chloride (0.559 g, 0.0044 mol) were added sequentially. The mixture was stirred for 2 hours and then the solvent was removed in vacuo. The residue was taken up in xylene (10 ml), 5-amino-4-chloro-3-methylisothiazole was added and the mixture was heated under reflux for 2 hours. The mixture was cooled to room temperature, diluted with ethyl acetate and washed-with brine. The organic solution was dried over anhydrous magnesium sulfate, filtered and the filtrate was evaporated in vacuo. The residue was further purified by flash column chromatography on silica gel, eluting with a 2:1 mixture of hexane:ethyl acetate, to give Compound 4 (Table A3) as a yellow-orange solid.

EXAMPLE 2

This Example illustrates the preparation of Compound 3 (Table A3).

Step 1

4-Methoxyphenylacetic acid (33.2 g, 0.2 mol) and N,N-dimethylformamide (1 ml) were dissolved in dichloromethane (300 ml) and the mixture was cooled in an ice-bath. Oxalyl chloride (27.9 g, 0.22 mol) was added dropwise and once the addition was complete the cooling bath was removed and the mixture was stirred for 3 hours. The solvent was removed in vacuo, the residue taken up in xylene (300 ml) and 5-amino-4-chloro-3-methylisothiazole added. The mixture was heated under reflux for 2 hours and was then cooled to room temperature before the solvent was evaporated in vacuo. The residue was taken up in ethyl acetate and washed with aqueous sodium hydroxide solution. On standing, N-(4-chloro-3-methyl-5-isothiazolyl)-4-methoxyphenylacetamide (27.3 g) precipitated from the aqueous solution.

¹H NMR (CDCl₃) δ: 2.4 (s, 3H); 3.8 (s, 2H); 3.85 (s, 3H); 6.95 (m, 2H); 7.25 (m, 2H); 8.1 (b, 1H) ppm.

Step 2

N-4-Chloro-3-methyl-5-isothiazolyl)-4-methoxyphenylacetamide (32.8 g, 0.11 mol) was dissolved in dichloromethane (300 ml) and the solution was then cooled to below −70° C. A solution of boron tribromide in dichloromethane (1M, 332 ml, 0.332 mol) was added dropwise, maintaining the internal temperature below −65° C. When the addition was complete, the mixture was allowed to warm to room temperature and stirring was continued for 3 hours. With ice-bath cooling, methanol (100 ml) was cautiously added and the mixture was stirred for several minutes. The solvent was removed in vacuo, methanol, was added, the mixture was stirred and then the solvent was evaporated once more. The residue was partitioned between ethyl acetate and saturated aqueous sodium bicarbonate solution. The organic extract was washed with brine, dried over magnesium sulfate, filtered and the filtrate was evaporated in vacuo. The residue was triturated with hexane to afford N-(4-chloro-3-methyl-5-isothiazolyl)-4-hydroxyphenylacetamide (28 g) as a solid.

¹H NMR (d₆-DMSO/CDCl₃) δ: 2.35 (s, 3H); 3.8 (s, 2H); 6.85 (m, 2H); 7.15 (m, 2H); 8.65 (b, 1H); 9.1 (b, 1H) ppm.

Step 3

The phenol (28 g, 0.099 mol) obtained in Step 2 was suspended in ethanol (200 ml) and ferric nitrate nonahydrate (40.0 g, 0.99 mol) was added. The mixture was stirred at 50° C. for 90 minutes and was then cooled to room temperature before the solvent was removed in vacuo. The residue was partitioned between 2M aqueous hydrochloric acid and ethyl acetate. The organic extract was washed sequentially with 2M aqueous hydrochloric acid and brine, dried over magnesium sulfate, filtered and the filtrate was evaporated in vacuo. Trituration with hexane afforded N-(-chloro-3-methyl-5-isothiazolyl)-4-hydroxy-3-nitrophenylacetamide (30.1 g) as a solid.

¹H NMR (d₆-DMSO/CDCl₃) δ: 2.4 (s, 3H); 3.9 (s, 2H); 7.1 (d, 1H); 7.65 (dd, 1H); 8.15 (d, 1H); 11.0 (s, 1H) ppm.

Step 4

N-(4-Chloro-3-methyl-5-isothiazolyl)-4-hydroxy-3-nitrophenylacetamide (374 g, 0.114 mol) was hydrogenated at 15 bar over a 3% w/w platinum on carbon catalyst (15 g) in N,N-dimethylformamide (180 ml). Once the reduction was complete, the catalyst was removed by filtration and the filtrate was evaporated in vacuo to give N-(4-chloro-3-methyl-5-isothiazolyl)-3-amino-4-hydroxyphenylacetamide (26.8 g) as a pale brown solid, which used without further purification in the next step.

¹H NMR (d₆-DMSO) δ: 2.25 (s, 3H); 3.6 (s, 3H), 6.3 (dd, 1H), 6.5 (m, 2H); 8.9, 1H); 11.5 (s, 1H) ppm.

Step 5

The product from Step 4 (0.58 g, 0.002 mol) was suspended in toluene (5 ml) and propionyl chloride (0.204 g, 0.0022 mol) and p-toluenesulfonic acid (0.125 g, 0.007 mol) were added. The mixture was heated to reflux for 2 hours, a further quantity of p-toluenesulfonic acid (0.125 g, 0.0007 mol) was added and heating was continued until cyclisation was complete. The mixture was cooled to room temperature, diluted with ethyl acetate and washed with brine. The organic solution was dried over anhydrous magnesium sulfate, filtered and the filtrate was evaporated in vacuo. The residue was further purified by flash column chromatography on silica gel, eluting with a 1:1 mixture of hexane:ethyl acetate, to give Compound 3 (Table A3) (0.188 g) as a colourless solid.

EXAMPLE 3

This Example illustrates the preparation of Compound 10 (Table A3).

Step 1

Methyl 4-hydroxy-3-nitrophenylacetate (21.1 g, 0.1 mol) was suspended in a mixture of water (55 ml) and methanol (105 ml). The suspension was stirred at room temperature while a solution of sodium hydroxide (8.8 g, 0.22 mol) in water (50 ml) was added dropwise over 20 minutes, maintaining the reaction temperature between 20 and 25° C. by water bath cooling. The resultant dark red solution was stirred at room temperature for 15 minutes, diluted with water and acidified to pH1–2 by addition of 2M hydrochloric acid and extracted with ethyl acetate. The organic extract was washed with brine (200 ml), dried over magnesium sulphate, filtered and concentrated under reduced pressure to give 4-hydroxy-3-nitrophenylacetic acid (19.6 g) as a yellow solid.

¹H NMR (CDCl₃) δ: 3.55 (s, 2H); 7.1 (d, 1H); 7.5 (dd, 1H); 8.0 (d, 1H) ppm.

Step 2

4-Hydroxy-3-nitrophenylacetic acid (10 g, 0.05 mol) was suspended in dichloroethane (50 ml) and stirred at room temperature under a nitrogen atmosphere. N,N-Dimethylformamide (0.1 ml) was added followed by dropwise addition of oxalyl chloride (6.77 g, 0.05 mol) over 20 minutes. The mixture was stirred at room temperature for 25 minutes and then at 40° C. for 20 minutes. The reaction mixture was then heated under reflux while a solution of 5-amino-4-chloro-3-methylisotiazole (7.54 g, 0.05 mol) in dichloroethane (30 ml) was added over 30 minutes. The resultant pale orange suspension was stirred at reflux for 2 hours and then cooled to room temperature, to give a precipitate, which was collected by filtration and washed with dichloromethane. The solid was suspended in water (150 ml), treated with 10% (w/v) sodium hydroxide (50 ml) and the resulting red solution was washed with dichloromethane (2×50 ml). The combined washings were extracted with water (50 ml) and the combined aqueous layers were acidified to pH4–5 by addition of concentrated hydrochloric acid (approximately 10 ml). The resultant yellow suspension was filtered and the solid was washed with water and dried under suction to give N-(4-chloro-3-methyl-5-isothiazolyl)-4-hydrox-3-nitrophenylacetamide (14.6 g) as a yellow solid.

$^1$H NMR (d$_6$-DMSO: δ: 2.3 (s, 3H); 3.9 (s, 2H); 7.05 (d, 1H); 7.4 (dd, 1H); 7.8 (d, 1H); 10.85 (s, 1H); 11.7 (s, 1H) ppm.

Step 3

N-(4-Chloro-3-methyl-5-isothiazolyl)-4-hydroxy-3-nitrophenylacetamide (50 g, 0.15 mol), 1% w/w platinum on carbon (15 g) and N,N-dimethylformamide (400 ml) were charged to a 600 ml stainless steel hydrogenation vessel. Once purged the vessel was pressurised to 35 bar with hydrogen, stirring was started and the reaction was heated to 35° C. After 6 hours the uptake of hydrogen had stopped; the stirring and heating were turned off and the mixture was allowed to cool to ambient temperature. The vessel was vented, purged with nitrogen and was heated to 50° C. to ensure complete solution. The reaction mixture was filtered to remove the catalyst and the liquors concentrated under high vacuum to remove the N,N-dimethylformamide. The resultant residue was slurried in dichloromethane (300 ml), filtered, washed with dichlorometane (200 ml) and dried to give give N-(4-chloro-3-methyl-5-isothiazolyl)-3-amino-4-hydroxy-phenylacetamide (43.9 g) as a buff solid, m.p. 239–243° C.

$^1$H NMR (d$_6$-DMSO) δ: 2.25 (s 3H); 3.6 (s, 2H); 4.6 (b, 2H); 6.3 (dd, 1H); 6.5 (2d, 2H); 8.8 (b, 1H); 11.6 (s, 1H) ppm.

Step 4

N-(4-chloro-3-methyl-5-isothiazolyl)-3-amino-4-hydroxy-phenylacetamide (0.42 g, 0.001 mol), 2-methylbutyryl chloride (0.37 g, 0.003 mol) and para-toluenesulfonic acid (0.05 g) were stirred together in 2-methoxyethyl either (5 ml) at 110° C. for 6 hours. The mixture was cooled to room temperature and partitioned between ethyl acetate and saturated aqueous sodium bicarbonate solution. The organic extract was dried over anhydrous magnesium sulfate, filtered and the filtrate was evaporated in vacuo. The residue was further purified by flash column chromatography on silica gel, eluting with a 1:1 mixture of hexane: ethyl acetate. Fractions containing the desired product were combined an the solvent was evaporated in vacuo to afford a yellow residue. Trituration with hexane gave Compound 10 (Table A3) as a colorless solid.

EXAMPLE 4

This Example illustrates the preparation of Compound 113 (Table A3).

Step 1

N,N'-Diisopropylcarbiimide (0.630 g, 0.005 mol) was added dropwise to a solution of both cyanoacetic acid (0.425 g, 0.005 mol) and N-4-chloro-3-methyl-5-isothiazolyl)-3-amino-4-hydroxy-phenylacetamide (1.49 g, 0.005 mol) in N,N-diethylacetamide (20 ml). The resultant mixture was stirred at room temperature for 1 hour and was then poured into water. The resultant precipitate (1.34 g) was collected by filtration, washed with water and dried.

Step 2

The product from Step 1 (0.365 g, 0.001 mol) was suspended in 1,1,2,2-tetrachloroethane (4 ml), para-toluenesulfonic acid (0.095 g) was added and the mixture was heated at 140° C. for 2 hours. The mixture was cooled to room temperature and partitioned between ethyl acetate and saturated aqueous sodium bicarbonate solution. The organic extract was dried over anhydrous magnesium sulfate, filtered and he filtrate was evaporated in vacuo. The residue was further purified by flash column chromatography on silica gel, eluting with a 2:1 mixture of hexane:ethyl acetate to give Compound 113 (Table A3) as a pale yellow solid.

EXAMPLE 5

This Example illustrates the preparation of Compound 221 (Table A3).

Step 1

Methyl 3-amino-4-hydroxyphenylacetate (5.43 g, 0.03 mol) was suspended in toluene (60 ml) and 1,1'-thiocarbonyldiimidazole (5.34 g, 0.03 mol) was added. The resultant mixture was stirred for 30 minutes, then acetic acid (10 ml) was added and the mixture was heated under reflux for 3 hours. The mixture was cooled to room temperature and the solvent was removed in vacuo. The residue was partitioned between water and ethyl acetate The organic extract was dried over magnesium sulfate, filtered and the filtrate was evaporated to give methyl (2,3-dihydro-2-thioxo-5-benzoxazolyl)acetate (6,2 g) as a light brown solid, m.p. 120–122° C.

$^1$H NMR (CDCl$_3$) δ: 3.7 (s, 2H); 3.75 (s, 3H; 7.15 (m, 2H); 7.3 (m, 1H) ppm.

Step 2

The compound prepared in Step 1 (1.12 g, 0.005 mol) and potassium carbonate (0.69 g, 0.005 mol) were together in acetone (20 ml). Ethyl iodide (0.78 g, 0.005 mol) was added and the mixture was heated under reflux for 1 hour. The mixture was cooled to room temperature and partitioned between water and ethyl acetate. The organic extract was dried over magnesium sulfate, filtered and the filtrate was evaporated in vacua to give methyl (2-ethylthio-5-benzoxalyl)acetate (1.22 g) as a brown liquid-used without further purification in the next step.

Step 3

The product from Step 2 (122 g, 0.0049 mol) was dissolved in a mixture of methanol (15 ml) and water (5 ml) and the mixture was cooled in an ice-bath. Potassium hydroxide flakes (0.302 g, 0.0054 mol) were added, and the mixture was stirred for 2 hours, warming slowly to room temperature. The solvent was evaporated in vacuo. The residue was taken up in water and extracted with diethyl ether and the aqueous fraction was acidified with 2M aqueous hydrochloric acid, with ice-bath cooling, to afford (2-ethylthio-5-benzoxazolyl)acetic acid (0.98 g).

$^1$H NMR (CDCl$_3$) δ: 1.5 (t, 3H); 3.3 (q, 2H); 3.75 (s, 2H); 7.15 (dd, 1H); 7.4 (d, 1H); 7.5 (d, 1H) ppm.

Step 4

The compound prepared in Step 3 (0.474 g, 0.002 mol) was suspended in dichloromethane (10 ml) and one drop of N,N-dimethylformamide and oxalyl chloride (0.254 g, 0.0022 mol) were added sequentially. The mixture was stirred for 2 hours and then the solvent was removed in vacuo. The residue was taken up in xylene (10 ml), 5-amino-4-chloro-3-methylisothiazole (0.32 g, 0.0021 mol) was added and the mixture was heated under reflux for 2 hours. The mixture was cooled to room temperature, diluted with ethyl acetate and washed sequentially with water and 2M aqueous hydrochloric acid. The organic solution was dried over anhydrous magnesium sulfate, filtered and the filtrate was evaporated in vacuo. The residue was further purified by flash column chromatography on silica gel, eluting with a 1:1 mixture of hexane:ethyl acetate, to give Compound 221 (Table A3) as a pale yellow solid.

EXAMPLE 6

This Example illustrates the preparation of Compound 224 (Table A3).

Step 1

Methyl 3-amino4-hydroxyphenylacetate (16.29 g, 0.09 mol) was suspended in toluene (180 ml) and 1,1'-thiocarbonyldiimidazole (15.96 g, 0.09 mol) was added and the was stirred until the exothermic reaction had subsided. Acetic acid (3 ml) was added and the mixture was heated at reflux for 4 hours, then cooled to room temperature and the solvent was removed in vacuo. The residue was partitioned between ethyl acetate and brine and the organic extract was dried over anhydrous magnesium sulfate, filtered and the filtrate was evaporated in vacuo. The residue was taken up in chloroform (200 ml) and the solution was saturated with chlorine. The mixture was stirred for 1 hour at room temperature, then diluted with chloroform and washed sequentially with a 10% (w/v) solution of aqueous sodium bicarbonate and water. The organic solution was dried over anhydrous magnesium sulfate, filtered and the filtrate was evaporated in vacuo. The residue was further purified by flash column chromatography on silica gel, eluting with a 3:1 mixture of hexane ethyl acetate, to give methyl (2-chloro-5-benzoxazolyl)acetate (8.4 g) as a pale yellow liquid which solidified on standing.

$^1$H NMR (CDCl$_3$) δ: 3.7 (s, 3H); 3.75 (s, 2H); 7.3 (dd, 1H); 7.45 (d, 1H); 7.6 (d, 1H) ppm.

Step 2

Sodium tert-butylthiolate (0.496 g, 0.0044 mol) was dissolved in N,N-dimethylformamide (5 ml) and the solution was cooled in an ice bath. A solution of methyl (2-chloro-5-benxazolyl)acetate (1.00 g, 0.0044 mol) in N,N-dimehylformamide (5 ml) was added dropwise and once the addition was complete the reaction mixture was stirred for 1 hour, being allowed to warm slowly to room temperature. The reaction mixture was poured onto ice-water and extracted with ethyl acetate. The organic extract was dried over anhydrous magnesium sulfate, filtered and the filtrate was evaporated in vacuo. The residue was further purified by flash column chromatography on silica gel, eluting with a 3:1 mixture of hexane:ethyl acetate, to give methyl (2-tert-butylthio-5-benxazol-yl)acetate (0.51 g) as a pale yellow liquid.

$^1$H NMR (CDCl$_3$) δ: 1.65 (s, 9H); 3.7 (s, 3H); 3.73 (s, 2H); 7.2 (dd, 1H); 7.4 (d, 1H); 7.55 (d, 1H) ppm.

Step 3

The product from Step 2 (0,44 g, 0.0016 mol) was dissolved in a mixture of methanol (10 ml) and water (5 ml) and the mixture was cooled in an ice-bath. Potassium hydroxide flakes (0.11 g, 0.016 mol) were added and the mixture was sired for 4 hours, being allowed to warm slowly to room temperature. The solvent was evaporated in vacuo. The residue was taken up in water and extracted with diethyl ether and the aqueous fraction was acidified with 2M aqueous hydrochloric acid, with ice-bath cooling, to afford (2-tert-butylthio-5-benezoxazolyl)acetic acid (0.41 g).

$^1$H NMR (CDCl$_3$) δ: 1.6 (s, 9H); 3.75 (s, 2H); 7.2 (dd, 1H); 7.4 (d, 1H); 7.55 (d, 1H) ppm.

Step 4

The acid prepared in Step 3 (0.39 g, 0.0015 mol) was suspended in dichloromethane (10 ml) and one drop of N,N-dimethylformamide and oxalyl chloride (0.205 g, 0.0016 mol) were added sequentially. The mixture was stirred for 2 hours and then the solvent was removed in vacuo. The residue was taken up in xylene (10 ml), 5-amino-4-chloro-3-methylisothiazole (0.33 g, 0.0022 mol) added and the mixture heated together under reflux for 2 hours. The mixture was cooled to room temperature and partitioned between ethyl acetate and brine. The organic solution was dried over anhydrous magnesium sulfate, filtered and the filtrate was evaporated in vacua. The residue was further purified by flash column chromatography on silica gel eluting with a 2:1 mixture of hexane ethyl acetate, to give Compound 224 (Table A3) as a sandy-brown solid.

EXAMPLE 7

This Example illustrates the preparation of Compound 183 (Table A3).

Step 1

A solution of methyl (2-chloro-5-benzoxazolyl)acetate (1.00 g, 0.004 mol) in dichloromethane (5 ml) was added dropwise to a chilled (ice-bath) solution of tert-butylamine (0.648 g, 0.009 mol) in dichloromethane (10 ml) and once the addition was complete the mixture was stirred for 2 hours, allowing it to warm to room temperature. 1,2-Diehloroethane (15 ml) was added and the mixture was heated to reflux for 17 hours. The mixture was cooled to room temperature, diluted with dichloromethane and washed with the water. The organic extract was dried over anhydrous magnesium sulfate, filtered and the filtrate was evaporated in vacua to give methyl (2-ter-butylamino-5-benzxazolyl)acetate as a yellow gum (1.09 g). The product was used without further purification in the next step.

Step 2

Potassium hydroxide flakes (0.236 g, 0.004 mol) were added to a chilled (ice-bath) solution of methyl (2-tert-butylamino-5-benzoxazolyl)cetate (1.00 g, 0.004 mol) in methanol (10 ml) and water (5 ml) and the mixture was stirred for 2 hours, being allowed to warm slowly to room temperature. The solvent was removed in vacuo, the residue taken up in water and extracted with diethyl ether. The aqueous extract was cooled in an-ice-bath and dilute aqueous hydrochloric acid was added until the solution reached pH3. The precipitate was collected by filtration and dried to give (2-tert-butylamino-5-benzoxazolyl)acetic acid (0.685 g) as a colourless solid, m.p. 175–176° C.

$^1$H NMR (CDCl$_3$) δ: 1.6 (s, 9H); 3.6 (s, 2H); 6.4 (b, 1H); 6.95 (dd, 1H); 7.2 (d, 1H); 7.3 (d 1H) ppm.

Step 3

The acid prepared in Step 2 (0.67 g, 0.003 mol) was suspended in dichloromethane (10 ml) and one drop of N,N-dimethylformamide and oxalyl chloride (0.38 g, 0.003 mol) were added sequentially. The mixture was stirred for 2 hours and then the solvent was removed in vacuo. The residue was taken up in 1,2-dichloroethne (20 ml) and the mixture was heated to reflux. 5-Amino-4-chloro-3-methylisothiazole (0.33 g, 0.0022 mol) was added and the mixture was heated under reflux for 2 hours. The mixture was cooled to room temperature, diluted with 1,2-dichloroethane and washed sequentially with saturated aqueous-sodium bicarbonate solution and brine. The organic extract was dried over anhydrous magnesium sulfate, filtered and the filtrate was evaporated in vacua. The residue was further purified by flash column chromatography on silica gel, eluting with a 2:1 mixture of hexane ethyl acetate to give an orange-yellow residue. The product was taken up in a small volume of ether and allowed to stand. Compound 183 (Table A3) precipitated as a cream coloured solid.

EXAMPLE 8

This Example illustrates the preparation of Compound 248 (Table A43).

Step 1

Methyl 3,4-diaminophenylacetate (0.38 g, 0.0021 mol) and triethyl orthobenzoate (0.8 ml, 0.0035 mol) were stirred together in refluxing ethanol (10 ml) for 8 hours. The mixture was cooled and partitioned between ethyl acetate and water. The organic solution was dried over anhydrous magnesium sulfate, filtered and the filtrate was evaporated in vacuo. The residue was further purified by flash column chromatography on silica gel, gradient eluting with a mixture of hexane:ethyl acetate, to give methyl (2-phenyl-5-benzidazolyl)acetate (0.34 g) as a brown oil.

$^1$H NMR (CDCl$_3$) δ: 3.5 (s, 3H), 3.52 (s, 2H), 7.15 (m, 1H), 7.5 (m, 5H), 8.0 (m, 2H) ppm.

Step 2

The ester (0.34 g, 0.0013 mol) prepared in Step 1 was dissolved in methanol (10 ml) and potassium hydroxide flakes (0.08 g, 0.0014 mol) were added. The mixture was heated at reflux for 2 hours, then cooled and the solvent was evaporated in vacuo. The residue was taken up in water and extracted with diethyl ether. The aqueous phase was collected, acidified to pH1 with dilute aqueous hydrochloric acid and the resultant precipitate (0.18 g) was collected and dried to give (2-phenyl-5-benzimidazolyl)acetic acid hydrochloride, which was used without further purification in the next step.

$^1$H NMR (CDCl$_3$) δ: 3.7 (s, 2H), 7.3 (m, 1H), 7.55 (m, 3H), 7.65 (m, 2H), 8.25(m, 2H) ppm.

Step 3

The benzimidazole prepared in Step 2 (0.18 g, 0.0007 mol) was suspended in chloroform (20 ml) and N,N-dimethylformamide (0.5 ml) and triethylamine (0.2 ml, 0.0014 mol) were added. To the resultant solution was added oxalyl chloride (0.07 ml, 0.00079 mol) and the mixture was stirred for 2 hours at room temperature. 5-Amino-4-chloro-3-methyl-isothiazole (0.107 g, 0.00072 mol) was added and the mixture was heated at room temperature for 15 hours and then under reflux for 48 hours. The mixture was cooled and partitioned between ethyl acetate and water. The organic solution was dried over anhydrous magnesium sulfate, filtered and the filtrate was evaporated in vacuo. The residue was further purified by flash column chromatography on silica gel, eluting with a 2:1 mixture of hexane: ethyl acetate, to give Compound 248 (Table A43) (0.012 g) as a yellow oil.

EXAMPLE 9

This illustrates the preparation of Compound 2 (Table A13).

Step 1

Methyl 4-hydroxy-3-nitrophenylacetate (21.1 g, 0.1 mol), dimethylthiocarbamoyl chloride (13.0 g, 0.1 mol) and potassium carbonate (14.0 g, 0.1 mol) were suspended in 4-methylpentan-2-one (150 ml) and the mixture was heated at reflux with stirring for 1 hour. The mixture was cooled and kept overnight at room temperature. The reaction mixture was diluted with water and was extracted with ethyl acetate. The organic extract was washed sequentially with dilute aqueous sodium hydroxide solution and brine and then dried over anhydrous magnesium sulfate, filtered and the filtrate was evaporated in vacuo to give a buff solid, which was triturated with diethyl ether to provide methyl 3-nitro-4-(O-dimethylthiocarbamoyl)phenylacetate (24.5 g).

$^1$H NMR (CDCl$_3$) δ: 3.40 (s, 2H); 3.45 (s, 3H); 3.75 (s, 6H); 7.25 (d, 1H); 7.6 (dd, 1H); 8.5 (d, 1H) ppm.

Step 2

The product from Step 1 (24.5 g, 0.083 mol), was dissolved in xylene (100 ml) and heated at reflux with stirring for 17 hours. The reaction was cooled and the xylene was evaporated in vacuo to afford an oil which crystallised on standing. Trituration with diethyl ether gave methyl 3-nitro-4-(S-dimethylthiocarbamoyl)phenylacetate (21.5 g) m.p. 56–57° C.

$^1$H NMR (CDCl$_3$) δ: 3.1 (bd, 6H); 3.7 (s, 5H); 7.5 (dd, 1H); 7.7 (d, 1H); 7.95 (d, 1H) ppm.

The product from Step 2 (6.0 g, 0.02 mol) was dissolved in methanol (250 ml) and a solution of sodium hydroxide pellets (2.0 g, 0.05 mol) in water (15 ml) was added. The mixture was stirred at room temperature for 17 hours, then acidified with concentrated hydrochloric acid, diluted with water and extracted with ethyl acetate. The organic extract was washed with brine, dried over anhydrous magnesium sulphate, filtered and the filtrate was evaporated in vacuo. Trituration with hexane gave a brown solid (4.5 g), comprising a mixture of 4-mercapto-3-nitrophenylacetic acid and bis(4-carboxymethyl-2-nitrophenyl) disulfide.

Step 4

The products of Step 3 (4.5 g, 0.015 ml) were dissolved in methanol (50 ml), and a few drops of concentrated hydrochloric acid were added. The mixture was refluxed for 2 hours and was then cooled and allowed to stand overnight at room temperature. The precipitate was collected and washed with diethylether and dried to give bis(4-carbomethoxymeltyl-2-nitrophenyl) disulfide as a yellow solid (1.2 g).

$^1$H NMR (CDCl$_3$) δ: 3.7 (s, 2H); 3.725 (s, 3H); 7.5 (dd, 1H); 7.8 (d, 1H); 8.3 (d, 1H) ppm.

The ethereal and methanol solution was evaporated in vacuo to afford a yellow solid (2.2 g) after trituration with diethyl ether. $^1$H NMR (CDCl$_3$) showed this to be a mixture of methyl 4-mercapto-3-nitrophenylacetate and bis(4-carbomethoxymethyl-2-nitrophenyl) disulfide.

Step 5

The product obtained in Step 4 (3.0 g, 0.013 mol) was dissolved in glacial acetic acid (30 ml). Iron power (52 g) was added to the solution and the mixture was heated and stirred at reflux for 3 hours. The mixture was cooled to room temperature, diluted with water and extracted with diethyl ether (200 ml). The ethereal extract was washed sequentially with water and aqueous sodium hydrogen carbonate solution, dried over anhydrous magnesium sulphate, filtered and the filtrate was evaporated in vacuo. The residue was further purified by flash column chromatography on silica gel, eluting with a 1:1 mixture of hexane:diethyl ether, to give methyl (2-methyl-5-benzothiazolyl)-acetate (0.95 g) as a yellow liquid.

$^1$H NMR (CDCl$_3$) δ: 2.85 (s, 3H); 3.7 (s, 2H); 3.8 (s, 3H); 7.3 (dd, 1H); 7.8 (d, 1H); 7.85 (d, 1H) ppm.

Step 6

The product from Step 5 (0.85 g, 0.0385 mol) was dissolved in methanol (10 ml) and a solution of potassium hydroxide pellets (0.35 g) in water (2 ml) was added. The mixture was then stirred at room temperature for 17 hours. The mixture was acidified with concentrated hydrochloric acid to pH4 and the solution was then diluted with water and extracted with ethyl acetate. The organic extract was washed with brine, dried over anhydrous magnesium sulfate, filtered and the filtrate was evaporated in vacuo. Trituration with hexane afforded (2-methyl-5-benzothioazolyl)acetic acid (0.62 g) as a buff solid, m.p. 194–196° C.

$^1$H NMR (CDCl$_3$) δ: 2.85 (s, 3H); 3.5 (s, 2H); 7.1 (dd, H); 7.55 (d, 1H); 7.65 (d, 1H) ppm.

Step 7

The acid prepared in Step 6 (0.2 g, 0.001 mol) was suspended in dicloromethane (10 ml) and one drop of N,N-dimethylformamide and oxalyl chloride (0.559 g, 0.0044 mol) were added sequentially. The mixture was stirred for 2 hours and then the solvent was removed in vacuo. The residue was taken up in xylene (10 ml), 5-amino-4-chloro-3-methylisothiazole was added and the mixture was heated under reflux for 2 hours. The mixture was cooled to room temperature, diluted with ethyl acetate and washed with brine. The organic solution was dried over anhydrous magnesium sulfate, filtered and the filtrate was evaporated in vacuo. The residue was further purified by flash column chromatography on silica gel, eluting with a 2:1 mixture of hexane:ethyl acetate, to give Compound 2 (Table A13) (0.125 g) as a buff solid.

EXAMPLE 10

This Example illustrates the preparation of Compound 15 (Table L3).

Step 1

[2-(2,2-Dimethylpropyl)-5-benzoxazolyl]acetic acid (0.800 g, 0.003 mol) was suspended in dichloromethane (10 ml) and one drop of N,N-dimethylformamide and oxalyl chloride (0.451 g, 0.004 mol) were added sequentially. The mixture was stirred for 2 hours and then the solvent was removed in vacuo. The residue was taken up in xylene (10 ml), 5-amino-4-chloro-3-methylisothiazole (0.829 g, 0.006 mol) was added and the mixture was heated under reflux for 2 hours. The mixture was cooled to room temperature, diluted with ethyl acetate and washed with brine. The organic solution was dried over anhydrous magnesium sulfate, filtered and the filtrate was evaporated in vacuo. The residue was further purified by flash column chromatography on silica gel, eluting with a 2:1 mixture of hexane:ethyl acetate, to give Compound 15 (Table A3) (0.325 g) as a pale orange solid.

Step 2

Compound 15 (Table A3) (1.7 g, 0.0045 mol) was dissolved in tetrahydrofuran (30 ml) and a 1M solution of lithium bis(trimethylsilyl)amide in tetrahydrofuran (4.95 ml) was added. The reaction mixture was stirred for 30 minutes at room temperature and then chloromethylethyl ether (0.851 g, 0.009 mol) was added. The reaction mixture was stirred for 2 hours at room temperature and then poured into water. The mixture was extracted with ethyl acetate, the organic extract washed with brine, dried over anhydrous magnesium sulfate filtered and the filtrate was evaporated in vacuo. The residue was further purified by flash column chromatography on silica gel, eluting with a 2:1 mixture of hexane:ethyl acetate, to give Compound 15 (Table L3) (0.55 g) as a viscous gum.

EXAMPLE 11

This Example illustrates the preparation of Compound 15 (Table C3).

[2-(2,2-Dimethylpropyl)-5-benzoxazolyl]acetic acid (0.729 g, 0.003 mol) was suspended in dichloromethane (10 ml) and a few drops of N,N-dimethylformamide and oxalyl chloride (0.419 g, 0.003 mol) were added sequentially. The mixture was stirred for 2 hours, and then the solvent removed in vacuo. The residue was taken up in 1,2-dichloroethane (2 ml) and xylene (10 ml), 4-chloro-5-ethylamino-3-methylisothiazole (0.590 g, 0.003 mol) were added and the mixture was then heated under reflux for 3 hours. The mixture was cooled to room temperature, the solvent evaporated in vacuo and the residue taken up in ethyl acetate and washed with brine. The organic solution was dried over anhydrous magnesium sulfate, filtered and the filtrate was evaporated in vacuo. The residue was further purified by flash column chromatography on silica gel, eluting with a 2:1 mixture of hexane:ethyl acetate, to give Compound 15 (Table C3) (0.62 g) as a yellowish gum.

EXAMPLE 12

This Example illustrates the preparation of Compound 15 (Table V3).

Compound 15 (Table A3) (1.88 g, 0.05 mol) and [2,4-bis(4-methoxyphenyl)-1,3-dithia-2-2,4-diphosphetane-2,4-disulfide] (3.03 g, 0.0075 mol) were heated in refluxing toluene for 6 hours. The mixture was cooled to room temperature, the solvent was removed in vacuo and the residue partitioned between ethyl acetate and water. The organic extract was dried over anhydrous magnesium sulfate, filtered and the filtrate was evaporated in vacuo. The residue was further purified by flash column chromatography on silica gel, eluting with a 2:1 mixture of hexane:ethyl acetate, to give Compound 15 (Table C3) (0.195 g).

EXAMPLE 13

This Example illustrates the preparation of Compound 204 (Table A3). Compound 220 (Table A3) (0.400 g, 0.001 mol) was dissolved in ethanol (10 ml) and potassium hydroxide flakes (0.126 g, 0.002 mol) were added. The mixture was stirred at room temperature for 1 hour, was then warmed to 50° C. for a further 1 hour and finally was heated at reflux for 30 minutes. The mixture was cooled to room temperature and the solvent was evaporated in vacuo. The residue was taken up in water, the solution was neutralized with dilute aqueous hydrochloric acid and extracted with ethyl acetate. The organic extract was dried over anhydrous magnesium sulfate, filtered and the filtrate was evaporated in vacuo. The residue was further purified by flash column chromatography on silica gel, eluting with a 2:1 mixture of hexane:ethyl acetate, to give Compound 204 (Table A3) (0.120 g) as a colourless solid.

EXAMPLE 14

This Example illustrates the preparation of Compound 9 (Table A13).

Step 1

Methyl 4-fluoro-3-nitrophenylacetate (5.0 g, 0.023 mol) and iron powder (3 g, 0.053 mol) were suspended in a mixture of propan-2-ol (50 ml) and water (5 ml). Concentrated hydrochloric acid (5 drops) was added at room temperature and the mixture was heated at reflux with stirring for 2 hours. The reaction mixture was cooled, diluted with diethyl ether, filtered through diatomaceous earth and the resulting filtrate was evaporated in vacuo. The residue was further purified by chromatography on silica gel, eluting with diethyl ether to yield methyl 3-amino-4-fluorophenylacetate (3.5 g) as a yellow oil.

$^1$H NMR (CDCl$_3$) δ: 3.50 (s, 2H); 3.8 (s, 3H); 3.5–3.9 (bs, 2H); 6.6 (m, 1H); 6.85 (dd, 1H); 7.9 (dd, 1H) ppm.

Step 2

The product from Step 1 (2.0 g, 0.01 mol), was dissolved in pyridine (10 ml) and was then cooled to 0° C. 2,2-Dimethylpropanoyl chloride (1.5 g, 0.012 mol) was added dropwise over 5 minutes. The reaction was stirred at 0° C. for 30 minutes and left to stand overnight at ambient temperature. The mixture was poured onto ice and extracted with diethyl ether. The ethereal extract was washed sequentially with water and brine, dried over anhydrous magnesium sulfate, filtered, and the filtrate was evaporated in vacuo to afford methyl 3-N-(2,2-dimethylpropanoyl)amino-4-fluorophenylacetate (2.9 g), which was used without further purification in the next step.

$^1$H NMR(CDCl$_3$) δ: 1.4 (s, 9H); 3.6 (s, 2H); 3.7 (s, 3H); 6.95 (m, 1H); 7.05 (m, 1H); 7.6 (bs, 1H); 8.3 (dd, 1H) ppm.

Step 3

The product from Step 2 (2.8 g, 0.6105 mol) and [2,4-bis(4-methoxyphenyl)-1,3-dithia-2-2,4-diphosphetane-2,4-disulfide] (8.5 g 0.021 mol) were dissolved in dry toluene (100 ml) and the mixture was heated under reflux for 17 hours. The reaction was cooled to a room temperature and the solvent was evaporated in vacuo. The residue was triturated with a 1:1 mixture of hexane:diethyl ether (100 ml), the solution was decanted and solvet was evaporated in vacuo to yield an oil, which was further purified by flash column chromatography on silica gel, eluting sequentially with dichloromethane and diethyl ether, to yield methyl 3-N-(2,2-dimethylthiopropionyl)amino-4-fluorophenylacetate (1.4 g) as a yellow oil.

$^1$H NMR (CDCl$_3$) δ: 1.5 (s, 9H); 3.65 (s, 2H); 3.75 (s, 3H); 7.1 (m, 2H); 8.4 (d, 1H); 8.7–8.9 (bs, 1H) ppm.

Step 4

The product from Step 3 (1.3 g, 0.046 mol) and potassium carbonate (0.7 g, 0.046 mol) were dissolved in dry N,N-dimethylacetamide (10 ml) with stirring and the mixture was brought to reflux for 15 minutes. The reaction mixture was cooled to room temperature, diluted with brine and extracted with diethyl ether. The ethereal extract was washed sequentially with water and brine, dried over anhydrous magnesium sulfate, filtered and the filtrate was evaporated in vacuo. The residue was further purified by flash column chromatography on silica gel, eluting sequentially with dichloromethane and diethyl ether, to yield methyl (2-tert-butyl-5-benzothiazolyl)acetate (1.0 g) as a yellow oil.

$^1$H NMR (CDCl$_3$) δ: 1.5 (s, 9H); 3.65 (s, 2H); 3.75 (s, 3H); 7.3 (d, 1H); 7.8 (d, 1H); 7.9 (dd, 1H) ppm.

Step 5

The product from Step 4 (1 g, 0.039 mol) was dissolved in methanol (8 ml) and a solution of potassium hydroxide pellets (0.35 g) in water (2 ml) was added. The mixture was stirred at room temperature for 17 hours. The mixture was acidified with concentrated hydrochloric acid to pH4 and the resultant solution was diluted with water and extracted with ethyl acetate. The organic extract was washed with brine, dried over anhydrous magnesiun sulfate, filtered and the filtrate was evaporated in vacuo to afford 2-tert-butyl-5-benzothioazolyl)acetic acid (0.62 g) as a viscous oil.

$^1$H NMR (CDCl$_3$) δ: 1.5 (s, 9H); 3.8 (s, 2H); 7.3 (d, 1H); 7.8 (d, 1H); 8.1 (s, 1H) ppm.

Step 6

The acid prepared in Step 5 (0.2 g, 0.001 mol) was suspended in dichloromethane (10 ml) and one drop of N,N-dimethylformamide and oxalyl chloride (0.559 g, 0.0044 mol) were added sequentially. The mixture was stirred for 2 hours and then the solvent was removed in vacuo. The residue was takes up in xylene (10 ml), 5-amino-4-chloro-3-methylisothiazole was added and the mixture was heated under reflux for 2 hours. The mixture was cooled to room temperature, diluted with ethyl acetate and washed with brine. The organic solution was dried over anhydrous magnesium sulfate, filtered and the filtrate was evaporated in vacuo. The residue was further purified by flash column chromatography on silica gel, eluting with a 1:1 mixture of hexane:diethyl ether, to give Compound 9 (Table A13) (0.04 g).

EXAMPLE 15

This Example illustrates an alternative preparation of 2-tert-butyl-5-benzothialylacetic acid (XX) (used in Example 14).

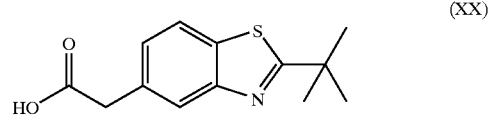

Step 1

2-Fluoro-4-methylaniline (12.5 g, 0.1 mol), was dissolved in pyridine (50 ml) and cooled to 5° C. 2,2-Dimethylpropanoyl chloride (12.5 g 0.1 mol) was added dropwise over 15 minutes. The reaction was stirred at 5° C. for 30 minutes and then at ambient temperature for 1 hour. The reaction mixture was poured onto ice and the precipitate was collected by filtration, washed with water and dried to afford 3-fluoro-4 (N-2,2-dimethylethanoyl)aminotoluene 9.5 g (46%) as a white solid, m.p. 88–89° C.

$^1$H NMR (CDCl$_3$) δ: 1.3 (s, 9H); 2.3 (s, 3H); 6.8 (m, 1H); 6.95 (dd, 1H); 7.6 (b, 1H); 8.2 (dd, 1H) ppm.

Step 2

The product from Step 1 (8.0 g, 0.039 mol) and [2,4-bis(4-methoxyphenyl)-1,3-dithia-2-2,4-diphosphetane-2,4-disulfide] (15.5 g, 0.039 mol) were dissolved in dry toluene (200 ml) with stirring and the mixture was heated at reflux for 6 hours. The reaction mixture was cooled to room temperature and the solvent-was evaporated in vacuo. The residue was further purified by passing through a plug of silica gel, eluting with a 9:1 mixture of hexane:diethyl ether (1000 ml) to afford 3-fluoro-4 (N-2,2-dimethylthioethanoyl) aminotoluene 8.0 g (91%) as a solid, m.p. 55–56° C.

$^1$H NMR (CDCl$_3$) δ: 1.5 (s, 9H); 2.3 (s, 3H); 7.0 (dd, 2H); 8.2 (dd, 1H); 8.8 (bs, 1H) ppm.

Step 3

The product from Step 2 (8.0 g, 0.036 mol) and potassium carbonate (6.0 g, 0.046 mol) were dissolved in dry N,N-dimethylacetamide (30 ml) with sing and the mixture was heated at reflux for 60 minutes. The reaction mixture was cooled to room temperature, diluted with brine and extracted with diethyl ether. The ethereal layer was washed sequentially with water and brine, dried over anhydrous magnesium sulfate and evaporated in vacuo to afford 2-tert-butyl-5-methylbenzothiazole as a colourless solid (5.4 g), m.p. 55–57° C.

$^1$H NMR (CDCl$_3$) δ: 1.5 (s, 9H); 2.5 (s, 3H); 7.15 (d, 1H); 7.7 (d, 1H); 7.8 (s, 1H) ppm.

Step 4

The product from Step 3 (5.1 g, 0.025 mol), N-bromosuccimide (4.8 g, 0.030 mol) and a catalytic quantity of 2,2'-azo-bis-isobutyronitrile were dissolved in carbon tetrachloride, with stirring and refluxed for about 30 minutes whilst being exposed to light generated from a 500 W spotlight. The reaction mixture was cooled to room temperature, the precipitate removed by filtration and the filtrate was evaporated to an orange liquid (6.1 g), which was used directly in the next step.

Step 5

A solution of potassium cyanide (2.0 g, 0.031 mol) in dimethyl sulphoxide (DMSO) (10 ml) was added, dropwise, to a solution of the product from Step 4 (2.0 g, 0.007 mol) in dry DMSO (5 ml). The mixture was stirred at room temperature for 10 minutes, then poured into water, diluted with brine and extracted with diethyl ether. The ethereal layer was washed sequentially with water and brine, dried over anhydrous magnesium sulfate, filtered and the filtrate was evaporated in vacuo. The residue was further purified by flashed column chromatography on silica gel, eluting with a 1:1 mixture of hexane diethylether, to give 2-tert-butyl-5-benzothiazolylacetonitrile as a yellow solid (0.90 g), m.p. 50–52° C.

$^1$H NMR (CDCl$_3$) δ: 1.5 (s, 9H); 3.9 (s, 2H); 7.3 (d, 1H); 7.85 (d, 1H); 8.0 (s, 1H) ppm.

Step 6

The product from Step 5 (0.90 g, 0.004 mol) was dissolved in methanol (8 ml) and a solution of potassium hydroxide pellets (0.35 g, 0.006 mol) in water (2 ml) was added. The mixture was refluxed for 17 hours and was then cooled to room temperature. The mixture was acidified with concentrated hydrochloric acid to pH4 and the resultant solution was diluted with water and extracted with ethyl acetate. The organic extract was washed with brine, dried over anhydrous magnesium sulfate, filtered and the filtrate was evaporated in vacuo to afford 2-tert-butyl-5-benzothiazolylacetic acid (0.5 g) as a viscous oil.

$^1$H NMR (CDCl) δ: 1.5 (s, 9H); 3.8 (s, 2H); 7.3 (d, 1H); 7.8 (d, 1H); 8.1 (s, 1H) ppm.

EXAMPLE 16

This Example illustrates the preparation of Compound 4 (Table A43).

Step 1

4-Aminophenylacetic acid (15 g, 0.1 mol) was sired in n-butyric anhydride (70 ml) at room temperature for 1 hour. The mixture was poured into iced water and the resultant precipitate was collected by filtration and washed with ethyl acetate to afford 4-N-(n-propionyl)amino-phenylacetic acid (11.4 g) as a pink solid.

$^1$H NMR (CDCl$_3$) δ: 1.0 (t, 3H); 1.8 (m, 2H); 2.3 (t, 2H); 3.6 (s, 2H); 7.2 (d, 2H); 7.5 (d, 2H); 8.0 (b, 1H) ppm.

Step 2

Concentrated nitric acid (8 ml) was added dropwise to a chilled (ice-bath) solution of 4-N-(n-propionyl) aminophenylacetic acid (11.4 g, 0.051 mol) in acetic anhydride (30 ml) and the mixture was stirred until the reaction was complete. The mixture was poured onto ice and the resultant precipitate was collected by filtration and dried to give 3-nitro-4-N-(n-propionyl)aminophenylacetic acid (7.6 g) as a yellow solid.

$^1$H NMR (CDCl$_3$) δ: 1.0 (t, 3H); 1.8 (m, 2H); 2.5 (t, 2H); 3.6 (s, 2H); 7.6 (dd, 1H); 8.2 (d, 1H); 8.7 (d, 1H) ppm.

Step 3

The acid prepared in Step 2 (5.4 g, 0.02 mol) was suspended in dichloromethane (30 ml) and one drop of N,N-dimethylformanide and oxalyl chloride (2.8 g, 0.022 mol) were added sequentially. The mixture was stirred for 2 hours and then the solvent was removed in vacuo. The residue was taken up in 1,2-dichloroethane (10 ml), 5-aminochloro-3-methylisothiazole (3.3 g, 0.02 mol) was added and the mixture was heated under reflux for 2 hours. The mixture was cooled to room temperature, diluted with ethyl acetate and washed with saturated aqueous sodium bicarbonate solution. The organic solution was dried over anhydrous magnesium sulfate, filtered and the filtrate was evaporated in vacuo. Trituration with dichloromethane gave N-(4-chloro-3-methyl-5-isothiazolyl)-[3-nitro-4-N-(n-propionyl)amino]phenylacetamide (0.42 g) as a cream solid.

$^1$H NMR (CDCl$_3$) δ: 1.0 (t, 3H); 1.8 (m, 2H); 2.4 (s, 3H); 2.5 (t, 2H); 4.0 (s, 2H); 7.7 (dd, 1H); 8.3 (d, 1H); 8.4 (d, 1H); 10.2 (s, 1H); 10.6 (s, 1H) ppm.

The dichlormethane washings were evaporated in vacuo, and triturated with a 1:1 mixture of ethyl acetate and hexane to give a fiber quantity (3.80 g) of desired product.

Step 4

A mixture of the product obtained in Step 3 (0.4 g, 0.001 mol) and iron powder (0.54 g) in a mixture of isopropanol (10 ml) and water (1 ml) were heated at reflux until tin layer chromotography showed the reaction to be complete. The mixture was cooled to room temperature, filtered through diatomaceous earth and the filtrate was evaporated in vacuo. Ethyl acetate was added and insoluble material was collected by filtration to give N-(4-chloro-3-methyl-5-isothiazolyl)-[3-amino-4-N-(n-propionyl)amino] phenylacetamide (0.085 g) as a grey solid.

$^1$H NMR (CDCl$_3$) δ: 1.0 (t, 3H); 1.8 (m, 2H); 2.3–2.5 (m, 5H); 3.8 (s, 2H); 6.7 (dd, 1H); 6.8 (d, 1H) ppm.

Step 5

The product obtained in Step 4 (0.085 g, 0.0002 mol) was suspended in 2-methoxyethyl ether (5 ml) and p-toluenesulfonic acid (0.045 g, 0.0002 mol) was added. The mixture was heated to reflux for 6 hours. The mixture was cooled to room temperature, diluted with ethyl acetate and washed with saturated aqueous sodium bicarbonate solution. The organic solution was dried over anhydrous magnesium sulfate, filtered and the filtrate was evaporated in vacuo. The residue was further purified by chromatography to afford Compound 4 (Table A43).

EXAMPLE 17

This Example illustrates an emulsifiable concentrate composition which is readily convertible, by addition to water, into a preparation suitable for spraying purposes. The emulsifiable concentrate has the following composition:

|  | % by weight |
|---|---|
| Compound No. 4 (Table A23) | 25.0 |
| SYNPERONIC NP13 | 2.5 |
| Calcium dodecylbenzenesulphonate | 2.5 |
| AROMASOL H | 70.0 |

EXAMPLE 18

This Example illustrates a wettable powder composition which is readily convertible, by addition to water, into a preparation suitable for spraying purposes. The wettable powder has the following composition:

|  | % by weight |
|---|---|
| Compound No. 272 (Table A3) | 25.0 |
| Silica | 25.0 |
| Sodium lignosulphonate | 5.0 |
| Sodium lauryl sulphate | 2.0 |
| Kaolin | 43.0 |

EXAMPLE 19

This Example illustrates a dustable powder which may be applied directly to plants or other surfaces. The dustable powder has the following composition:

| | % by weight |
|---|---|
| Compound No. 4 (Table K3) | 1.0 |
| Talc | 99.0 |

EXAMPLE 20

This Example illustrates an oil miscible liquid formulation suitable for application by ultra low volume techniques after mixing with an organic diluent. The formulation has the following composition:

| | % by weight |
|---|---|
| Compound No. 2 (Table D3) | 10.0 |
| SOLVESSO 200 | 90.0 |

EXAMPLE 21

This Example illustrates a capsule suspension concentrate which is readily convertible, by addition to water, into a preparation suitable for application as an aqueous spray. The capsule suspension concentrate has the following composition:

| | % by weight |
|---|---|
| Compound No. 15 (Table H3) | 10.0 |
| AROMASOL H | 10.0 |
| Toluene di-isocyanate | 3.0 |
| SYNPERONIC A7 | 1.0 |
| Polyvinyl alcohol | 2.0 |
| Bentonite | 1.5 |
| KELTROL | 0.1 |
| Water | 72.4 |

EXAMPLE 22

This Example illustrates a ready for use granular formulation which is prepared from a preformed granular carrier. The granular formulation has the following composition:

| | % by weight |
|---|---|
| Compound No. 251 (Table A43) | 0.5 |
| SOLVESSO 200 | 0.2 |
| SYNPERONIC A7 | 0.1 |
| Calcium carbonate granules (diameter 0.3–0.7 mm) | 99.2 |

EXAMPLE 23

This Example illustrates a ready for use granular formulation which is prepared by granulation of the powdered components. The granular formulation has the following composition:

| | % by weight |
|---|---|
| Compound No. 4 (Table E3) | 0.5 |
| Sodium lignosulphonate | 5.0 |
| Kaolin | 94.5 |

EXAMPLE 24

This Example illustrates an aqueous suspension concentrate composition which is readily convertible, by addition to water, into a preparation suitable for spraying purposes. The suspension concentrate has the following composition:

| | % by weight |
|---|---|
| Compound No. 331 (Table A3) | 25.0 |
| Sodium lignosulphonate | 3.0 |
| Propylene glycol | 10.0 |
| Bentonite | 2.0 |
| KELTROL | 0.1 |
| PROXEL | 0.1 |
| Water | 59.8 |

EXAMPLE 25

This Example illustrates a water dispersible granule formulation which is readily convertible, by addition to water, into a preparation suitable for spraying purposes. The water dispersible granule has the following composition:

| | % by weight |
|---|---|
| Compound No. 343 (Table A3) | 25.0 |
| Silica | 5.0 |
| Sodium lignosulphonate | 10.0 |
| Sodium lauryl sulphate | 5.0 |
| Sodium acetate | 10.0 |
| Montmorillonite powder | 45.0 |

EXAMPLE 26

This Example illustrates the pesticidal/insecticidal properties of compounds of formula (I). The activities of individual compounds of formula (I) were determined using a variety of pests. With the exception of nematodes, the pests were treated with a liquid composition containing 500 parts per million (ppm) by weight of a compound unless otherwise stated. Each composition was made by dissolving the compound in an acetone and ethanol (50:50 by volume) mixture and diluting the solution with water containing 0.05% by volume of a wetting agent, SYNPERONIC NP8, until the liquid composition contained the required concentration of the compound.

The test procedure adopted with regard to each pest, except nematodes, was essentially the same and composed supporting a number of the pests on a medium which was usually a substrate, a host plant or a foodstuff on which the pests feed, and treating either or both the medium and the pests with a composition. Pest mortality was assessed usually between three and five days after treatment Knockdown of housefly (*Musca domestica*) was assessed 15 minutes after treatment The test procedure for nematodes involved dissolving the compound in an acetone and ethanol (50:50 by volume)

mixture and diluting the solution with water to obtain a final concentration of the compound of 12.5 ppm. J2 infective juveniles of *Meloidogyne incognita* were suspended in the solution in a glass vial and mortality assessed after a period of three days.

The results of the tests are presented in Tables X1 and X2. The results indicate a grading of mortality (score) designated as 9, 5 or 0 wherein 9 indicates 80–100% mortality, 5 indicates 40–79% mortality and 0 indicates less than 40% mortality.

TABLE X1

| Compound No. (Table No.) | TETRUR | MYZUPE | MUSCDO AC | MUSCDO AK | HELIVI | LAPHEG | MELGIN |
|---|---|---|---|---|---|---|---|
| 4(A3) | 5 | 9 | 9 | 9 | 9 | 5 | 9 |
| 15(A3) | 9 | 9 | 9 | 0 | 9 | 9 | 0 |
| 2(A3) | 0 | 9 | 0 | 0 | 5 | 0 | 5 |
| 9(A3) | 9 | 5 | 9 | 0 | 9 | 5 | 0 |
| 248(A3) | 0 | 0 | 0 | 0 | 5 | 0 | 0 |
| 257(A3) | 9 | 0 | 0 | 5 | 5 | 0 | 5 |
| 1(A3) | 0 | 5 | 0 | 0 | 0 | 0 | 5 |
| 8(A3) | 0 | 5 | 9 | 9 | 5 | 5 | 0 |
| 3(A3) | 5 | 9 | 9 | 9 | 9 | 5 | 0 |
| 140(A3) | 0 | 0 | 0 | 0 | 0 | 0 | 0 |
| 220(A3) | 0 | 5 | 5 | 0 | 0 | 0 | 0 |
| 14(A3) | 9 | 9 | 9 | 5 | 9 | 9 | 0 |
| 221(A3) | 0 | 9 | 9 | 5 | 0 | 0 | 0 |
| 223(A3) | 0 | 9 | 0 | 0 | 5 | 0 | 0 |
| 10(A3) | 0 | 9 | 5 | 0 | 5 | 5 | 0 |
| 252(A3) | 0 | 0 | 0 | 0 | 0 | 0 | 0 |
| 46(A3) | 5 | 9 | 5 | 5 | 0 | 5 | 0 |
| 13(A3) | 9 | 9 | 9 | 5 | 0 | 0 | 0 |
| 329(A3) | 0 | 0 | 0 | 0 | 0 | 0 | N/T |
| 47(A3) | 0 | 9 | 0 | 0 | 0 | 0 | 0 |
| 247(A3) | 0 | 9 | 0 | 0 | 0 | 0 | 0 |
| 331(A3) | 0 | 0 | 0 | 0 | 0 | 0 | N/T |
| 98(A3) | 9 | 9 | 5 | 0 | 5 | 5 | 0 |
| 45(A3) | 5 | 9 | 9 | 9 | 5 | 9 | 0 |
| 5(A3) | 0 | 9 | 0 | 0 | 5 | 5 | 0 |
| 28(A3) | 9 | 9 | 5 | 9 | 9 | 5 | 0 |
| 172(A3) | 9 | 9 | 5 | 9 | 5 | 5 | 5 |
| 261(A3) | 0 | 0 | 0 | 0 | 0 | 0 | 0 |
| 224(A3) | 9 | 9 | 0 | 0 | 5 | 0 | 0 |
| 351(A3) | 0 | 0 | 0 | 0 | 0 | 0 | 0 |
| 15(B3) | 9 | 5 | 0 | 0 | 0 | 0 | 0 |
| 15(D3) | 9 | 9 | 0 | 0 | 5 | 5 | 0 |
| 15(K3) | 9 | 9 | 0 | 0 | 5 | 5 | 0 |
| 15(L3) | 9 | 9 | 9 | 9 | 9 | 5 | 0 |
| 15(M3) | 9 | 9 | 0 | 0 | 0 | 5 | 0 |
| 15(C3) | 9 | 9 | 9 | 0 | 0 | 9 | 0 |
| 73(A3) | 0 | 9 | 0 | 0 | 5 | 0 | 0 |
| 41(A3) | 5 | 9 | 0 | 9 | 5 | 5 | 0 |
| 2(A23) | 0 | 0 | 0 | 0 | 0 | 0 | 0 |
| 4(A23) | 0 | 9 | 0 | 0 | 0 | 0 | 0 |
| 15(A23) | 9 | 5 | 0 | 0 | 0 | 5 | 0 |
| 2(K3) | 9 | 9 | 9 | 0 | 0 | 0 | 0 |
| 2(B3) | 0 | 0 | 9 | 0 | 0 | 0 | 0 |
| 4(B3) | 0 | 5 | 0 | 0 | 0 | 5 | 0 |
| 15(F3) | 9 | 9 | 0 | 0 | 9 | 9 | 0 |
| 2(L3) | 9 | 9 | 9 | 0 | 9 | 5 | 0 |
| 2(M3) | 0 | 5 | 0 | 0 | 0 | 0 | 0 |
| 4(L3) | 9 | 9 | 9 | 5 | 9 | 9 | 0 |
| 4(K3) | 0 | 5 | 0 | 0 | 0 | 5 | 0 |
| 15(E3) | 9 | 9 | 0 | 0 | 9 | 5 | 0 |
| 2(C3) | 9 | 5 | 9 | 0 | 0 | 5 | 0 |
| 4(M3) | 0 | 9 | 0 | 0 | 0 | 0 | 0 |
| 4(C3) | 9 | 9 | 0 | 5 | 0 | 9 | 0 |
| 352(A3) | 0 | 5 | 0 | 0 | 0 | 0 | 0 |
| 2(E3) | 0 | 0 | 0 | 0 | 0 | 0 | 0 |
| 2(F3) | 0 | 9 | 0 | 0 | 0 | 0 | 0 |
| 4(F3) | 5 | 9 | 0 | 5 | 0 | 9 | 0 |
| 4(E3) | 5 | 9 | 0 | 0 | 0 | 0 | 0 |
| 2(D3) | 0 | 0 | 0 | 0 | 0 | 0 | 0 |
| 4(D3) | 9 | 5 | 0 | 0 | 0 | 5 | 0 |
| 228(A3) | 0 | 0 | 0 | 0 | 0 | 0 | 0 |
| 2(A13) | 0 | 0 | 0 | 0 | 0 | 0 | 5 |
| 15(V3) | 9 | 5 | 0 | 0 | 0 | 0 | 0 |
| 180(A3) | 0 | 0 | 0 | 0 | 0 | 5 | 0 |
| 4(A13) | 9 | 9 | 9 | 9 | 0 | N/T | 0 |
| 183(A3) | 9 | 0 | 0 | 5 | 5 | 5 | 0 |
| 203(A3) | 0 | 9 | 9 | 9 | 0 | 0 | 0 |
| 174(A3) | 0 | 5 | 0 | 0 | 0 | 0 | 0 |
| 2(A43) | 0 | 0 | 0 | 0 | 0 | 0 | 5 |

TABLE X1-continued

| Compound No. (Table No.) | TETRUR | MYZUPE | MUSCDO AC | MUSCDO AK | HELIVI | LAPHEG | MELGIN |
|---|---|---|---|---|---|---|---|
| 229(A3) | 0 | 0 | 0 | 0 | 0 | 0 | 0 |
| 191(A3) | 9 | 0 | 5 | 5 | 5 | 0 | 9 |
| 15(A1) | 9 | 0 | 5 | 0 | 0 | 0 | 0 |
| 15(A4) | 9 | 9 | 9 | 9 | 0 | 9 | 0 |
| 204(A3) | 0 | 9 | 9 | 9 | 5 | 9 | 0 |
| 2(A4) | 0 | 5 | 5 | 5 | 0 | N/T | 0 |
| 9(A43) | 5 | 9 | 0 | 0 | 0 | N/T | 0 |
| 339(A3) | 9 | 0 | 0 | 0 | 0 | N/T | 0 |
| 35(A3) | 9 | 9 | 0 | 0 | 5 | N/T | 0 |
| 15(N3) | 0 | 0 | 0 | 0 | 0 | N/T | 0 |
| 113(A3) | 9 | 0 | 0 | 0 | 0 | N/T | 0 |
| 80(A3) | 0 | 0 | 0 | 0 | 0 | N/T | 0 |

TABLE X2

| Compound No. (Table No.) | TETRUR | MYZUPE | HELIVI | MELGIN |
|---|---|---|---|---|
| 287(A3) | 0 | 0 | 0 | 0 |
| 15(A5) | 5 | 0 | 0 | 0 |
| 2(A5) | 0 | 5 | 0 | 5 |
| 2(A8) | 0 | 5 | 0 | 0 |
| 15(A8) | 9 | 9 | 5 | 0 |
| 330(A3) | 0 | 0 | 0 | 0 |
| 349(A3) | 0 | 0 | 0 | 0 |
| 173(A3) | 0 | 0 | 0 | 0 |
| 334(A3) | 0 | 0 | 0 | 0 |
| 272(A3) | 0 | 0 | 0 | 0 |
| 253(A3) | 0 | 5 | 0 | 0 |
| 42(A3) | 9 | 5 | 0 | 0 |
| 305(A3) | 0 | 0 | 0 | 0 |
| 86(A3) | 5 | 5 | 0 | 0 |
| 12(A3) | 5 | 5 | 0 | 9 |
| 93(A3) | 0 | 0 | 0 | 0 |
| 246(A3) | 0 | 0 | 0 | 0 |
| 36(A3) | 9 | 5 | 0 | 0 |
| 267(A3) | 0 | 5 | 0 | 0 |
| 79(A3) | 0 | 0 | 5 | 0 |
| 130(A3) | 5 | 9 | 0 | 0 |
| 95(A3) | 0 | 9 | 0 | 0 |
| 21(A3) | 0 | 5 | 0 | 0 |
| 343(A3) | 0 | 5 | 0 | 0 |
| 75(A3) | 0 | 9 | 0 | 0 |
| 15(H3) | 0 | 9 | 0 | 0 |
| 239(A3) | 0 | 9 | 0 | 0 |
| 244(A3) | 0 | 0 | 0 | 0 |
| 115(A3) | 0 | 5 | 0 | 0 |

Key to Tables X1 and X2:
TETRUR = *Tetranychus urticae*
MYZUPE = *Myzus persicae*
MUSCDO AK = *Musca domestica* (kill)
MUSCDO AC = *Musca domestica* (knockdown)
HELIVI = *Heliothis virescens*
LAPHEG = *Spodoptera exigua*
MELGIN = *Meloidogyne incognita*
N/T = Not tested

EXAMPLE 27

This Example illustrates the fungicidal properties of compounds of formula (I). The compounds were tested against a variety of foliar fungal diseases of plants. The technique employed was as follows.

Plants were grown in John Innes Potting Compost (No. 1 or 2) in 4 cm diameter, 3.5 cm depth minipots. The test compounds were individually formulated as a solution either in acetone or acetone/ethanol (1:1 by volume) which was diluted in deionised water to a concentration of 100 ppm (that is, 1 mg of compound in a final volume of 10 ml) immediately before use. When foliar sprays were applied to monocotyledonous crops, TWEEN 20 (0.1% by volume) was added. TWEEN is a registered trade mark.

Individual compounds of formula (I) were applied as a foliar (Folr) application (where the chemical solution was applied to the foliage of the test plants by spraying the plant to maximum droplet retention); as a systemic (Syst) application (where the chemical solution, 10 ml, was applied as a root drench treatment) or as a stem (Stem) application (where the chemical solution was applied to the stems of the test plants by spraying the plants to run off).

These tests were carried out against *Plasmopara viticola* (PLASVI) and *Uncinula necator* (UNCINE), on vines; *Phytophthora infestans lycopersici* (PHYTIN) and *Botrytis cinerea* (BOTRCI), on tomatoes; *Venturia inaequalis* (VENTIN), on apples; *Erysiphe graminis* f.sp. tritici (ERYSGT), *Septoria nodorum* (LEPTNO) and *Puccinia recondita* (PUCCRT), on wheat; and *Pyricularia oryzae* (PYRIOR) and *Rhizoctonia solani* (RHIZSO), on rice. Each treatment was applied to two or more replicate plants for *Plasmopara viticola*, *Phytophthora infestans lycopersici*, *Botrytis cinerea*, *Uncinula necator* and *Venturia inaequalis*. In tests on *Erysiphe graminis* f.sp. tritici, *Septoria nodorum*, *Puccinia recondita*, *Rhizoctonia solani* and *Pyricularia oryzae* two replicate pots each containing 6 to 10 plants were used for each treatment. The plants were inoculated with a calibrated fungal spore suspension one or two days before (Erad) or 6 hours, one day or two days after (Prot) chemical application.

After chemical application and inoculation, the plants were incubated under high humidity conditions and then put into an appropriate environment to allow infection to proceed, until the disease was ready for assessment. The *Erysiphe graminis* f.sp. tritici plants were inoculated using a 'shake' inoculation technique. The *Uncinula necator* plants were inoculated using a 'blowing' inoculation technique. For *Plasmopara viticola*, the plants were reincubated under high humidity conditions for 24 hours prior to assessment. The time period between chemical application and assessment varied from five to fourteen days according to the disease and environment. However, each individual disease was assessed after the same time period for all compounds.

Assessments were performed on a single leaf of each of the two replicate plants for *Plasmopara viticola* and *Venturia inaequalis* and on each of two leaves on each of the replicate plants for *Phytophthora infestans lycopersici* and *Botrytis cinerea*. Assessments were performed on a single leaf of each of the three replicate plants for *Uncinula necator*. For *Erysiphe graminis* f.sp. tritici, *Septoria nodorum*, *Puccinia recondita* and *Pyricularia recondita* assessments were carried out collectively on the plants in each replicate pot. For *Rhizoctonia solani*, the number of infected plants in each of two replicate pots were assessed.

The disease level present (that is, the percentage leaf area covered by actively sporulating disease) or percentage of infected plants per pot was assessed visually. For each treatment, the assessed values for all its replicates were meaned to provide mean disease values. Untreated control plants were assessed in the same manner. The data were then processed by either of two alternative methods, described hereinafter, each providing its own PRCO (Percentage Reduction from Control) value.

METHOD 1

This method uses banded assessment values.

The mean disease values are banded in the manner shown below. If the disease level value falls exactly mid-way between two of the points, the result will be the lower of the two points.

| | |
|---|---|
| 0 = 0% disease present | 10 = 5.1–10% disease present |
| 1 = 0.1–1% disease present | 20 = 10.1–20% disease present |
| 3 = 1.1–3% disease present | 30 = 20.1–30% disease present |
| 5 = 3.1–5% disease present | 60 = 30.1–60% disease present |
| | 90 = 60.1–100% disease present |

An example of a typical banded calculation is as follows:

Mean disease level for treatment A=25%

Therefore banded mean disease level for treatment A=30

Mean disease level on untreated controls=85%

Therefore banded mean disease level on untreated controls=90

$$\text{PRCO} = 100 - \frac{\{\text{Banded mean disease level for treatment A}\}}{\{\text{Banded mean disease level on treated controls}\}} \times 100$$

$$= 100 - \left(\frac{30}{90} \times 100\right) = 66.7$$

The PRCO is then rounded to the nearest whole number, therefore, in this particular example, the PRCO result is 67.

METHOD 2

This method uses unbanded assessment values (that is, the mean disease values are used in the PRCO calculation without a banding step).

An example of a typical unbanded calculation is as follows:

Mean disease level for treatment A=25%

Mean disease level on untreated controls=85%

$$\text{PRCO} = 100 - \frac{\{\text{Mean disease level for treatment A}\}}{\{\text{Mean disease level on untreated controls}\}} \times 100$$

$$= 100 - \left(\frac{25}{85} \times 100\right) = 70.6$$

The PRCO is then rounded to the nearest whole number, therefore, in this particular example, the PRCO result is 71.

It is possible for negative PRCO values to be obtained. PRCO results are shown below.

TABLE Y1

| COMPOUND NO. (TABLE NO.) | ERYSGT 6 hr Prot/Foir | ERYSGT 1 d Prot/Foir | PLASVI 1 d Prot/Foir | LEPTNO 1 d Prot/Foir | PUCCRT 1 d Prot/Foir | PHYTIN 1 d Prot/Foir |
|---|---|---|---|---|---|---|
| 4(A3) | 100* | | 34 | 50 | 100* | 100* |
| 15(A3) | 100* | | 100 | 71 | 100 | 100* |
| 2(A3) | 100* | | 0* | 21 | 100* | 100* |
| 9(A3) | 100* | | 100* | 55 | 100 | 100 |
| 248(A3) | 0* | | 97* | 0* | 100* | 17* |
| 257(A3) | 0* | | 79* | 0* | 100* | 0* |
| 1(A3) | | 88 | 6 | | 59 | 100 |
| 8(A3) | | 20 | 6 | 0 | 90 | |
| 3(A3) | | 4 | 14 | 33 | 98 | |
| 140(A3) | | 44 | 63 | 13 | 96 | |
| 220(A3) | | 12 | 6 | 17 | 100* | 100* |
| 14(A3) | | 90 | 89 | 28 | 97 | 100 |
| 221(A3) | | 50 | 84 | 20 | 99 | 99 |
| 223(A3) | | 73 | 55 | 12 | 99 | 93 |
| 10(A3) | | 98 | 87 | 28 | 100 | 100 |
| 252(A3) | | 30 | 38 | −13 | 97 | |
| 46(A3) | | 97 | 99 | 88 | 100 | |
| 13(A3) | | 100 | 100 | 58 | 100 | 93 |
| 329(A3) | | 30 | 8 | 0 | 46 | |
| 47(A3) | | 86 | 92 | 63 | 99 | |
| 247(A3) | | 61 | 62 | 13 | 95 | 97 |
| 331(A3) | | 33 | 49 | 17 | 95 | |
| 98(A3) | | 98 | 99 | 30 | 98 | 100 |
| 5(A3) | | 40 | 39 | 30 | 88 | 100 |
| 28(A3) | | 46 | 0 | 20 | 86 | 100 |
| 172(A3) | | 40 | 44 | 10 | 96 | 100 |
| 261(A3) | | 19 | 25 | −7 | 3 | 0 |
| 224(A3) | | 88 | 99 | 16 | 98 | 100 |
| 15(B3) | | 75 | 79 | −2 | 15 | 99 |
| 15(D3) | | 55 | | 70 | 25 | 99 |
| 15(L3) | | 100 | | 40 | 17 | 97 |
| 15(M3) | | | | | 6 | 98 |
| 15(C3) | | 38 | | 93 | 13 | 97 |
| 73(A3) | | 93 | | 57 | 100 | 100 |
| 41(A3) | | 59 | | 77 | 98 | 100 |
| 2(A23) | | −3 | | 53 | 77 | 100 |

TABLE Y1-continued

| COMPOUND NO. (TABLE NO.) | ERYSGT 6 hr Prot/Foir | ERYSGT 1 d Prot/Foir | PLASVI 1 d Prot/Foir | LEPTNO 1 d Prot/Foir | PUCCRT 1 d Prot/Foir | PHYTIN 1 d Prot/Foir |
|---|---|---|---|---|---|---|
| 4(A23) | | 59 | | 63 | 100 | 100 |
| 15(A23) | | 62 | | 83 | 98 | 100 |
| 2(K3) | | | | | 97 | 98 |
| 2(B3) | | | | | 96 | 100 |
| 4(B3) | | | | | 48 | 100 |
| 15(F3) | | | | | 95 | 100 |
| 2(L3) | | | | | 93 | 82 |
| 2(M3) | | | | | 68 | 83 |
| 4(L3) | | | | | 100 | 100 |
| 4(K3) | | | | | 100 | 98 |
| 15(E3) | | | | | 74 | 83 |
| 2(C3) | | | | | 74 | 150 |
| 4(M3) | | | | | 85 | 81 |
| 4(C3) | | | | | 96 | 79 |
| 352(A3) | | | | | 100 | 100 |
| 2(E3) | | | | | 99 | 98 |
| 2(F3) | | | | | 90 | 100 |
| 4(F3) | | | | | 100 | 99 |
| 4(E3) | | | | | 97 | 95 |
| 2(D3) | | | | | 96 | 59 |
| 4(D3) | | | | | 90 | 96 |
| 228(A3) | | | | | 6 | 66 |
| 2(A13) | | 31 | | 62 | 99 | 100 |
| 15(V3) | | 87 | | -2 | 100 | 100 |
| 180(A3) | | 29 | | 14 | 69 | |
| 4(A13) | | 100 | | 20 | 100 | |
| 183(A3) | | 99 | | 19 | 99 | 100 |
| 203(A3) | | 98 | | -3 | 100 | 85 |
| 2(A43) | | 20 | | -3 | 7 | 18 |
| 229(A3) | | 21 | | 2 | 6 | 92 |
| 191(A3) | | 94 | | 36 | 99 | 92 |
| 15(A1) | | 43 | | 4 | 96 | 100 |
| 15(A4) | | 91 | | 19 | 99 | 100 |
| 204(A3) | | 87 | | 67 | 99 | 100 |
| 4(A43) | | | | 0 | 31 | 0 |
| 15(A43) | | | | 0 | | 80 |
| 2(A4) | | 97 | | -12 | 100 | 100 |
| 9(A43) | | 7 | | -4 | 25 | 0 |
| 339(A3) | | -7 | | 0 | 31 | 0 |
| 35(A3) | | 93 | | -15 | 100 | 84 |
| 15(N3) | | 8 | | -2 | 3 | 3 |
| 113(A3) | | 5 | | 20 | 41 | 38 |
| 287(A3) | | 34 | | -2 | 94 | 3 |
| 80(A3) | | 99 | | -2 | 100 | 45 |
| 15(A5) | | 15 | | -2 | 84 | 45 |
| 2(A5) | | 18 | | -2 | 28 | 19 |
| 2(A8) | | 54 | | 9 | 100 | 74 |
| 15(A8) | | 80 | | -2 | | 99 |
| 63(A3) | | 40 | | 2 | 69 | 66 |
| 330(A3) | | 87 | | 37 | 99 | 99 |
| 173(A3) | | 16 | | 2 | 63 | 77 |
| 253(A3) | 94 | 94 | | 8 | 99 | 98 |
| 42(A3) | 92 | 92 | | 11 | 99 | 100 |
| 305(A3) | 16 | 16 | | -2 | 81 | 74 |
| 12(A3) | | 95 | | 17 | 100 | 100 |
| 93(A3) | | 32 | | 24 | 38 | 49 |
| 246(A3) | | 16 | | 27 | 13 | 79 |
| 36(A3) | | 72 | | 2 | 91 | 100 |
| 79(A3) | | 100 | | 14 | 100 | |
| 130(A3) | | 87 | | 21 | 100 | |
| 95(A3) | | 68 | | 8 | 100 | |
| 21(A3) | | 35 | | 14 | 100 | |
| 75(A3) | | 90 | | 27 | 94 | |
| 15(H3) | | 16 | | 2 | 29 | |
| 239(A3) | | 23 | | | 3 | |
| 244(A3) | | 3 | | -2 | 84 | |
| 115(A3) | | -3 | | 8 | 45 | |

TABLE Y2

| COMPOUND NO. (TABLE NO.) | UNCINE 1 d Prot/Foir | PYRIOR 1 d Prot/Foir | RHIZSO 1 d Prot/Foir | VENTIN 1 d Prot/Foir | BOTRCI 1 d Prot/Foir |
|---|---|---|---|---|---|
| 4(A3) | 62 | 81 | | 49 | 49 |
| 15(A3) | 100 | 100 | 5 | 100 | 73 |
| 2(A3) | 93 | 92 | 24 | 97 | 0 |
| 9(A3) | 100 | 100 | 29 | 33 | 3 |
| 248(A3) | 7 | | 7 | 100 | |
| 257(A3) | 61 | | 11 | 0 | |
| 1(A3) | 43 | 91 | | 25 | |
| 8(A3) | 40 | | 0 | 26 | |
| 3(A3) | 27 | | 0 | 67 | |
| 140(A3) | 99 | | 0 | 70 | |
| 220(A3) | −5 | | 0 | 11 | |
| 14(A3) | 98 | 90 | 12 | 10 | |
| 221(A3) | 23 | 93 | 0 | 25 | |
| 223(A3) | 30 | 63 | 0 | 60 | |
| 10(A3) | 96 | 77 | 0 | 40 | |
| 252(A3) | 79 | 46 | 0 | −47 | |
| 46(A3) | 100 | 92 | 0 | 84 | |
| 13(A3) | 100 | 96 | 19 | 53 | |
| 329(A3) | 6 | 38 | 0 | −16 | |
| 47(A3) | 98 | 88 | 0 | 37 | |
| 247(A3) | 95 | 85 | 0 | −11 | |
| 331(A3) | 76 | 81 | | 5 | |
| 98(A3) | 100 | 81 | | 96 | |
| 5(A3) | 72 | 31 | | −10 | |
| 28(A3) | 9 | 81 | | 53 | |
| 172(A3) | 36 | 19 | | 69 | |
| 261(A3) | 17 | 31 | 0 | 0 | |
| 224(A3) | 91 | 91 | 0 | 60 | |
| 351(A3) | 11 | | | | |
| 15(B3) | 100 | 69 | 29 | 5 | |
| 15(D3) | 100 | 27 | | −14 | |
| 15(L3) | 99 | 20 | | −21 | |
| 15(C3) | 100 | 7 | | 64 | |
| 73(A3) | 93 | 100 | 0 | | |
| 41(A3) | 91 | 33 | | 50 | |
| 2(A3) | −17 | 47 | 89 | | |
| 4(A3) | 99 | 90 | | 95 | |
| 15(A23) | 100 | 80 | 0 | 100 | |
| 2(A13) | 72 | 47 | 43 | | |
| 15(V3) | 100 | 100 | 0 | 10 | |
| 180(A3) | 42 | 42 | | 0 | |
| 4(A13) | 100 | 100 | | 55 | |
| 183(A3) | 98 | 99 | | 98 | |
| 203(A3) | 69 | 96 | | 65 | |
| 2(A43) | 11 | 48 | | 14 | |
| 229(A3) | −9 | 55 | | 10 | |
| 191(A3) | 100 | 92 | | 10 | |
| 15(A1) | 100 | 87 | | 54 | |
| 15(A4) | 100 | 98 | | 54 | |
| 204(A3) | 81 | 96 | | 22 | |
| 4(A43) | 35 | 38 | | | |
| 15(A43) | 63 | 63 | | | |
| 2(A4) | 90 | 99 | | 92 | |
| 9(A43) | 7 | 26 | | 38 | |
| 339((A3) | 26 | 33 | | 8 | |
| 35((A3) | 100 | 98 | | 70 | |
| 15(N3) | 87 | 13 | | 3 | |
| 113(A3) | 21 | 28 | | 8 | |
| 287(A3) | 20 | 19 | | 8 | |
| 80(A3) | 100 | 91 | | −8 | |
| 15(A5) | 83 | 81 | | 3 | |
| 2(A5) | 3 | 31 | | 19 | |
| 2(A8) | 74 | 75 | | 8 | |
| 15(A8) | 100 | 81 | | 24 | |
| 63(A3) | 14 | | | 13 | |
| 330(A3) | 14 | | | 6 | |
| 173(A3) | −12 | | | 50 | |
| 253(A3) | 100 | | | 34 | |
| 42(A3) | 100 | | | 74 | |
| 305(A3) | 19 | | | −6 | |
| 12(A3) | 100 | | | 63 | |
| 93(A3) | 10 | | | 6 | |
| 246(A3) | −7 | | | 13 | |
| 36(A3) | 99 | | | 44 | |
| 79(A3) | 90 | 98 | | 88 | |

TABLE Y2-continued

| COMPOUND NO. (TABLE NO.) | UNCINE 1 d Prot/Foir | PYRIOR 1 d Prot/Foir | RHIZSO 1 d Prot/Foir | VENTIN 1 d Prot/Foir | BOTRCI 1 d Prot/Foir |
|---|---|---|---|---|---|
| 130(A3) | 86 | 93 | | 60 | |
| 95(A3) | 100 | 96 | | 98 | |
| 21(A3) | 44 | 92 | | 50 | |
| 75(A3) | 53 | 78 | | 15 | |
| 15(H3) | 63 | 46 | | 0 | |
| 239(A3) | 51 | 11 | | 5 | |
| 244(A3) | | −2 | | 45 | |
| 115(A3) | 2 | 5 | | 15 | |

Key to Tables Y1 and Y2
* = METHOD 1 (otherwise METHOD 2)
6 h = 1 hour
1 d = 1 day
ERYSGT = *Erysiphe graminis tritici*
PHYTIN = *Phytophthora infestans lycopersici*
PLASVI = *Plasmopara viticoia*
PUCCRT = *Puccinia recondita*
LEPTNO = *Septoria nodorum*
UNCINE = *Uncinula necator*
PYRIOR = *Pyricularia oryzae*
RHIZO = *Rhizocionia solani*
VENTIN = *Venturia inaequalis*
BOTRCI = *Botrytis cinerea*

EXAMPLE 28

This Example illustrates the synergistic fungicidal properties of compounds of formula (I) when used in mixture with other compounds. The compounds were tested against a variety of foliar fungal diseases of plants. The technique employed was as follows.

Plants were grown in John Innes Potting Compost (No. 1 or 2) in 4 cm diameter, 3.5 cm depth minipots or 8 cm diameter, 7 cm depth pots. Compounds were tested individually or in two-compound mixtures. The test compounds were individually formulated as a solution either in acetone or acetone/ethanol (1:1 by volume) which was then diluted in deionised water to give a compound concentration such as 100 ppm (that is, 1 mg of a compound in a final volume of 10 ml) immediately before use. Solutions of two-compound mixtures were prepared by two appropriate solutions of individual compounds. Sprays were applied as foliar applications (where the chemical solution was applied to the foliage of the test plants by spraying the plant to maximum droplet retention). When applied to monocotyledonous crops, TWEEN 20 (0.1% by volume) was added. TWEEN is a registered trade mark. For each two-compound mixture tested, each of the two compounds was also tested individually, the concentration of an individual compound in an individual test being the same as the concentration of that same compound when present in the corresponding two-compound mixture test.

These tests were carried out against *Plasmopara viticola* (PLASVI), on vines; *Septoria nodorum* (LEPTNO), on wheat; and *Rhizoctonia solani* (RHIZSO), on turf. Each treatment was applied to four replicate plants for *Plasmopara viticola*. In tests on *Septoria nodorum* four replicate pots each containing 6 to 10 plants were used for each treatment. In tests on *Rhizoctonia solani* four replicate pots each containing a covering of turf were used for each treatment. The plants were inoculated with a calibrated fungal spore suspension one day after chemical application.

After chemical application and inoculation, the plants were incubated under high humidity conditions and then put into an appropriate environment to allow infection to proceed, until the disease was ready for assessment. For *Plasmopara viticola*, the plants were reincubated under high humidity conditions for 24 hours prior to assessment The time period between chemical application and assessment varied from four to fourteen days according to the disease and environment. However, each individual disease was assessed after the same time period for all compounds and mixtures.

Assessments were performed on a single leaf of each of the replicate plants for *Plasmopara viticola*. For *Septoria nodorum* and *Rhizoctonia solani* assessments were carried out collectively on the plants in each replicate pot.

Step 1. Determination of Fungicidal Control.

For each replicate of a treatment the disease level present (that is, the percentage leaf area covered by actively sporulating disease for *Plasmopara viticola*, lesion area caused by *Septoria nodorum* and percentage area of turf infected for *Rhizoctonia solani*) was assessed visually. The data obtained were then processed according to METHOD 2 of Example 27 in order to obtain PRCO (Percentage Reduction from Control) values.

Step 2. Synergy Assessment.

Limpel's formula (Pesticide Science (1987) 19 309–315 at 312) is used to determine the PRCO which a two-compound mixture is expected to provide, assuming that in mixture the compounds provide fungicide control in an additive manner. The expected control of the mixture is based on the PRCO data for the two individual compounds, when each is applied individually at the same rate as that used in mixture. If in tests the observed PRCO of the mixture is greater than the expected PRCO, then according to Limpel the two compounds are displaying synergistic behaviour when applied in mixture.

Limpel's formula is:

$$E = X + Y - \frac{XY}{100}$$

where:
- X is the PRCO of substance A applied at a rate of p mg/l;
- Y is the PRCO of substance B applied at a rate of q mg/l; and
- E is the expected PRCO of two-compound mixture [A+B] (A and B applied respectively at p and q mg/l).

the table below provides example data for two compounds tested individually and in mixture together.

| Application rate/ (mg of compound/litre) | | Observed | Expected |
|---|---|---|---|
| Compound A | Compound B | PRCO (/%) | PRCO (/%) |
| 100 | 0 | 21 | — |
| 0 | 0.1 | 48 | — |
| 100 | 0.1 | 81 | 59.2 |

In this example the PRCO observed for the mixture is greater than the value E calculated according to Limpel, therefore this mixture of A and B is synergistic.

The following tables contain observed and expected disease control data for a number of two-compound mixtures, each of which contains Compound 15 of Table A3.

TABLE Z1

*SEPTORIA NODORUM* - Compound 15 (A3) and azoxystrobin.

| COMPOUND APPLICATION RATE /(mg/l) | | Test 1 (Disease on untreated: 52%) % disease control | | Test 2 (Disease on untreated: 64%) % disease control | |
|---|---|---|---|---|---|
| Compound 15(A3) | azoxystrobin | Observed | Expected | Observed | Expected |
| 100 | 0 | 27 | / | 21 | / |
| 50 | 0 | 16 | / | 21 | / |
| 0 | 0.25 | 37 | / | 71 | / |
| 0 | 0.1 | 41 | / | 48 | / |
| 100 | 0.25 | 89 | 54.01 | 92 | |
| 100 | 0.1 | 84 | 56.93 | 81 | 58.92 |
| 50 | 0.25 | 82 | 47.08 | 80 | 77.09 |
| 50 | 0.1 | 73 | 50.44 | 75 | 58.92 |

Conclusion: The mixtures show synergy.

TABLE Z2

*PLASMOPARA VITICOLA* - Compound 15(A3) and azoxystrobin.

| COMPOUND APPLICATION RATE /(mg/l) | | (Disease on untreated: 95%) % disease control | |
|---|---|---|---|
| Compound 15(A3) | azoxystrobin | Observed | Expected |
| 0.2 | 0 | 45 | / |
| 0 | 0.2 | 61 | / |
| 0.2 | 0.2 | 100 | 79 |

Conclusion: The mixture shows synergy.

TABLE Z3

*PLASMOPARA VITICOLA* - Compound 15(A3) and fluazinam.

| COMPOUND APPLICATION RATE /(mg/l) | | (Disease on untreated: 95%) % disease control | |
|---|---|---|---|
| Compound 15(A3) | fluazinam | Observed | Expected |
| 0.2 | 0 | 45 | / |
| 0 | 1 | 4 | / |
| 0.2 | 1 | 96 | 47 |

Conclusion: The mixture shows synergy.

TABLE Z4

*PLASMOPARA VITICOLA* - Compound 15(A3) and fenamidone.

| COMPOUND APPLICATION RATE /(mg/l) | | (Disease on untreated: 95%) % disease control | |
|---|---|---|---|
| Compound 15(A3) | fenamidone | Observed | Expected |
| 0.2 | 0 | 45 | / |
| 0 | 0.2 | 65 | / |
| 0.2 | 0.2 | 100 | 83 |

Conclusion: The mixture shows synergy.

TABLE Z5

*RHIZOCTONIA SOLANI* - Compound 15(A3) and azoxystrobin.

| COMPOUND APPLICATION RATE /(mg/l) | | Test 1 (Disease on untreated 100%; assessed 5 days after treatment) % desease control | | Test 2 (Disease on untreated 100%; assessed 5 days after treatment) % disease control | |
|---|---|---|---|---|---|
| Compound 15(A3) | azoxystrobin | Observed | Expected | Observed | Expected |
| 300 | 0 | 2.5 | / | 6.1 | / |
| 0 | 0.1 | 38.25 | / | 19.7 | / |
| 0 | 0.3 | 71.25 | / | / | / |
| 300 | 0.1 | 66.25 | 40.3 | 51 | 26.4 |
| 300 | 0.3 | 87.5 | 71.97 | / | / |

Conclusion: The mixtures show synergy.

TABLE Z6

*RHIZOCTONIA SOLANI* - Compound 15(A3) and fluazinam.

| COMPOUND APPLICATION RATE /(mg/l) | | Test 1 (Disease on untreated 100%; assessed 5 days after treatment) % desease control | | Test 2 (Disease on untreated 100%; assessed 5 days after treatment) % disease control | |
|---|---|---|---|---|---|
| Compound 15(A3) | fluazinam | Observed | Expected | Observed | Expected |
| 300 | 0 | 2.5 | / | 6.1 | / |
| 0 | 10 | 48.75 | / | 18.4 | / |
| 0 | 3 | 15 | / | / | / |
| 300 | 10 | 86 | 50.0 | 79.6 | 23.37 |
| 300 | 3 | 40 | 17.125 | / | / |

Conclusion: The mixtures show synergy.

Chemical Formulae in the Description
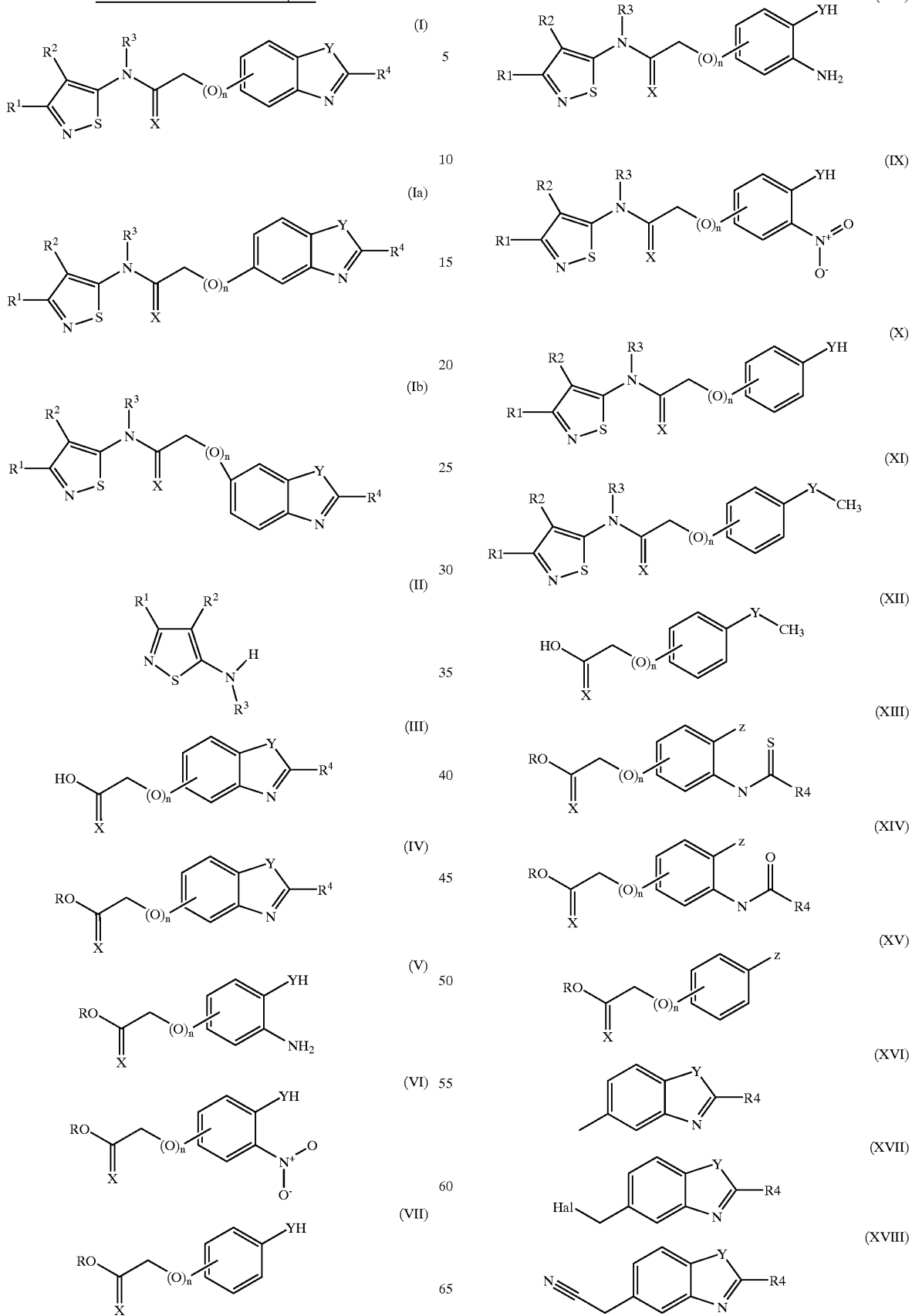

-continued

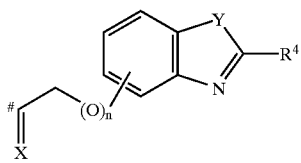
(XIX)

What is claimed is:
1. A compound of formula (I):

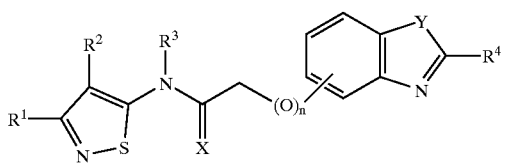
(I)

wherein X is O or S; n is 0 or 1; Y is O, S or $NR^7$; $R^1$ is hydrogen, halogen, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{3-6}$ cycloalkyl, $C_{1-6}$ alkoxy($C_{1-6}$)alkyl or $SF_5$; $R^2$ is hydrogen, halogen, $C_{1-6}$ alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{1-6}$ haloalkyl, cyano, nitro, CHO, CH=$NOR^5$, $C_{1-6}$ alkylcarbonyl, $C_{1-6}$ alkoxycarbonyl or $SF_5$; or together $R^1$ and $R^2$ form a five or six membered saturated or unsaturated carbocyclic ring, optionally substituted by one or two $C_{1-6}$ alky groups; $R^3$, is hydrogen, $C_{1-6}$ alkyl, $CH_2(C_{1-4}$ haloalkyl), $C_{1-6}$ cyanoalkyl, $C_{3-6}$ alkenyl, $C_{3-6}$ alkynyl, $C_{1-6}$-alkoxy($C_{1-6}$)alkyl, $C_{1-6}$ alkylthio($C_{1-6}$)alkyl, $C_{1-6}$ alkoxy($C_{1-6}$)alkoxy($C_{1-6}$)alkyl, $C_{1-6}$ alkylcarbonyl, $C_{1-6}$ alkoxycarbonyl, formyl, $C_{1-6}$ alkylcarbonyl($C_{1-6}$)alkyl, $C_{1-6}$ alkoxycarbonyl($C_{1-6}$)alkyl, $C_{1-6}$ alkylaminocarbonyl, di($C_{1-6}$)alkylaminocarbonyl, optionally substituted phenoxycarbonyl, optionally substituted phenyl($C_{1-4}$)alkyl or $S(O)_qR^6$; $R^4$ is hydrogen, halogen, cyano, $C_{1-8}$ alkyl, $C_{1-6}$ haloalkyl, $C_{1-6}$ cyanoalkyl, $C_{2-6}$ alkenyl, $C_{2-6}$ alkynyl, $C_{3-7}$ cycloalkyl, $C_{3-7}$ halocycloalkl, $C_{3-7}$ cyanocycloalkyl, $C_{1-3}$ alkyl($C_{3-7}$)cycloalkyl, $C_{1-3}$ alkyl($C_{3-7}$)halocycloalkyl, $C_{3-6}$ cycloalkyl($C_{1-6}$)alkyl, $C_{5-6}$ cycloalkenyl, $C_{5-6}$ cycloalkenyl ($C_{1-6}$)alkyl, $C_{2-6}$ haloalkenyl, $C_{1-6}$cyanoalkenyl, $C_{1-6}$ alkoxy ($C_{1-6}$)alkyl, formyl, $C_{1-6}$ carboxyalkyl, $C_{1-6}$ alkylcarbonyl ($C_{1-6}$)alkyl, $C_{1-6}$ alkoxycarbonyl($C_{1-6}$)alkyl, $C_{1-6}$ alkylthio ($C_{1-6}$)alkyl, $C_{1-6}$ alkylsulfinyl($C_{1-6}$)alkyl, $C_{1-6}$ alkylsulfonyl ($C_{1-6}$alkyl, aminocarbonyl($C_{1-6}$)alkyl, $C_{1-6}$ alkylaminocarbonyl($C_{1-6}$)alkyl, di($C_{1-6}$)alkylaminocarbonyl ($C_{1-6}$)alkyl, $C_{1-6}$ alkoxycarbonyl, $C_{1-6}$ alkylcarbonyl, aminocarbonyl, $C_{1-6}$ alkylaminocarbonyl, di($C_{1-6}$) alkylaminocarbonyl, optionally substituted phenyl, optionally substituted phenyl($C_{1-4}$)alkyl, optionally substituted phenyl($C_{2-4}$)alkenyl, optionally substituted heteroaryl, optionally substituted heteroaryl($C_{1-4}$)alkyl, optionally substituted heterocyclyl, optionally substituted heterocyclyl($C_{1-4}$)alkyl, a group $OR^8$, a group SH, a group $S(O)_pR^9$, a group $NR^{10}R^{11}$ or a group $C(R^{12})$=$NOR^{13}$; $R^5$ is hydrogen, $C_{1-6}$ alkyl, optionally substituted phenyl or optionally substituted phenyl($C_{1-4}$)alkyl; $R^6$ is $C_{1-6}$ alkyl, $C_{1-6}$ haloalkyl or optionally substituted phenyl; $R^7$ is hydrogen, cyano, $C_{1-8}$ alkyl, $C_{1-6}$ haloalkyl, $C_{1-6}$ cyanoalkyl, $C_{2-6}$ alkenyl, $C_{2-6}$ alkynyl, $C_{3-7}$ cycloalkyl, $C_{2-6}$ haloalkenyl, $C_{3-6}$ cycloalkyl($C_{1-6}$)alkyl, $C_{1-6}$ alkoxy($C_{1-6}$) alkyl, $C_{1-6}$ alkoxycarbonyl, $C_{1-6}$ alkylcarbonyl, $C_{1-6}$ alkylaminocarbonyl, di($C_{1-6}$)alkylaminocarbonyl, optionally substituted phenyl or optionally substituted heteroaryl; $R^8$ is hydrogen, $C_{1-6}$ alkyl, $C_{1-6}$ haloalkyl, $C_{3-6}$ alkenyl, $C_{1-4}$ cyanoalkyl, $C_{1-6}$ alkoxycarbonyl($C_{1-6}$)alkyl, optionally substituted phenyl, optionally substituted phenyl($C_{1-4}$)alkyl, optionally substituted heteroaryl, N=$C(CH_3)_2$; $R^9$ is $C_{1-6}$ alkyl, $C_{1-6}$ haloalkyl, $C_{3-6}$ alkenyl, cyano, $C_{1-4}$ cyanoalkyl, $C_{1-6}$ alkoxycarbonyl($C_{1-6}$)alkyl, optionally substituted phenyl, optionally substituted phenyl($C_{1-4}$)alkyl or optionally substituted heteroaryl; $R^{10}$ and $R^{11}$ are, independently, hydrogen, $C_{1-8}$ alkyl, $C_{3-7}$, cycloalkyl, $C_{3-6}$ alkenyl, $C_{3-6}$ alkynyl, $C_{2-6}$ haloalkyl, $C_{1-6}$ alkoxy($C_{1-6}$)alkyl, $C_{1-6}$ alkoxycarbonyl, optionally substituted phenoxycarbonyl, formyl, $C_{1-6}$ alkylcarbonyl, $C_{1-6}$ alkyl$SO_2$, optionally substituted phenyl$SO_2$ or optionally substituted phenyl($C_{1-4}$) alkyl; $R^{12}$ is $C_{1-3}$ alkyl $R^{13}$ is $C_{1-6}$ alkyl, optionally substituted phenyl($C_{1-2}$)alkyl; and p and q are, independently, 0, 1 or 2.

2. A compound of formula (Ia) or a compound of formula (Ib):

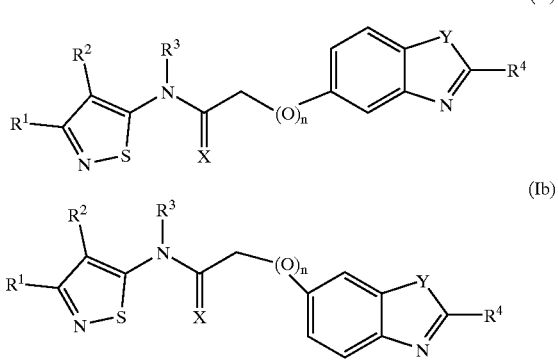

wherein X is O or S; n is 0 or 1; Y is O, S or $NR^7$; $R^1$ is hydrogen, halogen, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{3-6}$ cycloalkyl, $C_{1-6}$ alkoxy($C_{1-6}$)alkyl or $SF_5$; $R^2$ is hydrogen, halogen, $C_{1-6}$ alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{1-6}$ haloalkyl, cyano, nitro, CHO, CH=$NOR^5$, $C_{1-6}$ alkylcarbonyl, $C_{1-6}$ alkoxycarbonyl or $SF_5$; or together $R^1$ and $R^2$ form a five or six membered saturated or unsaturated carbocyclic ring, optionally substituted by one or two $C_{1-6}$ alkyl groups; $R^3$ is hydrogen, $C_{1-6}$ alkyl, $CH_2(C_{1-6}$ haloalkyl), $C_{1-6}$ cyanoalkyl, $C_{3-6}$ alkenyl, $C_{3-6}$ alkynyl, $C_{1-6}$ alkoxy($C_{1-6}$)alkyl, $C_{1-6}$ alkylthio($C_{1-6}$)alkyl, $C_{1-6}$ alkoxy ($C_{1-6}$)alkoxy($C_{1-6}$)alkyl, $C_{1-6}$ alkylcarbonyl, $C_{1-6}$ alkoxycarbonyl, formyl, $C_{1-6}$ alkylcarbonyl($C_{1-6}$)alkyl, $C_{1-6}$ alkoxycarbonyl($C_{1-6}$)alkyl, $C_{1-6}$ alkylaminocarbonyl, di($C_{1-6}$)alkylaminocarbonyl, optionally substituted phenoxycarbonyl, optionally substituted phenyl($C_{1-4}$)alkyl or $S(O)_qR^6$; $R^4$ is hydrogen, halogen, cyano, $C_{1-8}$ alkyl, $C_{1-6}$ haloalkyl, $C_{1-6}$ cyanoalkyl, $C_{2-6}$ alkenyl, $C_{2-6}$ alkynyl, $C_{3-7}$ cycloalkyl, $C_{3-7}$ halocycloalkyl, $C_{3-7}$ cyanocycloalkyl, $C_{1-3}$ alkyl($C_{3-7}$)cycloalkyl, $C_{1-3}$ alkyl($C_{3-7}$)halocycloalkyl, $C_{3-6}$ cycloalkyl($C_{1-6}$)alkyl, $C_{5-6}$ cycloalkenyl, $C_{5-6}$ cycloalkenyl ($C_{1-6}$)alkyl,$C_{2-6}$ haloalkenyl, $C_{1-6}$ cyanoalkenyl, $C_{1-6}$ alkoxy ($C_{1-6}$)alkyl, formyl, $C_{1-6}$ alkylcarbonyl($C_{1-6}$)alkyl, $C_{1-6}$ alkoxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$) alkyl, di($C_{1-6}$)alkylaminocarbonyl($C_{1-6}$)alkyl, $C_{1-6}$ alkoxycarbonyl, $C_{1-6}$ alkylcarbonyl, aminocarbonyl, $C_{1-6}$ alkylaminocarbonyl, di($C_{1-6}$)alkylaminocarbonyl, optionally substituted phenyl, optionally substituted phenyl(C$_{1-4}$) alkyl, optionally substituted phenyl(C$_{2-4}$)alkenyl, optionally substituted heteroaryl, optionally substituted heteroaryl(C$_{1-4}$)alkyl, optionally substituted heterocyclyl, optionally substituted heterocyclyl(C$_{1-4}$)alkyl, a group OR$^8$, a group SH, a group S(O)$_p$R$^9$, a group NR$^{10}$R$^{11}$ or a group C(R$^{12}$)=NOR$^{13}$; R$^5$ is hydrogen, C$_{1-6}$ alkyl, optionally substituted phenyl or optionally substituted phenyl(C$_{1-4}$) alkyl; R$^6$ is C$_{1-6}$ alkyl, C$_{1-6}$ haloalkyl or optionally substituted phenyl; R$^7$ is hydrogen, cyano, C$_{1-8}$ alkyl, C$_{1-6}$ haloalkyl, C$_{1-6}$ cyanoalkyl, C$_{2-6}$ alkenyl, C$_{2-6}$ alkynyl, C$_{3-7}$ cycloalkyl, C$_{2-6}$ haloalkenyl, C$_{3-6}$ cycloalkyl(C$_{1-6}$)alkyl, C$_{1-6}$ alkoxy(C$_{1-6}$)alkyl, C$_{1-6}$ alkoxycarbonyl, C$_{1-6}$ alkylcarbonyl, C$_{1-6}$ alkylaminocarbonyl, di(C$_{1-6}$) alkylaminocarbonyl, optionally substituted phenyl or optionally substituted heteroaryl; R$^8$ is hydrogen, C$_{1-6}$ alkyl, C$_{1-6}$ haloalkyl, C$_{3-6}$ alkenyl, C$_{1-4}$ cyanoalkyl, C$_{1-6}$ alkoxycarbonyl(C$_{1-6}$)alkyl, optionally substituted phenyl, optionally substituted phenyl(C$_{1-4}$)alkyl, optionally substituted heteroaryl, N=C(CH$_3$)$_2$; R$^9$ is C$_{1-6}$ alkyl, C$_{1-6}$ haloalkyl, C$_{3-6}$ alkenyl, cyano, C$_{1-4}$ cyanoalkyl, C$_{1-6}$ alkoxycarbonyl(C$_{1-6}$ optionally substituted phenyl, optionally substituted phenyl(C$_{1-4}$)alkyl or optionally substituted heteroaryl; R$^{10}$ and R$^{11}$ are, independently, hydrogen, C$_{1-8}$ alkyl, C$_{3-7}$ cycloalkyl, C$_{3-6}$ alkenyl, C$_{3-6}$ alkynyl, C$_{2-6}$ haloalkyl, C$_{1-6}$ alkoxy(C$_{1-6}$)alkyl, C$_{1-6}$ alkoxycarbonyl, optionally substituted phenoxycarbonyl, formyl, C$_{1-6}$ alkylcarbonyl, C$_{1-6}$ alkylSO$_2$, optionally substituted phenylSO$_2$ or optionally substituted phenyl(C$_{1-4}$)alkyl; R$^{12}$ is C$_{1-3}$ alkyl; R$^{13}$ is C$_{1-6}$ alkyl, optionally substituted phenyl (C$_{1-2}$)alkyl; and p and q are, independently, 0, 1 or 2.

3. A compound of formula (I) as claimed in claim 1 wherein n is zero.

4. A compound of formula (Ia) or a compound of formula (Ib) as claimed in claim 3 wherein R$^1$ is C$_{1-2}$ alkyl.

5. A compound of formula (Ia) or a compound of formula (Ib) as claimed in claim 3 wherein R$^2$ is hydrogen, cyano or halogen.

6. A compound of formula (Ia) or a compound of formula (Ib) as claimed in claim 3, wherein R$^3$ is hydrogen, C$_{1-6}$ alkyl or C$_{1-6}$ alkoxy(C$_{1-6}$)alkyl.

7. A compound of formula (Ia) or a compound of formula (Ib) as claimed in claim 3, wherein R$^4$ is hydrogen, SH, C$_{1-6}$ alkyl, C$_{3-6}$ cycloalkyl, C$_{2-6}$ alkenyl, C$_{2-5}$ alkynyl, C$_{1-4}$ haloalkyl, C$_{1-4}$ cyanoalkyl, C$_{2-6}$ haloalkenyl, optionally substituted heterocyclyl(C$_{1-4}$)alkyl, C$_{2-6}$ cyanoalkenyl, phenyl (optionally substituted with fluoro, chloro, bromo, nitro, cyano, C$_{1-6}$ alkyl, C$_{1-2}$ alkoxy, C$_{1-4}$ haloalkyl, C$_{1-4}$ haloalkoxy, methanesulfonyl, methylenedioxy or di(C$_{1-4}$ alkyl)amino), phenyl(C$_{1-3}$)alkyl (phenyl optionally substituted with halogen, nitro, cyano, C$_{1-6}$ alkyl, C$_{1-2}$ alkoxy, C$_{1-4}$ haloalkyl, C$_{1-4}$ haloalkoxy, methanesulfonyl, or methylenedioxy), formyl, optionally substituted heterocyclyl, optionally substituted heteroaryl, optionally substituted heteroaryl(C$_{1-4}$)alkyl, C$_{1-2}$ alkylcarbonyl, C$_{1-4}$ alkoxycarbonyl, C$_{1-5}$ alkoxycarbonyl(C$_{1-6}$)alkyl, a group NR$^{10}$R$^{11}$, a group OR$^8$, C$_{1-4}$ alkoxymethyl, chlorine, a group SR$^9$, or a group C(R$^{12}$)=NOR$^{13}$; R$^8$ is hydrogen, C$_{1-5}$ alkyl, C$_{1-4}$ haloalkyl, C$_{2-4}$ alkenyl, phenyl (optionally substituted with fluoro, chloro, bromo, nitro, cyano, C$_{1-6}$ alkyl, C$_{1-2}$ alkoxy, C$_{1-4}$ haloalkyl, C$_{1-4}$ haloalkoxy, methanesulfonyl, or methylenedioxy), phenyl(CH$_2$) (phenyl optionally substituted with fluoro, chloro, bromo, nitro, cyano, C$_{1-6}$ alkyl, C$_{1-2}$ alkoxy, C$_{1-4}$ haloalkyl, C$_{1-4}$ haloalkoxy, methanesulfonyl, or methylenedioxy), N=C(CH$_3$)$_2$; R$^9$ is C$_{1-5}$ alkyl, phenyl (optionally substituted with fluoro, chloro, bromo, nitro, cyano, C$_{1-6}$ alkyl, C$_{1-2}$ alkoxy, C$_{1-4}$ haloalkyl, C$_{1-4}$ haloalkoxy, methanesulfonyl, methylenedioxy or di(C$_{1-4}$ alkyl)amino), C$_{1-2}$ haloalkyl, cyano, cyanomethyl or C$_{1-2}$ alkoxycarbonylmethyl; R$^{10}$ and R$^{11}$ are, independently, hydrogen, C$_{1-4}$ alkyl, C$_{5-6}$ cycloalkyl, formyl, C$_{1-3}$ alkylcarbonyl, phenoxycarbonyl, C$_{1-2}$ alkylSO$_2$ or phenylSO$_2$; R$^{12}$ is C$_{1-2}$ alkyl; and R$^{13}$ is C$_{1-2}$ alkyl or benzyl.

8. A compound of formula (I) as claimed in claim 1 wherein log$_{10}$K$_{o/w}$ (calculated using the CLOGP3 program, available from BioByte Corp.) of the compound is in the range zero to 8.

9. A compound of formula (I) as claimed in claim wherein in the side chain portion of formula (XIX):

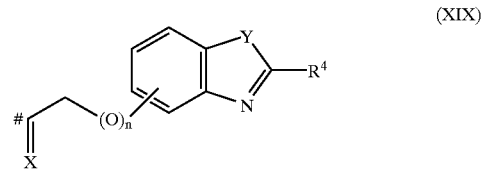

(XIX)

no atom having an atomic weight greater than 10 Daltons is more than four bond lengths away from at least one atom present in the longest bond path or, when there is a set of longest bond paths, no atom having an atomic weight greater than 10 Daltons is more than four bond lengths away from at least one atom present in each of the longest bond paths.

10. Processes for making compounds of formula (I) as defined in claim 1 comprising:

(i) acylation of a compound of formula (II) by a compound of formula (III):

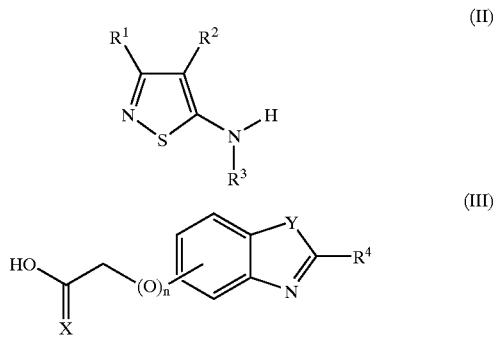

wherein R$^1$, R$^2$, R$^3$, R$^4$, X, Y and n are as described in claim 1; or (ii) acylation of a compound of formula (VIII):

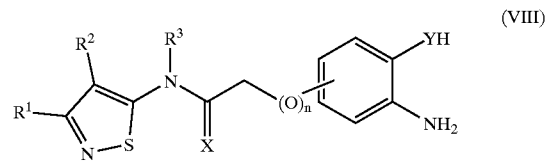

(VIII)

wherein R$^1$, R$^2$, R$^3$, X, Y and n are as described in claim 1, followed by cyclisation of the resultant product.

11. A fungicidal, insecticidal, acaricidal, molluscicidal or nematicidal composition comprising a fingicidally, insecticidally, acaricidally, molluscicidally or nematicidally effective amount of a compound of formula (I) as claimed in claim 1 and a carrier or diluent therefor.

12. A method of combating and controlling fungi comprising applying to a plant, to a seed of a plant, to the locus of the plant or seed or to the soil a fungicidally effective amount of a compound of formula (1) as claimed in claim 1.

13. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as claimed in claim 1.

14. A method as claimed in claim 13 wherein the insect pests are insect pests of plants.

15. A method of combating and controlling fungi comprising applying to a plant, to a seed of a plant, to the locus of the plant or seed or to the soil a fungicidally effective composition containing a compound of formula (I) as claimed in claim 11.

16. A method of combating and controlling insects, acarines, nematodes or molluscs which comprises applying to a pest, to a locus of a pest, or to a plant susceptible to attack by a pest an insecticidally, acaricidally nematicidally or molluscicidally effective amount of a composition containing a compound of formula (I) as claimed in claim 11.

17. A compound of formula (Ia) or a compound of formula (Ib) as claimed in claim 2, wherein n is zero.

18. A compound of formula (I) as claimed in claim 17, wherein $R^1$ is $C_{1-2}$ alkyl.

19. A compound of formula (I) as claimed in claim 17, wherein $R^2$ is hydrogen, cyano or halogen.

20. A compound of formula (I) as claimed in claim 17, wherein $R^3$ is hydrogen, $C_{1-6}$ alkyl or $C_{1-6}$ alkoxy ($C_{1-6}$) alkyl.

21. A compound of formula (I) as claimed in claim 17, wherein $R^4$ is hydrogen, SH, $C_{1-6}$- alkyl, $C_{3-6}$ cycloalkyl, $C_{2-6}$ alkenyl, $C_{2-5}$ alkynyl, $C_{1-4}$ haloalkyl, $C_{1-4}$ cyanoalkyl, $C_{2-6}$ haloalkenyl, optionally substituted heterocyclyl($C_{1-4}$) alkyl, $C_{2-6}$ cyanoalkenyl, phenyl (optionally substituted with fluoro, chloro, bromo, nitro, cyano, $C_{1-6}$ alkyl, $C_{1-2}$ alkoxy, $C_{1-4}$ haloalkyl, $C_{1-4}$ haloalkoxy, methanesulfonyl, methylenedioxy or di($C_{1-4}$ alkyl)amino), phenyl($C_{1-3}$)alkyl (phenyl optionally substituted with halogen, nitro, cyano, $C_{1-6}$ alkyl, $C_{1-2}$ alkoxy, $C_{1-4}$ haloalkyl, $C_{1-4}$ haloalkoxy, methanesulfonyl, or methylenedioxy), formyl, optionally substituted heterocyclyl, optionally substituted heteroaryl, optionally substituted heteroaryl($C_{1-4}$)alkyl, $C_{1-2}$ alkylcarbonyl, $C_{1-4}$ alkoxycarbonyl, $C_{1-5}$ alkoxycarbonyl ($C_{1-4}$)alkyl, a group $NR^{10}R^{11}$, a group $OR^8$, $C_{1-4}$ alkoxymethyl, chlorine, a group $SR^9$, or a group $C(R^{12})$ =$NOR^{13}$; $R^8$ is hydrogen, $C_{1-5}$ alkyl, $C_{1-4}$ haloalkyl, $C_{2-4}$ alkenyl, phenyl (optionally substituted with fluoro, chloro, bromo, nitro, cyano, $C_{1-6}$ alkyl, $C_{1-2}$ alkoxy, $C_{1-4}$ haloalkyl, $C_{1-4}$ haloalkoxy, methanesulfonyl, or methylenedioxy), phenyl($CH_2$) (phenyl optionally substituted with fluoro, chloro, bromo, nitro, cyano, $C_{1-6}$ alkyl, $C_{1-2}$ alkoxy, $C_{1-4}$ haloalkyl, $C_{1-4}$ haloalkoxy, methanesulfonyl, or methylenedioxy), N=$C(CH_3)_2$; $R^9$ is $C_{1-5}$ alkyl, phenyl (optionally substituted with fluoro, chloro, bromo, nitro, cyano, $C_{1-6}$ alkyl $C_{1-2}$ alkoxy, $C_{1-4}$ haloalkyl, $C_{1-4}$ haloalkoxy, methanesulfonyl, methylenedioxy or di($C_{1-4}$ alkyl)amino), $C_{1-2}$ haloalkyl, cyano, cyanomethyl or $C_{1-2}$ alkoxycarbonylmethyl; $R^{10}$ and $R^{11}$ are, independently, hydrogen, $C_{1-4}$. alkyl, $C_{5-6}$ cycloalkyl, formyl, $C_{1-3}$ alkylcarbonyl, phenoxycarbonyl, $C_{1-2}$ alkylSO$_2$ or phenylSO$_2$; $R^{12}$ is $C_{1-2}$ alkyl; and $R^{13}$ is $C_{1-2}$ alkyl or benzyl.

22. A compound of formula (Ia) or formula (Ib) as claimed in claim 2, wherein $\log_{10}K_{o/w}$ (calculated using the CLOGP3 program, available from BioByte Corp.) of the compound is in the range zero to 8.

23. A compound of formula (Ia) or formula (Ib) as claimed in claim 2, wherein in the side chain portion of formula (XIX):

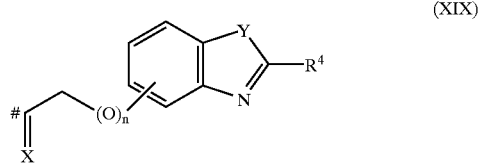

(XIX)

no atom having an atomic weight greater than 10 Daltons is more than four bond lengths away from at least one atom present in the longest bond path or, when there is a set of longest bond paths, no atom having an atomic weight greater than 10 Daltons is more than four bond lengths away from at least one atom present in each of the longest bond paths.

24. A compound of formula (Ia) or a compound of formula (Ib) as claimed in claim 2, wherein $R^1$ is methyl, $R^2$ is hydrogen, $R^3$ is hydrogen, X and Y are each oxygen, n is 0, and $R^4$ is $CH_2C(CH_3)_3$; wherein $R^1$ is methyl, $R^2$ is chloro, $R^3$ is hydrogen, X and Y are each oxygen, n is 0, and $R^4$ is hydrogen, methyl, $CH_2CH_3$, $CH_2CH_2CH_3$, $CH_2CH_2CH_2CH_3$, $CH(CH_3)_2$, $C(CH_3)_3$, $CH(CH_3)CH_2CH_3$, $CH(CH_3)CH_2CH_2CH_3$, $CH(CH_2CH_3)_2$, $CH_2CH(CH_3)_2$, $CH_2C(CH_3)_3$, cyclopropyl, cyclopentyl, cyclohexyl, 1-methylcyclohexyl, cyclopropylmethyl, cyclopentylmethyl, CH=$CHCH_3$, CH=$C(CH_3)_2$, $C(CH_3)$=$CHCH_3$, 4-nitrostyryl, $CH_2F$, $CF_3$, $CF_2CHF_2$, $CF_2CF_2CF_3$, $CF_2CF_2Cl$, $CH(Cl)CH_3$, $CH(Cl)CH_2CH_3$, $CCl_3$, $CH_2CN$, $CH(CH_3)CN$, $CH_2OCH_3$, $CH_2O$—$C_6H_5$, $CH_2CH_2SCH_3$, $CH_2S$—$C_6H_5$, Cl, $N(CH_3)CH_2CH_3$, NHC ($CH_3)_3$, morpholino, $OCH_3$, $OCH_2CH_3$, $OCH(CH_3)_2$, $SCH_3$, $SCH_2CH_3$, $SCH(CH_3)_2$, $SC(CH_3)_3$, $SCH_2CN$, $SCH_2CO_2CH_3$, $CH_2C_6F_5$, 2,6-diCl-4—$CF_3$—$C_6H_2$, $CH(C_6H_5)_2$, $CH_2CH_2C_6H_5$, $C_6H_5$, 4-ter-butyl-$C_6H_4$, 2-Cl—$C_6H_4$, 2,4-diCl—$C_6H_3$, 3,5-diCl—$C_6H_3$, 2-Cl-4-$NO_2$—$C_6H_3$, 2-F—$C_6H_4$, 2,6-diF—$C_6H_3$, $C_6F_5$, 2-$CH_3O$—$C_6H_4$, 4-$CH_3O$—$C_6H_4$, 6-carboxymethylphenyl, 2-thienyl, 3-chloro-2-thienyl, 2-thienylmethyl, pyridin-4-yl, 2-chloro-3-pyridyl, 5-isoxazolyl, OH, or SH; wherein $R^1$ is methyl, $R^2$ is bromo, $R^3$ is hydrogen, X and Y are each oxygen, n is 0, and $R^6$ is methyl or $CH_2C(CH_3)_3$; wherein $R^1$ is methyl, $R^2$ is cyano, $R^3$ is hydrogen, X and Y are each oxygen, n is 0, and $R^4$ is methyl or $CH_2C(CH_3)_3$; wherein $R^1$ is ethyl, $R^2$ is chloro, $R^3$ is hydrogen, X and Y are each oxygen, n is 0, and $R^4$ is methyl or $CH_2C(CH_3)_3$; wherein $R^1$ is methyl, $R^2$ is chloro, $R^3$ is hydrogen, X is oxygen, Y is sulfur, n is 0, and $R^6$ is methyl, $CH_2CH_2CH_3$, $CH(CH_3)_2$, $C(CH_3)_3$, or $CH_2C$ $(CH_3)_3$; wherein $R^1$ is methyl, $R^2$ is chloro, $R^3$ is hydrogen, X and Y are each oxygen, n is 0, and $R^4$ is methyl, $CH_2CH_2CH_3$, or $CH_2C(CH_3)_3$; wherein $R^1$ is methyl, $R^2$ is chloro, $R^3$ is hydrogen, X is oxygen, Y is $NR^7$, $R^7$ is hydrogen, n is 0, and $R^4$is methyl, $CH_2CH_2CH_3$, $C(CH_3)_3$, $CH_2C(CH_3)_3$, or $C_6H_5$; wherein $R^1$ is methyl, $R^2$ is chloro, $R^3$ is methyl, X and Y are each oxygen, n is 0, and $R^4$ is methyl, $CH_2CH_2CH_3$, or $CH_2C(CH_3)_3$; wherein $R^1$ is methyl, $R^2$ is chloro, $R^3$ is ethyl, X and Y are each oxygen, n is 0, and $R^4$ is methyl, $CH_2CH_2CH_3$, or $CH_2C(CH_3)_3$; wherein $R^1$ is methyl, $R^2$ is chloro, $R^3$ is $CH_2CH_2CH_3$, X and Y are each oxygen, n is 0, and $R^4$ is methyl, $CH_2CH_2CH_3$, or $CH_2C(CH_3)_3$; wherein $R^1$ is methyl, $R^2$ is chloro, $R^3$ is $CH_2CH$=$CH_2$, X and Y are each oxygen, n is 0, and $R^4$ is methyl, $CH_2CH_2CH_3$, or $CH_2C(CH_3)_3$; wherein $R^1$ is methyl, $R^2$ is chloro, $R^3$ is $CH_2CCH$, X and Y are each oxygen, n is 0, and $R^4$ is methyl, $CH_2CH_2CH_3$, or $CH_2C$ $(CH_3)_3$; wherein $R^1$ is methyl, $R^2$ is chloro, $R^3$ is $CH_2CF_3$, X and Y are each oxygen, n is 0, and $R^4$ is $CH_2C(CH_3)_3$; wherein $R^1$ is methyl, $R^2$ is chloro, $R^3$ is $CH_2OCH_3$, X and Y are each oxygen, n is 0, and $R^4$ is methyl, $CH_2CH_2CH_3$, or $CH_2C(CH_3)_3$; wherein $R^1$ is methyl, $R^2$ is chloro, $R^3$ is $CH_2OCH_2CH_3$, X and Y are each oxygen, n is 0, and $R^4$ is methyl, $CH_2CH_2CH_3$, or $CH_2C(CH_3)_3$; wherein $R^1$ is methyl, $R^2$ is chloro, $R^3$ is $CH_2OCH_2CH_2OCH_3$, X and Y are each oxygen, n is 0, and $R^4$ is methyl, $CH_2CH_2CH_3$, or $CH_2C(CH_3)_3$; wherein $R^1$ is methyl, $R^2$ is chloro, $R^3$ is $CH(CH_3)_2$, X and Y are each oxygen, n is 0, and $R^4$ is $CH_2C(CH_3)_3$; or wherein $R^1$ is methyl, $R^2$ is chloro, $R^3$ is hydrogen, X is sulfur, Y is oxygen, n is 0, and $R^4$ is $CH_2C(CH_3)_3$; or wherein $R^1$ is methyl, $R^2$ is chloro, $R^3$ is hydrogen, X is sulfur, Y is oxygen, n is 0, and $R^4$ is $CH_2C(CH_3)_3$.

25. A fungicidal, insecticidal, acaricidal, molluscicidal or nematicidal composition comprising a fungicidally, insecticidally, acaricidally, molluscicidally or nematicidally effective amount of a compound of formula (Ia) or a compound of formula (Ib) as claimed in claim 2 and a carrier or diluent therefor.

26. A method of combating and controlling fungi comprising applying to a plant, to a seed of a plant, to the locus of the plant or seed or to the soil a fungicidally effective amount of a compound of formula (Ia) or a compound of formula (Ib) as claimed in claim 2.

27. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (Ia) or a compound of formula (Ib) as claimed in claim 2.

28. The method as claimed in claim 27, wherein the insect pests are insect pests of plants.

29. A method of combating and controlling fungi comprising applying to a plant, to a seed of a plant, to the locus of the plant or seed or to the soil a fungicidally effective composition containing a compound of formula (Ia) or a compound of formula (Ib) as claimed in claim 25.

30. A method of combating and controlling insects, acarines, nematodes or molluscs which comprises applying to a pest, to a locus of a pest, or to a plant susceptible to attack by a pest an insecticidally, acaricidally nematicidally or molluscicidally effective amount of a composition containing a compound of formula (Ia) or a compound of formula (Ib) as claimed in claim 25.

* * * * *